(12) United States Patent
Duncia et al.

(10) Patent No.: US 10,618,903 B2
(45) Date of Patent: Apr. 14, 2020

(54) HETEROARYL SUBSTITUTED AMINOPYRIDINE COMPOUNDS

(71) Applicant: BRISTOL-MYERS SQUIBB COMPANY, Princeton, NJ (US)

(72) Inventors: John V. Duncia, Newtown, PA (US); Daniel S. Gardner, Furlong, PA (US); John Hynes, Washington Crossing, PA (US); John E. Macor, Washington Crossing, PA (US); Natesan Murugesan, Princeton Junction, NJ (US); Joseph B. Santella, Springfield, PA (US); Hong Wu, New Hope, PA (US); Durgarao Kantheti, Bangalore (IN); Satheesh Kesavan Nair, Bangalore (IN); Venkatram Reddy Paidi, Bangalore (IN); Sreekantha Ratna Kumar, Bangalore (IN); Kandhasamy Sarkunam, Hosur (IN); Ramesh Kumar Sistla, Bangalore (IN); Subba Rao Polimera, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 77 days.

(21) Appl. No.: 16/314,574

(22) PCT Filed: Jun. 23, 2016

(86) PCT No.: PCT/US2016/038861
§ 371 (c)(1),
(2) Date: Dec. 31, 2018

(87) PCT Pub. No.: WO2016/210036
PCT Pub. Date: Dec. 29, 2016

(65) Prior Publication Data
US 2019/0292191 A1  Sep. 26, 2019

(30) Foreign Application Priority Data
Jun. 24, 2015 (IN) .............................. 1876/DEL/15

(51) Int. Cl.
*C07D 487/04* (2006.01)
*C07D 401/14* (2006.01)
*C07D 413/04* (2006.01)
*C07D 471/04* (2006.01)
*A61P 29/00* (2006.01)
*A61P 11/00* (2006.01)
*A61P 1/00* (2006.01)
*A61P 25/04* (2006.01)
(Continued)

(52) U.S. Cl.
CPC ......... *C07D 487/04* (2013.01); *C07D 401/14* (2013.01); *C07D 413/04* (2013.01); *C07D 471/04* (2013.01)

(58) Field of Classification Search
CPC .. C07D 487/04; C07D 401/14; C07D 471/04; C07D 413/04; A61P 29/00; A61P 11/00; A61P 1/00; A61P 25/04; A61P 19/02; A61P 37/06; A61P 11/06; A61P 17/06; A61P 35/00; A61P 37/00; A61K 31/519; A61K 31/435
See application file for complete search history.

(56) References Cited

U.S. PATENT DOCUMENTS 8,586,751 B2  11/2013  De Lucca et al.
8,987,311 B2   3/2015  Dodd et al.
(Continued)

FOREIGN PATENT DOCUMENTS

WO  WO02102800 A1  12/2002
WO  WO03013523 A1   2/2003
(Continued)

OTHER PUBLICATIONS

Annual Reports in Medicinal Chemistry, vol. 49, pp. 117-133.
(Continued)

*Primary Examiner* — John M Mauro
(74) *Attorney, Agent, or Firm* — Gary Greenblatt

(57) ABSTRACT

Disclosed are compounds of Formula (I) Formula (I) or salts thereof, wherein HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 $R_b$; and $R_1$, $R_3$, and $R_b$ are define herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

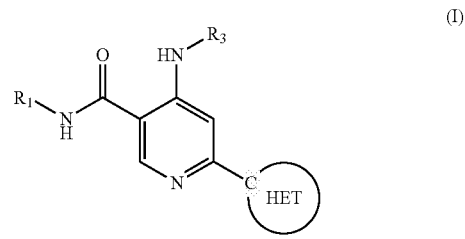

10 Claims, No Drawings

(51) Int. Cl.

| | |
|---|---|
| *A61P 19/02* | (2006.01) |
| *A61P 37/06* | (2006.01) |
| *A61P 11/06* | (2006.01) |
| *A61P 17/06* | (2006.01) |
| *A61P 37/00* | (2006.01) |
| *A61P 35/00* | (2006.01) |
| *A61K 31/519* | (2006.01) |
| *A61K 31/435* | (2006.01) |

(56) References Cited

U.S. PATENT DOCUMENTS

| | | | |
|---|---|---|---|
| 9,169,252 | B2 | 10/2015 | Santella et al. |
| 2005/0272753 | A1 | 12/2005 | Nagashima et al. |
| 2006/0148800 | A1 | 7/2006 | Stadtmueller et al. |
| 2009/0082329 | A1 | 3/2009 | Halley et al. |
| 2015/0011532 | A1 | 1/2015 | Paidi et al. |
| 2015/0018344 | A1 | 1/2015 | Paidi et al. |

FOREIGN PATENT DOCUMENTS

| | | |
|---|---|---|
| WO | GB2388596 A1 | 11/2003 |
| WO | WO2004065378 A1 | 8/2004 |
| WO | WO2005007646 A1 | 1/2005 |
| WO | WO2005075468 A2 | 8/2005 |
| WO | WO2008148889 A1 | 12/2008 |
| WO | WO2009046416 A1 | 4/2009 |
| WO | WO2011053701 A1 | 5/2011 |
| WO | WO2012149567 A1 | 11/2012 |
| WO | 2532656 A1 | 12/2012 |
| WO | WO2014074657 A1 | 5/2014 |
| WO | WO2014074660 A1 | 5/2014 |
| WO | WO2014074675 A1 | 5/2014 |

OTHER PUBLICATIONS

Buckley, IRAK-4 inhibitors. Part 1: A series of amides, Apr. 26, 2008, 3211-3214, 18, Bioorganic & Medicinal Chemistry Letters.
Buckley_etal_Bioorganic_Medicinal_Chem_Letters_Vol18_No11_2008_3291.
Buckley_etal_Bioorganic_Medicinal_Chem_Letters_Vol18_No11_2008_3656.
International Preliminary Report on Patentability for PCT/US2016/038861.

HETEROARYL SUBSTITUTED AMINOPYRIDINE COMPOUNDS

CROSS-REFERENCE TO RELATED APPLICATIONS

This application claims the benefit of Indian Provisional Patent Application Serial No. 1876/DEL/15, filed Jun. 24, 2015, which is incorporated herein in its entirety.

DESCRIPTION

The present invention generally relates to heteroaryl substituted aminopyridine compounds useful as kinase inhibitors, including the modulation of IRAK-4. Provided herein are heteroaryl substituted aminopyridine compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.,* 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.,* 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature,* 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., *Biochem. Pharmacol.,* 80:1981-1991 (2010)). A subset of human patients was identified who lack IRAK4 expression (Picard, C. et al., *Science,* 299:2076-2079 (2003)). Cells from these patients fail to respond to all TLR agonists with the exception of TLR3 as well as to members of the IL-1 family including IL-13 and IL-18 (Ku, C. et al., *J. Exp. Med.,* 204:2407-2422 (2007)). Deletion of IRAK4 in mice results in a severe block in IL-1, IL-18 and all TLR dependent responses with the exception of TLR3 (Suzuki, N. et al., *Nature,* 416:750-754 (2002)). In contrast, deletion of either IRAK1 (Thomas, J. A. et al., *J. Immunol.,* 163:978-984 (1999); Swantek, J. L. et al., *J. Immunol.,* 164:4301-4306 (2000) or IRAK2 (Wan, Y. et al., *J. Biol. Chem.,* 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.,* 282:13552-13560 (2007); Kawagoe, T. et al., *J. Exp. Med.,* 204:1013-1024 (2007); and Fraczek, J. et al., *J. Biol. Chem.,* 283:31697-31705 (2008)).

As compared to wild type animals, IRAK4 KDKI mice show greatly reduced disease severity in mouse models of multiple sclerosis (Staschke, K. A. et al., *J. Immunol.,* 183:568-577 (2009)), rheumatoid arthritis (Koziczak-Holbro, M. et al., *Arthritis Rheum.,* 60:1661-1671 (2009)), atherosclerosis (Kim, T. W. et al., *J. Immunol.,* 186:2871-2880 (2011) and Rekhter, M. et al., *Biochem. Biophys. Res. Comm.,* 367:642-648 (2008)), and myocardial infarction (Maekawa, Y. et al., *Circulation,* 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.,* 32:435-442 (2011); Mann, D. L., *Circ. Res.,* 108:1133-1145 (2011); Horton, C. G. et al., *Mediators Inflamm.,* Article ID 498980 (2010), doi:10.1155/2010/498980; Goldstein, D. R. et al., *J Heart Lung Transplant.,* 24:1721-1729 (2005); and Cario, E., *Inflamm. Bowel Dis.,* 16:1583-1597 (2010)). Oncogenically active MyD88 mutations in diffuse large B cell lymphomas have been identified that are sensitive to IRAK4 inhibition (Ngo, V. N. et al., *Nature,* 470:115-121 (2011)). Whole genome sequencing also identified mutations in MyD88 associated with chronic lymphatic leukemia suggesting that IRAK4 inhibitors may also have utility in treating leukemia (Puente, X. S. et al., *Nature,* 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.,* 41:1203-1217 (2011) and Couillin, I. et al., *J Immunol.,* 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.,* 187:6539-6549 (2011)). IL-1 has also been shown to be a critical link to adaptive immunity, driving differentiation of the TH17 effector T cell subset (Chung, Y. et al., *Immunity,* 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.,* 32:603-661 (2011)).

WO2013/106612, WO2013/106614, WO2013/106641, WO2014/074657, and WO2014/074675 disclose substituted pyridyl compounds useful as kinase inhibitors, including the modulation of IRAK4.

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

The present invention relates to a new class of heteroaryl substituted aminopyridine compounds found to be effective inhibitors of protein kinases including IRAK-4. These compounds are provided to be useful as pharmaceuticals with desirable stability, bioavailability, therapeutic index, and toxicity values that are important to their drugability.

SUMMARY OF THE INVENTION

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancer.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

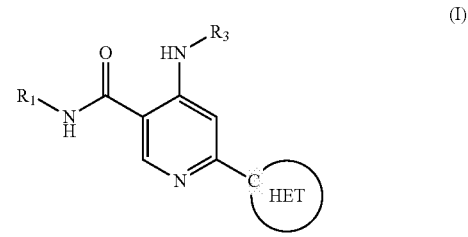

or a salt thereof, wherein:

HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 $R_b$;

each $R_b$ is independently selected from H, F, Cl, —CN, —NH$_2$, $C_{1-3}$ alkyl, $C_{1-2}$ fluoroalkyl, $C_{1-3}$ alkoxy, $C_{3-6}$ cycloalkyl, —NH($C_{1-3}$ alkyl), —NH($C_{1-4}$ hydroxyalkyl), cyanophenyl, pyridinyl, and hydroxypyrrolidinyl;

$R_1$ is:
(i) $C_{3-6}$ alkyl substituted with 1 to 4 substituents independently selected from F, —CN, —OH, —OCH$_3$, —OCD$_3$, —NHC(O)($C_{1-3}$ alkyl), —S(O)$_2$($C_{1-3}$ alkyl), and $C_{1-2}$ fluoroalkoxy;
(ii) —(CR$_y$R$_y$)$_{1-3}$R$_x$ or —(CH$_2$)$_{1-3}$C(O)R$_x$, wherein R$_x$ is phenyl, oxetanyl, tetrahydropyranyl, morpholinyl, piperidinyl, imidazolyl, pyridinyl, thiophenyl, or $C_{4-6}$ cycloalkyl, each substituted with zero to 3 substituents independently selected from F, Cl, —OH, $C_{1-3}$ alkyl, $C_{1-2}$ alkoxy, and —S(O)$_2$NH$_2$;
(iii) $C_{4-6}$ cycloalkyl substituted with zero to 2 substituents independently selected from —OH, $C_{1-4}$ hydroxyalkyl, $C_{1-3}$ alkoxy, —(CH$_2$)$_{1-3}$O($C_{1-3}$ alkyl), —C(O)NH($C_{1-4}$ alkyl), —C(O)NH($C_{3-6}$ cycloalkyl), —N($C_{1-3}$ alkyl)$_2$, —NHC(O)($C_{1-3}$ alkyl), —NHC(O)O($C_{1-3}$ alkyl), and —NHC(O)($C_{1-4}$ hydroxyalkyl);
(iv) tetrahydrofuranyl, tetrahydropyranyl, piperidinyl, piperazinyl, pyrrolyl, pyrazolyl, imidazolyl, or triazolyl, each substituted with zero to 2 substituents independently selected from $C_{1-4}$ hydroxyalkyl, —S(O)$_2$($C_{1-3}$ alkyl), —CH$_2$C(O)NH($C_{1-3}$ alkyl), —CH$_2$C(O)NH($C_{1-6}$ hydroxyalkyl), —CH$_2$C(O)NH($C_{1-6}$ fluoroalkyl), and —CH$_2$C(O)NH($C_{1-6}$ hydroxy-fluoroalkyl); or
(v) 1-oxa-7-azaspiro[3.5]nonanyl;

each $R_y$ is independently H, F, or —OH; and $R_3$ is:
(i) $C_{2-5}$ alkyl, $C_{2-5}$ fluoroalkyl, $C_{2-5}$ hydroxyalkyl, —(CH$_2$)$_{1-3}$R$_z$, —CH(CH$_3$)R$_z$, or —CH(CH$_2$OH)CH$_2$R$_z$, wherein R$_z$ is $C_{4-6}$ cycloalkyl, oxetanyl, tetrahydrofuranyl, tetrahydropyranyl, or phenyl, each substituted with zero to 1 substituent selected from —OH and —CH$_3$;

(ii) C$_{3-6}$ cycloalkyl substituted with zero to 3 substituents independently selected from F, Cl, —CN, —OH, C$_{1-3}$ alkyl, C$_{1-3}$ fluoroalkyl, C$_{1-4}$ hydroxyalkyl, C$_{1-4}$ alkoxy, —C(O)NH$_2$, —C(O)NH(C$_{1-3}$ alkyl), and —C(O)(C$_{1-3}$ fluoroalkyl);

(iii) oxetanyl, tetrahydrofuranyl, tetrahydropyranyl, pyrrolidinyl, piperidinyl, pyrazolyl, thiazolyl, bicyclo[1.1.1]pentanyl, bicyclo[2.2.1]heptanyl, or 4,5,6,7-tetrahydropyrazolo[1,5-a]pyrazinyl, each substituted with zero to 2 substituents independently selected from F, —OH, C$_{1-4}$ alkyl, C$_{1-3}$ hydroxyalkyl, C$_{1-4}$ fluoroalkyl, —CH$_2$(C$_{3-6}$ cycloalkyl), —(CH$_2$)$_{1-3}$O(C$_{1-3}$ alkyl), —C(O)(C$_{1-3}$ fluoroalkyl), —S(O)$_2$(C$_{1-3}$ alkyl), C$_{3-6}$ cycloalkyl, C$_{3-6}$ fluorocycloalkyl, oxetanyl, tetrahydrofuranyl, tetrahydropyranyl, pyrimidinyl, fluoropyrimidinyl, and methoxypyrimidinyl; or (iv) phenyl substituted with zero to 3 substituents independently selected from F, Cl, —CN, —OH, —C(O)NH$_2$, —C(O)NH(C$_{1-3}$ alkyl), and —C(O)(C$_{1-3}$ fluoroalkyl).

One embodiment provides at least one compound of Formula (I) or salt thereof, wherein:

HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 R$_b$;

each R$_b$ is independently selected from H, F, Cl, —CN, —NH$_2$, C$_{1-3}$ alkyl, C$_{1-3}$ alkoxy, C$_{3-6}$ cycloalkyl, —NH(C$_{1-3}$ alkyl), —NH(C$_{1-4}$ hydroxyalkyl), cyanophenyl, pyridinyl, and hydroxypyrrolidinyl;

R$_1$ is:

(i) C$_{3-6}$ alkyl substituted with 1 to 4 substituents independently selected from F, —OH, —OCH$_3$, and —OCD$_3$;

(ii) —(CR$_y$R$_y$)$_{1-3}$R$_x$ or —(CH$_2$)$_{1-3}$C(O)R$_x$, wherein R$_x$ is phenyl, tetrahydropyranyl, oxetanyl, morpholinyl, or C$_{4-6}$ cycloalkyl, each substituted with zero to 3 substituents independently selected from F, Cl, —OH, C$_{1-3}$ alkyl, C$_{1-2}$ alkoxy, and —S(O)$_2$NH$_2$;

(iii) C$_{4-6}$ cycloalkyl substituted with C$_{1-4}$ hydroxyalkyl, C$_{1-3}$ alkoxy, —C(O)NH(C$_{1-4}$ alkyl), —C(O)NH(C$_{3-6}$ cycloalkyl), —NHC(O)(C$_{1-3}$ alkyl), or —NHC(O)(C$_{1-4}$ hydroxyalkyl);

(iv) tetrahydrofuranyl, tetrahydropyranyl, piperidinyl, piperazinyl, pyrrolyl, pyrazolyl, imidazolyl, or triazolyl, each substituted with zero to 2 substituents independently selected from C$_{1-4}$ hydroxyalkyl, —S(O)$_2$(C$_{1-3}$ alkyl), —CH$_2$C(O)NH(C$_{1-3}$ alkyl), —CH$_2$C(O)NH(C$_{1-6}$ hydroxyalkyl), —CH$_2$C(O)NH(C$_{1-6}$ fluoroalkyl), and —CH$_2$C(O)NH(C$_{1-6}$ hydroxy-fluoroalkyl); or (v) 1-oxa-7-azaspiro[3.5]nonanyl;

each R$_y$ is independently H, F, or —OH; and

R$_3$ is:

(i) C$_{2-5}$ alkyl, C$_{2-5}$ fluoroalkyl, C$_{2-5}$ hydroxyalkyl, —(CH$_2$)$_{1-3}$R$_z$, —CH(CH$_3$)R$_z$, or —CH(CH$_2$OH)CH$_2$R$_z$, wherein R$_z$ is C$_{4-6}$ cycloalkyl, oxetanyl, tetrahydrofuranyl, tetrahydropyranyl, or phenyl, each substituted with zero to 1 substituent selected from —OH and —CH$_3$;

(ii) C$_{3-6}$ cycloalkyl substituted with zero to 3 substituents independently selected from F, Cl, —CN, —OH, C$_{1-3}$ alkyl, C$_{1-3}$ fluoroalkyl, C$_{1-4}$ hydroxyalkyl, C$_{1-4}$ alkoxy, —C(O)NH$_2$, —C(O)NH(C$_{1-3}$ alkyl), and —C(O)(C$_{1-3}$ fluoroalkyl);

(iii) oxetanyl, tetrahydrofuranyl, tetrahydropyranyl, pyrrolidinyl, piperidinyl, pyrazolyl, thiazolyl, bicyclo[1.1.1]pentanyl, or bicyclo[2.2.1]heptanyl, each substituted with zero to 2 substituents independently selected from F, —OH, C$_{1-3}$ alkyl, C$_{1-3}$ hydroxyalkyl, C$_{1-3}$ fluoroalkyl, —C(O)(C$_{1-3}$ fluoroalkyl), —S(O)$_2$(C$_{1-3}$ alkyl), oxetanyl, tetrahydrofuranyl, tetrahydropyranyl, pyrimidinyl, fluoropyrimidinyl, and methoxypyrimidinyl; or (iv) phenyl substituted with zero to 3 substituents independently selected from F, Cl, —CN, —OH, —C(O)NH$_2$, —C(O)NH(C$_{1-3}$ alkyl), and —C(O)(C$_{1-3}$ fluoroalkyl).

One embodiment provides a compound of Formula (I) or a salt thereof wherein:

HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 R$_b$;

each R$_b$ is independently selected from H, F, Cl, —CN, —NH$_2$, —CH$_3$, —CHF$_2$, —OCH$_3$, cyclopropyl, —NHCH$_2$CH$_2$OH, —NHCH$_2$C(CH$_3$)$_2$OH, cyanophenyl, pyridinyl, and hydroxypyrrolidinyl;

R$_1$ is:

(i) —CH$_2$CH$_2$C(CH$_3$)$_3$, —CH$_2$CH$_2$C(CH$_3$)$_2$OH, —CH$_2$CH$_2$C(CH$_3$)$_2$F, —CH$_2$CHFC(CH$_3$)$_2$F, —CH$_2$CH$_2$C(CH$_3$)$_2$CN, —CH$_2$CHFC(CH$_3$)$_2$OH, —CH$_2$CHFC(CH$_2$OH)$_2$OH, —CH$_2$CF$_2$C(CH$_3$)$_2$OH, —CH$_2$CH$_2$CH(CH$_3$)NHC(O)CH$_3$, —CH$_2$CHFC(CH$_3$)$_2$OCD$_3$, —CH$_2$CHFC(CH$_3$)$_2$OCHF$_2$, or —CH$_2$CH$_2$CH$_2$S(O)$_2$CH$_3$;

(ii) —CH$_2$CH$_2$(sulfamoylphenyl), —CH$_2$CH$_2$(fluorotetrahydropyranyl), —CH$_2$CH$_2$(hydrotetrahydropyranyl), —CH$_2$CHF(hydroxyoxetanyl), —CH$_2$CH$_2$C(O)(morpholinyl), —CH$_2$CH$_2$(pyridinyl), —CH$_2$CH$_2$(thiophenyl), —CH$_2$CH$_2$(hydroxycyclopentyl), —CH$_2$CH$_2$(hydroxy, methoxycyclohexyl), —CH$_2$CH$_2$(dihydroxy, methylcyclohexyl), —CH$_2$CH$_2$CH$_2$(imidazolyl), —CH$_2$CHF(piperidinyl), or —CH$_2$CHF(dimethyl tetrahydropyranyl);

(iii) cyclohexyl substituted with —OH, —C(CH$_3$)$_2$OH, —C(CH$_3$)$_2$OCH$_3$, —OCH$_3$, —OCH$_2$CH$_3$, —N(CH$_3$)$_2$, —C(O)NHCH$_3$, —C(O)NHCH(CH$_3$)$_2$, —C(O)NH(cyclopropyl), —NHC(O)CH$_3$, —NHC(O)OCH$_3$, —NHC(O)C(CH$_3$)$_2$OH, or —NHC(O)CH(OH)CH$_3$;

(iv) piperidinyl, pyrazolyl, or tetrahydropyranyl, each substituted with —CH$_2$OH, —S(O)$_2$CH(CH$_3$)$_2$, —CH$_2$C(O)NHCH$_3$, or —CH$_2$C(O)NHCH$_2$CHFC(CH$_3$)$_2$OH; or (iv) 1-oxa-7-azaspiro[3.5]nonanyl; and R$_3$ is:

(i) —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CF$_3$, —CH$_2$CH$_2$CF$_3$, —CH$_2$CF$_2$CH$_3$, —CH$_2$CHF$_2$, —CH$_2$CH$_2$CHF$_2$, —CH$_2$CH(CH$_3$)F, —CH$_2$CH$_2$CHFCH$_3$, —CH$_2$C(CH$_3$)$_2$F, —CH(CH$_3$)CH$_2$F, —CH(CH$_3$)CH$_2$CH$_2$F, —CH(CH$_3$)CH$_2$OH, —C(CH$_3$)$_2$CH$_2$OH, —CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$ (hydroxycyclobutyl), —CH$_2$(hydroxytetrahydropyranyl), or —CH(CH$_2$OH)CH$_2$(phenyl);
(ii) C$_{3-6}$ cycloalkyl substituted with zero to 3 substituents independently selected from F, —OH, —CH$_3$, —C(CH$_3$)$_2$OH, —C(CH$_3$)$_2$F, —OCH$_3$, and —OCH(CH$_3$)$_2$;
(iii) oxetanyl, tetrahydrofuranyl, tetrahydropyranyl, pyrrolidinyl, piperidinyl, pyrazolyl, thiazolyl, bicyclo[1.1.1]pentanyl, bicyclo[2.2.1]heptanyl, or 4,5,6,7-tetrahydropyrazolo[1,5-a]pyrazinyl; each substituted with zero to 2 substituents independently selected from F, —OH, C$_{1-4}$ alkyl, C$_{1-4}$ fluoroalkyl, —C(CH$_3$)$_2$OH, —CH$_2$CH$_2$OCH$_3$, —CH$_2$(cyclopropyl), C$_{3-4}$ cycloalkyl, —S(O)$_2$CH$_3$, difluorocyclobutyl, oxetanyl, tetrahydropyranyl, pyrimidinyl, fluoropyrmidinyl, and methoxypyrimidinyl; or
(iv) phenyl substituted with 1 to 2 substituents independently selected from F, —CN, —C(O)NH$_2$, and —C(O)NHCH$_3$.

One embodiment provides a compound of Formula (I) or a salt thereof wherein: HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 R$_b$;
each R$_b$ is independently selected from H, F, Cl, —CN, —NH$_2$, —CH$_3$, —OCH$_3$, cyclopropyl, —NHCH$_2$CH$_2$OH, —NHCH$_2$C(CH$_3$)$_2$OH, cyanophenyl, pyridinyl, and hydroxypyrrolidinyl;
R$_1$ is:
(i) —CH$_2$CH$_2$C(CH$_3$)$_2$OH, —CH$_2$CH$_2$C(CH$_3$)$_2$F, —CH$_2$CHFC(CH$_3$)$_2$OH, —CH$_2$CHFC(CH$_2$OH)$_2$OH, or —CH$_2$CHFC(CH$_3$)$_2$OCD$_3$;
(ii) —CH$_2$CH$_2$(sulfamoylphenyl), —CH$_2$CH$_2$(fluorotetrahydropyranyl), —CH$_2$CH$_2$(hydrotetrahydropyranyl), —CH$_2$CHF(hydroxyoxetanyl), —CH$_2$CH$_2$C(O)(morpholinyl), —CH$_2$CH$_2$(hydroxy, methoxycyclohexyl), or —CH$_2$CH$_2$(dihydroxy, methylcyclohexyl);
(iii) cyclohexyl substituted with —C(CH$_3$)$_2$OH, —OCH$_3$, —C(O)NHCH$_3$, —C(O)NHCH(CH$_3$)$_2$, —C(O)NH(cyclopropyl), —NHC(O)CH$_3$, —NHC(O)C(CH$_3$)$_2$OH, or —NHC(O)CH(OH)CH$_3$;
(iv) piperidinyl, pyrazolyl, or tetrahydropyranyl, each substituted with —CH$_2$OH, —S(O)$_2$CH(CH$_3$)$_2$, —CH$_2$C(O)NHCH$_3$, or —CH$_2$C(O)NHCH$_2$CHFC(CH$_3$)$_2$OH; or
(iv) 1-oxa-7-azaspiro[3.5]nonanyl;
R$_3$ is:
(i) —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CF$_3$, —CH$_2$CH$_2$CF$_3$, —CH$_2$CH(CH$_3$)F, —CH$_2$C(CH$_3$)$_2$F, —CH(CH$_3$)CH$_2$F, —CH(CH$_3$)CH$_2$CH$_2$F, —CH(CH$_3$)CH$_2$OH, —C(CH$_3$)$_2$CH$_2$OH, —CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$(hydroxycyclobutyl), —CH$_2$(hydroxytetrahydropyranyl), or —CH(CH$_2$OH)CH$_2$(phenyl);
(ii) C$_{3-5}$ cycloalkyl substituted with zero to 3 substituents independently selected from F, —OH, —CH$_3$, —C(CH$_3$)$_2$OH, —OCH$_3$, and —OCH(CH$_3$)$_2$;
(iii) oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl; or
(iv) phenyl substituted with 1 to 2 substituents independently selected from F, —CN, —C(O)NH$_2$, and —C(O)NHCH$_3$.

One embodiment provides a compound of Formula (I) or a salt thereof wherein HET is a heteroaryl selected from imidazo[1,2-b]pyridazin-3-yl and pyrazolo[1,5-a]pyrimidin-3-yl, each substituted with zero to 2 R$_b$; and R$_1$, R$_3$, and R$_b$ are defined in the first aspect. Included in this embodiment are compounds in which HET is imidazo[1,2-b]pyridazin-3-yl or pyrazolo[1,5-a]pyrimidin-3-yl substituted with Cl or —CN. Also included are compounds in which R$_3$ is —CH(CH$_3$)$_2$.

One embodiment provides a compound of Formula (I) or a salt thereof wherein HET is pyrazolo[1,5-a]pyrimidin-3-yl substituted with zero to 2 R$_b$; each R$_b$ is independently H, F, Cl, —CN, —NH$_2$, or cyclopropyl; R$_1$ is: (i) —CH$_2$CH$_2$C(CH$_3$)$_2$F, —CH$_2$CH$_2$C(CH$_3$)$_2$CN, —CH$_2$CHFC(CH$_3$)$_2$OH, —CH$_2$CHFC(CH$_2$OH)$_2$OH, —CH$_2$CHFC(CH$_3$)$_2$OCHF$_2$, —CH$_2$CHFC(CH$_3$)$_2$OCD$_3$, —CH$_2$CH$_2$CH$_2$S(O)$_2$CH$_3$, or —CH$_2$CH$_2$CH(CH$_3$)NHC(O)CH$_3$; (ii) —CH$_2$CH$_2$(sulfamoylphenyl), —CH$_2$CH$_2$(fluorotetrahydropyranyl), —CH$_2$CH$_2$(hydrotetrahydropyranyl), —CH$_2$CHF(hydroxyoxetanyl), —CH$_2$CH$_2$C(O)(morpholinyl), —CH$_2$CH$_2$(hydroxy, methoxycyclohexyl), or —CH$_2$CH$_2$(dihydroxy, methylcyclohexyl); (iii) cyclohexyl substituted with —C(CH$_3$)$_2$OH, —OCH$_3$, —OCH$_2$CH$_3$, —C(O)NHCH$_3$, —C(O)NHCH(CH$_3$)$_2$, —C(O)NH(cyclopropyl), —NHC(O)CH$_3$, —NHC(O)C(CH$_3$)$_2$OH, or —NHC(O)CH(OH)CH$_3$; (iv) piperidinyl, pyrazolyl, or tetrahydropyranyl, each substituted with —CH$_2$OH, —S(O)$_2$CH(CH$_3$)$_2$, —CH$_2$C(O)NHCH$_3$, or —CH$_2$C(O)NHCH$_2$CHFC(CH$_3$)$_2$OH; or (v) 1-oxa-7-azaspiro[3.5]nonanyl; and R$_3$ is: (i) —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CF$_3$, —CH$_2$CF$_2$CH$_3$, —CH$_2$CH$_2$CF$_3$, —CH(CH$_3$)CH$_2$F, —CH$_2$CH(CH$_3$)F, —CH$_2$CHFCH$_2$CH$_3$, —CH$_2$CH$_2$CHFCH$_3$, —CH$_2$C(CH$_3$)$_2$F, —CH(CH$_3$)CH$_2$CH$_2$F, —CH$_2$CH$_2$CH$_2$OH, —CH(CH$_3$)CH$_2$OH, —C(CH$_3$)$_2$CH$_2$OH, —CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$(hydroxycyclobutyl), —CH$_2$(hydroxytetrahydropyranyl), or —CH(CH$_2$OH)CH$_2$(phenyl);
(ii) C$_{3-5}$ cycloalkyl substituted with zero to 3 substituents independently selected from F, —OH, —CH$_3$, —C(CH$_3$)$_2$OH, —OCH$_3$, and —OCH(CH$_3$)$_2$; (iii) oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, bicyclo[2.2.1]heptanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl; or (iv) phenyl substituted with 1 to 2 substituents independently selected from F, —CN, —C(O)NH$_2$, —C(O)NHCH$_3$, and —C(O)CH$_2$CF$_3$. Included in this embodiment are compounds in which R$_b$ is H, Cl, or —CN. Also included are compounds in which R$_1$ is —CH$_2$CHFC(CH$_3$)$_2$OH.

One embodiment provides a compound of Formula (I) or a salt thereof wherein HET is pyrazolo[1,5-a]pyrimidin-3-yl substituted with zero to 2 R$_b$; each R$_b$ is independently H, F, Cl, —CN, —NH$_2$, or cyclopropyl; R$_1$ is: (i) —CH$_2$CH$_2$C(CH$_3$)$_2$F, —CH$_2$CHFC(CH$_3$)$_2$OH, —CH$_2$CHFC(CH$_2$OH)$_2$OH, or —CH$_2$CHFC(CH$_3$)$_2$OCD$_3$; (ii) —CH$_2$CH$_2$(sulfamoylphenyl), —CH$_2$CH$_2$(fluorotetrahydropyranyl), —CH$_2$CH$_2$(hydrotetrahydropyranyl), —CH$_2$CHF(hydroxyoxetanyl), —CH$_2$CH$_2$C(O)(morpholinyl), —CH$_2$CH$_2$(hydroxy, methoxycyclohexyl), or —CH$_2$CH$_2$(dihydroxy, methylcyclohexyl); (iii) cyclohexyl substituted with —C(CH$_3$)$_2$OH, —OCH$_3$, —C(O)NHCH$_3$, —C(O)NHCH(CH$_3$)$_2$, —C(O)NH(cyclopropyl), —NHC(O)CH$_3$, —NHC(O)C(CH$_3$)$_2$OH, or —NHC(O)CH(OH)CH$_3$; (iv) piperidinyl, pyrazolyl, or tetrahydropyranyl, each substituted with —CH$_2$OH, —S(O)$_2$CH(CH$_3$)$_2$, —CH$_2$C(O)NHCH$_3$, or —CH$_2$C(O)NHCH$_2$CHFC(CH$_3$)$_2$OH; or (v) 1-oxa-7-azaspiro[3.5]nonanyl; and R$_3$ is: (i) —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CF$_3$, —CH$_2$CH$_2$CF$_3$, —CH$_2$CH(CH$_3$)F, —CH$_2$C(CH$_3$)$_2$F, —CH(CH$_3$)CH$_2$F, —CH(CH$_3$)CH$_2$CH$_2$F, —CH(CH$_3$)CH$_2$OH, —C(CH$_3$)$_2$CH$_2$OH, —CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$(hydroxycyclobutyl), —CH$_2$(hydroxytetrahydropyranyl), or —CH(CH$_2$OH)CH$_2$(phenyl); (ii) C$_{3-5}$ cycloalkyl substituted with zero to 3 substituents independently selected from F, —OH, —CH$_3$, —C(CH$_3$)$_2$OH, —OCH$_3$, and —OCH(CH$_3$)$_2$; (iii) oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, bicyclo[2.2.1]heptanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl; or (iv) phenyl substituted with 1 to 2 substituents independently selected from F, —CN, —C(O)NH$_2$, —C(O)NHCH$_3$, and —C(O)CH$_2$CF$_3$. Included in this embodiment are compounds in which R$_b$ is H, Cl, or —CN. Also included are compounds in which R$_1$ is —CH$_2$CHFC(CH$_3$)$_2$OH.

One embodiment provides a compound of Formula (I) or a salt thereof wherein HET is imidazo[1,2-b]pyridazin-3-yl substituted with zero to 1 R$_b$; R$_b$ is H, Cl, —CN, —NH$_2$, —CH$_3$, —CHF$_2$, —OCH$_3$, —NHCH$_2$CH$_2$OH, —NHCH$_2$C(CH$_3$)$_2$OH, or hydroxypyrrolidinyl; R$_1$ is (i) —CH$_2$CH$_2$C(CH$_3$)$_3$, —CH$_2$CH$_2$C(CH$_3$)$_2$OH, —CH$_2$CF$_2$C(CH$_3$)$_2$OH, —CH$_2$CHFC(CH$_3$)$_2$OH, or —CH$_2$CHFC(CH$_3$)$_2$F; (ii) cyclohexyl substituted with —OH, —C(CH$_3$)$_2$OH, —C(CH$_3$)$_2$OCH$_3$, —N(CH$_3$)$_2$, —NHC(O)CH$_3$, or —NHC(O)OCH$_3$; or (iii) —CH$_2$CH$_2$(pyridinyl), —CH$_2$CH$_2$(thiophenyl), —CH$_2$CH$_2$(hydroxycyclopentyl), —CH$_2$CHF(piperidinyl), —CH$_2$CHF(dimethyl tetrahydropyranyl), or —CH$_2$CH$_2$CH$_2$(imidazolyl); and R$_3$ is (i) —CH$_2$CH$_3$, —CH(CH$_3$)$_2$, —CH(CH$_3$)CH$_2$CH$_3$, —C(CH$_3$)$_3$, —CH$_2$CH$_2$CHF$_2$, —CH$_2$CH$_2$CF$_3$, —CH(CH$_3$)CH$_2$F, —CH$_2$C(CH$_3$)$_2$F, —CH(CH$_3$)CH$_2$OH, or —CH$_2$C(CH$_3$)$_2$OH; (ii) C$_{3-6}$ cycloalkyl substituted with zero to 2 substituents independently selected from H, —CH$_3$, —OCH$_3$, —C(CH$_3$)$_2$OH, and —C(CH$_3$)$_2$F; or (iii) oxetanyl, tetrahydrofuranyl, tetrahydropyranyl, pyrrolyl, pyrazolyl, pyrrolidinyl, or 4,5,6,7-tetrahydropyrazolo[1,5-a]pyrazinyl, each substituted with zero to 2 substituents independently selected from —OH, —CH$_3$, —CH$_2$CH$_3$, —CH(CH$_3$)$_2$, —CH$_2$CH(CH$_3$)$_2$, —CHF$_2$, —CH$_2$CHF$_2$, —CH$_2$CF$_3$, —CH$_2$CH$_2$F, —CH$_2$CF$_2$CH$_3$, —CH$_2$C(CH$_3$)$_2$F, —CH$_2$CH$_2$OCH$_3$, —CH$_2$(cyclopropyl), cyclopropyl, cyclobutyl, difluorocyclobutyl, and fluoropyrimidinyl. Included in this embodiment are compounds in which R$_1$ is —CH$_2$CHFC(CH$_3$)$_2$OH. Also included are compounds in which R$_3$ is —CH(CH$_3$)$_2$, oxetanyl, or pyrazolyl substituted with zero to 2 substituents independently selected from —CH$_3$, —CH$_2$CH$_3$, —CH(CH$_3$)$_2$, —CH$_2$CH(CH$_3$)$_2$, —CHF$_2$, —CH$_2$CHF$_2$, —CH$_2$CF$_3$, —CH$_2$CH$_2$CH$_2$F, —CH$_2$CF$_2$CH$_3$, —CH$_2$C(CH$_3$)$_2$F, —CH$_2$CH$_2$OCH$_3$, —CH$_2$(cyclopropyl), cyclopropyl, cyclobutyl, difluorocyclobutyl, and fluoropyrimidinyl.

One embodiment provides a compound of Formula (I) or a salt thereof wherein HET is imidazo[1,2-b]pyridazin-3-yl substituted with zero to 1 R$_b$; R$_b$ is H, Cl, —CN, —NH$_2$, —CH$_3$, —OCH$_3$, —NHCH$_2$CH$_2$OH, —NHCH$_2$C(CH$_3$)$_2$OH, or hydroxypyrrolidinyl; R$_1$ is —CH$_2$CH$_2$C(CH$_3$)$_2$OH or cyclohexyl substituted with —C(CH$_3$)$_2$OH; and R$_3$ is —CH(CH$_3$)$_2$, —CH(CH$_3$)CH$_2$OH, —CH$_2$C(CH$_3$)$_2$OH, cyclopropyl, oxetanyl, tetrahydrofuranyl, or hydroxytetrahydrofuranyl. Included in this embodiment are compounds in which R$_1$ is —CH$_2$CHFC(CH$_3$)$_2$OH. Also included are compounds in which R$_3$ is —CH(CH$_3$)$_2$ or oxetanyl.

One embodiment provides a compound of Formula (I) or a salt thereof wherein HET is a heteroaryl selected from oxazolyl and pyrazolyl, each substituted with zero to 2 R$_b$; and R$_1$, R$_3$, and R$_b$ are defined in the first aspect. Included in this embodiment are compounds in which HET is oxazolyl or pyrazolyl substituted with cyanophenyl or pyridinyl. Also included are compounds in which R$_3$ is —CH(CH$_3$)$_2$.

One embodiment provides a compound of Formula (I) or a salt thereof wherein R$_1$ is C$_{3-6}$ alkyl substituted with 1 to 4 substituents independently selected from F, —CN, —OH, —OCH$_3$, —OCD$_3$, —NHC(O)(C$_{1-3}$ alkyl), —S(O)$_2$(C$_{1-3}$ alkyl), and C$_{1-2}$ fluoroalkoxy; and HET and R$_3$ are defined in the first aspect. Included in this embodiment are compounds in which R$_1$ is C$_{4-6}$ alkyl substituted with 1 to 4 substituents independently selected from F, —CN, —OH, —OCH$_3$, and —OCD$_3$; and compounds in which R$_1$ is pentyl substituted with 1 to 4 substituents independently selected from F, —OH, —OCH$_3$, —OCHF$_2$, —OCD$_3$, and —S(O)$_2$CH$_3$. Also included are compounds in which R$_1$ is —CH$_2$CF$_2$C(CH$_3$)$_2$OH, —CH$_2$CH$_2$C(CH$_3$)$_2$CN, —CH$_2$CH$_2$C(CH$_3$)$_2$F, —CH$_2$CH$_2$C(CH$_3$)$_2$OH, —CH$_2$CH$_2$C(CH$_3$)$_3$, —CH$_2$CH$_2$CH(CH$_3$)NHC(O)CH$_3$, —CH$_2$CH$_2$CH$_2$S(O)$_2$CH$_3$, —CH$_2$CHFC(CH$_2$OH)$_2$OH, —CH$_2$CHFC(CH$_3$)$_2$F, —CH$_2$CHFC(CH$_3$)$_2$OCD$_3$, —CH$_2$CHFC(CH$_3$)$_2$OCHF$_2$, and —CH$_2$CHFC(CH$_3$)$_2$OH.

One embodiment provides a compound of Formula (I) or a salt thereof wherein R$_1$ is C$_{3-6}$ alkyl substituted with 1 to 4 substituents independently selected from F, —OH, —OCH$_3$, and —OCD$_3$; and HET and R$_3$ are defined in the first aspect. Included in this embodiment are compounds in which R$_1$ is C$_{4-6}$ alkyl substituted with 1 to 4 substituents independently selected from F, —OH, —OCH$_3$, and —OCD$_3$; and compounds in which R$_1$ is pentyl substituted with 1 to 4 substituents independently selected from F, —OH, —OCH$_3$, and —OCD$_3$. Also included are compounds in which R$_1$ is —CH$_2$CH$_2$C(CH$_3$)$_2$OH, —CH$_2$CH$_2$C(CH$_3$)$_2$F, —CH$_2$CHFC(CH$_3$)$_2$OH, —CH$_2$CHFC(CH$_2$OH)$_2$OH, or —CH$_2$CHFC(CH$_3$)$_2$OCD$_3$.

One embodiment provides a compound of Formula (I) or a salt thereof wherein R$_1$ is —(CR$_y$R$_y$)$_{1-3}$R$_x$ or —(CH$_2$)$_{1-3}$C(O)R$_x$, wherein R$_x$ is phenyl, tetrahydropyranyl, oxetanyl, morpholinyl, piperidinyl, imidazolyl, thiophenyl, pyridinyl, or C$_{4-6}$ cycloalkyl, each substituted with zero to 3 substituents independently selected from F, Cl, —OH, C$_{1-3}$ alkyl, C$_{1-2}$ alkoxy, and —S(O)$_2$NH$_2$; and HET, R$_3$, and R$_y$ are defined in the first aspect. Included in this embodiment are compounds in which R$_1$ is —(CR$_y$R$_y$)$_{1-3}$R$_x$ or —(CH$_2$)$_{1-2}$C (O)$R_x$ or compounds in which $R_1$ is —(CR$_y$R$_y$)$_3$R$_x$ or —(CH$_2$)$_2$C(O)R$_x$, wherein R$_x$ is phenyl, tetrahydropyranyl, oxetanyl, morpholinyl, or C$_{4-6}$ cycloalkyl, each substituted with zero to 3 substituents independently selected from F, —OH, —CH$_3$, —OCH$_3$, and —S(O)$_2$NH$_2$. Also included are compounds in which $R_1$ is —CH$_2$CH$_2$(hydroxytetrahydropyranyl), —CH$_2$CH$_2$(fluorotetrahydropyranyl), —CH$_2$CH$_2$(sulfamoylphenyl), —CH$_2$CHF(hydroxyoxetanyl), —CH$_2$CH$_2$(dihydroxy, methylcyclohexyl), —CH$_2$CH$_2$C(O)(morpholinyl), —CH$_2$CH$_2$(hydroxy, methoxycyclohexyl), —CH$_2$CHF(dimethyltetrahydropyranyl), —CH$_2$CHF(piperidinyl), —CH$_2$CHF(dimethyltetrahydropyranyl), —CH$_2$CH$_2$(thiophenyl), —CH$_2$CH$_2$CH$_2$(imidazolyl), —CH$_2$CH$_2$(pyridinyl), or —CH$_2$CH$_2$(hydroxycyclopentyl).

One embodiment provides a compound of Formula (I) or a salt thereof wherein $R_1$ is —(CR$_y$R$_y$)$_{1-3}$R$_x$ or —(CH$_2$)$_{1-3}$C(O)R$_x$, wherein R$_x$ is phenyl, tetrahydropyranyl, oxetanyl, morpholinyl, or C$_{4-6}$ cycloalkyl, each substituted with zero to 3 substituents independently selected from F, Cl, —OH, C$_{1-3}$ alkyl, C$_{1-2}$ alkoxy, and —S(O)$_2$NH$_2$; and HET, $R_3$, and R$_y$ are defined in the first aspect. Included in this embodiment are compounds in which $R_1$ is —(CR$_y$R$_y$)$_{1-2}$R$_x$ or —(CH$_2$)$_{1-2}$C(O)R$_x$ or compounds in which $R_1$ is —(CR$_y$R$_y$)$_2$R$_x$ or —(CH$_2$)$_2$C(O)R$_x$, wherein R$_x$ is phenyl, tetrahydropyranyl, oxetanyl, morpholinyl, or C$_{4-6}$ cycloalkyl, each substituted with zero to 3 substituents independently selected from F, Cl, —OH, —CH$_3$, —OCH$_3$, and —S(O)$_2$NH$_2$. Also included are compounds in which $R_1$ is —CH$_2$CH$_2$(sulfamoylphenyl), —CH$_2$CH$_2$(fluorotetrahydropyranyl), —CH$_2$CH$_2$(hydrotetrahydropyranyl), —CH$_2$CHF(hydroxyoxetanyl), —CH$_2$CH$_2$C(O)(morpholinyl), —CH$_2$CH$_2$(hydroxy, methoxycyclohexyl), or —CH$_2$CH$_2$(dihydroxy, methylcyclohexyl).

One embodiment provides a compound of Formula (I) or a salt thereof wherein $R_1$ is C$_{4-6}$ cycloalkyl substituted with —OH, C$_{1-4}$ hydroxyalkyl, C$_{1-3}$ alkoxy, —(CH$_2$)$_{1-3}$O(C$_{1-2}$ alkyl), —N(C$_{1-2}$ alkyl)$_2$, —C(O)NH(C$_{1-4}$ alkyl), —C(O)NH(C$_{3-6}$ cycloalkyl), —NHC(O)(C$_{1-3}$ alkyl), —NHC(O)O(C$_{1-3}$ alkyl), or —NHC(O)(C$_{1-4}$ hydroxyalkyl); and HET and $R_3$ are defined in the first aspect. Included in this embodiment are compounds in which $R_1$ is C$_{5-6}$ cycloalkyl substituted with —OH, C$_{2-4}$ hydroxyalkyl, C$_{1-2}$ alkoxy, —(CH$_2$)$_{2-3}$OCH$_3$, —N(CH$_3$)$_2$, —C(O)NH(C$_{1-3}$ alkyl), —C(O)NH(C$_{3-4}$ cycloalkyl), —NHC(O)(C$_{1-2}$ alkyl), or —NHC(O)(C$_{2-4}$ hydroxyalkyl); and compounds in which $R_1$ is cyclohexyl substituted with C$_{2-4}$ hydroxyalkyl, C$_{1-2}$ alkoxy, —C(O)NH(C$_{1-3}$ alkyl), —C(O)NH(C$_{3-4}$ cycloalkyl), —NHC(O)(C$_{1-2}$ alkyl), or —NHC(O)(C$_{2-4}$ hydroxyalkyl). Also included are compounds in which $R_1$ is cyclohexyl substituted with —OH, —C(CH$_3$)$_2$OH, C$_{1-2}$ alkoxy, —C(CH$_3$)$_2$OCH$_3$, —N(CH$_3$)$_2$, —C(O)NHCH$_3$, —C(O)NHCH(CH$_3$)$_2$, —C(O)NH(cyclopropyl), —NHC(O)CH$_3$, —NHC(O)OCH$_3$, —NHC(O)C(CH$_3$)$_2$OH, or —NHC(O)CH(OH)CH$_3$.

One embodiment provides a compound of Formula (I) or a salt thereof wherein $R_1$ is C$_{4-6}$ cycloalkyl substituted with C$_{1-4}$ hydroxyalkyl, C$_{1-3}$ alkoxy, —C(O)NH(C$_{1-4}$ alkyl), —C(O)NH(C$_{3-6}$ cycloalkyl), —NHC(O)(C$_{1-3}$ alkyl), or —NHC(O)(C$_{1-4}$ hydroxyalkyl); and HET and $R_3$ are defined in the first aspect. Included in this embodiment are compounds in which $R_1$ is C$_{5-6}$ cycloalkyl substituted with C$_{2-4}$ hydroxyalkyl, C$_{1-2}$ alkoxy, —C(O)NH(C$_{1-3}$ alkyl), —C(O)NH(C$_{3-4}$ cycloalkyl), —NHC(O)(C$_{1-2}$ alkyl), or —NHC(O)(C$_{2-4}$ hydroxyalkyl); and compounds in which $R_1$ is cyclohexyl substituted with C$_{2-4}$ hydroxyalkyl, C$_{1-2}$ alkoxy, —C(O)NH(C$_{1-3}$ alkyl), —C(O)NH(C$_{3-4}$ cycloalkyl), —NHC(O)(C$_{1-2}$ alkyl), or —NHC(O)(C$_{2-4}$ hydroxyalkyl). Also included are compounds in which $R_1$ is cyclohexyl substituted with —C(CH$_3$)$_2$OH, —OCH$_3$, —C(O)NHCH$_3$, —C(O)NHCH(CH$_3$)$_2$, —C(O)NH(cyclopropyl), —NHC(O)CH$_3$, —NHC(O)C(CH$_3$)$_2$OH, or —NHC(O)CH(OH)CH$_3$.

One embodiment provides a compound of Formula (I) or a salt thereof wherein $R_1$ is tetrahydrofuranyl, tetrahydropyranyl, piperidinyl, piperazinyl, pyrrolyl, pyrazolyl, imidazolyl, or triazolyl, each substituted with zero to 2 substituents independently selected from C$_{1-4}$ hydroxyalkyl, —S(O)$_2$(C$_{1-3}$ alkyl), —CH$_2$C(O)NH(C$_{1-3}$ alkyl), —CH$_2$C(O)NH(C$_{1-6}$ hydroxyalkyl), —CH$_2$C(O)NH(C$_{1-6}$ fluoroalkyl), and —CH$_2$C(O)NH(C$_{1-6}$ hydroxy-fluoroalkyl); and HET and $R_3$ are defined in the first aspect. Included in this embodiment are compounds in which $R_1$ is tetrahydrofuranyl, tetrahydropyranyl, piperidinyl, or piperazinyl, each substituted with zero to 1 substituent selected from C$_{1-2}$ hydroxyalkyl, —S(O)$_2$(C$_{1-3}$ alkyl), —CH$_2$C(O)NH(C$_{1-2}$ alkyl), —CH$_2$C(O)NH(C$_{3-6}$ hydroxyalkyl), —CH$_2$C(O)NH(C$_{3-6}$ fluoroalkyl), and —CH$_2$C(O)NH(C$_{3-6}$ hydroxy-fluoroalkyl); and compounds in which $R_1$ is pyrrolyl, pyrazolyl, imidazolyl, or triazolyl, each substituted with zero to 1 substituent selected from C$_{1-2}$ hydroxyalkyl, —S(O)$_2$(C$_{1-3}$ alkyl), —CH$_2$C(O)NH(C$_{1-2}$ alkyl), —CH$_2$C(O)NH(C$_{3-6}$ hydroxyalkyl), —CH$_2$C(O)NH(C$_{3-6}$ fluoroalkyl), and —CH$_2$C(O)NH(C$_{3-6}$ hydroxy-fluoroalkyl). Also included in this embodiment are compounds in which $R_1$ is piperidinyl, pyrazolyl, or tetrahydropyranyl, each substituted with —CH$_2$OH, —S(O)$_2$CH(CH$_3$)$_2$, —CH$_2$C(O)NHCH$_3$, or —CH$_2$C(O)NHCH$_2$CHFC(CH$_3$)$_2$OH.

One embodiment provides a compound of Formula (I) or a salt thereof wherein $R_3$ is C$_{2-5}$ alkyl, C$_{2-5}$ fluoroalkyl, C$_{2-5}$ hydroxyalkyl, —(CH$_2$)$_{1-3}$R$_z$, —CH(CH$_3$)R$_z$, or —CH(CH$_2$OH)CH$_2$R$_z$, wherein R$_z$ is C$_{4-6}$ cycloalkyl, oxetanyl, tetrahydrofuranyl, tetrahydropyranyl, or phenyl, each substituted with zero to 1 substituent selected from —OH and —CH$_3$; and HET and $R_1$ are defined in the first aspect. Included in this embodiment are compounds in which $R_3$ is C$_{2-4}$ alkyl, C$_{2-4}$ fluoroalkyl, or C$_{3-5}$ hydroxyalkyl or compounds in which $R_3$ is —(CH$_2$)$_{1-2}$R$_z$, —CH(CH$_3$)R$_z$, or —CH(CH$_2$OH)CH$_2$R$_z$, wherein R$_z$ is C$_{4-5}$ cycloalkyl, oxetanyl, tetrahydrofuranyl, tetrahydropyranyl, or phenyl, each substituted with zero or 1 substituent selected from —OH and —CH$_3$. Also included in this embodiment are compounds in which $R_3$ is —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CHF$_2$, —CH$_2$CF$_3$, —CH$_2$CF$_2$CH$_3$, —CH$_2$CH$_2$CHF$_2$, —CH$_2$CH$_2$CF$_3$, —CH$_2$CHFCH$_2$CH$_3$, —CH$_2$CH$_2$CHFCH$_3$, —CH$_2$CH(CH$_3$)F, —CH$_2$C(CH$_3$)$_2$F, —CH(CH$_3$)CH$_2$F, —CH(CH$_3$)CH$_2$CH$_2$F, —CH$_2$CH$_2$CH$_2$OH, —CH(CH$_3$)CH$_2$OH, —C(CH$_3$)$_2$CH$_2$OH, CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$(hydroxycyclobutyl), —CH$_2$(hydroxytetrahydropyranyl), or —CH(CH$_2$OH)CH$_2$(phenyl).

One embodiment provides a compound of Formula (I) or a salt thereof wherein $R_3$ is C$_{2-5}$ alkyl, C$_{2-5}$ fluoroalkyl, C$_{2-5}$ hydroxyalkyl, —(CH$_2$)$_{1-3}$R$_z$, —CH(CH$_3$)R$_z$, or —CH(CH$_2$OH)CH$_2$R$_z$, wherein R$_z$ is C$_{4-6}$ cycloalkyl, oxetanyl, tetrahydrofuranyl, tetrahydropyranyl, or phenyl, each substituted with zero to 1 substituent selected from —OH and —CH$_3$; and HET and $R_1$ are defined in the first aspect. Included in this embodiment are compounds in which $R_3$ is C$_{2-4}$ alkyl, C$_{2-4}$ fluoroalkyl, or C$_{3-5}$ hydroxyalkyl or compounds in which $R_3$ is —(CH$_2$)$_{1-2}$R$_z$, —CH(CH$_3$)R$_z$, or —CH(CH$_2$OH)CH$_2$R$_z$, wherein R$_z$ is C$_{4-5}$ cycloalkyl, oxetanyl, tetrahydrofuranyl, tetrahydropyranyl, or phenyl, each substituted with zero or 1 substituent selected from —OH and —CH$_3$. Also included in this embodiment are compounds in which R$_3$ is —CH$_2$CH$_3$, —CH$_2$CH$_2$CH$_3$, —CH(CH$_3$)$_2$, —C(CH$_3$)$_3$, —CH(CH$_3$)CH$_2$CH$_3$, —CH$_2$CF$_3$, —CH$_2$CH$_2$CF$_3$, —CH$_2$CH(CH$_3$)F, —CH$_2$C(CH$_3$)$_2$F, —CH(CH$_3$)CH$_2$F, —CH(CH$_3$)CH$_2$CH$_2$F, —CH(CH$_3$)CH$_2$OH, —C(CH$_3$)$_2$CH$_2$OH, CH$_2$C(CH$_3$)$_2$OH, —CH$_2$CH(OH)CH$_2$CH$_3$, —CH$_2$CH$_2$CH(CH$_3$)OH, —CH(CH$_3$)C(CH$_3$)$_2$OH, —CH(CH$_3$)phenyl, —CH$_2$(hydroxyoxetanyl), —CH$_2$(methyloxetanyl), —CH$_2$(hydroxycyclobutyl), —CH$_2$(hydroxytetrahydropyranyl), or —CH(CH$_2$OH)CH$_2$(phenyl).

One embodiment provides a compound of Formula (I) or a salt thereof wherein R$_3$ is C$_{3-6}$ cycloalkyl substituted with zero to 3 substituents independently selected from F, Cl, —CN, —OH, C$_{1-3}$ alkyl, C$_{1-3}$ fluoroalkyl, C$_{1-4}$ hydroxyalkyl, C$_{1-4}$ alkoxy, —C(O)NH$_2$, —C(O)NH(C$_{1-3}$ alkyl), and —C(O)(C$_{1-3}$ fluoroalkyl); and HET and R$_1$ are defined in the first aspect. Included in this embodiment are compound in which R$_3$ is C$_{3-6}$ cycloalkyl substituted with zero to 3 substituents independently selected from F, Cl, —CN, —OH, C$_{1-2}$ alkyl, C$_{1-3}$ fluoroalkyl, C$_{1-3}$ hydroxyalkyl, and C$_{1-3}$ alkoxy. Also included are compounds in which R$_3$ is C$_{3-5}$ cycloalkyl substituted with zero to 3 substituents independently selected from F, —OH, —CH$_3$, —C(CH$_3$)$_2$F, —C(CH$_3$)$_2$OH, —OCH$_3$, and —OCH(CH$_3$)$_2$.

One embodiment provides a compound of Formula (I) or a salt thereof wherein R$_3$ is C$_{3-6}$ cycloalkyl substituted with zero to 3 substituents independently selected from F, Cl, —CN, —OH, C$_{1-3}$ alkyl, C$_{1-3}$ fluoroalkyl, C$_{1-4}$ hydroxyalkyl, C$_{1-4}$ alkoxy, —C(O)NH$_2$, —C(O)NH(C$_{1-3}$ alkyl), and —C(O)(C$_{1-3}$ fluoroalkyl); and HET and R$_1$ are defined in the first aspect. Included in this embodiment are compound in which R$_3$ is C$_{3-6}$ cycloalkyl substituted with zero to 3 substituents independently selected from F, Cl, —CN, —OH, C$_{1-2}$ alkyl, C$_{1-2}$ fluoroalkyl, C$_{1-2}$ hydroxyalkyl, and C$_{1-3}$ alkoxy. Also included are compounds in which R$_3$ is C$_{3-5}$ cycloalkyl substituted with zero to 3 substituents independently selected from F, —OH, —CH$_3$, —C(CH$_3$)$_2$OH, —OCH$_3$, and —OCH(CH$_3$)$_2$.

One embodiment provides a compound of Formula (I) or a salt thereof wherein R$_3$ is oxetanyl, tetrahydrofuranyl, tetrahydropyranyl, pyrrolidinyl, piperidinyl, pyrrolyl, pyrazolyl, thiazolyl, bicyclo[1.1.1]pentanyl, bicyclo[2.2.1]heptanyl, or 4,5,6,7-tetrahydropyrazolo[1,5-a]pyrazinyl, each substituted with zero to 2 substituents independently selected from F, —OH, C$_{1-4}$ alkyl, C$_{1-3}$ hydroxyalkyl, C$_{1-4}$ fluoroalkyl, —CH$_2$(C$_{3-6}$ cycloalkyl), —(CH$_2$)$_{1-3}$O(C$_{1-3}$ alkyl), —C(O)(C$_{1-3}$ fluoroalkyl), —S(O)$_2$(C$_{1-3}$ alkyl), C$_{3-6}$ cycloalkyl, C$_{3-6}$ fluorocycloalkyl, oxetanyl, tetrahydrofuranyl, tetrahydropyranyl, pyrimidinyl, fluoropyrimidinyl, and methoxypyrimidinyl; and HET and R$_1$ are defined in the first aspect. Included in this embodiment are compounds in which R$_3$ is oxetanyl, tetrahydrofuranyl, tetrahydropyranyl, pyrrolidinyl, piperidinyl, pyrrolyl, pyrazolyl, thiazolyl, bicyclo[1.1.1]pentanyl, bicyclo[2.2.1]heptanyl, or 4,5,6,7-tetrahydropyrazolo[1,5-a]pyrazinyl, each substituted with zero to 2 substituents independently selected from F, —OH, C$_{1-3}$ alkyl, C$_{1-2}$ hydroxyalkyl, C$_{1-4}$ fluoroalkyl, —(CH$_2$)$_{1-3}$OCH$_3$, —CH$_2$(C$_{3-4}$ cycloalkyl), —C(O)(C$_{1-2}$ fluoroalkyl), —S(O)$_2$(C$_{1-2}$ alkyl), C$_{3-6}$ cycloalkyl, C$_{4-6}$ fluorocycloalkyl, oxetanyl, tetrahydrofuranyl, tetrahydropyranyl, pyrimidinyl, fluoropyrimidinyl, and methoxypyrimidinyl. Also included are compounds in which R$_3$ is oxetanyl, tetrahydrofuranyl, tetrahydropyranyl, pyrrolidinyl, piperidinyl, pyrrolyl, pyrazolyl, thiazolyl, bicyclo[1.1.1]pentanyl, bicyclo[2.2.1]heptanyl, or 4,5,6,7-tetrahydropyrazolo[1,5-a]pyrazinyl, each substituted with zero to 2 substituents independently selected from F, —OH, C$_{1-4}$ alkyl, —CHF$_2$, —CH$_2$CH$_2$F, —CH$_2$CF$_2$CH$_3$, —CH$_2$CHF$_2$, —CH$_2$CF$_3$, —CH$_2$C(CH$_3$)$_2$F, —C(O)CH$_2$CF$_3$, —CH$_2$CH$_2$OCH$_3$, —CH$_2$(cyclopropyl), —S(O)CH$_3$, cyclopropyl, cyclobutyl, difluorocyclobutyl, oxetanyl, tetrahydrofuranyl, tetrahydropyranyl, pyrimidinyl, fluoropyrimidinyl, and methoxypyrimidinyl.

One embodiment provides a compound of Formula (I) or a salt thereof wherein R$_3$ is oxetanyl, tetrahydrofuranyl, tetrahydropyranyl, pyrrolidinyl, piperidinyl, pyrazolyl, thiazolyl, bicyclo[1.1.1]pentanyl, or bicyclo[2.2.1]heptanyl, each substituted with zero to 2 substituents independently selected from F, —OH, C$_{1-3}$ alkyl, C$_{1-3}$ hydroxyalkyl, C$_{1-3}$ fluoroalkyl, —C(O)(C$_{1-3}$ fluoroalkyl), —S(O)$_2$(C$_{1-3}$ alkyl), oxetanyl, tetrahydrofuranyl, tetrahydropyranyl, pyrimidinyl, fluoropyrimidinyl, and methoxypyrimidinyl; and HET and R$_1$ are defined in the first aspect. Included in this embodiment are compounds in which R$_3$ is oxetanyl, tetrahydrofuranyl, tetrahydropyranyl, pyrrolidinyl, piperidinyl, pyrazolyl, thiazolyl, bicyclo[1.1.1]pentanyl, or bicyclo[2.2.1]heptanyl, each substituted with zero or 1 substituent selected from F, —OH, C$_{1-2}$ alkyl, C$_{1-2}$ hydroxyalkyl, C$_{1-2}$ fluoroalkyl, —C(O)(C$_{1-2}$ fluoroalkyl), —S(O)$_2$(C$_{1-2}$ alkyl), oxetanyl, tetrahydrofuranyl, tetrahydropyranyl, pyrimidinyl, fluoropyrimidinyl, and methoxypyrimidinyl. Also included are compounds in which R$_3$ is oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl.

One embodiment provides a compound of Formula (I) or a salt thereof wherein R$_3$ is phenyl substituted with zero to 3 substituents independently selected from F, Cl, —CN, —OH, —C(O)NH$_2$, —C(O)NH(C$_{1-3}$ alkyl), and —C(O)(C$_{1-3}$ fluoroalkyl); and HET and R$_1$ are defined in the first aspect. Included in this embodiment are compounds in which R$_3$ is phenyl substituted with zero to 2 or with 1 to 2 substituents independently selected from F, Cl, —CN, —C(O)NH$_2$, and —C(O)NHCH$_3$. Also included are compounds in which R$_3$ is phenyl substituted with 1 to 2 substituents independently selected from F, —CN, —C(O)NH$_2$, and —C(O)NHCH$_3$.

One embodiment provides a compound of Formula (I) or a salt thereof, wherein said compound is selected from: (R)-6-(6-chloropyrazolo[1,5-a]pyrimidin-3-yl)-N-(2-fluoro-3-hydroxy-3-methylbutyl)-4-(isopropylamino)nicotinamide (1); (R)-6-(6-chloropyrazolo[1,5-a]pyrimidin-3-yl)-N-(2-fluoro-3-hydroxy-3-methylbutyl)-4-((5-(2-hydroxypropan-2-yl) thiazol-2-yl)amino)nicotinamide (2); 6-(6-chloropyrazolo[1,5-a]pyrimidin-3-yl)-N—((R)-2-fluoro-3-hydroxy-3-methylbutyl)-4-((tetrahydro-2H-pyran-3-yl)amino) nicotinamide (3 and 4); (R)-6-(6-chloropyrazolo[1,5-a]pyrimidin-3-yl)-N-(2-fluoro-3-hydroxy-3-methylbutyl)-4-(oxetan-3-ylamino)nicotinamide (5); N-(2-(4-hydroxytetrahydro-2H-pyran-4-yl)ethyl)-4-(isopropylamino)-6-(pyrazolo[1,5-a]pyrimidin-3-yl) nicotinamide (6); (R)-6-(6-chloropyrazolo[1,5-a]pyrimidin-3-yl)-N-(2-fluoro-3-hydroxy-3-methylbutyl)-4-((1-hydroxy-2-methylpropan-2-yl)amino) nicotinamide (7); 6-(6-chloropyrazolo[1,5-a]pyrimidin-3-yl)-N-(2-fluoro-2-(3-hydroxyoxetan-3-yl)ethyl)-4-(isopropylamino) nicotinamide (8); 6-(6-chloropyrazolo[1,5-a]pyrimidin-3-yl)-N-(2-fluoro-3,4-dihydroxy-3-(hydroxymethyl)butyl)-4-(isopropylamino)nicotinamide (9); (R)-6-(6-chloropyrazolo[1,5-a]pyrimidin-3-yl)-N-(1-(2-((2-fluoro-3-hydroxy-3-methylbutyl)amino)-2-oxoethyl)-1H-pyrazol-4-yl)-4-(isopropylamino)nicotinamide (10); 6-(6-chloropyrazolo[1,5-a]pyrimidin-3-yl)-4-(isopropylamino)-N-((1R,4R)-4-methoxycyclohexyl)nicotinamide (11); 6-(6-chloropyrazolo[1,5-a]pyrimidin-3-yl)-N-(3-fluoro-3-methylbutyl)-4-(oxetan-3-ylamino) nicotinamide (12); 6-(6-chloropyrazolo[1,5-a]pyrimidin-3-yl)-4-((3,3-difluoro-4-methoxycyclopentyl)amino)-N—((R)-2-fluoro-3-hydroxy-3-methylbutyl)nicotinamide (13 and 14); 6-(6-chloropyrazolo[1,5-a]pyrimidin-3-yl)-4-((3,3-difluoro-4-isopropoxycyclopentyl)amino)-N—((R)-2-fluoro-3-hydroxy-3-methylbutyl)nicotinamide (15 and 16); 6-(6-chloropyrazolo[1,5-a]pyrimidin-3-yl)-N-(2-(1-fluoro-4-methoxycyclohexyl)ethyl)-4-(oxetan-3-ylamino) nicotinamide (17); 6-(6-chloropyrazolo[1,5-a]pyrimidin-3-yl)-4-((4,4-difluorotetrahydrofuran-3-yl)amino)-N—((R)-2-fluoro-3-hydroxy-3-methylbutyl)nicotinamide (18 and 19); 6-(6-chloropyrazolo[1,5-a]pyrimidin-3-yl)-N-(3-fluoro-3-methylbutyl)-4-(isopropylamino)nicotinamide (20); (R)—N-(2-fluoro-3-hydroxy-3-methylbutyl)-6-(imidazo[1,2-b]pyridazin-3-yl)-4-(isopropylamino) nicotinamide (21); (R)-6-(6-chloropyrazolo[1,5-a]pyrimidin-3-yl)-4-(cyclopropylamino)-N-(2-fluoro-3-hydroxy-3-methylbutyl)nicotinamide (22); N-((1r,4r)-4-acetamidocyclohexyl)-6-(6-chloropyrazolo[1,5-a]pyrimidin-3-yl)-4-(isopropylamino) nicotinamide (23); 6-(6-chloropyrazolo[1,5-a]pyrimidin-3-yl)-4-((2-fluoro-2-methylpropyl)amino)-N-((1r,4r)-4-(methylcarbamoyl)cyclohexyl)nicotinamide (24); 6-(6-chloropyrazolo[1,5-a]pyrimidin-3-yl)-4-(cyclopropylamino)-N-((1r,4r)-4-(methylcarbamoyl)cyclohexyl)nicotinamide (25); 6-(6-chloropyrazolo[1,5-a]pyrimidin-3-yl)-4-(isopropylamino)-N-(4-sulfamoylphenethyl)nicotinamide (26); 6-(6-chloropyrazolo[1,5-a]pyrimidin-3-yl)-4-(isopropylamino)-N-((1r,4r)-4-(methylcarbamoyl)cyclohexyl) nicotinamide (27); 6-(6-chloropyrazolo[1,5-a]pyrimidin-3-yl)-N-((1r,4r)-4-(cyclopropylcarbamoyl)cyclohexyl)-4-(isopropylamino) nicotinamide (28); 6-(6-chloropyrazolo[1,5-a]pyrimidin-3-yl)-4-(isopropylamino)-N-((1r,4r)-4-(isopropylcarbamoyl)cyclohexyl)nicotinamide (29); (R)-6-(6-chloropyrazolo[1,5-a]pyrimidin-3-yl)-N-(2-fluoro-3-hydroxy-3-methylbutyl)-4-((tetrahydro-2H-pyran-4-yl)amino)nicotinamide (30); 6-(6-chloropyrazolo[1,5-a]pyrimidin-3-yl)-N—((R)-2-fluoro-3-hydroxy-3-methylbutyl)-4-(((S)-1-hydroxypropan-2-yl)amino)nicotinamide (31); 6-(6-chloropyrazolo[1,5-a]pyrimidin-3-yl)-N—((R)-2-fluoro-3-hydroxy-3-methylbutyl)-4-(((S)-1-fluoropropan-2-yl)amino) nicotinamide (32); (R)-4-((4-carbamoylphenyl)amino)-6-(6-chloropyrazolo[1,5-a]pyrimidin-3-yl)-N-(2-fluoro-3-hydroxy-3-methylbutyl) nicotinamide (33); (R)-6-(6-chloropyrazolo[1,5-a]pyrimidin-3-yl)-N-(2-fluoro-3-hydroxy-3-methylbutyl)-4-((4-(methylcarbamoyl)phenyl)amino)nicotinamide (34); (R)-6-(6-chloropyrazolo[1,5-a]pyrimidin-3-yl)-4-((3-cyano-2-fluorophenyl)amino)-N-(2-fluoro-3-hydroxy-3-methylbutyl)nicotinamide (35); 6-(6-chloropyrazolo[1,5-a]pyrimidin-3-yl)-N—((R)-2-fluoro-3-hydroxy-3-methylbutyl)-4-(((R)-1-(5-fluoropyrimidin-2-yl)pyrrolidin-3-yl)amino)nicotinamide (36); 6-(6-chloropyrazolo[1,5-a]pyrimidin-3-yl)-N-(2-fluoro-2-(3-hydroxyoxetan-3-yl)ethyl)-4-(isopropylamino)nicotinamide (37); (R)-6-(6-chloropyrazolo[1,5-a]pyrimidin-3-yl)-N-(2-fluoro-3-hydroxy-3-methylbutyl)-4-(((3-methyloxetan-3-yl)methyl) amino)nicotinamide (38); (R)-6-(6-chloropyrazolo[1,5-a]pyrimidin-3-yl)-N-(2-fluoro-3-hydroxy-3-methylbutyl)-4-(((3-hydroxyoxetan-3-yl)methyl)amino)nicotinamide (39); 6-(6-chloropyrazolo[1,5-a]pyrimidin-3-yl)-N-((1r,4r)-4-(2-hydroxypropan-2-yl)cyclohexyl)-4-(oxetan-3-ylamino) nicotinamide (40); 6-(6-chloropyrazolo[1,5-a]pyrimidin-3-yl)-N-((1r,4r)-4-(cyclopropylcarbamoyl)cyclohexyl)-4-(oxetan-3-ylamino)nicotinamide (41); 6-(6-chloropyrazolo[1,5-a]pyrimidin-3-yl)-N—((R)-2-fluoro-3-hydroxy-3-methylbutyl)-4-(((3R,4S)-4-hydroxytetrahydrofuran-3-yl)amino) nicotinamide (42); 6-(6-chloropyrazolo[1,5-a]pyrimidin-3-yl)-N—((R)-2-fluoro-3-hydroxy-3-methylbutyl)-4-(((3R,4S)-4-fluorotetrahydrofuran-3-yl)amino)nicotinamide (43); 6-(6-chloropyrazolo[1,5-a]pyrimidin-3-yl)-N—((R)-2-fluoro-3-hydroxy-3-methylbutyl)-4-(((3R,4S)-4-fluorotetrahydrofuran-3-yl)amino)nicotinamide (44); 6-(6-chloropyrazolo[1,5-a]pyrimidin-3-yl)-4-(isopropylamino)-N-(1-(2-(methylamino)-2-oxoethyl)-1H-pyrazol-4-yl)nicotinamide (45); (R)-6-(6-chloropyrazolo[1,5-a]pyrimidin-3-yl)-N-(2-fluoro-3-hydroxy-3-methylbutyl)-4-((3,3,3-trifluoropropyl)amino) nicotinamide (46); 6-(6-chloropyrazolo[1,5-a]pyrimidin-3-yl)-N-(3-hydroxy-3-methylbutyl)-4-(oxetan-3-ylamino)nicotinamide (47); (R)-6-(6-chloropyrazolo[1,5-a]pyrimidin-3-yl)-N-(2-fluoro-3-hydroxy-3-methylbutyl)-4-((1-(oxetan-3-yl)-1H-pyrazol-4-yl)amino)nicotinamide (48); 6-(6-chloropyrazolo[1,5-a]pyrimidin-3-yl)-N-((1S,4r)-4-((S)-2-hydroxypropanamido)cyclohexyl)-4-(isopropylamino)nicotinamide (49); 6-(6-chloropyrazolo[1,5-a]pyrimidin-3-yl)-N—((R)-2-fluoro-3-hydroxy-3-methylbutyl)-4-(((1S,3S)-3-(2-hydroxypropan-2-yl)cyclopentyl)amino) nicotinamide (50); (R)-6-(6-chloropyrazolo[1,5-a]pyrimidin-3-yl)-N-(2-fluoro-3-hydroxy-3-methylbutyl)-4-(((1-hydroxycyclobutyl)methyl)amino)nicotinamide (51); (R)-6-(6-chloropyrazolo[1,5-a]pyrimidin-3-yl)-N-(2-fluoro-3-hydroxy-3-methylbutyl)-4-((1-(tetrahydro-2H-pyran-4-yl)-1H-pyrazol-4-yl)amino)nicotinamide (52); 6-(6-chloropyrazolo[1,5-a]pyrimidin-3-yl)-N—((R)-2-fluoro-3-hydroxy-3-methylbutyl)-4-((tetrahydrofuran-3-yl)amino) nicotinamide (53 and 54); 6-(6-chloropyrazolo[1,5-a]pyrimidin-3-yl)-N-(2-(1,4-dihydroxy-4-methylcyclohexyl) ethyl)-4-(isopropylamino)nicotinamide (55); (R)-6-(6-chloropyrazolo[1,5-a]pyrimidin-3-yl)-4-(ethylamino)-N-(2-fluoro-3-hydroxy-3-methylbutyl) nicotinamide (56); (R)-6-(6-chloropyrazolo[1,5-a]pyrimidin-3-yl)-N-(2-fluoro-3-trideuteromethoxy-3-methylbutyl)-4-(isopropylamino) nicotinamide (57); (R)-6-(6-chloropyrazolo[1,5-a]pyrimidin-3-yl)-N-(2-fluoro-3-hydroxy-3-methylbutyl)-4-((2-hydroxy-2-methylpropyl)amino)nicotinamide (58); 6-(6-chloropyrazolo[1,5-a]pyrimidin-3-yl)-N—((R)-2-fluoro-3-hydroxy-3-methylbutyl)-4-(((1r,3R)-3-(2-hydroxypropan-2-yl)cyclobutyl)amino)nicotinamide (59); (R)-6-(6-chloropyrazolo[1,5-a]pyrimidin-3-yl)-4-(cyclobutylamino)-N-(2-fluoro-3-hydroxy-3-methylbutyl)nicotinamide (60); 6-(6-chloropyrazolo[1,5-a]pyrimidin-3-yl)-N—((R)-2-fluoro-3-hydroxy-3-methylbutyl)-4-(((S)-2-fluoropropyl) amino)nicotinamide (61); 6-(6-chloropyrazolo[1,5-a]pyrimidin-3-yl)-4-(isopropylamino)-N-(3-morpholino-3-oxopropyl)nicotinamide (62); 6-(6-chloropyrazolo[1,5-a]pyrimidin-3-yl)-4-(isopropylamino)-N-(2-oxo-2-(1-oxa-7-azaspiro[3.5]nonan-7-yl)ethyl)nicotinamide (63); (R)-6-(6-chloropyrazolo[1,5-a]pyrimidin-3-yl)-N-(2-fluoro-3-hydroxy-3-methylbutyl)-4-((2,2,2-trifluoroethyl)amino) nicotinamide (64); (R)-6-(6-chloropyrazolo[1,5-a]pyrimidin-3-yl)-4-((3,3-difluorocyclobutyl)amino)-N-(2-fluoro-3-hydroxy-3-methylbutyl)nicotinamide (65); (R)-6-(6-chloropyrazolo[1,5-a]pyrimidin-3-yl)-N-(2-fluoro-3-hydroxy-3-methylbutyl)-4-(propylamino)nicotinamide (66); (R)-6-(6-chloropyrazolo[1,5-a]pyrimidin-3-yl)-4-(cyclopentylamino)-N-(2-fluoro-3-hydroxy-3-methylbutyl)nicotinamide (67); (R)-6-(6-chloropyrazolo[1,5-a]pyrimidin-3-yl)-N-(2-fluoro-3-hydroxy-3-methylbutyl)-4-((1-(methylsulfonyl)piperidin-4-yl)amino) nicotinamide (68); 4-(((R)-sec-butyl)amino)-6-(6-chloropyrazolo[1,5-a]pyrimidin-3-yl)-N—((R)-2-fluoro-3-hydroxy-3-methylbutyl) nicotinamide (69 and 70); (R)-6-(6-chloropyrazolo[1,5-a]pyrimidin-3-yl)-4-((1-(2,2-difluoroethyl)-1H-pyrazol-4-yl)amino)-N-(2-fluoro-3-hydroxy-3-methylbutyl)nicotinamide (71); (R)-4-(tert-butylamino)-6-(6-chloropyrazolo[1,5-a]pyrimidin-3-yl)-N-(2-fluoro-3-hydroxy-3-methylbutyl) nicotinamide (72); (R)-6-(6-chloropyrazolo[1,5-a]pyrimidin-3-yl)-N-(2-fluoro-3-hydroxy-3-methylbutyl)-4-((4-hydroxybicyclo[2.2.1]heptan-1-yl)amino)nicotinamide (73); 6-(6-chloropyrazolo[1,5-a]pyrimidin-3-yl)-4-(isopropylamino)-N-(1-(isopropylsulfonyl)piperidin-4-yl)nicotinamide (74); (R)-4-(bicyclo[1.1.1]pentan-1-ylamino)-6-(6-chloropyrazolo[1,5-a]pyrimidin-3-yl)-N-(2-fluoro-3-hydroxy-3-methylbutyl)nicotinamide (75 and 76); 6-(6-chloropyrazolo[1,5-a]pyrimidin-3-yl)-N-((3R,6S)-6-(hydroxymethyl)tetrahydro-2H-pyran-3-yl)-4-(isopropylamino)nicotinamide (77); 6-(6-chloropyrazolo[1,5-a]pyrimidin-3-yl)-N-((1r,4r)-4-(2-hydroxy-2-methylpropanamido)cyclohexyl)-4-(isopropylamino) nicotinamide (78); 6-(6-chloropyrazolo[1,5-a]pyrimidin-3-yl)-N-(2-(1-hydroxy-4-methoxycyclohexyl)ethyl)-4-(oxetan-3-ylamino)nicotinamide (79); (R)-6-(6-chloropyrazolo[1,5-a]pyrimidin-3-yl)-N-(2-fluoro-3-hydroxy-3-methylbutyl)-4-((1-methylcyclopropyl)amino)nicotinamide (80); 6-(6-chloropyrazolo[1,5-a]pyrimidin-3-yl)-N—((R)-2-fluoro-3-hydroxy-3-methylbutyl)-4-(((S)-2-hydroxybutyl)amino)nicotinamide (81); 6-(6-chloropyrazolo[1,5-a]pyrimidin-3-yl)-N—((R)-2-fluoro-3-hydroxy-3-methylbutyl)-4-((3-hydroxybutyl)amino) nicotinamide (82); 6-(6-chloropyrazolo[1,5-a]pyrimidin-3-yl)-N—((R)-2-fluoro-3-hydroxy-3-methylbutyl)-4-((3-fluorocyclopentyl)amino)nicotinamide (83 and 84); 6-(6-chloropyrazolo[1,5-a]pyrimidin-3-yl)-N—((R)-2-fluoro-3-hydroxy-3-methylbutyl)-4-((3-fluorocyclopentyl)amino) nicotinamide (85); 6-(6-chloropyrazolo[1,5-a]pyrimidin-3-yl)-N—((R)-2-fluoro-3-hydroxy-3-methylbutyl)-4-((3-fluorocyclopentyl)amino)nicotinamide (86); (R)-6-(6-cyanopyrazolo[1,5-a]pyrimidin-3-yl)-N-(2-fluoro-3-hydroxy-3-methylbutyl)-4-(isopropylamino)nicotinamide (87); 6-(6-cyanopyrazolo[1,5-a]pyrimidin-3-yl)-4-(isopropylamino)-N-((1r,4r)-4-(methylcarbamoyl)cyclohexyl)nicotinamide (88); N-((1r,4r)-4-acetamidocyclohexyl)-6-(6-cyanopyrazolo[1,5-a]pyrimidin-3-yl)-4-(isopropylamino) nicotinamide (89); (R)-6-(6-cyanopyrazolo[1,5-a]pyrimidin-3-yl)-N-(2-fluoro-3-hydroxy-3-methylbutyl)-4-((tetrahydro-2H-pyran-4-yl)amino)nicotinamide (90); (R)-6-(6-cyanopyrazolo[1,5-a]pyrimidin-3-yl)-4-((2-fluoro-2-methylpropyl)amino)-N-(2-fluoro-3-hydroxy-3-methylbutyl)nicotinamide (91); (R)-6-(6-cyanopyrazolo[1,5-a]pyrimidin-3-yl)-4-(cyclopropylamino)-N-(2-fluoro-3-hydroxy-3-methylbutyl) nicotinamide (92); (R)-6-(6-cyanopyrazolo[1,5-a]pyrimidin-3-yl)-4-(ethylamino)-N-(2-fluoro-3-hydroxy-3-methylbutyl)nicotinamide (93); 6-(6-cyanopyrazolo[1,5-a]pyrimidin-3-yl)-N—((R)-2-fluoro-3-hydroxy-3-methylbutyl)-4-((tetrahydro-2H-pyran-3-yl)amino) nicotinamide (94); 6-(6-cyanopyrazolo[1,5-a]pyrimidin-3-yl)-N—((R)-2-fluoro-3-hydroxy-3-methylbutyl)-4-((tetrahydro-2H-pyran-3-yl)amino) nicotinamide (95); (R)-6-(6-cyanopyrazolo[1,5-a]pyrimidin-3-yl)-4-(cyclobutylamino)-N-(2-fluoro-3-hydroxy-3-methylbutyl)nicotinamide (96); 4-(((R)-sec-butyl)amino)-6-(6-cyanopyrazolo[1,5-a]pyrimidin-3-yl)-N—((R)-2-fluoro-3-hydroxy-3-methylbutyl)nicotinamide (97); 6-(6-cyanopyrazolo[1,5-a]pyrimidin-3-yl)-N—((R)-2-fluoro-3-hydroxy-3-methylbutyl)-4-(((R)-1-hydroxypropan-2-yl)amino)nicotinamide (98); (R)-6-(6-cyanopyrazolo[1,5-a]pyrimidin-3-yl)-N-(2-fluoro-3-hydroxy-3-methylbutyl)-4-(oxetan-3-ylamino) nicotinamide (99); 6-(6-cyanopyrazolo[1,5-a]pyrimidin-3-yl)-N—((R)-2-fluoro-3-hydroxy-3-methylbutyl)-4-(((S)-3-hydroxy-3-methylbutan-2-yl)amino)nicotinamide (100); 6-(6-cyanopyrazolo[1,5-a]pyrimidin-3-yl)-N—((R)-2-fluoro-3-hydroxy-3-methylbutyl)-4-(((R)-1-hydroxy-3-phenylpropan-2-yl)amino)nicotinamide (101); 6-(6-cyanopyrazolo[1,5-a]pyrimidin-3-yl)-4-((2-fluoro-2-methylpropyl)amino)-N-((1r,4r)-4-(methylcarbamoyl)cyclohexyl)nicotinamide (102); 6-(6-cyanopyrazolo[1,5-a]pyrimidin-3-yl)-N—((R)-2-fluoro-3-hydroxy-3-methylbutyl)-4-((2-hydroxycyclopentyl)amino)nicotinamide (103); 6-(6-cyanopyrazolo[1,5-a]pyrimidin-3-yl)-N-((1r,4r)-4-(2-hydroxypropan-2-yl)cyclohexyl)-4-(isopropylamino)nicotinamide (104); 6-(6-cyanopyrazolo[1,5-a]pyrimidin-3-yl)-N—((R)-2-fluoro-3-hydroxy-3-methylbutyl)-4-(((1R,2S)-2-fluorocyclopentyl)amino) nicotinamide (105); 6-(6-cyanopyrazolo[1,5-a]pyrimidin-3-yl)-N—((R)-2-fluoro-3-hydroxy-3-methylbutyl)-4-((4-fluorobutan-2-yl)amino)nicotinamide (106); 6-(6-cyanopyrazolo[1,5-a]pyrimidin-3-yl)-4-((3,3-difluoro-2-hydroxycyclopentyl)amino)-N—((R)-2-fluoro-3-hydroxy-3-methylbutyl)nicotinamide (107); 6-(6-cyano-6H-pyrazolo[4,3-b]pyridin-3-yl)-N—((R)-2-fluoro-3-hydroxy-3-methylbutyl)-4-(((R)-1-(3,3,3-trifluoropropanoyl) piperidin-3-yl)amino)nicotinamide (108); 6-(6-cyanopyrazolo[1,5-a]pyrimidin-3-yl)-N—((R)-2-fluoro-3-hydroxy-3-methylbutyl)-4-(((R)-1-(5-fluoropyrimidin-2-yl)pyrrolidin-3-yl)amino)nicotinamide (109); (R)-6-(6-cyanopyrazolo[1,5-a]pyrimidin-3-yl)-N-(2-fluoro-3-hydroxy-3-methylbutyl)-4-((4-(methylcarbamoyl)phenyl)amino) nicotinamide (110); (R)-4-((3-carbamoylphenyl)amino)-6-(6-cyanopyrazolo[1,5-a]pyrimidin-3-yl)-N-(2-fluoro-3-hydroxy-3-methylbutyl)nicotinamide (111); (R)-4-((4-carbamoylphenyl)amino)-6-(6-cyanopyrazolo[1,5-a]pyrimidin-3-yl)-N-(2-fluoro-3-hydroxy-3-methylbutyl) nicotinamide (112); 6-(6-cyanopyrazolo[1,5-a]pyrimidin-3-yl)-N—((R)-2-fluoro-3-hydroxy-3-methylbutyl)-4-((1-(pyridin-3-yl)ethyl)amino)nicotinamide (113); (R)-6-(6-cyanopyrazolo[1,5-a]pyrimidin-3-yl)-N-(2-fluoro-3-hydroxy-3-methylbutyl)-4-((1-hydroxy-2-methylpropan-2-yl)amino)nicotinamide (114); 6-(6-cyanopyrazolo[1,5-a]pyrimidin-3-yl)-N—((R)-2-fluoro-3-hydroxy-3-methylbutyl)-4-(((R)-1-(5-methoxypyrimidin-2-yl)pyrrolidin-3-yl)amino)nicotinamide (115); 6-(6-cyanopyrazolo[1,5-a]pyrimidin-3-yl)-N—((R)-2-fluoro-3-hydroxy-3-methylbutyl)-4-(((3S,4R)-4-fluorotetrahydrofuran-3-yl)amino)nicotinamide (116 and 117); 6-(6-cyanopyrazolo[1,5-a]pyrimidin-3-yl)-N—((R)-2-fluoro-3-hydroxy-3-methylbutyl)-4-(((R)-1-(pyrimidin-2-yl)pyrrolidin-3-yl)amino)nicotinamide (118); 6-(6-cyanopyrazolo[1,5-a]pyrimidin-3-yl)-N—((R)-2-fluoro-3-hydroxy-3-methylbutyl)-4-(((R)-1-(pyrimidin-5-yl) pyrrolidin-3-yl)amino)nicotinamide (119); 6-(6-cyanopyrazolo[1,5-a]pyrimidin-3-yl)-N-((1r,4r)-4-(2-hydroxypropan-2-yl)cyclohexyl)-4-(oxetan-3-ylamino)nicotinamide (120); (R)-6-(6-cyanopyrazolo[1,5-a]pyrimidin-3-yl)-N-(2-fluoro-3-hydroxy-3-methylbutyl)-4-(((3-hydroxyoxetan-3-yl)methyl)amino)nicotinamide (121); 6-(6-cyanopyrazolo[1,5-a]pyrimidin-3-yl)-N—((R)-2-fluoro-3-hydroxy-3-methylbutyl)-4-(((3-hydroxytetrahydro-2H-pyran-3-yl)methyl)amino)nicotinamide (122 and 123); 6-(6-cyanopyrazolo[1,5-a]pyrimidin-3-yl)-N-((1r,4r)-4- methoxycyclohexyl)-4-(oxetan-3-ylamino)nicotinamide (124); 6-(6-cyanopyrazolo[1,5-a]pyrimidin-3-yl)-N—((R)-2-fluoro-3-hydroxy-3-methylbutyl)-4-(((S)-2-hydroxybutyl)amino)nicotinamide (125); (R)—N-(2-fluoro-3-hydroxy-3-methylbutyl)-6-(pyrazolo[1,5-a]pyrimidin-3-yl)-4-((tetrahydro-2H-pyran-4-yl)amino)nicotinamide (126); (R)—N-(2-fluoro-3-hydroxy-3-methylbutyl)-4-(isopropylamino)-6-(pyrazolo[1,5-a]pyrimidin-3-yl)nicotinamide (127); (R)-6-(6-cyclopropylpyrazolo[1,5-a]pyrimidin-3-yl)-N-(2-fluoro-3-hydroxy-3-methylbutyl)-4-(isopropylamino) nicotinamide (128); (R)-6-(5-amino-6-fluoropyrazolo[1,5-a]pyrimidin-3-yl)-N-(2-fluoro-3-hydroxy-3-methylbutyl)-4-(isopropylamino)nicotinamide (129); (R)—N-(2-fluoro-3-hydroxy-3-methylbutyl)-6-(6-fluoropyrazolo[1,5-a]pyrimidin-3-yl)-4-(isopropylamino)nicotinamide (130); (R)—N-(2-fluoro-3-hydroxy-3-methylbutyl)-6-(imidazo[1,2-b]pyridazin-3-yl)-4-(oxetan-3-ylamino)nicotinamide (131); (R)—N-(2-fluoro-3-hydroxy-3-methylbutyl)-6-(imidazo[1,2-b]pyridazin-3-yl)-4-((tetrahydro-2H-pyran-4-yl)amino)nicotinamide (132); N-((1r,4r)-4-(2-hydroxypropan-2-yl)cyclohexyl)-6-(imidazo[1,2-b]pyridazin-3-yl)-4-(oxetan-3-ylamino)nicotinamide (133); N—((R)-2-fluoro-3-hydroxy-3-methylbutyl)-4-((4-hydroxytetrahydrofuran-3-yl)amino)-6-(imidazo[1,2-b]pyridazin-3-yl)nicotinamide (134); N—((R)-2-fluoro-3-hydroxy-3-methylbutyl)-4-((4-hydroxytetrahydrofuran-3-yl)amino)-6-(imidazo[1,2-b]pyridazin-3-yl)nicotinamide (135); N—((R)-2-fluoro-3-hydroxy-3-methylbutyl)-4-(((S)-1-hydroxypropan-2-yl)amino)-6-(imidazo[1,2-b]pyridazin-3-yl)nicotinamide (136); (S)—N-(3-hydroxy-3-methylbutyl)-4-((1-hydroxypropan-2-yl)amino)-6-(imidazo[1,2-b]pyridazin-3-yl)nicotinamide (137); (R)—N-(2-fluoro-3-hydroxy-3-methylbutyl)-4-((2-hydroxy-2-methylpropyl)amino)-6-(imidazo[1,2-b]pyridazin-3-yl)nicotinamide (138); (R)—N-(2-fluoro-3-hydroxy-3-methylbutyl)-6-(6-((2-hydroxyethyl)amino)imidazo[1,2-b]pyridazin-3-yl)-4-(isopropylamino)nicotinamide (139); (R)—N-(2-fluoro-3-hydroxy-3-methylbutyl)-6-(6-((2-hydroxyethyl)amino)imidazo[1,2-b]pyridazin-3-yl)-4-(oxetan-3-ylamino)nicotinamide (140); (R)-6-(7-chloroimidazo[1,2-b]pyridazin-3-yl)-N-(2-fluoro-3-hydroxy-3-methylbutyl)-4-(oxetan-3-ylamino)nicotinamide (141); (R)-6-(7-chloroimidazo[1,2-b]pyridazin-3-yl)-N-(2-fluoro-3-hydroxy-3-methylbutyl)-4-(isopropylamino)nicotinamide (142); (R)-6-(7-chloroimidazo[1,2-b]pyridazin-3-yl)-N-(2-fluoro-3-hydroxy-3-methylbutyl)-4-((tetrahydro-2H-pyran-4-yl)amino)nicotinamide (143); (R)-6-(7-chloroimidazo[1,2-b]pyridazin-3-yl)-4-(cyclopropylamino)-N-(2-fluoro-3-hydroxy-3-methylbutyl)nicotinamide (144); (R)-6-(7-cyanoimidazo[1,2-b]pyridazin-3-yl)-N-(2-fluoro-3-hydroxy-3-methylbutyl)-4-(isopropylamino)nicotinamide (145); (R)-6-(7-cyanoimidazo[1,2-b]pyridazin-3-yl)-N-(2-fluoro-3-hydroxy-3-methylbutyl)-4-((tetrahydro-2H-pyran-4-yl)amino)nicotinamide (146); (R)-6-(7-cyanoimidazo[1,2-b]pyridazin-3-yl)-N-(2-fluoro-3-hydroxy-3-methylbutyl)-4-(oxetan-3-ylamino) nicotinamide (147); (R)—N-(2-fluoro-3-hydroxy-3-methylbutyl)-4-(isopropylamino)-6-(7-methylimidazo[1,2-b]pyridazin-3-yl)nicotinamide (148); (R)—N-(2-fluoro-3-hydroxy-3-methylbutyl)-4-(isopropylamino)-6-(6-methoxyimidazo[1,2-b]pyridazin-3-yl) nicotinamide (149); (R)-6-(6-aminoimidazo[1,2-b]pyridazin-3-yl)-N-(2-fluoro-3-hydroxy-3-methylbutyl)-4-(isopropylamino)nicotinamide (150); (R)—N-(2-fluoro-3-hydroxy-3-methylbutyl)-6-(6-((2-hydroxy-2-methylpropyl)amino)imidazo[1,2-b]pyridazin-3-yl)-4-(isopropylamino)nicotinamide (151); N—((R)-2-fluoro-3-hydroxy-3-methylbutyl)-6-(6-((R)-3-hydroxypyrrolidin-1-yl)imidazo[1,2-b]pyridazin-3-yl)-4-(isopropylamino)nicotinamide (152); (R)—N-(2-fluoro-3-hydroxy-3-methylbutyl)-4-(isopropylamino)-6-(7-methoxyimidazo[1,2-b]pyridazin-3-yl) nicotinamide (153); (R)—N-(2-fluoro-3-hydroxy-3-methylbutyl)-6-(7-methoxyimidazo[1,2-b]pyridazin-3-yl)-4-(oxetan-3-ylamino)nicotinamide (154); (R)-6-(2-(3-cyanophenyl)oxazol-5-yl)-N-(2-fluoro-3-hydroxy-3-methylbutyl)-4-(isopropylamino)nicotinamide (155); (R)—N-(2-fluoro-3-hydroxy-3-methylbutyl)-4-(isopropylamino)-6-(1-(pyridin-4-yl)-1H-pyrazol-3-yl)nicotinamide (156); (R)-6-(6-chloropyrazolo[1,5-a]pyrimidin-3-yl)-N-(3-(difluoromethoxy)-2-fluoro-3-methylbutyl)-4-(isopropylamino)nicotinamide (157); 6-(6-chloropyrazolo[1,5-a]pyrimidin-3-yl)-N—((R)-2-fluoro-3-hydroxy-3-methylbutyl)-4-(((S)-2-fluorobutyl)amino)nicotinamide (158); (R)-6-(6-chloropyrazolo[1,5-a]pyrimidin-3-yl)-N-(2-fluoro-3-hydroxy-3-methylbutyl)-4-(propylamino)nicotinamide (159); 6-(6-chloropyrazolo[1,5-a]pyrimidin-3-yl)-N—((R)-2-fluoro-3-hydroxy-3-methylbutyl)-4-((3-fluorobutyl)amino)nicotinamide (160); (R)-6-(6-chloropyrazolo[1,5-a]pyrimidin-3-yl)-N-(2-fluoro-3-hydroxy-3-methylbutyl)-4-((3,3,3-trifluoropropyl)amino)nicotinamide (161); (R)-6-(6-chloropyrazolo[1,5-a]pyrimidin-3-yl)-N-(3-(difluoromethoxy)-2-fluoro-3-methylbutyl)-4-(isopropylamino)nicotinamide (162); (R)-6-(6-chloropyrazolo[1,5-a]pyrimidin-3-yl)-4-((2,2-difluoroethyl)amino)-N-(2-fluoro-3-hydroxy-3-methylbutyl) nicotinamide (163); (R)-6-(6-chloropyrazolo[1,5-a]pyrimidin-3-yl)-N-(2-fluoro-3-hydroxy-3-methylbutyl)-4-((3-hydroxypropyl)amino)nicotinamide (164); 6-(6-chloropyrazolo[1,5-a]pyrimidin-3-yl)-N—((R)-2-fluoro-3-hydroxy-3-methylbutyl)-4-(((1r,4R)-4-methoxycyclohexyl)amino) nicotinamide (165); 6-(6-chloropyrazolo[1,5-a]pyrimidin-3-yl)-N-((1r,4r)-4-ethoxycyclohexyl)-4-(isopropylamino) nicotinamide (166); (R)—N-(3-acetamidobutyl)-6-(6-chloropyrazolo[1,5-a]pyrimidin-3-yl)-4-(isopropylamino)nicotinamide (167); 6-(6-chloropyrazolo[1,5-a]pyrimidin-3-yl)-4-(isopropylamino)-N-(3-(methylsulfonyl)propyl)nicotinamide (168); N-(3-cyano-3-methylbutyl)-6-(6-cyanopyrazolo[1,5-a]pyrimidin-3-yl)-4-(isopropylamino) nicotinamide (169); (R)-6-(6-cyanopyrazolo[1,5-a]pyrimidin-3-yl)-N-(3-(difluoromethoxy)-2-fluoro-3-methylbutyl)-4-(isopropylamino)nicotinamide (170); (R)-6-(6-cyanopyrazolo[1,5-a]pyrimidin-3-yl)-4-((2,2-difluoroethyl)amino)-N-(2-fluoro-3-hydroxy-3-methylbutyl)nicotinamide (171); (R)-6-(6-cyanopyrazolo[1,5-a]pyrimidin-3-yl)-4-((2,2-difluoropropyl)amino)-N-(2-fluoro-3-hydroxy-3-methylbutyl)nicotinamide (172); 6-(7-cyanoimidazo[1,2-b]pyridazin-3-yl)-N-(2,2-difluoro-3-hydroxy-3-methylbutyl)-4-(isopropylamino)nicotinamide (173); 6-(7-cyanoimidazo[1,2-b]pyridazin-3-yl)-4-(isopropylamino)-N-((1r,4r)-4-(2-methoxypropan-2-yl)cyclohexyl) nicotinamide (174); 6-(7-chloroimidazo[1,2-b]pyridazin-3-yl)-N—((R)-2-fluoro-3-hydroxy-3-methylbutyl)-4-(((1r,4R)-4-(2-fluoropropan-2-yl)cyclohexyl)amino) nicotinamide (175); 6-(7-cyanoimidazo[1,2-b]pyridazin-3-yl)-N-(2-(2,6-dimethyltetrahydro-2H-pyran-4-yl)-2-fluoroethyl)-4-(isopropylamino)nicotinamide (176); (R)—N-(2-fluoro-3-hydroxy-3-methylbutyl)-6-(imidazo[1,2-b]pyridazin-3-yl)-4-(isopropylamino)nicotinamide (177); (R)-6-(7-chloroimidazo[1,2-b]pyridazin-3-yl)-4-(ethylamino)-N-(2-fluoro-3-hydroxy-3-methylbutyl)nicotinamide (178); (R)-6-(7-chloroimidazo[1,2-b]pyridazin-3-yl)-N-(2-fluoro-3-hydroxy-3-methylbutyl)-4-(propylamino)nicotinamide (179); (R)-6-(7-chloroimidazo[1,2-b]pyridazin-3-yl)-4-(cyclobutylamino)-N-(2-fluoro-3-hydroxy-3-methylbutyl)nicotinamide (180); 6-(7-chloroimidazo[1,2-b]pyridazin-3-yl)-

N—((R)-2-fluoro-3-hydroxy-3-methylbutyl)-4-(((S)-1-hydroxypropan-2-yl)amino)nicotinamide (181); (R)-6-(7-cyanoimidazo[1,2-b]pyridazin-3-yl)-4-(cyclopropylamino)-N-(2-fluoro-3-hydroxy-3-methylbutyl)nicotinamide (182); (R)-6-(7-cyanoimidazo[1,2-b]pyridazin-3-yl)-4-(cyclobutylamino)-N-(2-fluoro-3-hydroxy-3-methylbutyl)nicotinamide (183); (R)-4-(cyclopropylamino)-N-(2-fluoro-3-hydroxy-3-methylbutyl)-6-(7-methylimidazo[1,2-b]pyridazin-3-yl)nicotinamide (184); (R)-4-(cyclobutylamino)-N-(2-fluoro-3-hydroxy-3-methylbutyl)-6-(7-methylimidazo[1,2-b]pyridazin-3-yl)nicotinamide (185); 6-(7-cyanoimidazo[1,2-b]pyridazin-3-yl)-N-(3-hydroxy-3-methylbutyl)-4-(isopropylamino) nicotinamide (186); (R)-4-(tert-butylamino)-6-(7-cyanoimidazo[1,2-b]pyridazin-3-yl)-N-(2-fluoro-3-hydroxy-3-methylbutyl)nicotinamide (187); (R)-6-(7-cyanoimidazo[1,2-b]pyridazin-3-yl)-4-(ethylamino)-N-(2-fluoro-3-hydroxy-3-methylbutyl)nicotinamide (188); (R)-6-(7-chloroimidazo[1,2-b]pyridazin-3-yl)-N-(2,3-difluoro-3-methylbutyl)-4-(oxetan-3-ylamino)nicotinamide (189); (R)-6-(7-chloroimidazo[1,2-b]pyridazin-3-yl)-N-(2-fluoro-3-hydroxy-3-methylbutyl)-4-((3,3,3-trifluoropropyl)amino)nicotinamide (190); 6-(7-chloroimidazo[1,2-b]pyridazin-3-yl)-N-((1r,4r)-4-(2-methoxypropan-2-yl)cyclohexyl)-4-(oxetan-3-ylamino) nicotinamide (191); 6-(7-chloroimidazo[1,2-b]pyridazin-3-yl)-N-(3,3-dimethylbutyl)-4-(oxetan-3-ylamino) nicotinamide (192); (R)-6-(3-cyanopyrrolo[1,2-b]pyridazin-7-yl)-N-(2-fluoro-3-hydroxy-3-methylbutyl)-4-(isopropylamino)nicotinamide (193); (S)-6-(7-cyanoimidazo[1,2-b]pyridazin-3-yl)-N-(2-fluoro-3-hydroxy-3-methylbutyl)-4-(isopropylamino)nicotinamide (194); (R)-6-(7-cyanoimidazo[1,2-b]pyridazin-3-yl)-4-((3,3-difluorocyclobutyl)amino)-N-(2-fluoro-3-hydroxy-3-methylbutyl)nicotinamide (195); 6-(7-cyanoimidazo[1,2-b]pyridazin-3-yl)-N—((R)-2-fluoro-3-hydroxy-3-methylbutyl)-4-(((1r,4R)-4-methoxycyclohexyl)amino) nicotinamide (196); 6-(7-cyanoimidazo[1,2-b]pyridazin-3-yl)-N-(2-fluoro-2-(piperidin-4-yl)ethyl)-4-(isopropylamino) nicotinamide (197); (S)-6-(7-chloroimidazo[1,2-b]pyridazin-3-yl)-N-(2-fluoro-3-hydroxy-3-methylbutyl)-4-((1-methylcyclopropyl)amino) nicotinamide (198); (R)-6-(7-chloroimidazo[1,2-b]pyridazin-3-yl)-N-(2-fluoro-3-hydroxy-3-methylbutyl)-4-((3-fluorocyclobutyl)amino) nicotinamide (199); 6-(7-cyanoimidazo[1,2-b]pyridazin-3-yl)-N—((R)-2-fluoro-3-hydroxy-3-methylbutyl)-4-(((S)-1-fluoropropan-2-yl)amino)nicotinamide (200); 6-(7-cyanoimidazo[1,2-b]pyridazin-3-yl)-N—((R)-2-fluoro-3-hydroxy-3-methylbutyl)-4-((tetrahydrofuran-3-yl)amino) nicotinamide (201); 4-(((R)-sec-butyl)amino)-6-(7-chloroimidazo[1,2-b]pyridazin-3-yl)-N—((R)-2-fluoro-3-hydroxy-3-methylbutyl)nicotinamide (202); 6-(7-cyanoimidazo[1,2-b]pyridazin-3-yl)-N-(2-(2,6-dimethyltetrahydro-2H-pyran-4-yl)-2-fluoroethyl)-4-(isopropylamino) nicotinamide (203); 6-(7-cyanoimidazo[1,2-b]pyridazin-3-yl)-N—((R)-2-fluoro-3-hydroxy-3-methylbutyl)-4-(((1r,4R)-4-(2-hydroxypropan-2-yl)cyclohexyl)amino) nicotinamide (204); (R)-6-(7-cyanoimidazo[1,2-b]pyridazin-3-yl)-N-(2-fluoro-3-hydroxy-3-methylbutyl)-4-((3,3,3-trifluoropropyl)amino)nicotinamide (205); (R)-6-(7-chioroimidazo[1,2-b]pyridazin-3-yl)-4-((3,3-difluorocyclobutyl)amino)-N-(2-fluoro-3-hydroxy-3-methylbutyl)nicotinamide (206); (S)-6-(7-chloroimidazo[1,2-b]pyridazin-3-yl)-N-(2-fluoro-3-hydroxy-3-methylbutyl)-4-((1-methylcyclopropyl)amino)nicotinamide (207); 6-(7-cyanoimidazo[1,2-b]pyridazin-3-yl)-N—((R)-2-fluoro-3-hydroxy-3-methylbutyl)-4-((3-fluorocyclopentyl)amino) nicotinamide (208); (S)-6-(7-(difluoromethyl)imidazo[1,2-b]pyridazin-3-yl)-N-(2-fluoro-3-hydroxy-3-methylbutyl)-4-(isopropylamino)nicotinamide (209); (R)-6-(7-chloroimidazo[1,2-b]pyridazin-3-yl)-4-((3,3-difluoropropyl)amino)-N-(2-fluoro-3-hydroxy-3-methylbutyl)nicotinamide (210); (R)-6-(7-cyanoimidazo[1,2-b]pyridazin-3-yl)-4-((3,3-difluoropropyl)amino)-N-(2-fluoro-3-hydroxy-3-methylbutyl)nicotinamide (211); (S)—N-(2-fluoro-3-hydroxy-3-methylbutyl)-6-(7-fluoroimidazo[1,2-b]pyridazin-3-yl)-4-(isopropylamino)nicotinamide (212); 6-(7-cyanoimidazo[1,2-b]pyridazin-3-yl)-4-(isopropylamino)-N-(2-(thiophen-2-yl)ethyl)nicotinamide (213); N-(3-(1H-imidazol-1-yl)propyl)-6-(7-cyanoimidazo[1,2-b]pyridazin-3-yl)-4-(isopropylamino)nicotinamide (214); 6-(7-cyanoimidazo[1,2-b]pyridazin-3-yl)-N-(4-(dimethylamino)cyclohexyl)-4-(isopropylamino)nicotinamide (215); 6-(7-cyanoimidazo[1,2-b]pyridazin-3-yl)-4-(isopropylamino)-N-(2-(pyridin-2-yl)ethyl)nicotinamide (216); 6-(7-cyanoimidazo[1,2-b]pyridazin-3-yl)-N-(2-(1-hydroxycyclopentyl)ethyl)-4-(isopropylamino)nicotinamide (217); 6-(7-chloroimidazo[1,2-b]pyridazin-3-yl)-N-(3-hydroxy-3-methylbutyl)-4-(oxetan-3-ylamino)nicotinamide (218); N-((1r,4r)-4-acetamidocyclohexyl)-6-(7-chloroimidazo[1,2-b]pyridazin-3-yl)-4-(isopropylamino)nicotinamide (219); N-((1r,4r)-4-acetamidocyclohexyl)-6-(7-cyanoimidazo[1,2-b]pyridazin-3-yl)-4-(isopropylamino)nicotinamide (220); (S)-6-(7-cyanoimidazo[1,2-b]pyridazin-3-yl)-4-((1-fluoropropan-2-yl)amino)-N-(3-hydroxy-3-methylbutyl)nicotinamide (221); (R)-6-(7-(difluoromethyl)imidazo[1,2-b]pyridazin-3-yl)-N-(2-fluoro-3-hydroxy-3-methylbutyl)-4-(oxetan-3-ylamino)nicotinamide (222); methyl((1r,4r)-4-(6-(7-cyanoimidazo[1,2-b]pyridazin-3-yl)-4-(isopropylamino)nicotinamido)cyclohexyl)carbamate (223); methyl ((1r,4r)-4-(6-(7-cyanoimidazo[1,2-b]pyridazin-3-yl)-4-((1-methylcyclopropyl)amino)nicotinamido)cyclohexyl)carbamate (224); (R)-6-(6-cyanopyrazolo[1,5-a]pyrimidin-3-yl)-4-((1-(2,2-difluoroethyl)-1H-pyrrol-3-yl)amino)-N-(2-fluoro-3-hydroxy-3-methylbutyl)nicotinamide (225); (R)-6-(6-chloropyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino)nicotinamide (226); (R)-6-(6-chloropyrazolo[1,5-a]pyrimidin-3-yl)-4-((1-(2-fluoro-2-methylpropyl)-1H-pyrazol-4-yl)amino)-N-(2-fluoro-3-hydroxy-3-methylbutyl)nicotinamide (227); (R)-6-(6-chloropyrazolo[1,5-a]pyrimidin-3-yl)-4-((1-(2,2-difluoroethyl)-1H-pyrrol-3-yl)amino)-N-(2-fluoro-3-hydroxy-3-methylbutyl)nicotinamide (228); (R)-6-(6-chloropyrazolo[1,5-a]pyrimidin-3-yl)-4-((1-(2-fluoro-2-methylpropyl)-1H-pyrazol-3-yl)amino)-N-(2-fluoro-3-hydroxy-3-methylbutyl)nicotinamide (229); (R)-6-(6-cyanopyrazolo[1,5-a]pyrimidin-3-yl)-4-((1-(2,2-difluoroethyl)-1H-pyrazol-3-yl)amino)-N-(2-fluoro-3-hydroxy-3-methylbutyl)nicotinamide (230); (R)-6-(6-chloropyrazolo[1,5-a]pyrimidin-3-yl)-4-((1-(difluoromethyl)-1H-pyrazol-4-yl)amino)-N-(2-fluoro-3-hydroxy-3-methylbutyl) nicotinamide (231); (R)-6-(6-chloropyrazolo[1,5-a]pyrimidin-3-yl)-4-((1-ethyl-1H-pyrazol-4-yl)amino)-N-(2-fluoro-3-hydroxy-3-methylbutyl) nicotinamide (232); (R)-6-(6-chloropyrazolo[1,5-a]pyrimidin-3-yl)-N-(2-fluoro-3-hydroxy-3-methylbutyl)-4-((1-isopropyl-1H-pyrazol-4-yl)amino)nicotinamide (233); (R)-6-(6-cyanopyrazolo[1,5-a]pyrimidin-3-yl)-4-((1-(difluoromethyl)-1H-pyrazol-4-yl)amino)-N-(2-fluoro-3-hydroxy-3-methylbutyl)nicotinamide (234); (R)-6-(6-cyanopyrazolo[1,5-a]pyrimidin-3-yl)-4-((1-(2-fluoro-2-methylpropyl)-1H-pyrazol-4-yl)amino)-N-(2-fluoro-3-hydroxy-3-methylbutyl)nicotinamide (235); (R)-6-(6-cyanopyrazolo[1,5-a]pyrimidin-3-yl)-N-(2-fluoro-3-hydroxy-3-methylbutyl)-4-((1-(2,2,2-trifluoroethyl)-1H- pyrazol-4-yl)amino) nicotinamide (236); (R)-6-(6-chloropyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino)nicotinamide (237); (R)-6-(6-cyanopyrazolo[1,5-a]pyrimidin-3-yl)-4-((1-(2,2-difluoropropyl)-1H-pyrazol-4-yl)amino)-N-(2-fluoro-3-hydroxy-3-methylbutyl) nicotinamide (238); (R)-6-(6-chloropyrazolo[1,5-a]pyrimidin-3-yl)-4-((1-(2,2-difluoropropyl)-1H-pyrazol-4-yl)amino)-N-(2-fluoro-3-hydroxy-3-methylbutyl) nicotinamide (239); (R)-6-(6-cyanopyrazolo[1,5-a]pyrimidin-3-yl)-N-(2-fluoro-3-hydroxy-3-methylbutyl)-4-((1-methyl-1H-pyrazol-4-yl)amino)nicotinamide (240); (R)-6-(6-cyanopyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino)nicotinamide (241); (R)-6-(6-chloropyrazolo[1,5-a]pyrimidin-3-yl)-N-(2-fluoro-3-hydroxy-3-methylbutyl)-4-((1-(2-methoxyethyl)-1H-pyrazol-4-yl)amino) nicotinamide (242); (R)-6-(6-cyanopyrazolo[1,5-a]pyrimidin-3-yl)-N-(2-fluoro-3-hydroxy-3-methylbutyl)-4-((1-(2-methoxyethyl)-1H-pyrazol-4-yl)amino)nicotinamide (243); (R)-6-(6-cyanopyrazolo[1,5-a]pyrimidin-3-yl)-4-((1,3-dimethyl-1H-pyrazol-5-yl)amino)-N-(2-fluoro-3-hydroxy-3-methylbutyl) nicotinamide (244); (R)-6-(6-cyanopyrazolo[1,5-a]pyrimidin-3-yl)-4-((1-(2,2-difluoropropyl)-1H-pyrazol-3-yl)amino)-N-(2-fluoro-3-hydroxy-3-methylbutyl) nicotinamide (245); (R)-6-(6-chloropyrazolo[1,5-a]pyrimidin-3-yl)-4-((1-cyclopropyl-1H-pyrazol-4-yl)amino)-N-(2-fluoro-3-hydroxy-3-methylbutyl)nicotinamide (246); (R)-6-(6-chloropyrazolo[1,5-a]pyrimidin-3-yl)-N-(2-fluoro-3-hydroxy-3-methylbutyl)-4-((1-isobutyl-1H-pyrazol-4-yl)amino)nicotinamide (247); (R)-6-(6-cyanopyrazolo[1,5-a]pyrimidin-3-yl)-4-((1-cyclopropyl-1H-pyrazol-4-yl)amino)-N-(2-fluoro-3-hydroxy-3-methylbutyl)nicotinamide (248); (R)-6-(6-cyanopyrazolo[1,5-a]pyrimidin-3-yl)-4-((1-(cyclopropylmethyl)-1H-pyrazol-4-yl)amino)-N-(2-fluoro-3-hydroxy-3-methylbutyl)nicotinamide (249); (R)-6-(6-chloropyrazolo[1,5-a]pyrimidin-3-yl)-4-((1-cyclobutyl-1H-pyrazol-4-yl)amino)-N-(2-fluoro-3-hydroxy-3-methylbutyl) nicotinamide (250); (R)-6-(6-chloropyrazolo[1,5-a]pyrimidin-3-yl)-4-((1-(cyclopropylmethyl)-1H-pyrazol-4-yl)amino)-N-(2-fluoro-3-hydroxy-3-methylbutyl) nicotinamide (251); 6-(6-chloropyrazolo[1,5-a]pyrimidin-3-yl)-4-((1-(2,2-difluoroethyl)-1H-pyrazol-4-yl)amino)-N-((1r,4r)-4-hydroxycyclohexyl) nicotinamide (252); 6-(6-chloropyrazolo[1,5-a]pyrimidin-3-yl)-4-((1-(2,2-difluoroethyl)-1H-pyrazol-4-yl)amino)-N-(3-hydroxy-3-methylbutyl)nicotinamide (253); 6-(6-chloropyrazolo[1,5-a]pyrimidin-3-yl)-4-((1-cyclopropyl-1H-pyrazol-4-yl)amino)-N-((1r,4r)-4-(2-hydroxypropan-2-yl)cyclohexyl) nicotinamide (254); 6-(6-chloropyrazolo[1,5-a]pyrimidin-3-yl)-N-(3-hydroxy-3-methylbutyl)-4-((1-methyl-1H-pyrazol-4-yl)amino)nicotinamide (255); 6-(6-chloropyrazolo[1,5-a]pyrimidin-3-yl)-N-((1r,4r)-4-(2-hydroxypropan-2-yl)cyclohexyl)-4-((1-methyl-1H-pyrazol-4-yl)amino) nicotinamide (256); methyl ((1r,4r)-4-(6-(6-chloropyrazolo[1,5-a]pyrimidin-3-yl)-4-((1-methyl-1H-pyrazol-4-yl)amino)nicotinamido)cyclohexyl)carbamate (257); (R)-6-(7-cyanoimidazo[1,2-b]pyridazin-3-yl)-N-(2,3-difluoro-3-methylbutyl)-4-((1-(2,2-difluoroethyl)-1H-pyrazol-4-yl)amino)nicotinamide (258); (R)-6-(7-cyanoimidazo[1,2-b]pyridazin-3-yl)-4-((1-(3,3-difluorocyclobutyl)-1H-pyrazol-4-yl)amino)-N-(2-fluoro-3-hydroxy-3-methylbutyl) nicotinamide (259); (R)-6-(7-cyanoimidazo[1,2-b]pyridazin-3-yl)-4-((1-(2,2-difluoroethyl)-1H-pyrazol-4-yl)amino)-N-(2-fluoro-3-hydroxy-3-methylbutyl) nicotinamide (260); (R)-6-(7-cyanoimidazo[1,2-b]pyridazin-3-yl)-N-(2,3-difluoro-3-methylbutyl)-4-((1-(2,2-difluoroethyl)-1H-pyrazol-4-yl)amino)nicotinamide (261); (R)-6-(7-chloroimidazo[1,2-b]pyridazin-3-yl)-4-((1-(2,2-difluoroethyl)-1H-pyrazol-4-yl)amino)-N-(2-fluoro-3-hydroxy-3-methylbutyl)nicotinamide (262); (R)-6-(7-chloroimidazo[1,2-b]pyridazin-3-yl)-N-(2,3-difluoro-3-methylbutyl)-4-((1-(2,2-difluoroethyl)-1H-pyrazol-4-yl)amino)nicotinamide (263); 6-(7-chloroimidazo[1,2-b]pyridazin-3-yl)-4-((1-(2,2-difluoroethyl)-1H-pyrazol-4-yl)amino)-N-((1r,4r)-4-(2-hydroxypropan-2-yl)cyclohexyl) nicotinamide (264); (R)-6-(7-cyanoimidazo[1,2-b]pyridazin-3-yl)-4-((1-(2,2-difluoropropyl)-1H-pyrazol-4-yl)amino)-N-(2-fluoro-3-hydroxy-3-methylbutyl)nicotinamide (265); (R)-6-(7-chloroimidazo[1,2-b]pyridazin-3-yl)-4-((1-ethyl-1H-pyrazol-4-yl)amino)-N-(2-fluoro-3-hydroxy-3-methylbutyl) nicotinamide (266); (R)-6-(7-cyanoimidazo[1,2-b]pyridazin-3-yl)-4-((1-ethyl-1H-pyrazol-4-yl)amino)-N-(2-fluoro-3-hydroxy-3-methylbutyl)nicotinamide (267); (R)-6-(7-cyanoimidazo[1,2-b]pyridazin-3-yl)-4-((1-(2,2-difluoropropyl)-1H-pyrazol-3-yl)amino)-N-(2-fluoro-3-hydroxy-3-methylbutyl)nicotinamide (268); (R)-6-(7-cyanoimidazo[1,2-b]pyridazin-3-yl)-N-(2,3-difluoro-3-methylbutyl)-4-((1-(2,2-difluoropropyl)-1H-pyrazol-4-yl)amino)nicotinamide (269); (R)-6-(7-chloroimidazo[1,2-b]pyridazin-3-yl)-4-((1-(difluoromethyl)-1H-pyrazol-4-yl)amino)-N-(2-fluoro-3-hydroxy-3-methylbutyl) nicotinamide (270); (R)-6-(7-chloroimidazo[1,2-b]pyridazin-3-yl)-N-(2-fluoro-3-hydroxy-3-methylbutyl)-4-((1-methyl-1H-pyrazol-4-yl)amino)nicotinamide (271); (R)-6-(7-cyanoimidazo[1,2-b]pyridazin-3-yl)-4-((1-(2-fluoro-2-methylpropyl)-1H-pyrazol-3-yl)amino)-N-(2-fluoro-3-hydroxy-3-methylbutyl)nicotinamide (272); (R)-6-(7-cyanoimidazo[1,2-b]pyridazin-3-yl)-4-((1-(difluoromethyl)-1H-pyrazol-4-yl)amino)-N-(2-fluoro-3-hydroxy-3-methylbutyl)nicotinamide (273); (R)-6-(7-cyanoimidazo[1,2-b]pyridazin-3-yl)-N-(2-fluoro-3-hydroxy-3-methylbutyl)-4-((1-methyl-1H-pyrazol-4-yl)amino)nicotinamide (274); (R)-6-(7-chloroimidazo[1,2-b]pyridazin-3-yl)-N-(2-fluoro-3-hydroxy-3-methylbutyl)-4-((1-(2,2,2-trifluoroethyl)-1H-pyrazol-4-yl)amino) nicotinamide (275); (R)-6-(7-cyanoimidazo[1,2-b]pyridazin-3-yl)-N-(2-fluoro-3-hydroxy-3-methylbutyl)-4-((1-(2,2,2-trifluoroethyl)-1H-pyrazol-4-yl)amino) nicotinamide (276); (R)-6-(7-chloroimidazo[1,2-b]pyridazin-3-yl)-4-((1-(3,3-difluorocyclobutyl)-1H-pyrazol-4-yl)amino)-N-(2-fluoro-3-hydroxy-3-methylbutyl) nicotinamide (277); (R)-6-(7-cyanoimidazo[1,2-b]pyridazin-3-yl)-N-(2-fluoro-3-hydroxy-3-methylbutyl)-4-((1-propyl-1H-pyrazol-4-yl)amino)nicotinamide (278); (R)-6-(7-cyanoimidazo[1,2-b]pyridazin-3-yl)-4-((1-(2-fluoro-2-methylpropyl)-1H-pyrazol-4-yl)amino)-N-(2-fluoro-3-hydroxy-3-methylbutyl)nicotinamide (279); (R)-6-(7-cyanoimidazo[1,2-b]pyridazin-3-yl)-4-((5-(2,2-difluoroethyl)-4,5,6,7-tetrahydropyrazolo[1,5-a]pyrazin-2-yl)amino)-N-(2-fluoro-3-hydroxy-3-methylbutyl) nicotinamide (280); (R)-6-(7-cyanoimidazo[1,2-b]pyridazin-3-yl)-N-(2-fluoro-3-hydroxy-3-methylbutyl)-4-((1-(3-fluoropropyl)-1H-pyrazol-4-yl)amino)nicotinamide (281); (R)-6-(7-cyanoimidazo[1,2-b]pyridazin-3-yl)-N-(2,3-difluoro-3-methylbutyl)-4-((1-(2-fluoro-2-methylpropyl)-1H-pyrazol-4-yl)amino)nicotinamide (282); (R)-6-(7-chloroimidazo[1,2-b]pyridazin-3-yl)-N-(2-fluoro-3-hydroxy-3-methylbutyl)-4-((1-(3-fluoropropyl)-1H-pyrazol-4-yl)amino)nicotinamide (283); (R)-6-(7-cyanoimidazo[1,2-b]pyridazin-3-yl)-4-((1-cyclopropyl-1H-pyrazol-4-yl)amino)-N-(2-fluoro-3-hydroxy-3-methylbutyl)nicotinamide (284); (R)-6-(7-chloroimidazo[1,2-b]pyridazin-3-yl)-4-((1-cyclobutyl-1H-pyrazol-4-yl)amino)-N-(2-fluoro-3-hydroxy-3-methylbutyl)nicotinamide (285); 6-(7-cyanoimidazo[1,2-b]pyridazin-3-yl)-4-((1-cyclopropyl-1H-pyrazol-4-yl)amino)-N-((1r,4r)-4-(2-hydroxypropan-2-yl)cyclohexyl) nicotinamide (286); 6-(7-cyanoimidazo[1,2-b]pyridazin-3-yl)-N-(3-hydroxy-3-methylbutyl)-4-((1-isopropyl-1H-pyrazol-4-yl)amino)nicotinamide (287); and 6-(7-cyanoimidazo[1,2-b]pyridazin-3-yl)-N—((R)-2-fluoro-3-hydroxy-3-methylbutyl)-4-(((R)-1-(5-fluoropyrimidin-2-yl)pyrrolidin-3-yl)amino)nicotinamide (288).

One embodiment provides compounds of the Formula (I) having IRAK4 IC$_{50}$ values of ≤0.1 µM.

One embodiment provides compounds of the Formula (I) having IRAK4 IC$_{50}$ values of ≤0.050 µM.

One embodiment provides compounds of the Formula (I) having IRAK4 IC$_{50}$ values of ≤0.025 µM.

One embodiment provides compounds of the Formula (I) having IRAK4 IC$_{50}$ values of ≤0.015 µM.

One embodiment provides compounds of the Formula (I) having IRAK4 IC$_{50}$ values of ≤0.01 µM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and C$_{1-4}$ hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) Hydrolysis in Drug and Prodrug Metabolism, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncological and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of the general Formula (I) can be prepared according to the method outlined in Scheme 1. Hydrolysis of ester (1) to the acid 1.1 followed by reaction with an amine using standard amide bond forming conditions can afford the dichloro amide 1.2. Selective displacement of the C4 chloride by reacting with an amine can afford the mono-chloro product 1.3. Reaction of 1.3 with an appropriate heterocyclic boron containing coupling partner, in the presence of a catalyst, such as palladium, can afford compounds of the general formula I.

SCHEME 1

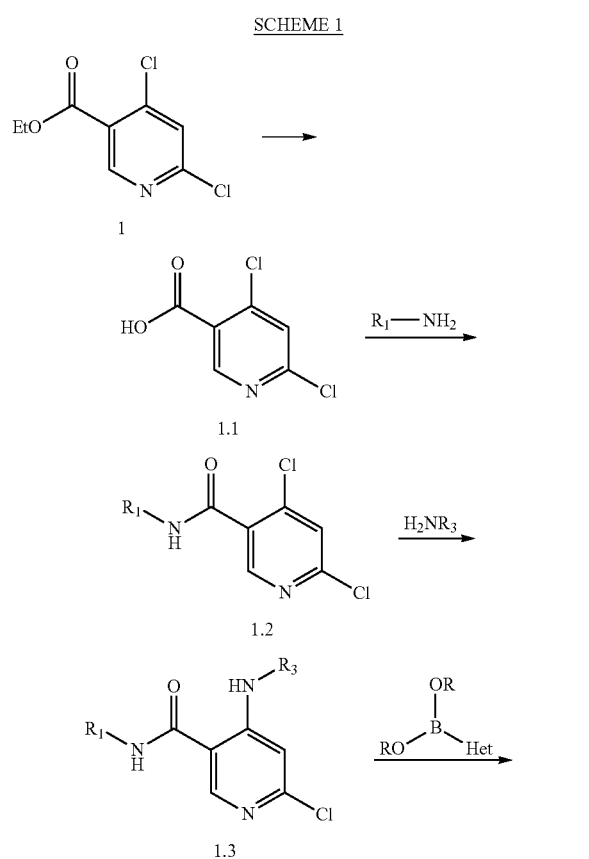

Alternatively, the order of reactions can be modified to change the overall synthesis to allow for variations at different positions of the molecule at different stages of the preparation. For example, in Scheme 2, the chloride 1 may be reacted with an amine first to form the mono-chlorinated ester 2.1. Subsequent reaction with a heterocyclic boron containing coupling partner, may form the disubstituted intermediate 2.2. Hydrolysis of the ester to acid 2.3 followed by amide bond formation can afford the final analog 2.4.

SCHEME 2

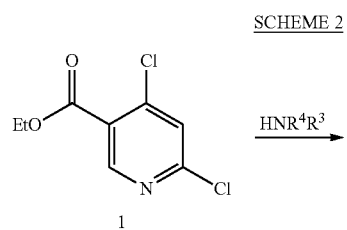

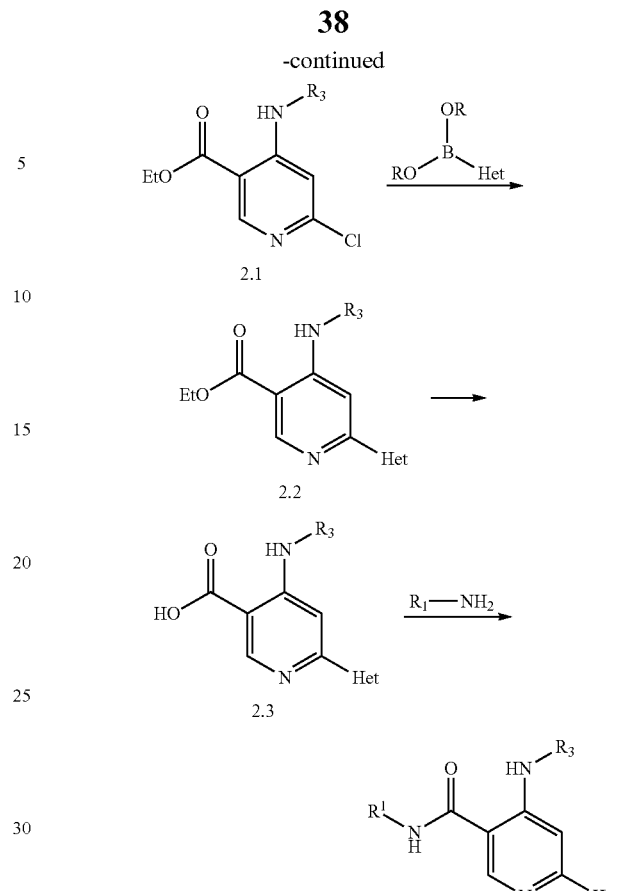

An additional variation on the order of substitution is shown in Scheme 3. First, reacting the dichloride with an amine may afford compound 3.1. Hydrolysis of the ester with a base, such as NaOH or KOH, may afford the acid 3.2. This acid may be reacted with an amine using standard amide bond forming reaction conditions, such as HOBt, EDC and DIPEA, in an appropriate solvent to form the amide 3.3, similar to amide 1.3 in Scheme 1. Subsequent heterocyclic boron containing coupling in the presence of a metal catalyst such as palladium, may afford the final compound 3.4.

SCHEME 3

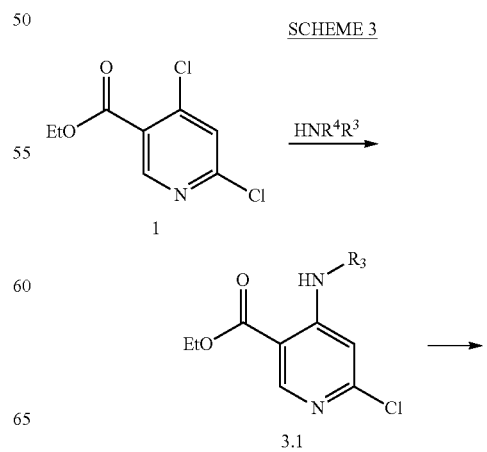

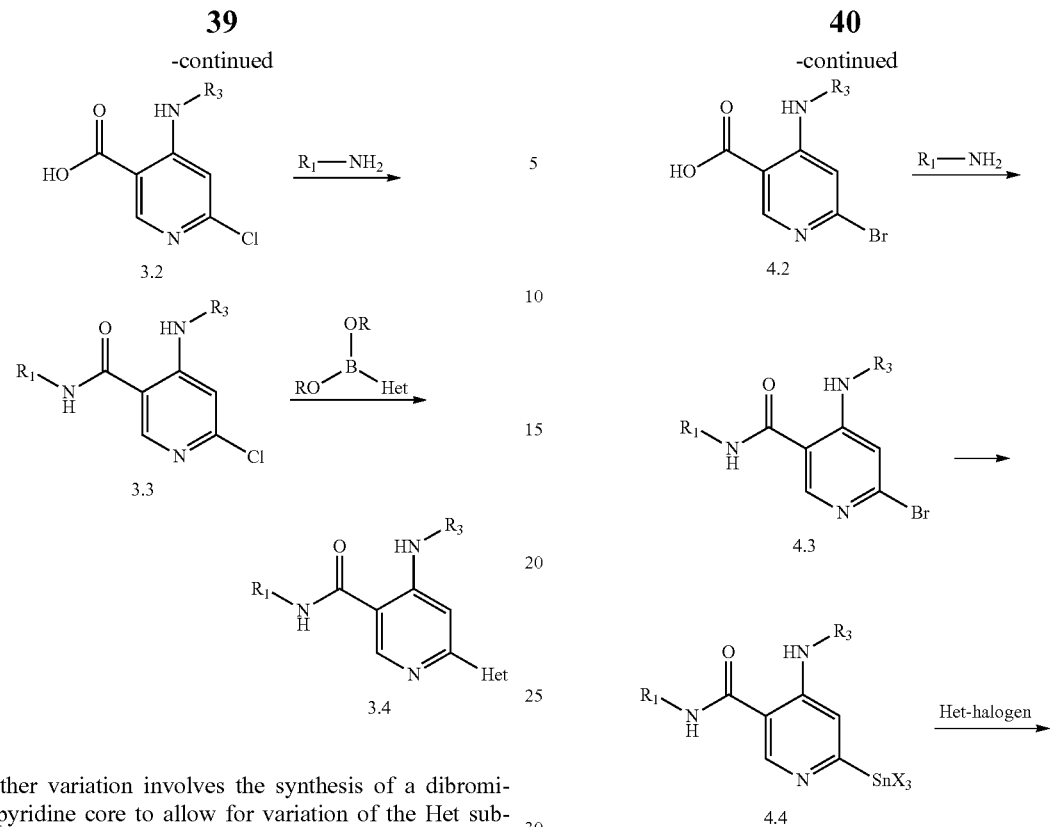

Another variation involves the synthesis of a dibrominated pyridine core to allow for variation of the Het substituent at the last stage of the synthesis. Ethyl 4,6-dibromonicotinate may be reacted with an amine, such as isopropyl amine to afford the C4 amine substituted 4.1. This may be further reacted with a saponification reagent, such as LiOH or NaOH to form the acid 4.2. This acid may be reacted with an amine using standard amide bond forming reaction conditions, such as HOBt, EDC and DIPEA, in an appropriate solvent to form the amide 4.3. Amide 4.3 may be reacted with a stannylating reagent, such as hexamethylditin, to afford compound 4.4. Finally, compound 4.4 may be reacted with a halogenated heterocycle, in the presence of a catalyst such as Pd, to afford compound 4.5. Alternatively, a change in the order of transformations, such as ester hydrolysis—amide bond coupling—C4 amination could be utilized to prepare 4.3 and ultimately 4.5.

SCHEME 4

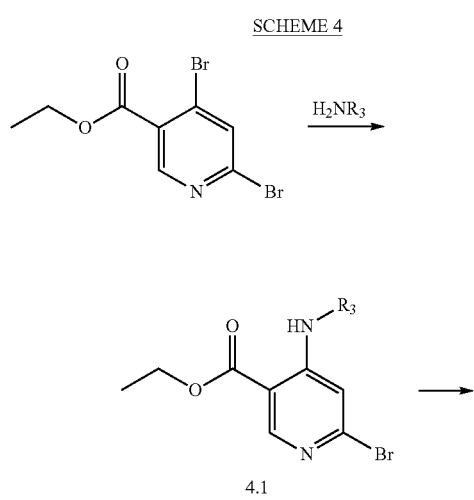

It should be also noted, and obvious to those skilled in the art, that synthetic manipulations of the incorporated $R_1$, HET, and $R_3$ groups are possible. An illustrative example is shown in Scheme 5. The secondary alcohol incorporated in compound 5.1 may be converted to the fluoro analog 5.2 upon treatment with a fluorinating reagent, such as DAST, in an appropriate solvent, such as DCM. It should be obvious to those skilled in the art that other functionalities than an alcohol may be present for subsequent functionalization. For example, nitro groups can be converted readily to amines and subsequently functionalized, and esters can be readily converted to acids, amides or heterocycles. Additionally, aryl or heteroaryl groups incorporated into compound 5.3 may be converted, through standard chemical manipulations, to analogs of varying degrees of substitution. For example, when Y is nitro, the functionality may be converted to an amine under standard reducing conditions and further functionalized as an amide (Z is $NHCOCH_3$) or sulfonamide (Z is $NHSO_2CH_3$). The order of synthetic manipulations, of course, may be carried out in a fashion that is consistent with the methods outlined in Schemes 1-4 and should not be limited to the final step of the example preparation.

SCHEME 5

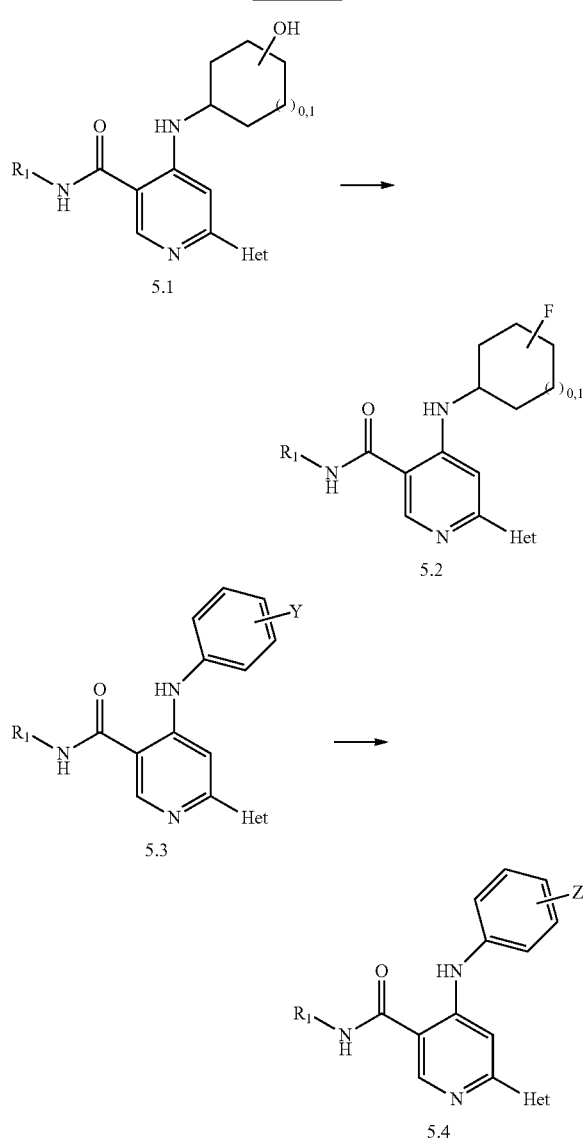

Additionally, variations to the $R_1$ group can be made via functionalization after incorporating onto the pyridine scaffold. For example, in Scheme 6, an appropriately protected amine, sulfide or ester may be coupled to the pyridine acid 6.1 via standard amide bond forming conditions to form 6.2. Compound 6.2 may be further manipulated (amine deprotection/functionalization; sulfide oxidation; ester hydrolysis/amide or heterocycle formation) to form compounds of the general formula 6.3.

SCHEME 6

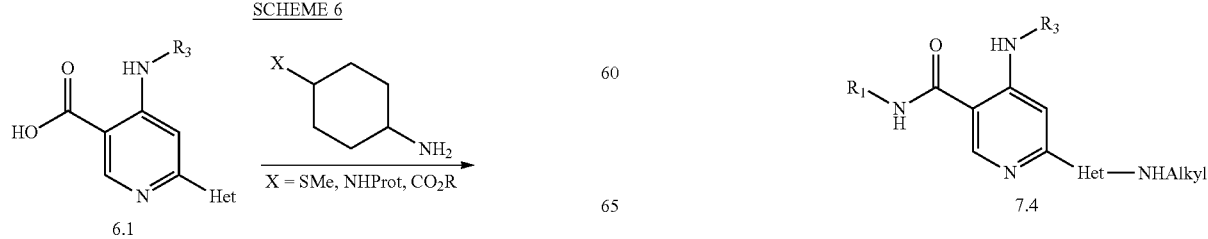

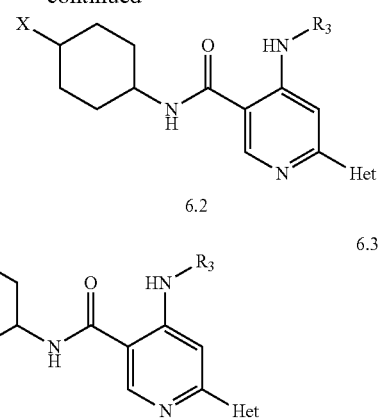

Substitution on the heterocyclic substituent may be accomplished via the methods outlined in Scheme 7. Preparation of an appropriately functionalized precursor, such as compound 7.1 ($R^x$ is a functional group such as an amine, ester or halogen), and reaction with a variety of reagents, such as amines, aryl cross coupling partners, cyanide may form compounds of the formula 9.2 ($R^x$). For example, compound 7.3 may be converted to compound 7.4 via reaction with an aldehyde in the presence of a reducing agent.

SCHEME 7

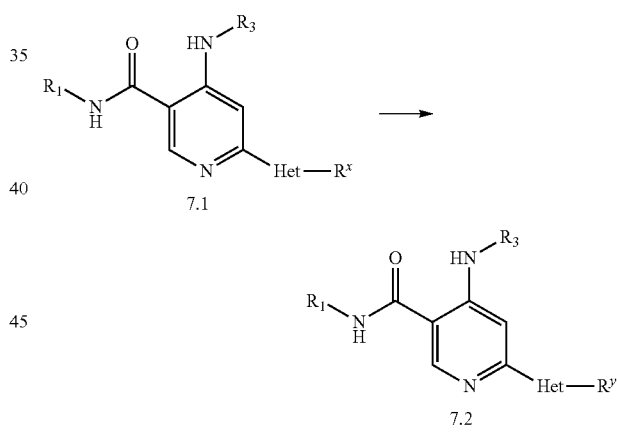

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire C18, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

ACN acetonitrile
aq. aqueous
BOC tert-butoxycarbonyl
$BOC_2O$ di-tert-butyl dicarbonate
BOP benzotriazol-1-yloxytris-(dimethylamino)-phosphonium hexafluorophosphate
brine saturated aqueous sodium chloride
DAST (diethylamino)sulfur trifluoride
DCM dichloromethane
DIPEA N,N-diisopropylethylamine
DMA N,N-dimethylacetamide
DMF N,N-dimethylformamide
DMSO dimethyl sulfoxide
DTBAD di-tert-butyl azodicarboxylate
EDC N-(3-dimethylaminopropyl)-N'-ethylcarbodiimide hydrochloride
$Et_3N$ triethylamine
EtOAc ethyl acetate
EtOH ethanol
g gram(s)
h hour(s)
HATU O-(7-azabenzotriazol-1-yl)-N,N,N',N'-tetramethyluronium hexafluorophosphate
HOBt hydroxybenzotriazole
HPLC High Performance Liquid Chromatography
hrs hours
LCMS Liquid Chromatography-Mass Spectroscopy
LDA lithium diisopropylamide
mCPBA 3-chloroperbenzoic acid
MeCN acetonitrile
MeI methyl iodide
MeOH methanol
Min minute(s)
MTBE methyl t-butyl ether
NBS N-bromosuccinimide
$NH_4OAc$ ammonium acetate
$PdCl_2(dppf)$ [1,1'-bis(diphenylphosphino)ferrocene]dichloropalladium(II)
$Pd(PPh_3)_4$ tetrakis(triphenylphosphine)palladium
pet ether petroleum ether
t-BuOH t-butyl alcohol
TEA triethylamine
TFA trifluoroacetic acid
THF tetrahydrofuran
TMS-Cl chlorotrimethylsilane
TMS-CN cyanotrimethylsilane HPLC Conditions:

A. Sunfire C18 (4.6×150 mm), 3.5 micron, mobile phase A: 95:5 water/MeCN, 0.05% TFA; mobile phase B: 95:5 MeCN/water, 0.05% TFA; 1 mL\min, 12 min gradient.

B. Xbridge Phenyl (4.6×150 mm), 3.5 micron, mobile phase A: 95:5 water/MeCN, 0.05% TFA; mobile phase B: 95:5 MeCN/water, 0.05% TFA; 1 mL\min, 12 min gradient.

C. Ascentis Express C18 (2.1×50 mm), 2.7 micron, mobile phase A: 95:5 water/MeCN, 10 mM $NH_4OAc$; mobile phase B: 5:95 water/MeCN, 10 mM $NH_4OAc$; 1.1 mL\min, 3 min gradient, 50° C.

D. Ascentis Express C18 (2.1×50 mm), 2.7 micron, mobile phase A: 95:5 water/MeCN, 0.01% TFA; mobile phase B: 5:95 water/MeCN, 0.01% TFA; 1.1 mL\min, 3 min gradient, 50° C.

E. Waters Acquity UPLC BEH C18, 2.1×50 mm, 1.7 micron; mobile phase A: 5:95 MeCN:water with 10 mM ammonium acetate; mobile phase B: 95:5 MeCN:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

F. Column: Waters Acquity UPLC BEH C18, 2.1×50 mm, 1.7 micron; mobile phase A: 5:95 MeCN:water with 0.1% trifluoroacetic acid; mobile phase B: 95:5 MeCN:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

G. Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min.

H. Column: Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min.

Example 1

(R)-6-(6-chloropyrazolo[1,5-a]pyrimidin-3-yl)-N-(2-fluoro-3-hydroxy-3-methylbutyl)-4-(isopropylamino)nicotinamide

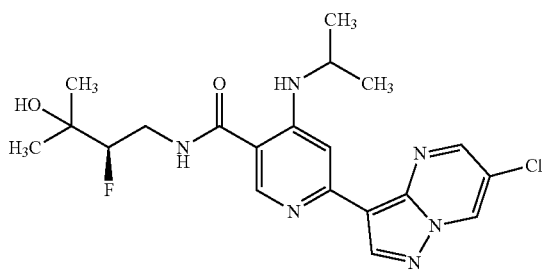

(1)

Intermediate 1A: ethyl 6-chloro-4-(isopropylamino)nicotinate

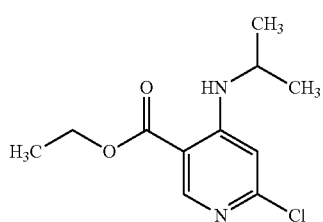

(1A)

To a solution of ethyl 4,6-dichloronicotinate (10 g, 45 mmol) in DMA (40 mL) was added propan-2-amine (5.3 g, 91 mmol) and DIPEA (31.7 mL, 182 mmol). The reaction mixture was stirred at room temperature for 48 h. The reaction mixture was diluted with MTBE and washed with water (3×). The organic layer was dried over $Na_2SO_4$, filtered and concentrated to afford the crude product. The product was purified by flash chromatography through silica gel (10% EtOAc:pet ether as eluent) to afford ethyl 6-chloro-4-(isopropylamino)nicotinate (8.3 g, 75% yield) as a crystalline solid. LCMS m/z 243.7 (M+H); $^1$H NMR (400 MHz, DMSO-$d_6$) δ 8.54 (s, 1H), 7.98 (d, J=7.6 Hz, 1H), 6.85 (s, 1H), 4.29 (q, J=7.2 Hz, 2H), 3.86 (m, 1H), 1.32 (d, J=6.8 Hz, 3H), 1.20 (s, 3H), 1.19 (s, 3H).

Intermediate 1B: 6-chloro-4-(isopropylamino)nicotinic acid

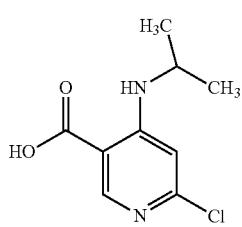

(1B)

To a solution of ethyl 6-chloro-4-(isopropylamino)nicotinate (7 g, 28.8 mmol) in EtOH (70 mL) was added water (30 mL) and LiOH (2.1 g, 87 mmol). The mixture was stirred at room temperature for 3 h, concentrated in vacuo and acidified with 1.5 N HCl. The resultant solids were collected and dried to afford 6-chloro-4-isopropylaminonicotic acid (5.3 g, 85% yield) as a white solid. LCMS m/z 215.3 (M+H)+; $^1$H NMR (400 MHz, DMSO-$d_6$) δ 13.32 (br s, 1H), 8.51 (s, 1H), 8.19 (d, J=7.6 Hz, 1H), 6.79 (s, 1H), 2.50 (m, 1H), 1.20 (s, 3H), 1.18 (s, 3H).

Intermediate 1C: (R)-6-chloro-N-(2-fluoro-3-hydroxy-3-methylbutyl)-4-(isopropylamino)nicotinamide

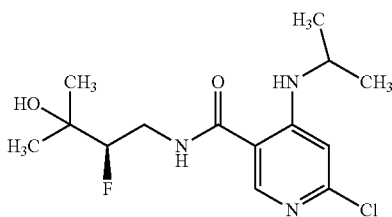

(1C)

To a stirred solution of 6-chloro-4-(isopropylamino)nicotinic acid (2.9 g, 13.51 mmol) in DMF was added (R)-4-amino-3-fluoro-2-methylbutan-2-ol (1.637 g, 13.51 mmol) (WO 2014/074675 A1), HATU (6.16 g, 16.21 mmol) and DIPEA (9.44 mL, 54.0 mmol). The reaction mixture was stirred at room temperature for 18 h. The reaction mixture was diluted with ethyl acetate and washed with water (3×). The organic layer was dried over $Na_2SO_4$ and concentrated in vacuo to provide the crude compound which was purified via column chromatography (10-40% ethyl acetate/pet ether) to afford (R)-6-chloro-N-(2-fluoro-3-hydroxy-3-methylbutyl)-4-(isopropylamino)nicotinamide (2.8 g, 65% yield) as an off-white solid. LCMS m/z 318.1 (M+H): $^1$H NMR (400 MHz, DMSO-$d_6$) δ 8.75 (t, J=7.6 Hz, 1H), 8.44 (br d, J=10.4 Hz, 1H), 8.38 (s, 1H), 6.71 (s, 1H), 4.24 (m, 1H), 3.64 (m 2H), 3.42 (m, 1H), 1.16 (m, 12H).

Intermediate 1D: 3-bromo-6-chloropyrazolo[1,5-a]pyrimidine

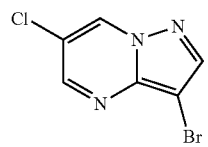

(1D)

To a stirred solution of 6-chloropyrazolo[1,5-a]pyrimidine (0.3 g, 1.954 mmol) in DCM (10 mL) was added NBS (0.348 g, 1.954 mmol) at 0° C. The reaction mixture was stirred for 5 h at the same temperature. The mixture was diluted with water and extracted with ethyl acetate (3×15 mL). The combined organic layers were dried over anhydrous $Na_2SO_4$ and evaporated under reduced pressure to afford the crude compound. The crude compound was taken to the next step without further purification. LCMS m/z 231.8 (M+H); $^1$H NMR (300 MHz, DMSO-$d_6$) d=9.63 (d, J=2.3 Hz, 1H), 8.70 (d, J=2.3 Hz, 1H), 8.43 (s, 1H).

Intermediate 1E: 6-chloro-3-(4,4,5,5-tetramethyl-1,3,2-dioxaborolan-2-yl)pyrazolo[1,5-a]pyrimidine

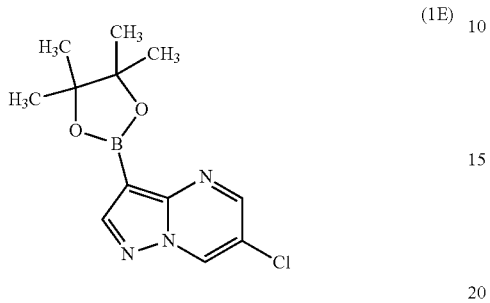

(1E)

To a solution of 3-bromo-6-chloropyrazolo[1,5-a]pyrimidine (0.290 g, 1.247 mmol) in 1,4-dioxane (10 mL) was added 4,4,4',4',5,5,5',5'-octamethyl-2,2'-bi(1,3,2-dioxaborolane) (1.426 g, 5.61 mmol) followed by potassium acetate (0.441 g, 4.49 mmol) and the solution was degassed for 5 min with nitrogen. To this reaction mixture, bis(triphenylphosphine)palladium(II) dichloride (0.044 g, 0.062 mmol) was added and the mixture was degassed for another 15 min. The reaction vessel was sealed and heated to 110° C. for 16 h. The reaction mixture was filtered through a celite bed and washed with dioxane. The filtrate was concentrated under reduced pressure. The crude compound was purified by column to afford 6-chloro-3-(4,4,5,5-tetramethyl-1,3,2-dioxaborolan-2-yl)pyrazolo[1,5-a]pyrimidine. LCMS m/z 198.0 (M+H); $^1$H NMR (400 MHz, DMSO-$d_6$) δ 9.63 (d, J=2.0 Hz, 1H), 8.74 (d, J=2.5 Hz, 1H), 8.37 (s, 1H), 1.31 (s, 13H).

Example 1

(R)-6-Chloro-N-(2-fluoro-3-hydroxy-3-methylbutyl)-4-(isopropylamino) nicotinamide (0.085 g, 0.267 mmol) was dissolved in 1,4-dioxane (4 mL) and 0.2 mL of water. 6-Chloro-3-(4,4,5,5-tetramethyl-1,3,2-dioxaborolan-2-yl)pyrazolo[1,5-a]pyrimidine (0.075 g, 0.267 mmol) was added and the mixture was degassed for 10 min. Potassium acetate (0.079 g, 0.802 mmol) was then added followed by palladium tetrakis (0.062 g, 0.053 mmol) and the reaction mixture was heated to 100° C. for 1 h in a microwave. The reaction mixture was filtered through celite and concentrated in vacuo. The crude material was purified by preparative TLC. This procedure afforded (R)-6-(6-chloropyrazolo[1,5-a]pyrimidin-3-yl)-N-(2-fluoro-3-hydroxy-3-methylbutyl)-4-(isopropylamino)nicotinamide as a pale yellow solid (0.032 g, 27.4%). LCMS m/z 435 (M+H); $^1$H NMR (400 MHz, DMSO-$d_6$) δ 9.65-9.68 (m, 1H) 8.79-8.84 (m, 2H) 8.61-8.67 (m, 2H) 8.43 (d, J=7.53 Hz, 1H) 7.74 (s, 1H) 4.82 (s, 1H) 4.27-4.45 (m, 1H) 3.63-3.83 (m, 2H) 3.36-3.45 (m, 1H) 1.27 (d, J=6.53 Hz, 6H) 1.17 (dd, J=5.27, 1.25 Hz, 6H); HPLC rt 7.14 min, conditions B.

Example 2

(R)-6-(6-chloropyrazolo[1,5-a]pyrimidin-3-yl)-N-(2-fluoro-3-hydroxy-3-methylbutyl)-4-((5-(2-hydroxypropan-2-yl)thiazol-2-yl)amino)nicotinamide

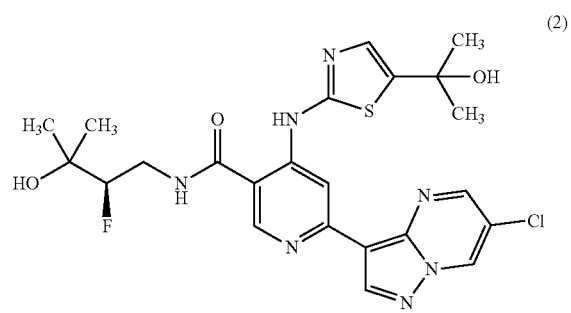 [SMILES: CC(C)(O)c1cnc(Nc2cc(-c3cnn4cc(Cl)cnc34)ncc2C(=O)NC[C@@H](F)C(C)(C)O)s1]

(2)

Intermediate 2A: 4,6-dichloronicotinic acid

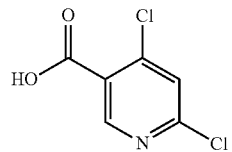

(2A)

To a solution of ethyl 4,6-dichloronicotinate (8 g, 36.4 mmol) in THF (50 mL), ethanol (25 mL) and water (25 mL) was added LiOH (2.61 g, 109 mmol). The mixture was stirred at 25° C. for 2 hours. The reaction mixture was concentrated in vacuo. The residue was dissolved in water and acidified to neutral pH with 1.5 N HCl. The precipitated solid was filtered and washed with water (2×30 mL). The solid was dried under vacuum to afford 4,6-dichloronicotinic acid (6.5 g, 83% yield). LCMS m/z 194.1 (M+2); $^1$H NMR (400 MHz, DMSO-$d_6$) δ 8.80 (s, 1H), 7.93 (s, 1H).

Intermediate 2B: (R)-4,6-dichloro-N-(2-fluoro-3-hydroxy-3-methylbutyl)nicotinamide

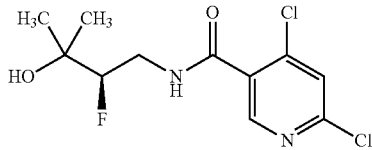

(2B)

To a solution of 4,6-dichloronicotinic acid (5 g, 26.0 mmol) in dichloromethane (30 mL) was added (R)-4-amino-3-fluoro-2-methylbutan-2-ol (3.16 g, 26.0 mmol) and TEA (18.15 mL, 130 mmol) at 0° C. followed by the addition of 1-propanephosphonic acid cyclic anhydride (50% in ethyl acetate) (24.86 g, 78 mmol). The reaction mixture was stirred at 25° C. for 16 h. The mixture was then diluted with dichloromethane and the organic layer was washed with water and brine. The organic layer was dried over anhydrous Na$_2$SO$_4$, filtered and concentrated in vacuo. The residue was purified via column chromatography (40% EtOAc/pet ether) to afford (R)-4,6-dichloro-N-(2-fluoro-3-hydroxy-3-methylbutyl)nicotinamide (3.6 g, 46% yield). LCMS m/z 297.2 (M+2); $^1$H NMR (400 MHz, DMSO) δ 8.98-8.81 (m, 1H), 8.48 (s, 1H), 7.92 (s, 1H), 4.85 (s, 1H), 4.46-4.33 (m, 1H), 4.30-4.20 (m, 1H), 3.89-3.66 (m, 2H), 1.17 (dd, J=7.5, 1.5 Hz, 9H).

Intermediate 2C: (R)-ethyl 2-((2-chloro-5-((2-fluoro-3-hydroxy-3-methylbutyl) carbamoyl)pyridin-4-yl)amino)thiazole-5-carboxylate

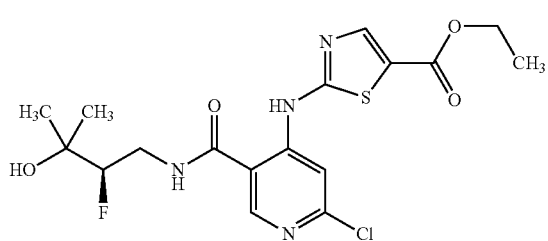

(2C)

To a solution of (R)-4,6-dichloro-N-(2-fluoro-3-hydroxy-3-methylbutyl) nicotinamide (1.1 g, 3.73 mmol) in DMF (15 mL) was added ethyl 2-aminothiazole-5-carboxylate (0.642 g, 3.73 mmol) and Cs$_2$CO$_3$ (2.429 g, 7.45 mmol) at room temperature. The reaction mixture was heated to 110° C. for 3 h. The reaction mixture was concentrated in vacuo and then extracted with EtOAc and water. The organic layer was separated and dried over anhydrous Na$_2$SO$_4$, filtered and concentrated in vacuo. The crude product was purified via column chromatography to afford (R)-ethyl 2-((2-chloro-5-((2-fluoro-3-hydroxy-3-methylbutyl) carbamoyl)pyridin-4-yl)amino)thiazole-5-carboxylate (1.0 g, 42% yield). LCMS m/z 431.3 (M+H).

Intermediate 2D: (R)-6-chloro-N-(2-fluoro-3-hydroxy-3-methylbutyl)-4-((5-(2-hydroxypropan-2-yl)thiazol-2-yl)amino)nicotinamide

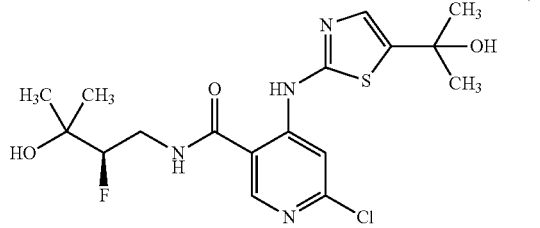

(2D)

To a solution of (R)-ethyl 2-((2-chloro-5-((2-fluoro-3-hydroxy-3-methylbutyl) carbamoyl)pyridin-4-yl)amino)thiazole-5-carboxylate (0.430 g, 0.998 mmol) in THF (15 mL) was added dropwise methyl magnesium chloride (3M in THF) (1.996 mL, 5.99 mmol) at 0° C. The reaction mixture was stirred at 25° C. for 2 h. The reaction mixture was quenched with an aqueous NH$_4$Cl solution at 0° C. and extracted with EtOAc. The combined organic layers were washed with water (50 mL), brine solution (50 mL), dried over anhydrous Na$_2$SO$_4$, filtered and concentrated in vacuo. The mixture was purified via column chromatography to give (R)-6-chloro-N-(2-fluoro-3-hydroxy-3-methylbutyl)-4-((5-(2-hydroxypropan-2-yl)thiazol-2-yl)amino)nicotinamide (0.17 g, 37% yield). LCMS m/z 417.3 (M+H).

Example 2

To a solution of (R)-6-chloro-N-(2-fluoro-3-hydroxy-3-methylbutyl)-4-((5-(2-hydroxypropan-2-yl)thiazol-2-yl)amino)nicotinamide (0.07 g, 0.168 mmol) in 1,4-dioxane (4 mL) was added 0.2 mL water followed by 6-chloro-3-(4,4,5,5-tetramethyl-1,3,2-dioxaborolan-2-yl)pyrazolo[1,5-a]pyrimidine (0.070 g, 0.252 mmol) and potassium acetate (0.049 g, 0.504 mmol). The reaction mixture was degassed for 10 min then tetrakis(triphenylphosphine)palladium(0) (0.039 g, 0.034 mmol) was added and the reaction mixture degassed for another 15 min. The reaction tube was sealed and heated to 100° C. for 1 h in a microwave. The reaction mixture was filtered through a bed of celite and washed with dioxane. The filtrate was concentrated in vacuo. The crude compound was purified by preparative HPLC to get (R)-6-(6-chloropyrazolo[1,5-a]pyrimidin-3-yl)-N-(2-fluoro-3-hydroxy-3-methylbutyl)-4-((5-(2-hydroxypropan-2-yl) thiazol-2-yl)amino)nicotinamide as an off-white solid. LCMS m/z 534.1 (M+H); $^1$H NMR (400 MHz, DMSO-d$_6$) δ 11.89 (br. s., 1H), 9.68 (s, 1H), 9.24 (br. s., 1H), 8.93-8.72 (m, 3H), 7.20 (br. s., 1H), 5.51 (br. s., 1H), 4.87 (br. s., 1H), 4.51-4.28 (m, 1H), 3.93-3.70 (m, 1H), 3.54-3.37 (m, 1H), 1.63-1.47 (m, 6H), 1.26-1.12 (m, 6H); HPLC rt 5.94 min, conditions A.

Examples 3 (Isomer 1) & Example 4 (Isomer 2)

6-(6-chloropyrazolo[1,5-a]pyrimidin-3-yl)-N—((R)-2-fluoro-3-hydroxy-3-methylbutyl)-4-((tetrahydro-2H-pyran-3-yl)amino)nicotinamide Isomer 1

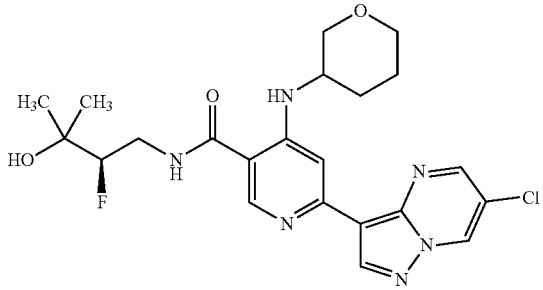

Isomer 2

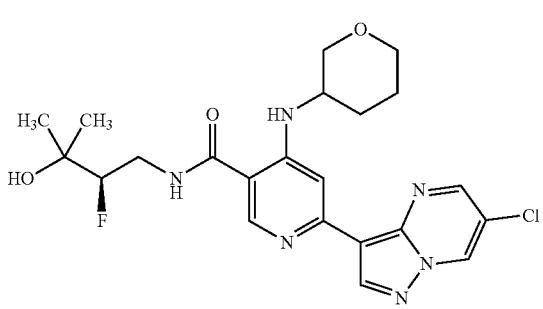

Intermediate 3A: 6-chloro-N—((R)-2-fluoro-3-hydroxy-3-methylbutyl)-4-((tetrahydro-2H-pyran-3-yl)amino)nicotinamide

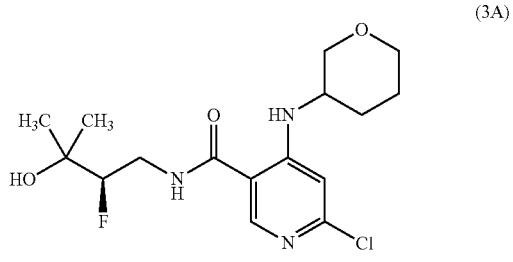 [SMILES: CC(C)(O)[C@H](F)CNC(=O)c1cnc(Cl)cc1NC1CCCOC1]

(3A)

To a stirred solution of 6-chloro-4-((tetrahydro-2H-pyran-3-yl)amino)nicotinic acid (0.5 g, 1.948 mmol) in DMF (10 mL) was added DIPEA (1.021 mL, 5.84 mmol) and HATU (1.111 g, 2.92 mmol) at 0° C. The reaction mixture was stirred for 10 min. (R)-4-amino-3-fluoro-2-methylbutan-2-ol (0.236 g, 1.948 mmol) was added to the reaction mixture and stirred for 3 h at 25° C. The solvent was evaporated under reduced pressure and the residue was extracted with ethyl acetate. The combined organic extracts were washed with water and 10% NaHCO$_3$ solution, dried over anhydrous Na$_2$SO$_4$, filtered and concentrated in vacuo. The crude compound was purified using column chromatography to afford 6-chloro-N—((R)-2-fluoro-3-hydroxy-3-methylbutyl)-4-((tetrahydro-2H-pyran-3-yl)amino)nicotinamide as an off-white solid (0.57 g, 81%). LCMS m/z 360.3 (M+H).

Examples 3 and 4

To a solution of 6-chloro-N—((R)-2-fluoro-3-hydroxy-3-methylbutyl)-4-((tetrahydro-2H-pyran-3-yl)amino)nicotinamide (0.1 g, 0.278 mmol) in 1,4-dioxane (4 mL) was added 0.2 mL water followed by 6-chloro-3-(4,4,5,5-tetramethyl-1,3,2-dioxaborolan-2-yl)pyrazolo[1,5-a]pyrimidine (0.117 g, 0.417 mmol) and potassium acetate (0.082 g, 0.834 mmol) at room temperature. The reaction mixture was degassed for 5 min and then tetrakis(triphenylphosphine)palladium(0) (0.064 g, 0.056 mmol) was added. The resulting solution was degassed for another 10 min. The reaction tube was sealed and heated to 100° C. for 1 h in a microwave. The reaction mixture was filtered through a bed of celite and washed with dioxane. The filtrate was concentrated under reduced pressure to afford the desired products as a mixture of diastereomers. The diastereomers were separated by SFC.

Example 3 (Isomer 1) LCMS m/z 477.2 (M+H); $^1$H NMR (400 MHz, DMSO-d$_6$) δ 9.68-9.64 (m, 1H), 8.85-8.79 (m, 2H), 8.73-8.63 (m, 3H), 7.74 (s, 1H), 4.84 (s, 1H), 4.46-4.28 (m, 1H), 3.91-3.73 (m, 1H), 3.71-3.54 (m, 2H), 3.47-3.36 (m, 1H), 2.01 (dd, J=8.8, 4.3 Hz, 1H), 1.79-1.54 (m, 3H), 1.18 (dd, J=5.8, 1.3 Hz, 6H); HPLC rt 7.17 min, conditions B.

Example 4 (Isomer 2) LCMS m/z 477.2 (M+H); $^1$H NMR (400 MHz, DMSO-d$_6$) δ 9.67 (d, J=2.5 Hz, 1H), 8.84-8.79 (m, 2H), 8.76-8.65 (m, 3H), 7.74 (s, 1H), 4.86 (br. s., 1H), 4.46-4.27 (m, 1H), 3.91-3.72 (m, 2H), 3.72-3.53 (m, 4H), 3.47-3.36 (m, 2H), 2.00 (dd, J=8.8, 4.3 Hz, 1H), 1.78-1.53 (m, 3H), 1.18 (dd, J=6.0, 1.0 Hz, 6H); HPLC rt 5.55 min, conditions A.

Example 5

(R)-6-(6-chloropyrazolo[1,5-a]pyrimidin-3-yl)-N-(2-fluoro-3-hydroxy-3-methylbutyl)-4-(oxetan-3-ylamino)nicotinamide

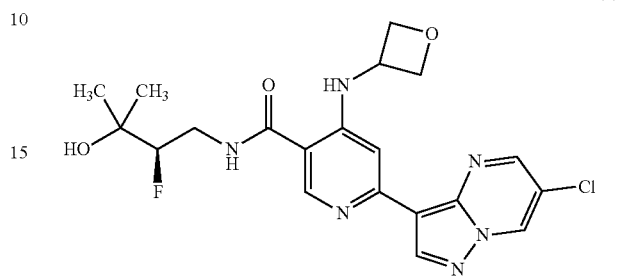

(5)

Intermediate 5A: ethyl 6-chloro-4-(oxetan-3-ylamino)nicotinate

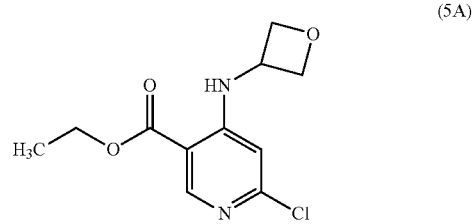 [SMILES: CCOC(=O)c1cnc(Cl)cc1NC1COC1]

(5A)

Ethyl 4,6-dichloronicotinate (3.91 g, 17.79 mmol) was transferred to a seal tube and DMA (10 mL), oxetan-3-amine (1.3 g, 17.79 mmol) and DIPEA (12.43 mL, 71.1 mmol) were added. The reaction mixture was stirred for 16 hrs at 25° C. The reaction mixture was extracted with ethyl acetate (50 mL), washed with water (100 mL) and the organic layer was dried over anhydrous Na$_2$SO$_4$, filtered and concentrated in vacuo. The residue was purified via column chromatography (15% EtOAc:pet ether) to afford ethyl 6-chloro-4-(oxetan-3-ylamino)nicotinate (2.4 g, 44% yield) as a colorless liquid. $^1$H NMR (400 MHz, DMSO-d$_6$) δ 8.56-8.60 (m, 1H) 8.45 (d, J=5.52 Hz, 1H) 6.63 (s, 1H) 4.87-4.93 (m, 2H) 4.77-4.87 (m, 1H) 4.46-4.52 (m, 2H) 4.34 (q, J=7.03 Hz, 2H) 1.30-1.37 (m, 3H).

Intermediate 5B: 6-chloro-4-(oxetan-3-ylamino)nicotinic acid

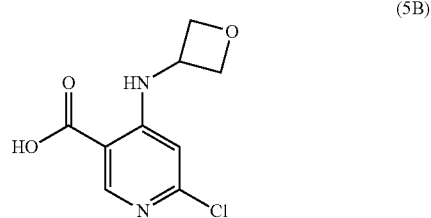 [SMILES: O=C(O)c1cnc(Cl)cc1NC1COC1]

(5B)

To a stirred solution of ethyl 6-chloro-4-(oxetan-3-ylamino)nicotinate (2.35 g, 9.16 mmol) in a mixture of THF (10 mL), ethanol (4 mL) and water (4 mL) was added LiOH (0.658 g, 27.5 mmol). The reaction mixture was stirred for 2 h at room temperature and concentrated in vacuo. The resulting residue was dissolved in water (5 mL) and acidified to pH 4 using saturated aqueous citric acid solution. The resulting solids were filtered, washed with water (2×30 mL), and dried to afford 6-chloro-4-(oxetan-3-ylamino)nicotinic acid (1.9 g, 79% yield) as an off-white solid. $^1$H NMR (400 MHz, DMSO-$d_6$) δ 8.92 (br. s., 1H) 8.53 (s, 1H) 6.56 (s, 1H) 4.87-4.93 (m, 2H) 4.75-4.84 (m, 1H) 4.43-4.49 (m, 2H).

Intermediate 5C: (R)-6-chloro-N-(2-fluoro-3-hydroxy-3-methylbutyl)-4-(oxetan-3-ylamino)nicotinamide

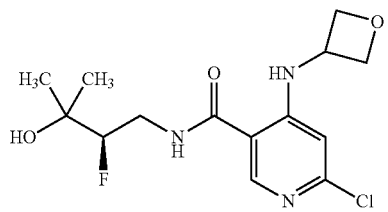

(5C)

To a stirred solution of 6-chloro-4-(oxetan-3-ylamino) nicotinic acid (0.6 g, 2.62 mmol) in DMF (10 mL) at 0° C. was added DIPEA (2.292 mL, 13.12 mmol), HATU (1.996 g, 5.25 mmol) and (R)-4-amino-3-fluoro-2-methylbutan-2-ol (0.318 g, 2.62 mmol). The reaction mixture was stirred for 16 hrs at 25° C. The reaction mixture was diluted with ethyl acetate, washed with water and brine. The organic extract was dried over anhydrous $Na_2SO_4$, filtered and concentrated in vacuo. The crude product was purified via column chromatography (3.5% MeOH:chloroform) to afford (R)-6-chloro-N-(2-fluoro-3-hydroxy-3-methylbutyl)-4-(oxetan-3-ylamino)nicotinamide (0.6 g, 65% yield) as an off-white solid. LCMS m/z 332 (M+H); $^1$H NMR (400 MHz, DMSO-$d_6$) δ 8.91 (d, J=6.53 Hz, 1H) 8.83 (t, J=5.52 Hz, 1H) 8.43 (s, 1H) 6.52 (s, 1H) 4.86-4.92 (m, 2H) 4.83 (s, 1H) 4.71-4.77 (m, 1H) 4.27-4.46 (m, 3H) 3.63-3.79 (m, 1H) 3.34-3.45 (m, 1H) 1.17 (dd, J=5.52, 1.51 Hz, 6H).

Example 5

(R)-6-Chloro-N-(2-fluoro-3-hydroxy-3-methylbutyl)-4-(oxetan-3-ylamino) nicotinamide (0.07 g, 0.211 mmol) was dissolved in 1,4-dioxane (4 mL) and 0.2 mL water. 6-Chloro-3-(4,4,5,5-tetramethyl-1,3,2-dioxaborolan-2-yl)pyrazolo[1,5-a]pyrimidine (0.088 g, 0.316 mmol) was added and the mixture was degassed for 10 min followed by the addition of potassium acetate (0.062 g, 0.633 mmol) and palladium tetrakis (0.049 g, 0.042 mmol). The reaction mixture was degassed for an additional 15 min and heated to 100° C. for 2 hours in a microwave. The reaction mixture was filtered through celite, washed with 10% MeOH\DCM (100 mL) and the filtrate was concentrated in vacuo. The crude product was purified via column chromatography (3.5% MeOH:chloroform) to afford (R)-6-(6-chloropyrazolo[1,5-a]pyrimidin-3-yl)-N-(2-fluoro-3-hydroxy-3-methylbutyl)-4-(oxetan-3-ylamino)nicotinamide (0.0046 g, 5% yield) as a pale yellow solid. LCMS m/z 449.2 (M+H); $^1$H NMR (400 MHz, DMSO-$d_6$) δ 9.68 (d, J=2.01 Hz, 1H) 8.88 (d, J=2.01 Hz, 1H) 8.79-8.82 (m, 2H) 8.74 (t, J=5.52 Hz, 1H) 8.70 (s, 1H) 7.44 (s, 1H) 4.99 (t, J=6.78 Hz, 2H) 4.84 (s, 1H) 4.70-4.77 (m, 1H) 4.53 (t, J=6.53 Hz, 2H) 4.30-4.47 (m, 1H) 3.66-3.82 (m, 1H) 3.36-3.48 (m, 1H) 1.16-1.21 (m, 6H); HPLC rt 5.58 min, conditions B.

Example 6

N-(2-(4-hydroxytetrahydro-2H-pyran-4-yl)ethyl)-4-(isopropylamino)-6-(pyrazolo[1,5-a]pyrimidin-3-yl)nicotinamide

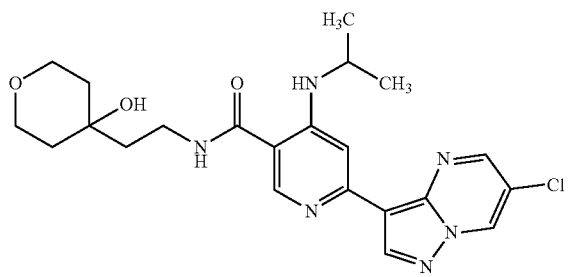

(6)

Intermediate 6A:
1,6-dioxaspiro[2.5]octane-2-carbonitrile

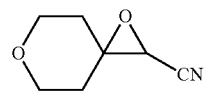

(6A)

To a mixture of dihydro-2H-pyran-4(3H)-one (2.5 g, 25 mmol) and 2-chloroacetonitrile (1.89 g, 25 mmol) was added a solution of potassium tert-butoxide in tert-butanol (1.0 M, 25 mL) dropwise. The reaction mixture was stirred overnight and quenched with water (50 mL). The mixture was extracted with ethyl acetate (100 mL). The organic layer was washed with water and brine, then dried over magnesium sulfate, filtered and concentrated in vacuo. The crude product was purified via column chromatography (10-60% ethyl acetate/pet ether) to afford 1,6-dioxaspiro[2.5]octane-2-carbonitrile (2.9 g, 83% yield) as a yellow oil. $^1$H NMR (400 MHz, CDCl$_3$) δ 3.95-3.80 (m, 4H), 3.35 (s, 1H), 2.18-2.01 (m, 1H), 1.96-1.76 (m, 2H), 1.67-1.50 (m, 1H).

Intermediate 6B:
4-(2-aminoethyl)tetrahydro-2H-pyran-4-ol

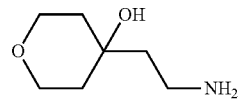

(6B)

A mixture of 1,6-dioxaspiro[2.5]octane-2-carbonitrile (3.0 g, 22 mmol) and 10% Pd on C (0.3 g) in methanol (40 mL) was stirred for 2 h under a balloon of hydrogen. The mixture was filtered through a pad of celite and the filtrate was concentrated in vacuo. The residue was dissolved in THF (50 mL). The solution was added dropwise to a mixture of lithium aluminum hydride (1.6 g, 43 mmol) and THF (100 mL) and the mixture was stirred for 2 h at reflux temperature. After cooling to 0° C., Na$_2$SO$_4$-10H$_2$O (16 g) and KF (2.5 g) were added and the mixture was stirred overnight. After filtration, the filtrate was concentrated in vacuo, and the residue was acidified with 4N HCl in 1,4-dioxane. The mixture was concentrated in vacuo and the residue was crystallized from ethanol-ether. The precipitate was filtered to afford 4-(2-aminoethyl)tetrahydro-2H-pyran-4-ol (2.1 g, 67% yield) as the HCl salt. $^1$H NMR (400 MHz, CDCl$_3$) δ 3.94-3.65 (m, 6H), 2.57 (s, 2H), 1.95-1.51 (m, 6H).

Intermediate 6C: 6-chloro-N-(2-(4-hydroxytetrahydro-2H-pyran-4-yl)ethyl)-4-(isopropylamino)nicotinamide

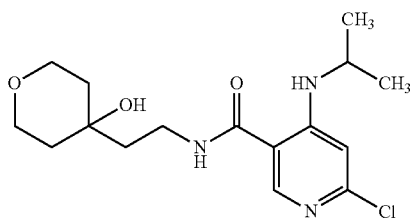

(6C)

To a solution of 6-chloro-4-(isopropylamino)nicotinic acid (0.1 g, 0.47 mmol) in DMF (1 mL) was added HOBt (0.7 g, 0.51 mmol) and EDC (0.1 g, 0.51 mmol). The mixture was stirred at room temperature for 0.5 h. To this mixture was then added 4-(2-aminoethyl)tetrahydro-2H-pyran-4-ol hydrochloride (0.09 g, 0.49 mmol) and DIPEA (0.17 mL, 0.978 mmol). The mixture was stirred for 2 h then quenched with water, stirred, and filtered to give 6-chloro-N-(2-(4-hydroxytetrahydro-2H-pyran-4-yl)ethyl)-4-(isopropylamino)nicotinamide (67 mg, 42% yield) as an off-white solid, which was used without purification.

Example 6

To a solution of 6-chloro-N-(2-(4-hydroxytetrahydro-2H-pyran-4-yl)ethyl)-4-(isopropylamino)nicotinamide (10 mg, 0.03 mmol) in 1,4-dioxane (1 mL) was added 6-chloro-3-(4,4,5,5-tetramethyl-1,3,2-dioxaborolan-2-yl)pyrazolo[1,5-a]pyrimidine (9.0 mg, 0.032 mmol), 2M aqueous solution of K$_3$PO$_4$ (0.044 mL, 0.088 mmol) and PdCl$_2$(dppf) (2.14 mg, 2.9 μmol). The mixture was purged with nitrogen, sealed and heated to 120° C. for 4 h. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10 mM ammonium acetate; Gradient: 5-55% B over 25 minutes, then a 5-minute hold at 55% B; Flow: 20 mL/min. Fractions containing the desired product were combined and dried via centrifugal evaporation. This procedure afforded N-(2-(4-hydroxytetrahydro-2H-pyran-4-yl)ethyl)-4-(isopropylamino)-6-(pyrazolo[1,5-a]pyrimidin-3-yl)nicotinamide (0.6 mg, 4.5% yield) as a TFA salt. LCMS m/z 460.2 (M+H)+; $^1$H NMR (500 MHz, DMSO-d$_6$) δ 9.65 (d, J=2.0 Hz, 1H), 8.88-8.75 (m, 2H), 8.56 (s, 1H), 8.44 (d, J=6.4 Hz, 2H), 7.72 (s, 1H), 4.23-4.21 (m, 1H), 3.76 (m, 4H), 3.69-3.61 (m, 2H), 3.44-3.27 (m, 1H), 1.72-1.62 (m, 2H), 1.60-1.41 (m, 4H), 1.33-1.18 (m, 6H); HPLC rt 1.57 min, conditions F.

Example 7

(R)-6-(6-chloropyrazolo[1,5-a]pyrimidin-3-yl)-N-(2-fluoro-3-hydroxy-3-methylbutyl)-4-((1-hydroxy-2-methylpropan-2-yl)amino)nicotinamide

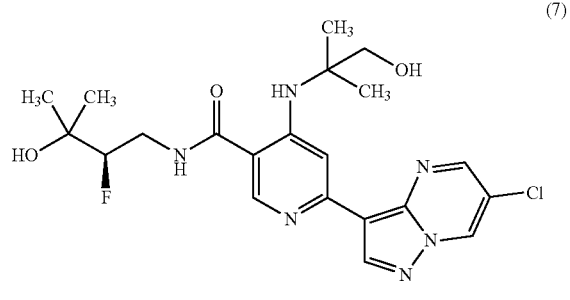 [SMILES: CC(C)(CO)Nc1cc(-c2cnn3cc(Cl)cnc23)ncc1C(=O)NC[C@@H](F)C(C)(C)O]

(7)

Intermediate 7A: ethyl 6-chloro-4-((1-hydroxy-2-methylpropan-2-yl)amino)nicotinate

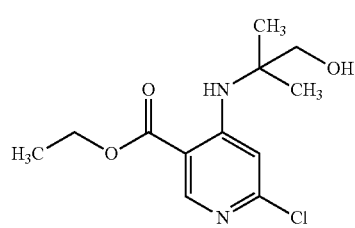

(7A)

To a stirred solution of ethyl 4,6-dichloronicotinate (2.5 g, 11.36 mmol) in DMA (12.5 mL) was added DIPEA (5.95 mL, 34.1 mmol) and the mixture was stirred at room temperature for 5 min. 2-Amino-2-methylpropan-1-ol (1.114 g, 12.50 mmol) was added and the mixture was stirred for 16 h at 25° C. followed by 16 h at 85° C. The reaction mixture was quenched by the addition of water and extracted with EtOAc (3×50 mL). The combined organic extracts were washed with water (100 mL) followed by brine solution, dried over Na$_2$SO$_4$, filtered and concentrated in vacuo. The crude product was purified via column chromatography (50% EtOAc/pet ether) to afford ethyl 6-chloro-4-((1-hydroxy-2-methylpropan-2-yl)amino)nicotinate (2.1 g, 68% yield). LCMS m/z 273.1 (M+H); $^1$H NMR (400 MHz, DMSO-d$_6$) δ 8.61 (s, 1H), 8.56 (s, 1H), 6.88 (s, 1H), 5.27 (t, J=5.3 Hz, 1H), 4.29 (q, J=7.2 Hz, 2H), 3.43 (d, J=5.0 Hz, 2H), 1.37-1.25 (m, 9H).

Intermediate 7B: 6-chloro-4-((1-hydroxy-2-methyl-propan-2-yl)amino)nicotinic acid

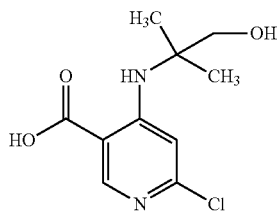

(7B)

To a stirred solution of ethyl 6-chloro-4-((1-hydroxy-2-methylpropan-2-yl)amino) nicotinate (600 mg, 2.200 mmol) in ethanol (12 mL) and water (6 mL) was added LiOH (79 mg, 3.30 mmol) and the mixture was stirred at room temperature for 3 h. The reaction mixture was concentrated in vacuo. The crude residue was dissolved in water (5 mL), acidified with 1.5 N HCl (pH 5) and stirred at room temperature for 10 min. The solid obtained was filtered, washed with water and dried in vacuo to afford 6-chloro-4-((1-hydroxy-2-methylpropan-2-yl)amino)nicotinic acid (450 mg, 83%) as an off-white solid. LCMS m/z 245 (M+H); $^1$H NMR (400 MHz, DMSO-$d_6$) δ 13.66-12.92 (m, 1H), 8.78 (s, 1H), 8.52 (s, 1H), 6.85 (s, 1H), 5.35-5.05 (m, 1H), 3.43 (s, 2H), 1.42-1.17 (m, 6H).

Intermediate 7C: (R)-6-chloro-N-(2-fluoro-3-hydroxy-3-methylbutyl)-4-((1-hydroxy-2-methylpropan-2-yl)amino)nicotinamide

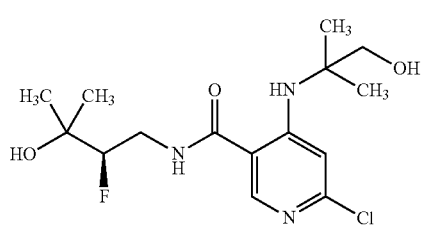

(7C)

To a stirred solution of 6-chloro-4-((1-hydroxy-2-methylpropan-2-yl)amino) nicotinic acid (500 mg, 2.044 mmol) in DMF (10 mL) was added DIPEA (1.785 ml, 10.22 mmol) and HATU (1554 mg, 4.09 mmol). The reaction mixture was stirred at room temperature for 5 min. (R)-4-Amino-3-fluoro-2-methylbutan-2-ol (272 mg, 2.248 mmol) in DMF (1 ml) was added and the reaction mixture was stirred at room temperature for 3 h. The reaction mixture was quenched by the addition of water and extracted with EtOAc (2×10 mL). The combined organic extracts were washed with saturated NaHCO$_3$ solution and water followed by brine solution, dried over Na$_2$SO$_4$ and concentrated in vacuo. The crude mixture was purified via column chromatography (60% EtOAc/pet ether) to provide (R)-6-chloro-N-(2-fluoro-3-hydroxy-3-methylbutyl)-4-((1-hydroxy-2-methylpropan-2-yl)amino)nicotinamide (300 mg, 38%) as an off-white solid. LCMS m/z 348.1 (M+H); $^1$H NMR (400 MHz, DMSO-$d_6$) δ 8.85 (s, 1H), 8.72 (t, J=5.5 Hz, 1H), 8.33 (s, 1H), 6.77 (s, 1H), 5.17 (t, J=5.3 Hz, 1H), 4.84 (s, 1H), 4.44-4.21 (m, 1H), 3.76-3.56 (m, 1H), 3.45-3.37 (m, 3H), 1.35-1.25 (m, 6H), 1.19-1.11 (m, 6H).

Example 7

To a stirred solution of (R)-6-chloro-N-(2-fluoro-3-hydroxy-3-methylbutyl)-4-((1-hydroxy-2-methylpropan-2-yl)amino)nicotinamide (50 mg, 0.144 mmol) and 6-chloro-3-(4,4,5,5-tetramethyl-1,3,2-dioxaborolan-2-yl)pyrazolo[1,5-a]pyrimidine (60.3 mg, 0.216 mmol) in 1,4-dioxane (10 mL)/water (0.5 mL) mixture was added potassium acetate (42.3 mg, 0.431 mmol). The mixture was degassed with nitrogen for 5 min and Pd(PPh$_3$)$_4$ (33.2 mg, 0.029 mmol) was added. The mixture was degassed for another 10 min and then heated to 100° C. for 2 h in a microwave. The reaction mixture was then cooled to 25° C. and concentrated in vacuo. The crude residue was dissolved in 10% MeOH/CHCl$_3$ and filtered through celite. The filtrate was concentrated in vacuo. The crude material was purified via preparative LC/MS with the following conditions: Waters Xbridge C18, 19×150 mm, 5 μm; Guard Column: Waters XBridge C18, 19×10 mm, 5 μm; Mobile Phase A: 5:95 Acetonitrile:water with 10 mM NH$_4$OAc; Mobile Phase B: 95:5 Acetonitrile:water with 10 mM NH$_4$OAc; Gradient: 5-35% B over 25 minutes, followed by a 10 minute hold at 35% B and 5 minute hold at 100% B; Flow: 15 ml/min. Fractions containing the desired product were combined and dried using a Genevac centrifugal evaporator. This procedure afforded (R)-6-(6-chloropyrazolo[1,5-a]pyrimidin-3-yl)-N-(2-fluoro-3-hydroxy-3-methylbutyl)-4-((1-hydroxy-2-methylpropan-2-yl)amino) nicotinamide (13.7 mg, 19% yield) as pale yellow solid. LCMS m/z 465.1 (M+H); $^1$H NMR (400 MHz, DMSO-$d_6$) δ 9.68 (d, J=2.0 Hz, 1H), 8.87-8.77 (m, 3H), 8.64-8.54 (m, 2H), 8.05 (s, 1H), 5.12 (t, J=5.0 Hz, 1H), 4.84 (s, 1H), 4.49-4.25 (m, 1H), 3.73 (br. s., 1H), 3.50 (d, J=5.0 Hz, 2H), 3.45-3.36 (m, 1H), 1.42 (s, 6H), 1.18 (dd, J=5.8, 1.3 Hz, 6H); HPLC rt 1.17 min, conditions C.

Examples 8 and 9

6-(6-chloropyrazolo[1,5-a]pyrimidin-3-yl)-N-(2-fluoro-2-(3-hydroxyoxetan-3-yl)ethyl)-4-(isopropylamino)nicotinamide & 6-(6-chloropyrazolo[1,5-a]pyrimidin-3-yl)-N-(2-fluoro-3,4-dihydroxy-3-(hydroxymethyl)butyl)-4-(isopropylamino)nicotinamide

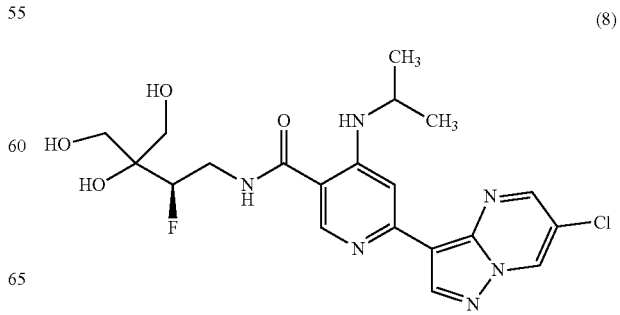

(8)

-continued

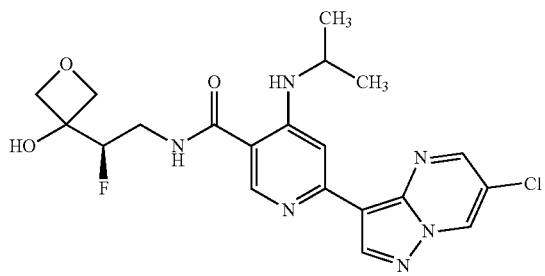

(9)

Intermediate 8A: 3-Vinyloxetan-3-ol

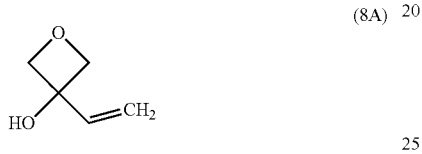

(8A)

In a dry flask, under a nitrogen atmosphere, a stirring solution of oxetan-3-one (2.1 g, 29.1 mmol) in anhydrous THF (100 mL) was cooled to 0° C. and treated dropwise with vinylmagnesium bromide (1M in THF) (50 mL, 50.0 mmol) at a rate which maintained an internal temperature below 10° C. The reaction mixture was stirred for 10 minutes, then allowed to warm to room temperature and stirred for 2 hours. The reaction mixture was poured into a solution of saturated ammonium chloride (200 mL). The mixture was stirred at room temperature for 5 minutes, the layers were separated, and the aqueous phase was extracted 4× with diethyl ether (75 mL). The combined organic phases were dried over sodium sulfate, filtered and concentrated in vacuo to afford 3-vinyloxetan-3-ol (2.66 g, 91% yield) as a pale yellow oil, which was used as is in the next step. $^1$H NMR (400 MHz, chloroform-d) δ 6.31 (dd, J=17.4, 10.8 Hz, 1H), 5.44 (dd, J=17.4, 0.7 Hz, 1H), 5.29 (dd, J=10.8, 0.7 Hz, 1H), 4.70 (q, J=7.0 Hz, 4H), 2.31 (s, 1H).

Intermediate 8B: 3-(benzyloxy)-3-vinyloxetane

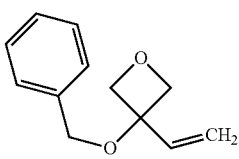

(8B)

A stirring solution of 3-vinyloxetan-3-ol (1.0 g, 9.99 mmol) in anhydrous THF (50 mL) was cooled to 5° C. and treated with sodium hydroxide (60% in mineral oil) (0.799 g, 19.98 mmol). The mixture was stirred at 5° C. for 1 hour, then treated with benzyl bromide (2.495 mL, 20.98 mmol) and tetrabutyl ammonium iodide (0.369 g, 0.999 mmol). The reaction mixture was allowed to slowly come to room temperature, and was stirred for 18 hours, at which point it was judged to be complete by TLC (3:1 hexanes/ethyl acetate; UV/KMnO$_4$). About half of the THF was evaporated via rotary evaporator, and the remaining solution was poured into saturated ammonium chloride. The turbid mixture was extracted three times with diethyl ether, then the combined ether phases were washed with brine, dried over sodium sulfate, filtered and concentrated in vacuo. The residue was chromatographed via MPLC over an 80 g silica gel column, eluting at 60 mL/min with 5% to 25% acetone/hexanes over 10 column volumes. Fractions containing the desired product were pooled and concentrated in vacuo to yield 3-(benzyloxy)-3-vinyloxetane (1.58 g, 83% yield). $^1$H NMR (400 MHz, chloroform-d) δ 7.45-7.29 (m, 5H), 6.14 (dd, J=17.6, 10.8 Hz, 1H), 5.54 (dd, J=17.6, 0.7 Hz, 1H), 5.49 (dd, J=10.9, 0.8 Hz, 1H), 4.81 (d, J=7.0 Hz, 2H), 4.65 (d, J=7.3 Hz, 2H), 4.42 (s, 2H).

Intermediate 8C:
3-(benzyloxy)-3-(oxiran-2-yl)oxetane

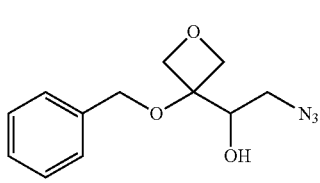

(8C)

A stirring solution of 3-(benzyloxy)-3-vinyloxetane (3.13 g, 16.45 mmol) in dichloromethane (50 mL) was cooled to 5° C. and treated with mCPBA (8.11 g, 36.2 mmol). The reaction mixture was allowed to slowly come to room temperature, heated at reflux for 1 hour, then cooled to room temperature and stirred for 42 hours, at which point it was judged to be complete by LCMS. The mixture was cooled to 5° C. and treated with half-saturated sodium bisulfite (150 mL). The mixture was allowed to come to room temperature and stirred for 30 minutes, then most of the DCM was evaporated via rotary evaporator. The resulting heterogeneous mixture was extracted 3× with ethyl acetate (30 mL), then the combined organic phases were washed 3× with a solution of saturated sodium bicarbonate and once with brine, then dried over sodium sulfate, filtered and concentrated in-vacuo to yield 3-(benzyloxy)-3-(oxiran-2-yl)oxetane (3.32 g, 98% yield). $^1$H NMR (400 MHz, chloroform-d) δ 7.45-7.30 (m, 5H), 4.75 (d, J=6.6 Hz, 1H), 4.68 (d, J=6.6 Hz, 1H), 4.66 (d, J=2.4 Hz, 1H), 4.60-4.54 (m, 1H), 4.48 (d, J=6.6 Hz, 1H), 4.40 (d, J=7.3 Hz, 1H), 3.35 (dd, J=3.6, 2.8 Hz, 1H), 3.00-2.95 (m, 1H), 2.94-2.90 (m, 1H).

Intermediate 8D:
2-azido-1-(3-(benzyloxy)oxetan-3-yl)ethanol (8D)

A mixture of 3-(benzyloxy)-3-(oxiran-2-yl)oxetane (3.7 g, 17.94 mmol) and sodium azide (1.749 g, 26.9 mmol) in acetone/water (1:1) (40 mL) was stirred at room temperature for 60 hours. Most of the acetone was evaporated, and the remainder of the reaction mixture was treated with saturated ammonium chloride (20 mL). The turbid solution was extracted three times with dichloromethane (30 mL), and the combined aqueous phases were washed once with water and once with brine, then dried over sodium sulfate, filtered and concentrated in vacuo. The residue was chromatographed via MPLC over a 40 g silica gel column, eluting at 40 mL/min with a 5% to 50% methylene chloride/hexanes gradient over 12 column volumes. Fractions containing the desired product were pooled and concentrated in vacuo to yield 2-azido-1-(3-(benzyloxy)oxetan-3-yl)ethanol (2.31 g, 52% yield) as an amber oil. $^1$H NMR (400 MHz, chloroform-d) δ 7.45-7.31 (m, 5H), 4.94-4.81 (m, 4H), 4.79 (d, J=7.7 Hz, 1H), 4.68-4.63 (m, 1H), 4.22-4.09 (m, 1H), 3.55-3.50 (m, 2H), 2.38 (d, J=6.6 Hz, 1H).

Intermediate 8E:
3-(2-azido-1-fluoroethyl)-3-(benzyloxy)oxetane

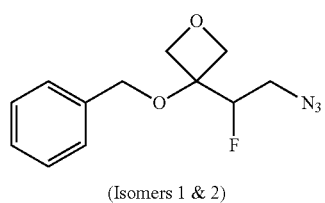

(8E)

(Isomers 1 & 2)

A stirring solution of 2-azido-1-(3-(benzyloxy)oxetan-3-yl)ethanol (1.2 g, 4.81 mmol) in anhydrous dichloromethane (30 mL) was cooled to −78° C. and treated with diethylaminosulfur trifluoride (1.209 mL, 9.15 mmol). The mixture was stirred at −78° C. for 2 hours, then allowed to come to room temperature and stirred for 42 hours. The reaction mixture was poured into stirring, ice-cold saturated sodium carbonate solution (200 mL), and the mixture was stirred for 30 minutes. The layers were separated, the aqueous phase was extracted twice with dichloromethane (50 mL), and the combined organic phases were dried over sodium sulfate, filtered and concentrated in vacuo. The residue was chromatographed via MPLC over a 80 g silica gel column, eluting at 60 mL/min with a 5% to 30% acetone/hexanes gradient over 10 column volumes. Fractions containing the product were pooled and concentrated in vacuo to yield 3-(2-azido-1-fluoroethyl)-3-(benzyloxy)oxetane (0.65 g, 54% yield) as a colorless oil. $^1$H NMR (400 MHz, CHLOROFORM-d) δ 7.46-7.31 (m, 5H), 5.04-4.82 (m, 5H), 4.81-4.74 (m, 1H), 4.63 (d, J=7.5 Hz, 1H), 3.70 (ddd, J=19.6, 13.6, 7.0 Hz, 1H), 3.58-3.43 (m, 1H). The enantiomers were resolved by supercritical fluid chromatography (SFC) using the following conditions: Instrument: Thar Preparative SFC-350; Column: Chiralpak AD (5×25 cm, 5 m); BPR pressure: 100 bars; Temperature: 30° C.; Flow rate: 270 mL/min; Mobile Phase: CO$_2$/MeOH (87/13); Detector Wavelength: 212 nm; Separation Program: Sequence injection; Injection: 0.90 mL with cycle time 3.25 min. The separation yielded: First-eluting isomer: 3-(2-azido-1-fluoroethyl)-3-(benzyloxy) oxetane, Isomer 1 (0.25 g, 77% yield); Second-eluting isomer: 3-(2-azido-1-fluoroethyl)-3-(benzyloxy)oxetane, Isomer 2 (0.19 g, 53% yield).

Intermediate 8F: tert-butyl (2-fluoro-2-(3-hydroxyoxetan-3-yl)ethyl)carbamate

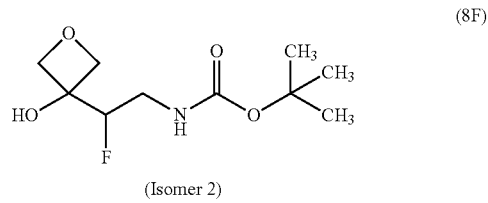 [SMILES: CC(C)(C)OC(=O)NCC(F)C1(O)COC1]

(8F)

(Isomer 2)

A Parr bottle was charged with 20% palladium hydroxide on carbon (100 mg, 0.142 mmol) under nitrogen, and the catalyst was wetted with methanol. The vessel was charged with a solution of 3-(2-azido-1-fluoroethyl)-3-(benzyloxy)oxetane, Isomer 2 (122 mg, 0.486 mmol) in methanol (5 mL) and BOC-anhydride (0.135 mL, 0.583 mmol), and the mixture was degassed by thrice evacuating the vessel under vacuum and repressurizing with nitrogen. The mixture was hydrogenated at 50 psi for 9 hours, at which point the reaction was judged to be complete by LCMS. The catalyst was removed by filtration and thoroughly rinsed with methanol. The combined filtrate and rinsings were concentrated in vacuo to yield tert-butyl (2-fluoro-2-(3-hydroxyoxetan-3-yl)ethyl) carbamate, Isomer 2 (135 mg) as a slightly yellow oil, which was used as is in the next step. $^1$H NMR (400 MHz, chloroform-d) δ 4.96 (bd, J=7.3 Hz, 1H), 4.89 (d, J=5.7 Hz, 1H), 4.76-4.67 (m, 2H), 4.66-4.48 (m, 3H), 3.77-3.58 (m, 1H), 3.45 (tdd, J=15.8, 6.2, 4.2 Hz, 1H), 1.47 (s, 9H).

Intermediate 8G:
3-(2-amino-1-fluoroethyl)oxetan-3-ol, TFA

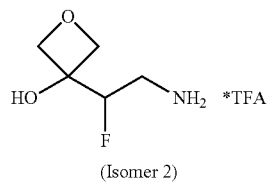

(Isomer 2)

A solution of tert-butyl (2-fluoro-2-(3-hydroxyoxetan-3-yl)ethyl)carbamate, Isomer 2 (0.6 g, 2.55 mmol) in anhydrous methylene chloride (3 mL) was cooled to 5° C. and treated with TFA (3 mL, 38.9 mmol). The reaction mixture was stirred at 5° C. for 1 hour, at which point it was judged to be complete by TLC. The mixture was concentrated in vacuo, and the residue was concentrated once from 1:1 DCM/toluene (10 mL), then twice from DCM (10 mL) to remove residual TFA. The residue was dried under vacuum for 3 hours to yield 3-(2-amino-1-fluoroethyl)oxetan-3-ol, isomer 2, TFA (0.66 g) as a colorless oil. $^1$H NMR (400 MHz, methanol-d$_4$) δ 5.11-4.94 (m, 1H), 4.75 (d, J=7.0 Hz, 1H), 4.66-4.58 (m, 3H), 3.30-3.23 (m, 1H).

Intermediate 8H: ethyl 6-(6-chloropyrazolo[1,5-a]pyrimidin-3-yl)-4-(isopropylamino)nicotinate

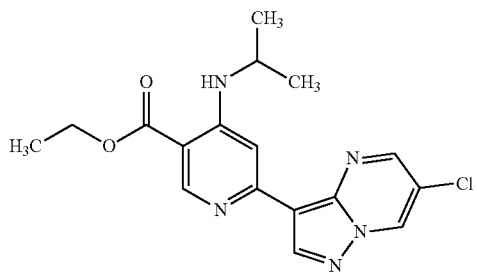

(8H)

In a heavy-walled glass vial, a mixture of ethyl 6-chloro-4-(isopropylamino) nicotinate (109 mg, 0.449 mmol), 6-chloro-3-(4,4,5,5-tetramethyl-1,3,2-dioxaborolan-2-yl) pyrazolo[1,5-a]pyrimidine (251 mg, 0.898 mmol), 2 M potassium phosphate (aq) (0.988 mL, 1.976 mmol) and dioxane (3 mL) was degassed with bubbling nitrogen for 10 minutes. $PdCl_2$(dppf) (32.9 mg, 0.045 mmol) was added, the mixture was degassed for another 5 minutes, and the vial was sealed. The reaction mixture was stirred at 120° C. for 3 hours, at which point it was judged to be complete by LCMS. Most of the dioxane was evaporated from the mixture, and the remainder was dissolved in ethyl acetate (100 mL). The mixture was filtered through glass-fiber filter paper, and the filtrate was washed 3× with saturated sodium bicarbonate, once with water and once with brine. The organic phase was dried over sodium sulfate and concentrated in vacuo. The residue was purified via column chromatography (1% to 10% methanol/methylene chloride gradient). This procedure afforded ethyl 6-(6-chloropyrazolo[1,5-a]pyrimidin-3-yl)-4-(isopropylamino)nicotinate (95 mg, 59% yield) as an amber solid. LCMS m/z 360.3 (M+H)+; $^1$H NMR (400 MHz, chloroform-d) δ 8.96 (s, 1H), 8.86 (s, 1H), 8.77 (d, J=2.4 Hz, 1H), 8.58 (d, J=2.4 Hz, 1H), 8.03 (d, J=6.8 Hz, 1H), 7.76 (s, 1H), 4.35 (q, J=7.2 Hz, 2H), 3.93 (dd, J=13.2, 6.4 Hz, 1H), 1.42-1.37 (m, 3H), 1.36 (d, J=6.4 Hz, 6H).

Intermediate 8I: Lithium 6-(6-chloropyrazolo[1,5-a]pyrimidin-3-yl)-4-(isopropylamino)nicotinate

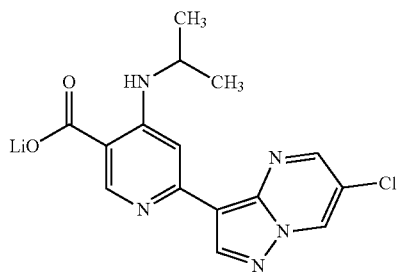

(8I)

A suspension of ethyl 6-(6-chloropyrazolo[1,5-a]pyrimidin-3-yl)-4-(isopropylamino)nicotinate (95 mg, 0.264 mmol) in methanol/THF/water (2:2:1) (5 mL) was treated with lithium hydroxide (14 mg, 0.585 mmol), and the mixture was stirred at 50° C. for 8 hours. The reaction was judged to be complete by LCMS. The reaction mixture was concentrated in vacuo, and the residue was concentrated twice from isopropanol to remove residual water to afford lithium 6-(6-chloropyrazolo[1,5-a]pyrimidin-3-yl)-4-(isopropylamino)nicotinate. This product was used as is in the next step. LCMS m/z 332.3 (M+H)+.

Examples 8 and 9

A stirring mixture of 3-(2-amino-1-fluoroethyl)oxetan-3-ol, isomer 2, TFA (26.9 mg, 0.108 mmol), lithium 6-(6-chloropyrazolo[1,5-a]pyrimidin-3-yl)-4-(isopropylamino) nicotinate (28 mg, 0.083 mmol) and triethylamine (0.046 mL, 0.332 mmol) in DMF (2 mL) was treated with BOP (55.0 mg, 0.124 mmol). The reaction mixture was stirred at room temperature for 18 hours, at which point it was judged to be complete by LCMS. Two products were detected. The reaction mixture was filtered and the products were isolated via HPLC using the following conditions.

Example 8

Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 25 minutes, then a 5-minute hold at 40% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 55% B; Flow: 20 mL/min. Fractions containing the desired product were combined and dried via centrifugal evaporation to yield 6-(6-chloropyrazolo[1,5-a]pyrimidin-3-yl)-N-(2-fluoro-3,4-dihydroxy-3-(hydroxymethyl)butyl)-4-(isopropylamino)nicotinamide (2.5 mg, 6% yield). LCMS m/z 467.3 (M+H)+; $^1$H NMR (500 MHz, DMSO-$d_6$) δ 9.66 (d, J=2.0 Hz, 1H), 8.85-8.79 (m, 2H), 8.66 (br. s., 1H), 8.62 (s, 1H), 8.49 (d, J=6.7 Hz, 1H), 7.74 (s, 1H), 4.79-4.62 (m, 2H), 3.88-3.29 (m, 4H), 1.27 (d, J=6.1 Hz, 6H); HPLC rt 1.21 min, conditions E.

Example 9

Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 25 minutes, then a 5-minute hold at 40% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 20 minutes, then a 5-minute hold at 100% B; Flow: 20 mL/min. Fractions containing the desired product were combined and dried via centrifugal evaporation to yield 6-(6-chloropyrazolo[1,5-a]pyrimidin-3-yl)-N-(2-fluoro-2-(3-hydroxyoxetan-3-yl)ethyl)-4-(isopropylamino)nicotinamide (4.9 mg, 13% yield). LCMS m/z 449.2 (M+H)+: $^1$H NMR (500 MHz, DMSO-d$_6$) δ 9.82 (s, 1H), 9.55-9.44 (m, 1H), 9.33-9.27 (m, 1H), 9.07 (s, 1H), 8.99 (s, 1H), 8.61 (s, 1H), 7.77 (s, 1H), 5.00-4.64 (m, 1H), 4.61 (d, J=6.7 Hz, 1H), 4.56-4.43 (m, 3H), 4.09-3.95 (m, 1H), 3.79-3.38 (m, 2H), 2.86-2.78 (m, 1H), 1.33 (d, J=6.1 Hz, 6H); HPLC rt 1.35 min, conditions E.

Example 10

(R)-6-(6-chloropyrazolo[1,5-a]pyrimidin-3-yl)-N-(1-(2-((2-fluoro-3-hydroxy-3-methylbutyl)amino)-2-oxoethyl)-1H-pyrazol-4-yl)-4-(isopropylamino)nicotinamide

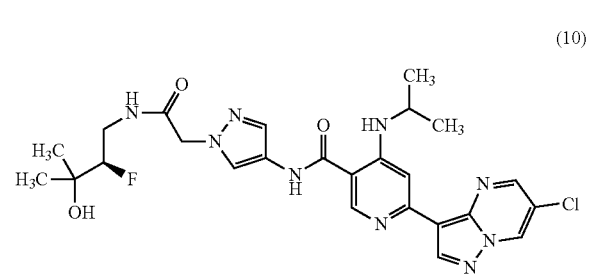 [SMILES: CC(C)Nc1cc(-c2cnn3cc(Cl)cnc23)ncc1C(=O)Nc1cnn(CC(=O)NC[C@@H](F)C(C)(C)O)c1]

(10)

Intermediate 10A: tert-butyl 2-(4-nitro-1H-pyrazol-1-yl)acetate

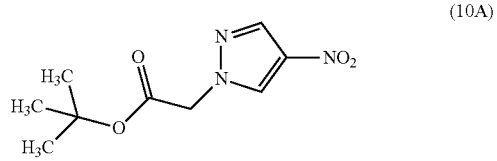 [SMILES: CC(C)(C)OC(=O)Cn1cc([N+](=O)[O-])cn1]

(10A)

To a stirred solution of KOH (9.9 g, 177 mmol) in water (75 mL) was added a solution of 4-nitro-1H-pyrazole (10 g, 88 mmol) in acetone (40 mL). The mixture was stirred at room temperature. A solution of tert-butyl 2-bromoacetate (17.3 g, 88 mmol) in acetone (40 mL) was added and the resulting mixture was stirred at room temperature for 12 h. The acetone was removed in vacuo and the aqueous phase was acidified to pH 4-5. The aqueous phase was extracted with EtOAc (2×50 mL). The combined organic extracts were washed with water, dried over Na$_2$SO$_4$ and concentrated in vacuo. The crude residue was purified by column chromatography (20% ethylacetate/pet ether) to afford tert-butyl 2-(4-nitro-1H-pyrazol-1-yl)acetate (13.8 g, 65% yield) as colorless crystals. $^1$H NMR (400 MHz, DMSO-d$_6$) δ 8.87 (s, 1H) 8.30 (s, 1H) 5.06 (s, 2H) 1.43 (s, 9H).

Intermediate 10B: tert-butyl 2-(4-amino-1H-pyrazol-1-yl)acetate

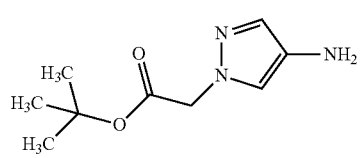

(10B)

To a solution of tert-butyl 2-(4-nitro-1H-pyrazol-1-yl)acetate (5 g, 22 mmol) in methanol (100 mL) was added Pd/C (1.2 g, 1.1 mmol) and the mixture was stirred at room temperature under an atmosphere of hydrogen (5 kg) for 2 h. The reaction mixture was filtered through celite and the filtrate was concentrated in vacuo to afford tert-butyl 2-(4-amino-1H-pyrazol-1-yl)acetate (4 g, 54% yield) which was used as is in the next reaction. LCMS m/z 198 (M+H).

Intermediate 10C: tert-butyl 2-(4-(6-chloro-4-(isopropylamino)nicotinamido)-1H-pyrazol-1-yl)acetate

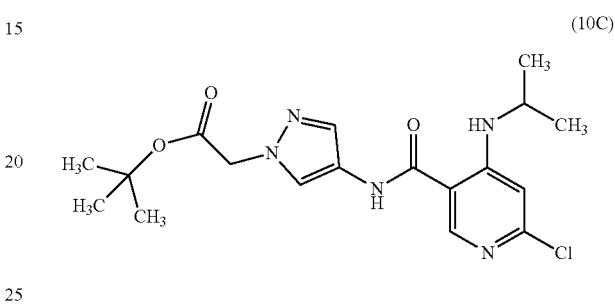

(10C)

A flask was charged with 6-chloro-4-(isopropylamino) nicotinic acid (2 g, 9.3 mmol), tert-butyl 2-(4-amino-1H-pyrazol-1-yl)acetate (1.8 g, 9.3 mmol) and DMF (50 mL). The reaction mixture was cooled to 0° C. To this mixture was added HATU (7.1 g, 18.6 mmol) and DIPEA (4.9 mL, 28 mmol). The reaction mixture was allowed to warm up to room temperature and was stirred for an additional 12 h. The reaction mixture was concentrated in vacuo. The residue obtained was extracted with EtOAc (50 mL). The organic extract was washed with 10% NaHCO$_3$, water, dried over Na$_2$SO$_4$, filtered and concentrated in vacuo. The crude product obtained was purified via column chromatography (10% EtOAc/Hexane) to afford tert-butyl 2-(4-(6-chloro-4-(isopropylamino)nicotinamido)-1H-pyrazol-1-yl)acetate (3.1 g, 80% yield) as an orange solid. $^1$H NMR (400 MHz, DMSO-d$_6$) 10.53 (s, 1H) 8.48 (s, 1H), 8.33-8.30 (m, 1H), 8.08 (s, 1H), 7.58 (s, 1H), 6.75 (s, 1H), 4.92 (s, 2H), 3.83-3.76 (m, 1H), 1.43 (s, 9H), 1.19-1.17 (m, 6H).

Intermediate 10D: tert-butyl 2-(4-(6-(6-chloropyrazolo[1,5-a]pyrimidin-3-yl)-4-(isopropylamino)nicotinamido)-1H-pyrazol-1-yl)acetate

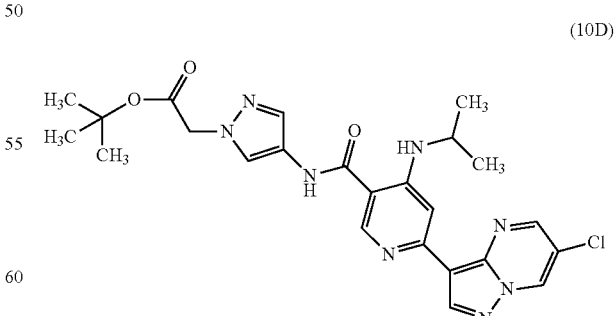

(10D)

To a solution of tert-butyl 2-(4-(6-chloro-4-(isopropylamino)nicotinamido)-1H-pyrazol-1-yl)acetate (1 g, 2.54 mmol) in 1,4-dioxane (10 mL) was added 0.2 mL water followed by 6-chloro-3-(4,4,5,5-tetramethyl-1,3,2-dioxaborolan-2-yl)pyrazolo[1,5-a]pyrimidine (1.065 g, 3.81 mmol) and potassium acetate (0.748 g, 7.62 mmol). The solution was degassed for 10 min. Tetrakis(triphenylphosphine)palladium(0) (0.587 g, 0.508 mmol) was added to the reaction mixture and the reaction mixture was degassed for another 15 min. The resulting reaction mixture was heated to 100° C. for 2 hours in a microwave. The reaction mixture was filtered through celite and washed with 10% MeOH\DCM (100 mL). The filtrate was concentrated in vacuo to afford a crude residue. The residue was purified via column chromatography to afford tert-butyl 2-(4-(6-(6-chloropyrazolo[1,5-a]pyrimidin-3-yl)-4-(isopropylamino)nicotinamido)-1H-pyrazol-1-yl)acetate (0.8 g, 47% yield) as pale yellow solid. LCMS m/z 511.2 (M+H); $^1$H NMR (400 MHz, DMSO-d$_6$) δ 10.45 (s, 1H), 9.69 (d, J=2.0 Hz, 1H), 8.86-8.81 (m, 2H), 8.75 (s, 1H), 8.31 (br. s., 1H), 8.10 (s, 1H), 7.78 (s, 1H), 7.61 (s, 1H), 4.93 (s, 2H), 3.82 (dd, J=13.3, 6.3 Hz, 1H), 1.96 (s, 1H), 1.47-1.43 (m, 9H), 1.30 (d, J=6.5 Hz, 6H).

Intermediate 10E: 2-(4-(6-(6-chloropyrazolo[1,5-a]pyrimidin-3-yl)-4-(isopropylamino)nicotinamido)-1H-pyrazol-1-yl)acetic acid

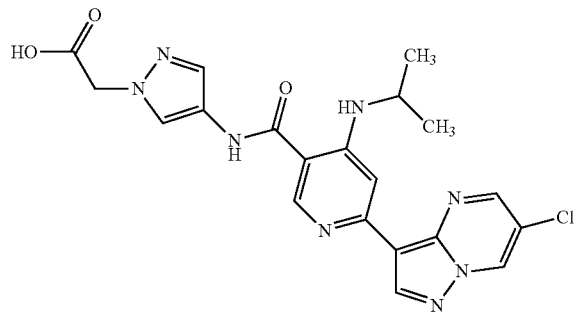

(10E)

To a stirred solution of tert-butyl 2-(4-(6-(6-chloropyrazolo[1,5-a]pyrimidin-3-yl)-4-(isopropylamino)nicotinamido)-1H-pyrazol-1-yl)acetate (0.8 g, 1.566 mmol) in DCM (10 mL) was added TFA (1.206 mL, 15.66 mmol) at room temperature. The reaction mixture was stirred for 16 h at 25° C. The solvent was removed under reduced pressure to afford a crude residue. The residue was triturated with pet ether to afford 2-(4-(6-(6-chloropyrazolo[1,5-a]pyrimidin-3-yl)-4-(isopropylamino)nicotinamido)-1H-pyrazol-1-yl)acetic acid (0.65 g, 77% yield). LCMS m/z 455.0 (M+H); $^1$H NMR (400 MHz, DMSO-d$_6$) δ 13.06 (s, 1H), 10.92 (br. s., 1H), 9.88 (d, J=2.0 Hz, 1H), 9.25 (br. s., 1H), 9.09 (s, 1H), 9.02 (d, J=2.5 Hz, 1H), 8.74 (s, 1H), 8.14 (s, 1H), 7.81 (s, 1H), 7.64 (s, 2H), 7.57-7.42 (m, 2H), 4.98 (s, 2H), 4.05 (dd, J=12.8, 6.8 Hz, 1H), 1.36 (d, J=6.5 Hz, 6H).

Example 10

To a stirred solution of 2-(4-(6-(6-chloropyrazolo[1,5-a]pyrimidin-3-yl)-4-(isopropylamino)nicotinamido)-1H-pyrazol-1-yl)acetic acid (0.05 g, 0.110 mmol) in DMF (4 mL) was added DIPEA (0.019 mL, 0.110 mmol) followed by HATU (0.042 g, 0.110 mmol) and (R)-4-amino-3-fluoro-2-methylbutan-2-ol (0.013 g, 0.110 mmol) at room temperature. The reaction mixture was stirred at 25° C. for 18 hours. The reaction mixture was then diluted with water and extracted with ethyl acetate (2×). The combined organic extracts were dried over anhydrous sodium sulphate, filtered and concentrated in vacuo to afford a crude residue. The crude material was purified via preparative LC/MS with the following conditions: Waters Xbridge C18, 19×150 mm, 5 μm; Guard Column: Waters XBridge C18, 19×10 mm, 5 μm; Mobile Phase A: 5:95 Acetonitrile:water with 0.1% TFA; Mobile Phase B: 95:5 Acetonitrile:water with 0.1% TFA; Gradient: 10-35% B over 25 minutes, followed by a 10 minute hold at 35% B and 5 minute hold at 100% B; Flow: 15 ml/min. Fractions containing the desired product were combined and dried using a Genevac centrifugal evaporator. This procedure afforded (R)-6-(6-chloropyrazolo[1,5-a]pyrimidin-3-yl)-N-(1-(2-((2-fluoro-3-hydroxy-3-methylbutyl)amino)-2-oxoethyl)-1H-pyrazol-4-yl)-4-(isopropylamino)nicotinamide (0.019 g, 30% yield) as a pale yellow solid. LCMS m/z 558.1 (M+H); $^1$H NMR (400 MHz, DMSO-d$_6$) δ 1.12 (dd, J=6.78, 1.25 Hz, 6H) 1.34 (d, J=6.52 Hz, 6H) 3.10-3.26 (m, 2H) 3.52-3.71 (m, 1H) 4.02 (d, J=6.53 Hz, 1H) 4.10-4.29 (m, 1H) 4.84 (s, 2H) 7.59-7.65 (m, 1H) 7.80 (s, 1H) 8.07-8.13 (m, 1H) 8.33 (t, J=5.52 Hz, 1H) 8.72 (s, 1H) 9.00 (d, J=1.76 Hz, 1H) 9.06 (s, 1H) 9.85 (s, 1H) 10.85 (br. s., 1H) 13.60 (br. s., 1H); HPLC rt 1.443 min, conditions C.

Example 11

6-(6-chloropyrazolo[1,5-a]pyrimidin-3-yl)-4-(isopropylamino)-N-((1R,4R)-4-methoxycyclohexyl)nicotinamide

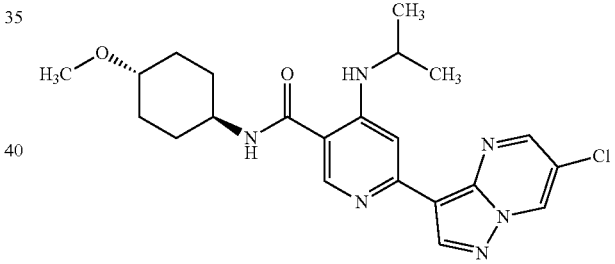

(11)

Intermediate 11A: tert-butyl ((1r,4r)-4-hydroxycyclohexyl)carbamate

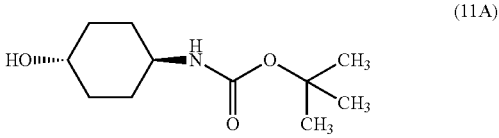

(11A)

To a solution of (1R,4R)-4-aminocyclohexanol (1.0 g, 8.68 mmol) in THF (10 mL) was added a solution of sodium bicarbonate (1.459 g, 17.37 mmol) in water (10 mL). The reaction mixture was cooled to 0° C. and di-tert-butyl dicarbonate (2.217 mL, 9.55 mmol) was added dropwise. The reaction mixture was allowed to stir at room temperature for 16 hrs. The reaction mixture was extracted with ethyl acetate. The organic extract was dried over Na$_2$SO$_4$, filtered and concentrated in vacuo. The crude product obtained was purified via column chromatography (10% ethylacetate/pet ether) to afford tert-butyl ((1R,4R)-4-hydroxycyclohexyl)carbamate (1.5 g, 80% yield) as a white solid. LCMS m/z 160.2 (M-tBu); $^1$H NMR (400 MHz, MeOD) δ 6.48 (s, 1H), 3.46-3.54 (m, 1H), 3.31-3.33 (m, 1H), 1.88-1.96 (m, 4H), 1.40-1.43 (m, 9H), 1.18-1.30 (m, 4H).

Intermediate 11B: tert-butyl ((1r,4r)-4-methoxycyclohexyl)carbamate

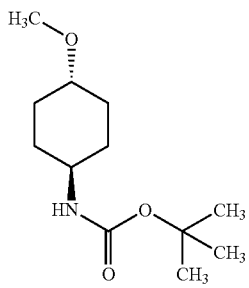

(11B)

Tert-butyl ((1R,4R)-4-hydroxycyclohexyl)carbamate (0.4 g, 1.858 mmol) was dissolved in tetrahydrofuran (10 mL) and the mixture was cooled to 0° C. Sodium hydride (0.067 g, 2.79 mmol) was added in portions. After stirring for 5 minutes, MeI (0.116 mL, 1.858 mmol) was added dropwise and the reaction mixture was allowed to stir at room temperature for 2 h. The reaction mixture was quenched with ice water and extracted with ethyl acetate (3×10 mL). The combined organic extracts were dried over Na$_2$SO$_4$, filtered and concentrated in vacuo. The crude product was purified via column chromatography (10% ethyl acetate/pet ether) to afford tert-butyl ((1R,4R)-4-methoxycyclohexyl) carbamate (0.32 g, 75% yield) as a colorless syrup. LCMS m/z 230.2 (M+H); $^1$HNMR (400 MHz, CDCl$_3$) δ 4.38 (s, 1H), 3.45-3.46 (m, 1H), 3.35 (s, 3H), 3.10-3.16 (m, 1H), 2.03-2.06 (m, 4H), 1.46 (s, 9H), 1.10-1.46 (m, 4H).

Intermediate 11C: (1r,4r)-4-methoxycyclohexanamine

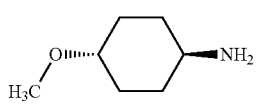

(11C)

Tert-butyl ((1R,4R)-4-methoxycyclohexyl)carbamate (0.4 g, 1.744 mmol) was added to a solution of 4M HCl (0.436 mL, 1.744 mmol) in 1,4-dioxane (3.0 mL) and stirred at room temperature for 2 hrs. The reaction mixture was concentrated in vacuo to afford (1R,4R)-4-methoxycyclohexanamineHCl (0.2 g, 89% yield) as a white solid. $^1$HNMR (400 MHz, MeOD) δ 3.19-3.30 (m, 1H), 2.97-3.06 (m, 1H), 2.68 (s, 3H), 2.16-2.18 (m, 4H), 1.37-1.51 (m, 4H).

Intermediate 11D: 6-chloro-4-(isopropylamino)-N-((1r,4r)-4-methoxycyclohexyl)nicotinamide

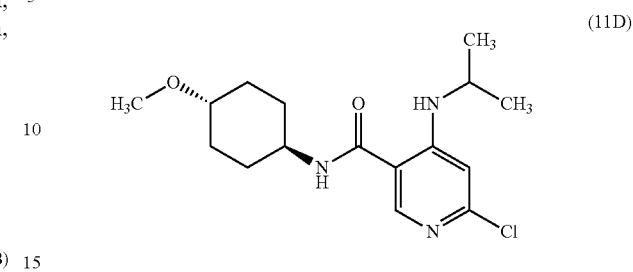

(11D)

To a solution of 6-chloro-4-(isopropylamino)nicotinic acid (0.3 g, 1.398 mmol) in DMF (5.0 mL), was added (1R,4R)-4-methoxycyclohexanamine (0.181 g, 1.398 mmol), HATU (0.531 g, 1.398 mmol) and triethylamine (0.205 mL, 1.468 mmol). The reaction mixture was stirred at room temperature for 2 hrs. The reaction mixture was then concentrated in vacuo. The crude residue obtained was extracted in ethyl acetate (15 mL). The organic extract was washed with water (5 mL), 10% NaHCO$_3$ (10 mL), dried over Na$_2$SO$_4$, filtered and concentrated in vacuo. The crude product was purified via column chromatography (3% methanol/chloroform) to afford 6-chloro-4-(isopropylamino)-N-((1s,4s)-4-methoxycyclohexyl)nicotinamide (0.45 g, 66% yield). LCMS m/z 326.1 (M+H).

Example 11

A microwave vial was charged with 6-chloro-4-(isopropylamino)-N-((1R,4R)-4-methoxycyclohexyl)nicotinamide (0.1 g, 0.307 mmol), (6-chloropyrazolo[1,5-a]pyrimidin-3-yl)boronic acid (0.091 g, 0.460 mmol) and 1,4-dioxane (5.0 mL). To this mixture was added potassium acetate (0.090 g, 0.921 mmol) and the reaction mixture was purged with nitrogen for 5 min. Pd(PPh$_3$)$_4$ (0.071 g, 0.061 mmol) was added and the reaction mixture was purged with nitrogen for an additional 5 min. The reaction mixture was heated to 100° C. for 2 h in a microwave. The reaction mixture was filtered through a bed of celite which was washed with DCM. The filtrate was concentrated in vacuo. The crude product obtained was purified via column chromatography (5% MeOH/CHCl$_3$) to afford 6-(6-chloropyrazolo[1,5-a]pyrimidin-3-yl)-4-(isopropylamino)-N-((1R,4R)-4-methoxycyclohexyl)nicotinamide (21 mg, 15%) as a pale yellow solid. LCMS m/z 443.2 (M+H); $^1$H NMR (400 MHz, MeOD) δ 1.13-1.25 (m, 4H), 1.29-1.39 (m, 8H), 1.45-1.49 (m, 2H), 1.93-2.07 (m, 2H), 2.13-2.16 (m, 2H), 3.37 (s, 1H), 3.82-3.89 (m, 1H), 4.07-4.14 (m, 1H), 7.78 (s, 1H), 8.48 (s, 1H), 8.89 (d, J=2.40 Hz, 1H), 8.92 (s, 1H), 9.48 (d, J=2.00 Hz, 1H); HPLC rt 6.885 min, conditions A.

Example 12

6-(6-chloropyrazolo[1,5-a]pyrimidin-3-yl)-N-(3-fluoro-3-methylbutyl)-4-(oxetan-3-ylamino)nicotinamide

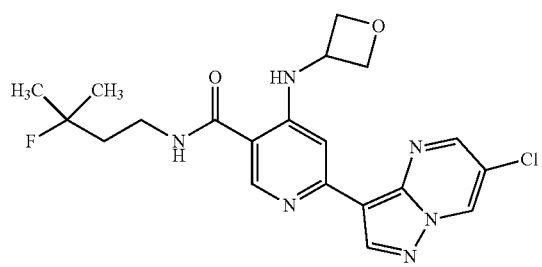

(12)

A solution of 6-(6-chloropyrazolo[1,5-a]pyrimidin-3-yl)-N-(3-hydroxy-3-methylbutyl)-4-(oxetan-3-ylamino)nicotinamide (20 mg, 0.046 mmol) in DCM (5 mL) was cooled to −78° C. To this solution was added DAST (0.012 mL, 0.093 mmol). The mixture was then allowed to warm up to room temperature and stirred for 16 h. The reaction mixture was concentrated in vacuo. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 20 minutes, then a 5-minute hold at 100% B; Flow: 20 mL/min. Fractions containing the desired product were combined and dried via centrifugal evaporation. This procedure afforded 6-(6-chloropyrazolo[1,5-a]pyrimidin-3-yl)-N-(3-fluoro-3-methylbutyl)-4-(oxetan-3-ylamino)nicotinamide (1.9 mg, 9% yield). LCMS m/z 433.2 (M+H); $^1$H NMR (500 MHz, DMSO-$d_6$) δ 9.71 (d, J=1.7 Hz, 1H), 9.04 (br. s., 2H), 8.90 (d, J=1.7 Hz, 1H), 8.86 (s, 1H), 8.70 (br. s., 1H), 8.62 (s, 1H), 7.42 (s, 1H), 4.98 (t, J=6.7 Hz, 2H), 4.80-4.72 (m, 1H), 4.54 (t, J=6.2 Hz, 2H), 3.47-3.30 (m, 1H), 1.90 (dt, J=19.8, 7.8 Hz, 2H), 1.39 (s, 3H), 1.35 (s, 3H); HPLC rt 1.31 min, conditions F.

Examples 13 and 14

6-(6-chloropyrazolo[1,5-a]pyrimidin-3-yl)-4-((3,3-difluoro-4-methoxycyclopentyl)amino)-N—((R)-2-fluoro-3-hydroxy-3-methylbutyl)nicotinamide

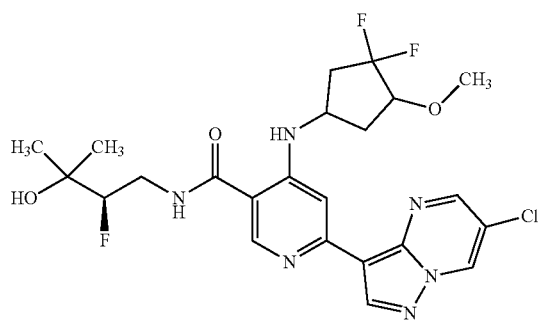

(13 and 14)

Intermediate 13A: ethyl 6-chloro-4-(cyclopent-3-en-1-ylamino)nicotinate

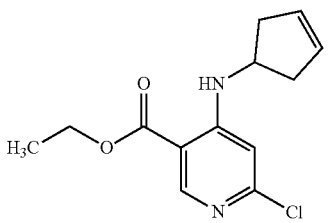

(13A)

To a stirred solution of ethyl 4,6-dichloronicotinate (2.2 g, 10.00 mmol) in DMA (20 mL) was added cyclopent-3-enamine (0.914 g, 11.00 mmol) and DIPEA (5.24 mL, 30.0 mmol). The reaction mixture was heated to 120° C. for 3 hrs. The reaction mixture was then concentrated in vacuo. The crude residue obtained was dissolved in ethyl acetate and washed with water. The organic layer was dried over $Na_2SO_4$, filtered and concentrated in vacuo. The crude product was purified via column chromatography (15% EtOAc/pet ether) to provide 6-chloro-4-(cyclopent-3-en-1-ylamino)nicotinate (0.2 g, 7% yield) as an off-white solid. LCMS m/z 267 (M+H).

Intermediate 13B: ethyl 4-(6-oxabicyclo[3.1.0]hexan-3-ylamino)-6-chloronicotinate

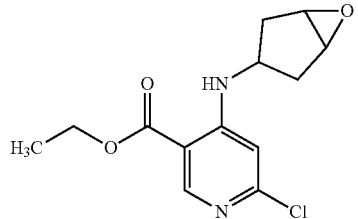

(13B)

Ethyl 6-chloro-4-(cyclopent-3-en-1-ylamino)nicotinate (1.5 g, 5.62 mmol) was dissolved in DCM (20 mL). To this solution was added mCPBA (9.70 g, 56.2 mmol) and the mixture was stirred at 25° C. for 16 hrs. The reaction mixture was quenched with a saturated solution of $NaHCO_3$ and extracted with DCM. The organic layer was dried over $Na_2SO_4$, filtered and concentrated in vacuo. The crude product was purified via column chromatography (20% ethyl acetate/pet ether) to provide ethyl 4-(6-oxabicyclo[3.1.0]hexan-3-ylamino)-6-chloronicotinate (0.5 g, 31% yield) as an off-white solid. LCMS m/z 283 (M+H).

Intermediate 13C: ethyl 6-chloro-4-((3-hydroxy-4-methoxycyclopentyl)amino)nicotinate

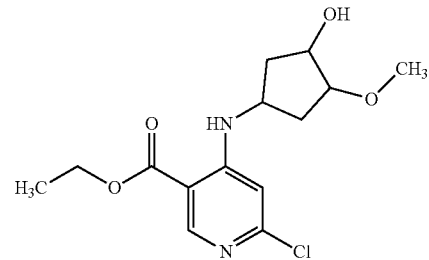

(13C)

Ethyl 4-(6-oxabicyclo[3.1.0]hexan-3-ylamino)-6-chloronicotinate (0.3 g, 1.061 mmol)) was dissolved in MeOH (10 mL). To this solution was added $H_2SO_4$ (0.057 mL, 1.061 mmol). The reaction mixture was stirred at 25° C. for 0.5 h. The reaction mixture was concentrated in vacuo. The residue obtained was dissolved in ethyl acetate and washed with a saturated solution of $NaHCO_3$. The organic extract was dried over $Na_2SO_4$, filtered and concentrated in vacuo to afford ethyl 6-chloro-4-((3-hydroxy-4-methoxycyclopentyl)amino)nicotinate which was used as is in the next reaction. LCMS m/z 315 (M+H).

Intermediate 13D: Ethyl 6-chloro-4-((3-methoxy-4-oxocyclopentyl)amino)nicotinate

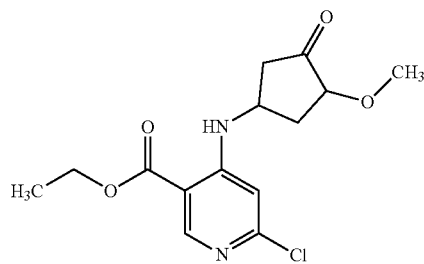

(13D)

To a stirred solution of ethyl 6-chloro-4-((3-hydroxy-4-methoxycyclopentyl)amino)nicotinate (0.23 g, 0.731 mmol) in DCM (10 mL) was added Dess-Martin periodinane (0.930 g, 2.192 mmol) and the resulting mixture was stirred at room temperature for 0.5 h. The reaction mixture was diluted with DCM and washed with a saturated solution of $NaHCO_3$. The organic extract was dried over $Na_2SO_4$, filtered and concentrated in vacuo. This procedure provided ethyl 6-chloro-4-((3-methoxy-4-oxocyclopentyl)amino)nicotinate which was used as is in the next reaction. LCMS m/z 313 (M+H).

Intermediate 13E: ethyl 6-chloro-4-((3,3-difluoro-4-methoxycyclopentyl)amino) nicotinate

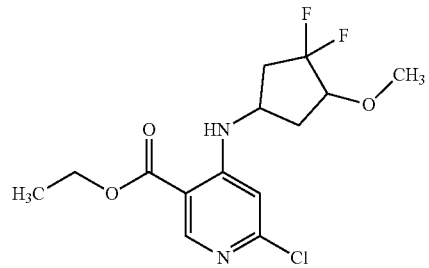

(13E)

To a solution of ethyl 6-chloro-4-((3-methoxy-4-oxocyclopentyl)amino)nicotinate (0.23 g, 0.735 mmol) in DCM (10 mL) was added DAST (0.291 mL, 2.206 mmol). The resulting mixture was stirred at 25° C. for 0.5 h. The reaction mixture was diluted with DCM and washed with a saturated solution of $NaHCO_3$. The organic extract was dried over $Na_2SO_4$, filtered and concentrated in vacuo. This procedure afforded ethyl 6-chloro-4-((3,3-difluoro-4-methoxycyclopentyl)amino)nicotinate which was used as is in the next reaction. LCMS m/z 335 (M+H).

Intermediate 13F: 6-chloro-4-((3,3-difluoro-4-methoxycyclopentyl)amino)nicotinic acid

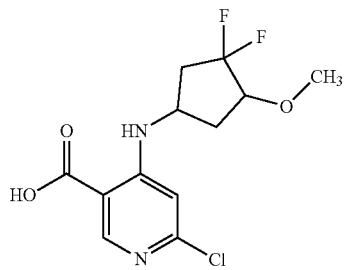

(13F)

Ethyl 6-chloro-4-((3,3-difluoro-4-methoxycyclopentyl)amino)nicotinate (0.22 g, 0.657 mmol) was dissolved in MeOH (10 mL) and water (2 mL). To this solution was added LiOH (0.047 g, 1.972 mmol). The reaction mixture was stirred at room temperature for 4 hrs. The reaction mixture was concentrated in vacuo. The crude residue obtained was dissolved in water and the pH adjusted to 4. The solid obtained was filtered and dried under vacuum. This procedure afforded 6-chloro-4-((3,3-difluoro-4-methoxycyclopentyl)amino)nicotinic acid as an off-white solid which was used as is in the next reaction. LCMS m/z 307 (M+H).

Intermediate 13G: 6-chloro-4-((3,3-difluoro-4-methoxycyclopentyl)amino)-N—((R)-2-fluoro-3-hydroxy-3-methylbutyl)nicotinamide

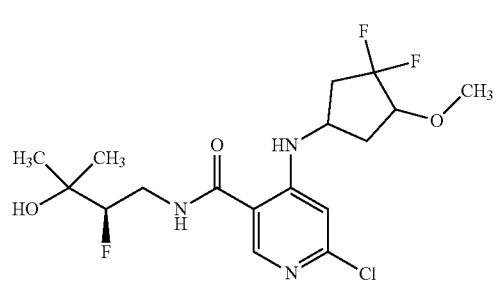

(13G)

To a solution of 6-chloro-4-((3,3-difluoro-4-methoxycyclopentyl)amino)nicotinic acid (0.15 g, 0.489 mmol) in DMF (5 mL) was added HATU (0.372 g, 0.978 mmol), (R)-4-amino-3-fluoro-2-methylbutan-2-ol (0.119 g, 0.978 mmol) and DIPEA (0.256 mL, 1.467 mmol). The mixture was stirred at 25° C. for 3 hrs. The reaction mixture was concentrated in vacuo. The residue obtained was purified via column chromatography (5% methanol/chloroform) to afford 6-chloro-4-((3,3-difluoro-4-methoxycyclopentyl)amino)-N—((R)-2-fluoro-3-hydroxy-3-methylbutyl)nicotinamide as an off-white solid. LCMS m/z 410 (M+H).

Examples 13 and 14

To a solution of 6-chloro-4-((3,3-difluoro-4-methoxycyclopentyl)amino)-N—((R)-2-fluoro-3-hydroxy-3-methylbutyl)nicotinamide (0.15 g, 0.366 mmol) in 1,4-dioxane (3 mL) was added 6-chloro-3-(4,4,5,5-tetramethyl-1,3,2-dioxaborolan-2-yl)pyrazolo[1,5-a]pyrimidine (0.205 g, 0.732 mmol) and potassium acetate (0.108 g, 1.098 mmol). The vial was degassed for 10 min. Pd(Ph₃P)₄ (0.085 g, 0.073 mmol) was added and the reaction mixture was degassed for an additional 15 min. The reaction mixture was then heated to 120° C. in a microwave for 2.5 h. The reaction mixture was filtered through celite and the filtrate was concentrated in vacuo. The crude product was purified via column chromatography (4% methanol/chloroform) to afford the desired product as a mixture of diastereoisomers in low purity (<70%). Repurification by preparative HPLC followed by purification by preparative chiral HPLC provided the desired chiral compounds.

Example 13

6-(6-chloropyrazolo[1,5-a]pyrimidin-3-yl)-4-((3,3-difluoro-4-methoxycyclopentyl)amino)-N—((R)-2-fluoro-3-hydroxy-3-methylbutyl)nicotinamide: LCMS m/z 527.2 (M+H); ¹H NMR (400 MHz, METHANOL-d₄) δ 1.31 (d, J=1.51 Hz, 6H) 2.04-2.19 (m, 2H) 2.45-2.53 (m, 1H) 2.76-2.94 (m, 1H) 3.54 (s, 4H) 3.81-4.03 (m, 2H) 4.28-4.41 (m, 1H) 4.47-4.61 (m, 1H) 7.84-7.89 (m, 1H) 8.52-8.61 (m, 1H) 8.74-8.78 (m, 1H) 8.79-8.83 (m, 1H) 9.23-9.34 (m, 1H); HPLC rt 8.42 min, conditions B.

Example 14

6-(6-chloropyrazolo[1,5-a]pyrimidin-3-yl)-4-((3,3-difluoro-4-methoxycyclopentyl)amino)-N—((R)-2-fluoro-3-hydroxy-3-methylbutyl)nicotinamide. LCMS m/z 527.2 (M+H); ¹H NMR (400 MHz, METHANOL-d₄) δ 1.31 (d, J=1.51 Hz, 6H) 2.04-2.19 (m, 2H) 2.45-2.53 (m, 1H) 2.76-2.94 (m, 1H) 3.54 (s, 4H) 3.81-4.03 (m, 2H) 4.28-4.41 (m, 1H) 4.47-4.61 (m, 1H) 7.84-7.89 (m, 1H) 8.52-8.61 (m, 1H) 8.74-8.78 (m, 1H) 8.79-8.83 (m, 1H) 9.23-9.34 (m, 1H); HPLC rt 8.40 min, conditions B.

Examples 15 and 16

6-(6-chloropyrazolo[1,5-a]pyrimidin-3-yl)-4-((3,3-difluoro-4-isopropoxycyclopentyl)amino)-N—((R)-2-fluoro-3-hydroxy-3-methylbutyl)nicotinamide (15 and 16)

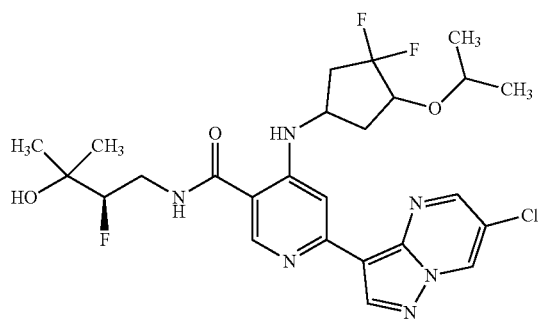

Intermediate 15A: Ethyl 6-chloro-4-((3-hydroxy-4-isopropoxycyclopentyl)amino) nicotinate (15A)

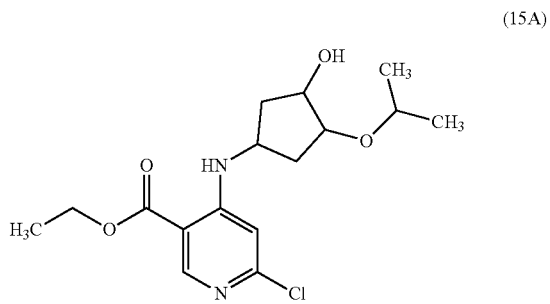 [SMILES: CCOC(=O)c1cnc(Cl)cc1NC1CC(O)C(OC(C)C)C1]

Ethyl 4-(6-oxabicyclo[3.1.0]hexan-3-ylamino)-6-chloronicotinate (0.5 g, 1.769 mmol) was dissolved in 2-propanol (20 mL). To this mixture was added H₂SO₄ (0.094 mL, 1.769 mmol). The reaction mixture was stirred at 25° C. for 0.5 h. The reaction mixture was concentrated in vacuo. The crude residue obtained was dissolved in ethyl acetate and washed with a saturated solution of NaHCO₃. The organic layer was dried over Na₂SO₄, filtered and concentrated in vacuo. This procedure afforded ethyl 6-chloro-4-((3-hydroxy-4-isopropoxycyclopentyl)amino)nicotinate (0.4 g, 66% yield), which was used as is in the next reaction. LCMS m/z 343 (M+H).

Intermediate 15B: ethyl 6-chloro-4-((3-isopropoxy-4-oxocyclopentyl)amino)nicotinate (15B)

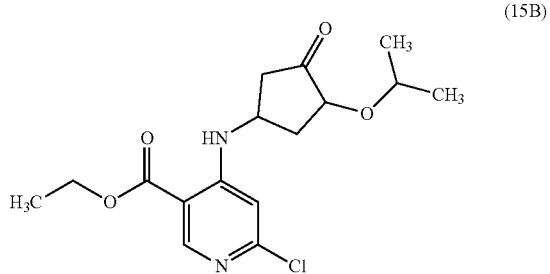 [SMILES: CCOC(=O)c1cnc(Cl)cc1NC1CC(=O)C(OC(C)C)C1]

To a stirred solution of ethyl 6-chloro-4-((3-hydroxy-4-isopropoxycyclopentyl)amino)nicotinate (0.4 g, 1.167 mmol) in DCM (20 mL) was added Dess-Martin periodinane (1.485 g, 3.50 mmol) and the resulting mixture was stirred at room temperature for 0.5 h. The reaction mixture was diluted with DCM and washed with a saturated solution of NaHCO₃. The organic layer was dried over Na₂SO₄, filtered and concentrated in vacuo. This procedure afforded ethyl 6-chloro-4-((3-isopropoxy-4-oxocyclopentyl)amino) nicotinate, which was used as is in the next reaction. LCMS m/z 341 (M+H).

Intermediate 15C: ethyl 6-chloro-4-((3,3-difluoro-4-isopropoxycyclopentyl)amino) nicotinate

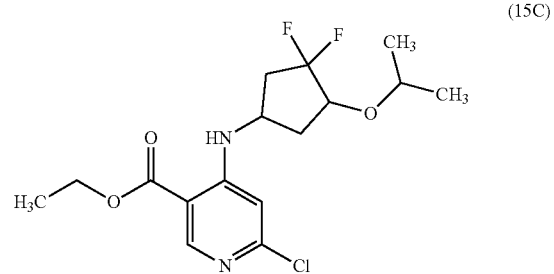 [SMILES: CCOC(=O)c1cnc(Cl)cc1NC1CC(OC(C)C)C(F)(F)C1]

(15C)

To a solution of ethyl 6-chloro-4-((3-isopropoxy-4-oxo-cyclopentyl)amino) nicotinate (0.23 g, 0.675 mmol) in DCM (10 mL) was added DAST (0.267 mL, 2.025 mmol) and the resulting mixture was stirred at 25° C. for 0.5 hr. The reaction mixture was diluted with DCM and washed with a saturated solution of NaHCO$_3$. The organic layer was dried over Na$_2$SO$_4$, filtered and concentrated in vacuo. This procedure afforded 6-chloro-4-((3,3-difluoro-4-isopropoxycyclopentyl)amino)nicotinate which was used as is in the next reaction. LCMS m/z 363 (M+H).

Intermediate 15D: 6-chloro-4-((3,3-difluoro-4-isopropoxycyclopentyl)amino)nicotinic acid

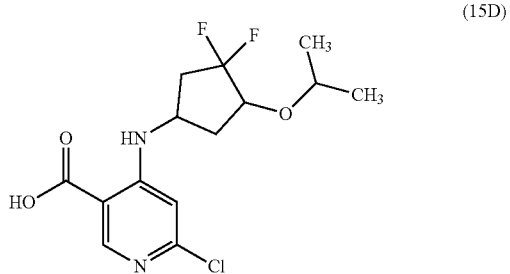 [SMILES: CC(C)OC1CC(Nc2cc(Cl)ncc2C(=O)O)CC1(F)F]

(15D)

Ethyl 6-chloro-4-((3,3-difluoro-4-isopropoxycyclopentyl)amino)nicotinate (0.22 g, 0.606 mmol) was dissolved in MeOH (10 mL) and water (2 mL). To this mixture was added LiOH (0.044 g, 1.819 mmol). The reaction mixture was stirred at room temperature for 4 h. The reaction mixture was concentrated in vacuo. The crude residue obtained was dissolved in water and the pH was adjusted to 4. The solid obtained was filtered and dried under vacuum to afford 4-((4-(isopropoxy)-3,3-difluorocyclopentyl)amino)-6-chloronicotinic acid as an off-white solid which was used as is in the next reaction. LCMS m/z 335 (M+H).

Intermediate 15E: 6-chloro-4-((3,3-difluoro-4-isopropoxycyclopentyl)amino)-N—((R)-2-fluoro-3-hydroxy-3-methylbutyl)nicotinamide

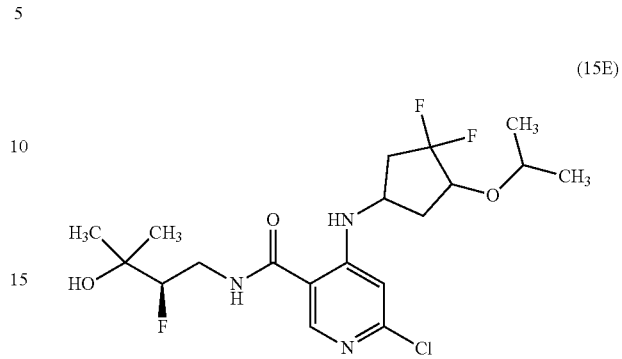

(15E)

To a solution of 4-((4-(isopropoxy)-3,3-difluorocyclopentyl)amino)-6-chloronicotinic acid (0.15 g, 0.430 mmol) in DMF (5 mL) was added HATU (0.327 g, 0.860 mmol), (R)-4-amino-3-fluoro-2-methylbutan-2-ol (0.052 g, 0.430 mmol) and DIPEA (0.300 mL, 1.720 mmol). The reaction mixture was stirred at 25° C. for 3 hrs. The reaction mixture was concentrated in vacuo. The residue obtained was purified via column chromatography (5% methanol/chloroform) to afford 6-chloro-4-((3,3-difluoro-4-isopropoxycyclopentyl)amino)-N—((R)-2-fluoro-3-hydroxy-3-methylbutyl) nicotinamide as an off-white solid. LCMS m/z 415 (M+H).

Examples 15 and 16

To a solution of 6-chloro-4-((3,3-difluoro-4-isopropoxycyclopentyl)amino)-N—((R)-2-fluoro-3-hydroxy-3-methylbutyl)nicotinamide (0.15 g, 0.343 mmol) in 1,4-dioxane (3 mL) was added 6-chloro-3-(4,4,5,5-tetramethyl-1,3,2-dioxaborolan-2-yl) pyrazolo[1,5-a]pyrimidine (0.192 g, 0.685 mmol) and potassium acetate (0.101 g, 1.028 mmol). The reaction mixture was degassed for 10 min. Pd(Ph$_3$P)$_4$ (0.079 g, 0.069 mmol) was added and the mixture was degassed for an additional 15 min. The reaction mixture was heated to 120° C. in a microwave for 2.5 hrs. The reaction mixture was then filtered through celite and the filtrate was concentrated in vacuo. The crude product was purified via column chromatography (4% methanol/chloroform) to afford the desired compound in partially pure form (<70%). The compound was repurified by preparative HPLC to afford the product as a mixture of diastereoisomers. Purification by preparative chiral HPLC provided the desired chiral compounds.

Example 15

6-(6-chloropyrazolo[1,5-a]pyrimidin-3-yl)-4-((3,3-difluoro-4-isopropoxycyclopentyl)amino)-N—((R)-2-fluoro-3-hydroxy-3-methylbutyl)nicotinamide: LCMS m/z 555.2 (M+H); $^1$H NMR (400 MHz, METHANOL-d$_4$) δ 1.21-1.25 (m, 6H) 1.30-1.32 (m, 6H) 1.90-2.21 (m, 1H) 2.35-2.47 (m, 1H) 2.70-2.96 (m, 2H) 3.44-3.54 (m, 1H) 3.77-3.99 (m, 2H) 4.14-4.26 (m, 1H) 4.30-4.42 (m, 1H) 4.46-4.61 (m, 1H) 7.79-7.92 (m, 1H) 8.53-8.60 (m, 1H) 8.71-8.83 (m, 2H) 9.26-9.35 (m, 1H); HPLC rt 6.11 min, conditions A.

Example 16

6-(6-chloropyrazolo[1,5-a]pyrimidin-3-yl)-4-((3,3-difluoro-4-isopropoxycyclopentyl)amino)-N—((R)-2-fluoro- 3-hydroxy-3-methylbutyl)nicotinamide. LCMS m/z 555.2 (M+H); $^1$H NMR (400 MHz, METHANOL-d$_4$) δ 1.21-1.25 (m, 6H) 1.30-1.32 (m, 6H) 1.90-2.21 (m, 1H) 2.35-2.47 (m, 1H) 2.70-2.96 (m, 2H) 3.44-3.54 (m, 1H) 3.77-3.99 (m, 2H) 4.14-4.26 (m, 1H) 4.30-4.42 (m, 1H) 4.46-4.61 (m, 1H) 7.79-7.92 (m, 1H) 8.53-8.60 (m, 1H) 8.71-8.83 (m, 2H) 9.26-9.35 (m, 1H); HPLC rt 6.19 min, conditions A.

Example 17

6-(6-chloropyrazolo[1,5-a]pyrimidin-3-yl)-N-(2-(1-fluoro-4-methoxycyclohexyl)ethyl)-4-(oxetan-3-ylamino)nicotinamide

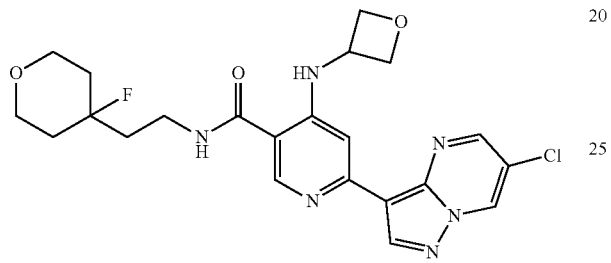

(17)

A solution of 6-(6-chloropyrazolo[1,5-a]pyrimidin-3-yl)-N-(2-(1-hydroxy-4-methoxycyclohexyl)ethyl)-4-(oxetan-3-ylamino)nicotinamide (10 mg, 0.020 mmol) in DCM (5 mL) was cooled to 0° C. To this solution was added DAST (5.27 μL, 0.040 mmol). The mixture was allowed to warm up to room temperature overnight. The reaction mixture was poured into an iced saturated sodium bicarbonate solution, extracted with DCM (20 mL) and washed with brine. The organic extract was concentrated in vacuo. The crude material was purified via preparative LC/MS with the following conditions: Column: Waters XBridge Shield RP18, 19×200 mm, 5-μm particles; Mobile Phase A: 5:95 acetonitrile:water with 10-mM ammonium acetate; Mobile Phase B: 95:5 acetonitrile:water with 10 mM ammonium acetate; Gradient: 10-65% B over 25 minutes, then a 5-minute hold at 100% B; Flow: 20 mL/min. Fractions containing the desired product were combined and dried via centrifugal evaporation. This procedure provided 6-(6-chloropyrazolo[1,5-a]pyrimidin-3-yl)-N-(2-(1-fluoro-4-methoxycyclohexyl)ethyl)-4-(oxetan-3-ylamino)nicotinamide (1.4 mg, 13% yield) as a TFA salt. LCMS m/z 503.2 (M+H)+; $^1$H NMR (500 MHz, DMSO-d$_6$) δ 9.72 (d, J=2.0 Hz, 1H), 9.58 (br. s., 1H), 8.99-8.90 (m, 3H), 8.54 (s, 1H), 7.41 (s, 1H), 5.03-4.95 (m, 2H), 4.90 (d, J=5.7 Hz, 1H), 4.58 (t, J=6.2 Hz, 2H), 3.40 (m, 3H), 3.20 (s, 3H), 1.94-1.59 (m, 10H); HPLC rt 1.36 min, conditions F.

Examples 18 and 19

6-(6-chloropyrazolo[1,5-a]pyrimidin-3-yl)-4-((4,4-difluorotetrahydrofuran-3-yl)amino)-N—((R)-2-fluoro-3-hydroxy-3-methylbutyl)nicotinamide

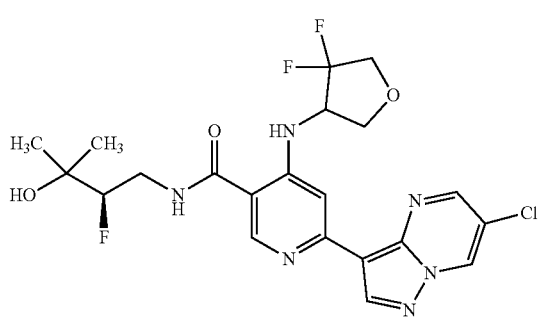

(18 and 19)

Intermediate 18A: ethyl 6-chloro-4-(((3R,4S)-4-hydroxytetrahydrofuran-3-yl)amino) nicotinate

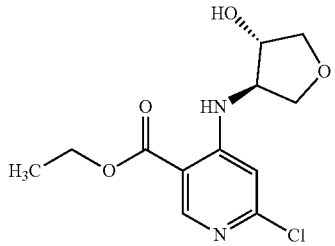

(18A)

To a stirred solution of ethyl 4,6-dichloronicotinate (2.134 g, 9.70 mmol) in DMA (20 mL) was added (3S,4R)-4-aminotetrahydrofuran-3-ol (1, 9.70 mmol)[trans racemic] and DIPEA (5.08 mL, 29.1 mmol). The reaction mixture was heated to 80° C. for 4 hrs. The reaction mixture was concentrated in vacuo. The residue obtained was dissolved in water and stirred for 30 min. The desired compound precipitated as off-white lumps. The solid was collected and purified via column chromatography using (10-25% ethyl acetate/pet ether) to afford ethyl 6-chloro-4-(((3R,4S)-4-hydroxytetrahydrofuran-3-yl)amino)nicotinate[trans racemate] (2.5 g, 87% yield) as a white solid. LCMS m/z 287 (M+H); $^1$H NMR (300 MHz, DMSO-d$_6$) δ 8.57 (s, 1H), 8.09 (d, J=7.18 Hz, 1H), 7.02 (s, 1H), 5.57 (d, J=3.02 Hz, 1H), 4.30 (q, J=7.18 Hz, 2H), 3.99-4.13 (m, 2H), 3.92 (dd, J=9.44, 4.53 Hz, 2H), 3.70 (dd, J=9.25, 1.70 Hz, 1H), 3.53 (dd, J=9.82, 1.89 Hz, 1H), 1.27-1.37 (m, 3H).

Intermediate 18B: Ethyl 6-chloro-4-((4-oxotetrahydrofuran-3-yl)amino)nicotinate

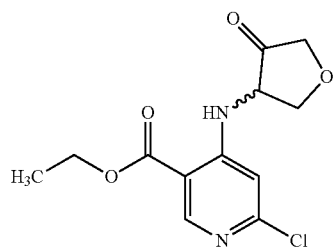

(18B)

A stirred solution of ethyl 6-chloro-4-(((3R,4S)-4-hydroxytetrahydrofuran-3-yl)amino)nicotinate (600 mg, 2.093 mmol) in DCM (10 mL) was cooled to 0° C. To this solution was added Dess-Martin periodinane (2.7 g, 6.28 mmol). The reaction mixture was allowed to warm up to room temperature and stirred for 12 hrs. Additional Dess-Martin periodinane (1.5 g, 3.49 mmol) was then added and the mixture was stirred at 25° C. for an additional 12 hrs. The reaction mixture was filtered through celite. The filtrate was washed with an aqueous solution of 10% NaHCO$_3$. The organic extract was dried over Na$_2$SO$_4$, filtered and concentrated in vacuo. The crude product was purified via column chromatography (5-15% ethyl acetate/pet ether) to afford ethyl 6-chloro-4-((4-oxotetrahydrofuran-3-yl)amino)nicotinate (450 mg, 76% yield) as an off-white solid. LCMS m/z 285 (M+H); $^1$H NMR (400 MHz, DMSO-d$_6$) δ 8.59 (s, 1H), 8.28 (d, J=8.0 Hz, 1H), 7.07 (s, 1H), 4.84-4.72 (m, 1H), 4.63 (t, J=8.3 Hz, 1H), 4.39-4.26 (m, 2H), 4.21 (d, J=16.1 Hz, 1H), 3.99 (d, J=17.1 Hz, 1H), 3.84 (dd, J=10.0, 8.5 Hz, 1H), 1.38-1.28 (m, 3H).

Intermediate 18C: ethyl 6-chloro-4-((4,4-difluorotetrahydrofuran-3-yl)amino)nicotinate

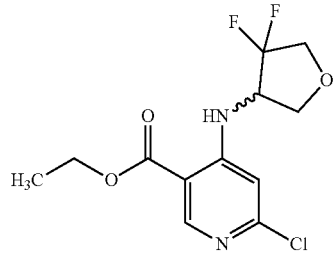

(18C)

To a stirred solution of ethyl 6-chloro-4-((4-oxotetrahydrofuran-3-yl)amino) nicotinate (0.250 g, 0.878 mmol) in DCM (5 mL) at 0° C. was added DAST (0.290 mL, 2.195 mmol) dropwise. The reaction mixture was allowed to warm up to room temperature and stirred for 12 hrs. The reaction mixture was then cooled to 0° C. and quenched by the addition of a 10% NaHCO$_3$ solution. The organic layer was separated and the aqueous layer was extracted with DCM (3×15 mL). The combined organic extracts were dried over Na$_2$SO$_4$, filtered and concentrated in vacuo. The crude product was purified via column chromatography (5-10% ethyl acetate/pet ether) to afford ethyl 6-chloro-4-((4,4-difluorotetrahydrofuran-3-yl)amino)nicotinate (110 mg, 41% yield) as an off-white solid. LCMS m/z 307 (M+H); $^1$H NMR (400 MHz, DMSO-d$_6$) δ 8.63 (s, 1H), 8.34 (d, J=8.0 Hz, 1H), 7.04 (s, 1H), 4.81 (dquin, J=14.4, 7.2 Hz, 1H), 4.43-4.26 (m, 3H), 4.21-3.98 (m, 2H), 3.83-3.72 (m, 1H), 1.38-1.28 (m, 3H).

Intermediate 18D: 6-chloro-4-((4,4-difluorotetrahydrofuran-3-yl)amino)nicotinic acid

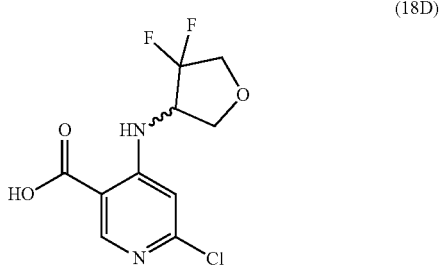 [SMILES: O=C(O)c1cnc(Cl)cc1NC1COCC1(F)F]

(18D)

To a stirred solution of ethyl 6-chloro-4-((4,4-difluorotetrahydrofuran-3-yl)amino)nicotinate (110 mg, 0.359 mmol) in ethanol (2 mL) and water (0.2 mL) was added LiOH (25.8 mg, 1.076 mmol). The reaction mixture was stirred at room temperature for 2 h. The reaction mixture was then concentrated in vacuo. The residue obtained was dissolved in water and neutralized using a solution of 1.5 N HCl. The resulting precipitate was extracted with ethyl acetate (3×10 mL). The combined organic extracts were dried over Na$_2$SO$_4$, filtered and concentrated in vacuo. This procedure afforded 6-chloro-4-((4,4-difluorotetrahydrofuran-3-yl)amino)nicotinic acid (80 mg, 80% yield) as an off-white solid. LCMS m/z 279 (M+H); $^1$H NMR (400 MHz, DMSO-d$_6$) δ 13.64 (br.s., 1H), 8.68-8.54 (m, 2H), 7.00 (s, 1H), 4.86-4.69 (m, 1H), 4.38 (dd, J=9.5, 7.5 Hz, 1H), 4.22-3.95 (m, 2H), 3.75 (dd, J=8.5, 7.0 Hz, 1H).

Intermediate 18E: 6-chloro-4-((4,4-difluorotetrahydrofuran-3-yl)amino)-N—((R)-2-fluoro-3-hydroxy-3-methylbutyl)nicotinamide

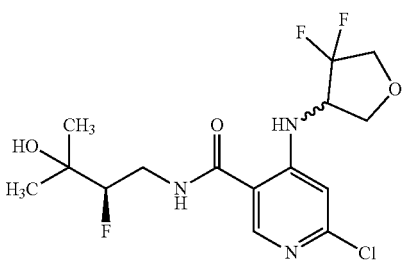

(18E)

To a stirred solution of 6-chloro-4-((4,4-difluorotetrahydrofuran-3-yl)amino) nicotinic acid (80 mg, 0.287 mmol) in DMF (0.8 mL) was added HATU (109 mg, 0.287 mmol), (R)-4-amino-3-fluoro-2-methylbutan-2-ol (34.8 mg, 0.287 mmol) and DIPEA (0.201 mL, 1.148 mmol). The reaction mixture was stirred at room temperature overnight. The reaction mixture was then concentrated in vacuo. The resulting crude residue was dissolved in ethyl acetate and washed with a 10% NaHCO$_3$ aqueous solution. The organic extract was dried over Na$_2$SO$_4$, filtered and concentrated in vacuo. The crude product was purified via column chromatography (20-50% ethyl acetate/pet ether) to afford 6-chloro-4-((4,4-difluorotetrahydrofuran-3-yl)amino)-N—((R)-2-fluoro-3-hydroxy-3-methylbutyl)nicotinamide (100 mg, 84% yield) as an off-white solid. LCMS m/z 382 (M+H; $^1$H NMR (400 MHz, DMSO-d$_6$) δ 8.98-8.87 (m, 2H), 8.50 (s, 1H), 6.93 (s, 1H), 4.84 (s, 1H), 4.70 (dt, J=14.3, 7.4 Hz, 1H), 4.43-4.25 (m, 2H), 4.31-4.25 (m, 1H), 4.18-3.96 (m, 2H), 3.80-3.61 (m, 2H), 3.48-3.35 (m, 1H), 3.19 (s, 1H), 1.16 (dd, J=6.0, 1.5 Hz, 6H).

Examples 18 and 19

To a solution of 6-chloro-4-((4,4-difluorotetrahydrofuran-3-yl)amino)-N—((R)-2-fluoro-3-hydroxy-3-methylbutyl) nicotinamide (0.1 g, 0.262 mmol) in 1,4-dioxane (20 mL) was added potassium acetate (0.077 g, 0.786 mmol). The reaction mixture was purged with nitrogen for 5 min. Pd(PPh$_3$)$_4$ (0.061 g, 0.052 mmol) was then added and the reaction mixture was heated in a microwave to 100° C. for 2 hrs. The reaction mixture was filtered through a bed of celite, the celite bed was washed with DCM and the filtrate was concentrated in vacuo. The crude product obtained was purified via column chromatography (5% MeOH/CHCl$_3$) to obtain a partially pure product, which was repurified by preparative HPLC to afford the desired product as a mixture of diastereoisomers. This mixture was subjected to chiral separation via preparative chiral HPLC to afford the individual diastereomers.

Example 18

6-(6-chloropyrazolo[1,5-a]pyrimidin-3-yl)-4-((4,4-difluorotetrahydrofuran-3-yl)amino)-N—((R)-2-fluoro-3-hydroxy-3-methylbutyl) nicotinamide (37 mg); LCMS m/z 499.2 (M+H); $^1$H NMR (400 MHz, MeOD) δ 9.38 (d, J=2.00 Hz, 1H), 8.86 (s, 1H), 8.82 (d, J=2.40 Hz, 1H), 8.64 (s, 1H), 7.98 (s, 1H), 4.60-4.70 (m, 1H), 4.49-4.57 (m, 2H), 4.36-4.39 (m, 1H), 3.95-4.19 (m, 2H), 3.80-3.90 (m, 1H), 3.53-3.55 (m, 1H), 1.40 (s, 6H); HPLC rt 5.915 min, conditions A.

Example 19

6-(6-chloropyrazolo[1,5-a]pyrimidin-3-yl)-4-((4,4-difluorotetrahydrofuran-3-yl)amino)-N—((R)-2-fluoro-3-hydroxy-3-methylbutyl) nicotinamide (18 mg). LCMS m/z 499.2 (M+H); $^1$H NMR (400 MHz, MeOD) δ 9.38 (d, J=2.00 Hz, 1H), 8.86 (s, 1H), 8.82 (d, J=2.40 Hz, 1H), 8.64 (s, 1H), 7.98 (s, 1H), 4.60-4.70 (m, 1H), 4.49-4.57 (m, 2H), 4.36-4.39 (m, 1H), 3.95-4.19 (m, 2H), 3.80-3.90 (m, 1H), 3.53-3.55 (m, 1H), 1.40 (s, 6H); HPLC rt 5.954 min, conditions A.

Example 20

6-(6-chloropyrazolo[1,5-a]pyrimidin-3-yl)-N-(3-fluoro-3-methylbutyl)-4-(isopropylamino)nicotinamide

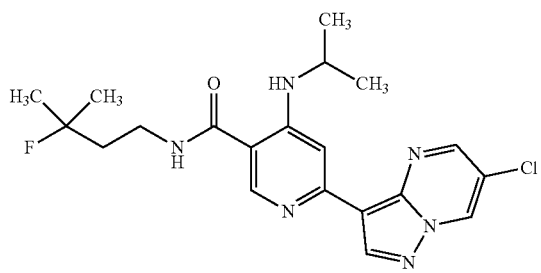

(20)

Intermediate 20A: 4,6-dichloro-N-(3-fluoro-3-methylbutyl)nicotinamide

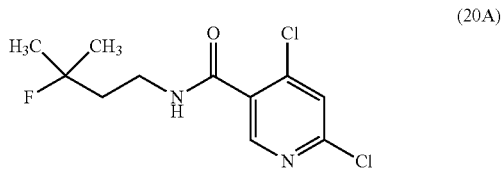 [SMILES: CC(C)(F)CCNC(=O)c1cnc(Cl)cc1Cl]

(20A)

To a solution of 4,6-dichloronicotinic acid (250 mg, 1.302 mmol), ethyl 3-aminopropanoate hydrochloride (210 mg, 1.367 mmol) and pyridine (0.263 mL, 3.26 mmol) in DCM (5 mL) at 0° C. was added phosphoryl trichloride (319 mg, 2.083 mmol). The mixture was stirred at room temperature for 2 hrs. The reaction mixture was poured into iced water, extracted with DCM (50 mL), washed with saturated NaHCO$_3$ (aq) and brine. The organic extract was dried over Na$_2$SO$_4$, filtered and concentrated in vacuo. The crude intermediate, ethyl 3-(4,6-dichloronicotinamido)propanoate, was then dissolved in dry THF (5 mL) and put under an atmosphere of nitrogen. The solution obtained was cooled to 0° C. Methylmagnesium bromide (2.60 mL, 7.81 mmol) was added and the mixture was stirred at room temperature for 3 h. The reaction mixture was quenched with a saturated solution of NH$_4$Cl (aq), extracted with ethyl acetate, washed with brine, dried over Na$_2$SO$_4$, filtered and concentrated in vacuo. The crude intermediate 4,6-dichloro-N-(3-hydroxy-3-methylbutyl)nicotinamide was dissolved in DCM (5 mL) and the mixture was cooled to 0° C. DAST (0.189 mL, 1.432 mmol) was added and the mixture was stirred at room temperature overnight. The reaction mixture was then quenched with a saturated solution of NaHCO$_3$ (aq), extracted with DCM, dried over Na$_2$SO$_4$, filtered and concentrated in vacuo. The crude product was purified via column chromatography to afford 4,6-dichloro-N-(3-fluoro-3-methylbutyl)nicotinamide (126 mg, 35% yield). LCMS m/z 279.2 (M+H)+; $^1$H NMR (400 MHz, CDCl$_3$) δ 8.67 (s, 1H), 7.48-7.38 (m, 1H), 6.70-6.50 (m, 1H), 3.74-3.59 (m, 2H), 2.06-1.90 (m, 2H), 1.48 (s, 3H), 1.43-1.42 (m, 3H).

Intermediate 20B: 6-chloro-N-(3-fluoro-3-methylbutyl)-4-(isopropylamino)nicotinamide

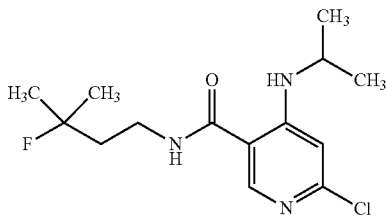
(20B)

To a solution of 4,6-dichloro-N-(3-fluoro-3-methylbutyl) nicotinamide (60 mg, 0.215 mmol) in DMA (0.2 mL) was added propan-2-amine hydrochloride (22.60 mg, 0.236 mmol) and DIPEA (0.078 mL, 0.451 mmol). The mixture was heated to 110° C. for 4 hrs. The crude product was purified via HPLC to afford 6-chloro-N-(3-fluoro-3-methylbutyl)-4-(isopropylamino)nicotinamide (42 mg, 65% yield).

Example 20

To a suspension of 6-chloro-N-(3-fluoro-3-methylbutyl)-4-(isopropylamino) nicotinamide (15 mg, 0.050 mmol) in 1,4-dioxane (1 mL), was added 6-chloro-2-(4,4,5,5-tetramethyl-1,3,2-dioxaborolan-2-yl)pyrazolo[1,5-a]pyrimidine (13.89 mg, 0.050 mmol), 2M aqueous solution of $K_3PO_4$ (0.075 mL, 0.149 mmol) and $PdCl_2(dppf)$ (2.91 mg, 3.98 mol). The reaction vial was purged with nitrogen, sealed and heated to 120° C. for 2 hrs. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10 mM ammonium acetate; Gradient: 25-100% B over 25 minutes, then a 5-minute hold at 100% B; Flow: 20 mL/min. Fractions containing the desired product were combined and dried via centrifugal evaporation. This procedure afforded 6-(6-chloropyrazolo[1,5-a]pyrimidin-3-yl)-N-(3-fluoro-3-methylbutyl)-4-(isopropylamino) nicotinamide (3.9 mg, 19% yield). LCMS m/z 419.2 (M+H)+; $^1$H NMR (500 MHz, DMSO-d6) δ 9.63 (s, 1H), 8.83-8.75 (m, 2H), 8.57-8.53 (m, 2H), 8.46 (d, J=7.1 Hz, 1H), 7.71 (s, 1H), 3.84-3.70 (m, 1H), 3.40-3.28 (m, 2H), 1.87 (dt, J=19.8, 7.8 Hz, 2H), 1.38 (s, 3H), 1.33 (s, 3H), 1.25 (d, J=6.1 Hz, 6H). HPLC rt 1.91 min. conditions F.

Example 21

(R)—N-(2-fluoro-3-hydroxy-3-methylbutyl)-6-(imidazo[1,2-b]pyridazin-3-yl)-4-(isopropylamino)nicotinamide

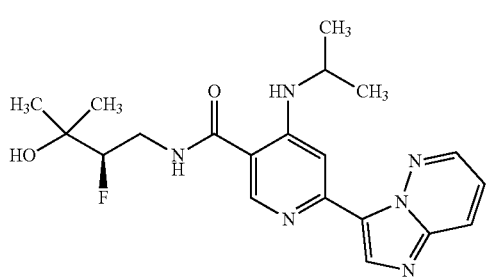
(21)

Intermediate 21A: Ethyl 4,6-dibromonicotinate

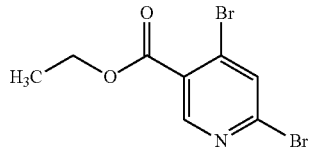
(21A)

To a solution of ethyl 4,6-dichloronicotinate (45 g, 204 mmol) in toluene (500 mL) was added phosphorous oxybromide (205 g, 716 mmol) and heated to 130° C. for 16 hrs. The reaction mixture was cooled to room temperature and was slowly added to a saturated $NaHCO_3$ solution. The organic layer was separated and the aqueous layer was extracted with MTBE (3×100 mL). The combined organic layer was washed with brine, dried over $Na_2SO_4$ and concentrated in vacuo. Purification by silica gel column using 10% ethylacetate/pet ether provided ethyl 4,6-dibromonicotinate (62 g, 98% yield) as colorless syrup. LCMS [m/z 307.9 (M+H); $^1$H NMR (300 MHz, DMSO-d6) δ 8.70-8.75 (m, 1H) 8.24 (s, 1H) 4.30-4.44 (m, 2H) 1.28-1.38 (m, 3H).

Intermediate 21B: Ethyl 6-bromo-4-(isopropylamino)nicotinate (21B)

To a stirred solution of ethyl 4,6-dibromonicotinate (25 g, 81 mmol), in DMA (100 mL) was added isopropylamine (20.80 mL, 243 mmol) and DIPEA (70.7 mL, 405 mmol) and heated to 50° C. for overnight. The reaction mixture was concentrated in vacuo to a residue, which was poured into water and extracted with diethyl ether (4×100 mL). The combined organic layer washed with brine, dried over $Na_2SO_4$, and concentrated. Purification by silica gel [ISCO, 120 g, liquid injection] column using 0-8% ethyl acetate/pet ether provided ethyl 6-bromo-4-(isopropylamino)nicotinate (22 g, 95% yield) as colorless syrup. LCMS [m/z 289 (M+H)] $^1$H NMR (400 MHz, DMSO-d6) δ 8.47 (s, 1H) 7.99 (br. s., 1H) 6.97 (s, 1H) 4.19-4.35 (m, 2H) 3.76-3.95 (m, 1H) 1.30 (t, J=7.28 Hz, 3H) 1.10-1.24 (m, 6H).

Intermediate 21C: 6-Bromo-4-(isopropylamino)nicotinic acid

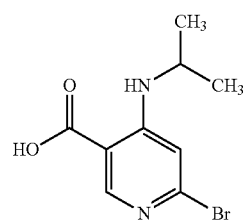
(21C)

To a stirred solution of ethyl 6-bromo-4-(isopropylamino) nicotinate (22 g, 77 mmol) in ethanol (80 mL) and water (10 mL) was added LiOH (3.67 g, 153 mmol) and stirred for 4 hrs. The reaction mixture was concentrated to give crude salt, which was dissolved in water and neutralized using 1.5N HCl. The solid obtained was filtered and dried to give 6-bromo-4-(isopropylamino)nicotinic acid (19 g, 96% yield) as off-white solid. LCMS [m/z 261 (M+H)] ¹H NMR (400 MHz, DMSO-d₆) δ 13.36 (br. s., 1H) 8.38-8.53 (m, 1H) 8.17 (d, J=7.53 Hz, 1H) 6.92 (s, 1H) 3.72-3.91 (m, 1H) 1.11-1.26 (m, 6H).

Intermediate 21D: (R)-6-Bromo-N-(2-fluoro-3-hydroxy-3-methylbutyl)-4-(isopropylamino)nicotinamide

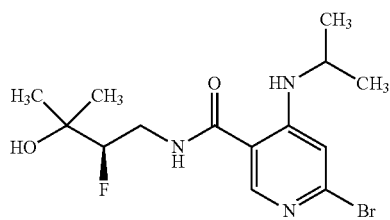

(21D)

To a stirred solution of 6-bromo-4-(isopropylamino)nicotinic acid (1.2 g, 4.63 mmol) in DMF (10 mL) was added HATU (1.761 g, 4.63 mmol), (R)-4-amino-3-fluoro-2-methylbutan-2-ol (0.561 g, 4.63 mmol) and DIPEA (0.809 mL, 4.63 mmol) successively. The reaction mixture was stirred for 1 hr and concentrated. Water (25 mL) was added to the crude compound and stirred for 15 minutes. The solid was filtered, washed with water and dried to give (R)-6-bromo-N-(2-fluoro-3-hydroxy-3-methylbutyl)-4-(isopropylamino)nicotinamide (1.2 g, 72% yield) as off-white solid. LCMS: [m/z 364 (M+H)] ¹H NMR (300 MHz, DMSO-d₆) δ 8.76 (t, J=5.29 Hz, 1H) 8.37-8.50 (m, 1H) 8.32 (s, 1H) 6.84 (s, 1H) 4.83 (s, 1H) 4.16-4.47 (m, 1H) 3.55-3.85 (m, 2H) 3.35-3.45 (m, 1H) 1.07-1.21 (m, 12H).

Intermediate 21E: (R)—N-(2-Fluoro-3-hydroxy-3-methylbutyl)-4-(isopropylamino)-6-(trimethylstannyl)nicotinamide

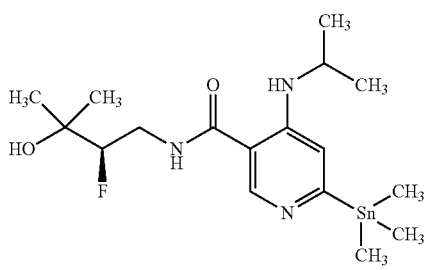

(21E)

To a stirred solution of (R)-6-bromo-N-(2-fluoro-3-hydroxy-3-methylbutyl)-4-(isopropylamino)nicotinamide (125 mg, 0.345 mmol) in a pressure tube, was added hexamethylditin (0.107 mL, 0.518 mmol) in toluene (4 mL). The mixture was degassed for 10 minutes. Pd(Ph₃P)₄ (80 mg, 0.069 mmol) was added and heated to 115° C. for 2 h. The reaction mixture was filtered through celite and concentrated to give (R)—N-(2-fluoro-3-hydroxy-3-methylbutyl)-4-(isopropylamino)-6-(trimethylstannyl)nicotinamide [200 mg] as black syrup, which was used without any purification. LCMS [m/z 448 (M+H)].

Intermediate 21F: 6-Chloroimidazo[1,2-b]pyridazine

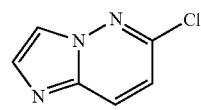

(21F)

To a solution of 2-chloroacetaldehyde (55.1 g, 386 mmol) was added 6-chloropyridazin-3-amine (5 g, 38.6 mmol) and heated to 100° C. for 5 hrs. The reaction mixture was concentrated, suspended in water and extracted with ethyl acetate. The aqueous layer was neutralized using NaHCO₃ solution and the resulting solid was filtered and washed with cold water to afford after drying 6-chloroimidazo[1,2-b]pyridazine (3 g, 51%) as pale brown solid. LCMS [m/z 153.9 (M+H)] ¹H NMR (300 MHz, DMSO-d₆) δ 8.36 (s, 1H) 8.19-8.27 (m, 1H) 7.85 (d, J=1.13 Hz, 1H) 7.37 (d, J=9.44 Hz, 1H).

Intermediate 21G: Imidazo[1,2-b]pyridazine

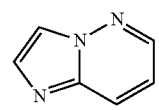

(21G)

To a stirred solution of 6-chloroimidazo[1,2-b]pyridazine (800 mg, 5.21 mmol) in methanol (20 mL) and tetrahydrofuran (20 mL) was added triethylamine (0.8 mL, 5.74 mmol) followed by Pd/C (100 mg, 0.094 mmol). The mixture was stirred under hydrogen atmosphere for 16 h. The reaction mixture was filtered through celite and the celite bed was washed with methanol. The combined filtrate was concentrated then suspended in water and extracted with ethyl acetate (3×). The organic layer was dried over Na₂SO₄ and filtered to give the imidazo[1,2-b]pyridazine (550 mg, 87%) as off white solid. LCMS[m/z 120 (M+H)]; ¹H NMR (300 MHz, DMSO-d₆) δ 8.51 (dd, J=4.53, 1.51 Hz, 1H) 8.29 (d, J=0.76 Hz, 1H) 8.05-8.19 (m, 1H) 7.79 (d, J=1.13 Hz, 1H) 7.22 (dd, J=9.44, 4.53 Hz, 1H).

Intermediate 21H: 3-Bromoimidazo[1,2-b]pyridazine

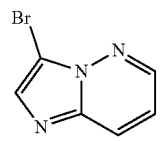

(21H)

To a stirred solution of imidazo[1,2-b]pyridazine (200 mg, 1.679 mmol) in acetic acid (10 mL) was added bromine (0.2 mL, 3.88 mmol) at 0° C. The reaction mixture was allowed to warm to room temperature and stir for 1 hr. The reaction mixture was neutralized with 1N sodium hydroxide, poured into EtOAc (20 mL) and 10% NaHCO₃ solution. The layers were separated and the aqueous layer extracted with EtOAC (3×20 ml). The combined organic layer was washed with brine, dried over Na₂SO₄, and concentrated to give 3-bromoimidazo[1,2-b]pyridazine (120 mg, 36%) as light brown solid. ¹H NMR (400 MHz, DMSO-d₆) δ 8.68 (dd, J=4.52, 1.51 Hz, 1H) 8.19 (dd, J=9.54, 1.51 Hz, 1H) 7.94 (s, 1H) 7.28-7.39 (m, 1H).

Example 21

To a stirred solution of compound (R)—N-(2-fluoro-3-hydroxy-3-methylbutyl)-4-(isopropylamino)-6-(trimethyl-stannyl)nicotinamide (200 mg, 0.448 mmol) in dioxane (10 mL), 3-bromoimidazo[1,2-b]pyridazine (98 mg, 0.493 mmol), CuI (8.54 mg, 0.045 mmol) and Pd(PPh₃)₄ (51.8 mg, 0.045 mmol) were added and degassed with nitrogen for 15 min then heated to 100° C. for 30 min in a microwave reactor. After cooling, the reaction mixture was concentrated to obtain dark brown solid which was purified by Prep TLC (10% MeOH/CHCl₃) to afford a pale yellow solid, which was further purified by Preparative HPLC to give (R)—N-(2-fluoro-3-hydroxy-3-methylbutyl)-6-(imidazo[1,2-b]pyridazin-3-yl)-4-(isopropylamino)nicotinamide (9.8 mg, 5%) as pale yellow solid. LCMS [401.2 (M+H)]; ¹H NMR (400 MHz, DMSO-d₆) δ 1.12-1.21 (m, 6H) 1.29 (d, J=5.52 Hz, 6H) 3.37-3.47 (m, 1H) 3.71-3.87 (m, 2H) 4.28-4.46 (m, 1H) 4.83 (s, 1H) 7.33-7.41 (m, 1H) 8.04 (s, 1H) 8.25-8.33 (m, 1H) 8.46 (s, 1H) 8.54 (d, J=7.03 Hz, 1H) 8.66-8.72 (m, 2H) 8.76 (dd, J=4.27, 1.76 Hz, 1H).

Intermediate I-1

(S)-ethyl 6-chloro-4-((1-fluoropropan-2-yl)amino)nicotinate

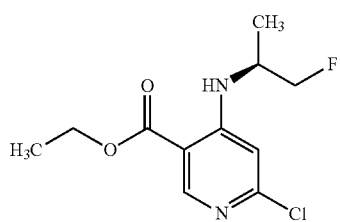

(I-1)

To a stirred solution of (S)-ethyl 6-chloro-4-((1-hydroxypropan-2-yl)amino) nicotinate (100 mg, 0.387 mmol) in DCM (10 mL) was added TEA (0.054 mL, 0.387 mmol) and Deoxofluor (0.107 mL, 0.580 mmol) dropwise at −20° C. and the reaction mixture was then stirred at room temperature for 4 hrs. The reaction was quenched with 10% NaHCO₃ solution and extracted with ethyl acetate. The organic layer was dried over Na₂SO₄, filtered and concentrated in vacuo. The crude material was purified by preparative TLC plate using 20% EtOAc:pet ether to afford (S)-ethyl 6-chloro-4-((1-fluoropropan-2-yl)amino)nicotinate (40 mg, 40% yield). LCMS m/z 261 (M+H); ¹H NMR (400 MHz, CHLOROFORM-d) δ 8.93-8.49 (m, 1H), 8.33 (br. s., 1H), 6.72-6.54 (m, 1H), 4.55-4.43 (m, 1H), 4.42-4.30 (m, 3H), 3.87 (td, J=12.8, 6.6 Hz, 1H), 1.64-1.51 (m, 3H), 1.45-1.30 (m, 3H).

Intermediate I-2

(R)-ethyl 6-chloro-4-((1-(5-fluoropyrimidin-2-yl)pyrrolidin-3-yl)amino)nicotinate

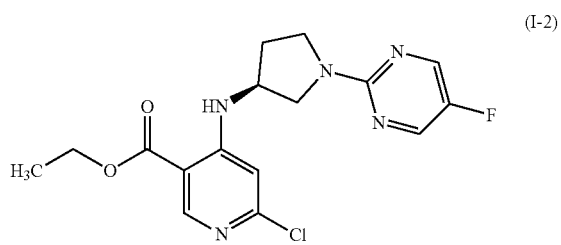 [SMILES: CCOC(=O)c1cnc(Cl)cc1N[C@H]1CCN(c2ncc(F)cn2)C1]

(I-2)

Intermediate I-2A: (R)-ethyl 4-((1-(tert-butoxycarbonyl)pyrrolidin-3-yl)amino)-6-chloronicotinate

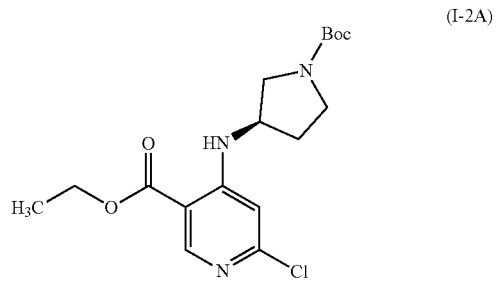 [SMILES: CCOC(=O)c1cnc(Cl)cc1N[C@@H]1CCN(C(=O)OC(C)(C)C)C1]

(I-2A)

To a stirred solution of ethyl 4,6-dichloronicotinate (1 g, 4.54 mmol) in DMA (10 mL) was added (R)-tert-butyl 3-aminopyrrolidine-1-carboxylate (1.016 g, 5.45 mmol) and DIPEA (3.17 mL, 18.18 mmol). The mixture was heated to 130° C. for 2 hrs. The reaction mixture was evaporated to dryness and partitioned between EtOAc and water. The organic layer was dried over Na₂SO₄, filtered and concentrated in vacuo. The crude product obtained was purified via column chromatography (10% ethylacetate:pet ether) to provide (R)-ethyl 4-((1-(tert-butoxycarbonyl)pyrrolidin-3-yl)amino)-6-chloronicotinate (1.3 g, 74% yield) as pale yellow solid. LCMS m/z 370.4 (M+H); ¹H NMR (400 MHz, DMSO-d₆) δ 8.55-8.61 (m, 1H) 8.13 (br. s., 1H) 6.99 (s, 1H) 4.31 (q, J=7.03 Hz, 3H) 3.63 (dd, J=10.54, 6.02 Hz, 1H) 3.35-3.42 (m, 2H) 3.16 (dd, J=11.04, 4.02 Hz, 1H) 2.21 (br. s., 1H) 1.88 (br. s., 1H) 1.37-1.47 (m, 9H) 1.28-1.36 (m, 3H).

Intermediate I-2B: (R)-ethyl 6-chloro-4-(pyrrolidin-3-ylamino)nicotinate

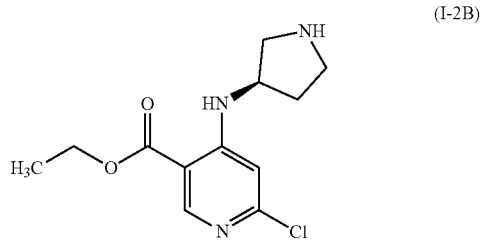 [SMILES: CCOC(=O)c1cnc(Cl)cc1N[C@@H]1CCNC1]

(I-2B)

To a stirred solution of (R)-ethyl 4-((1-(tert-butoxycarbonyl)pyrrolidin-3-yl)amino)-6-chloronicotinate (1.3 g, 3.52 mmol) in 1,4-dioxane (5 mL) was added HCl in 1,4-dioxane (5 ml, 20 mmol, 4.0 M) and stirred for 1 hr at room temperature. The reaction mixture was evaporated to dryness to get crude (R)-ethyl 6-chloro-4-(pyrrolidin-3-ylamino)nicotinate (800 mg, 84%), which was used without further purification. LCMS m/z 270.4 (M+H); $^1$H NMR (400 MHz, DMSO-$d_6$) δ 9.30-9.60 (m, 2H) 8.54-8.62 (m, 1H) 8.15 (d, J=7.53 Hz, 1H) 6.96 (s, 1H) 4.38-4.49 (m, 1H) 4.25-4.37 (m, 2H) 3.45-3.60 (m, 2H) 3.05-3.39 (m, 3H) 2.36 (dq, J=13.87, 6.92 Hz, 1H) 1.85-2.00 (m, 1H) 1.26-1.38 (m, 3H).

Intermediate I-2

To a stirred solution of (R)-ethyl 6-chloro-4-(pyrrolidin-3-ylamino)nicotinate (0.8 g, 2.97 mmol) in DMF (10 mL) was added 2-chloro-5-fluoropyrimidine (0.393 g, 2.97 mmol) and Et$_3$N (2.067 mL, 14.83 mmol) and the stirring was continued for 13 hrs. The reaction mixture was diluted with 100 mL of ethyl acetate and washed with water (2×30 mL). The organic layer was dried over Na$_2$SO$_4$, filtered and concentrated in vacuo. The crude product was purified via column chromatography (10% ethyl acetate:pet ether) to provide (R)-ethyl 6-chloro-4-((1-(5-fluoropyrimidin-2-yl)pyrrolidin-3-yl)amino) nicotinate (0.8 g, 71% yield) as a white solid. LCMS m/z 366.1 (M+H); $^1$H NMR (400 MHz, CHLOROFORM-d) δ 8.68-8.72 (m, 1H) 8.42 (d, J=6.00 Hz, 1H) 8.21-8.26 (m, 2H) 6.62 (s, 1H) 4.29-4.37 (m, 2H) 4.18-4.27 (m, 1H) 3.96 (dd, J=11.51, 6.00 Hz, 1H) 3.72-3.81 (m, 2H) 3.60 (dd, J=11.51, 3.75 Hz, 1H) 2.43 (dtd, J=13.16, 7.80, 7.80, 5.75 Hz, 1H) 2.08-2.20 (m, 1H) 1.34-1.42 (m, 3H).

Intermediate I-3

2-((1R,4R)-4-aminocyclohexyl)propan-2-ol

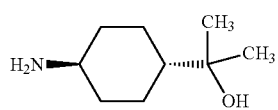

Intermediate I-3A: (1r,4r)-benzyl 4-(dibenzylamino)cyclohexanecarboxylate

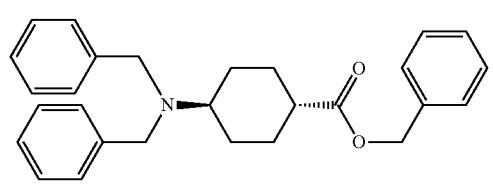

To a stirred suspension of (1R,4R)-4-aminocyclohexanecarboxylic acid hydrochloride (5.6 g, 31.2 mmol) in acetonitrile (120 mL) was added potassium carbonate (15.08 g, 109 mmol) and the mixture was heated to 80° C. for 1 hr. The reaction mixture was cooled to room temperature and a solution of benzyl bromide (12.98 mL, 109 mmol) in acetonitrile (30 mL) was added dropwise. The reaction mixture was heated to reflux for 16 hrs. The reaction mixture was allowed to cool to room temperature and it was filtered through celite and washed with acetonitrile. The filtrate was concentrated in vacuo to obtain (1R,4R)-benzyl 4-(dibenzylamino)cyclohexanecarboxylate which was used further without purification. LCMS m/z 414.8 (M+H); $^1$H NMR (400 MHz, CHLOROFORM-d) δ 7.53-7.10 (m, 15H), 5.08 (s, 2H), 3.62 (s, 4H), 2.64-2.41 (m, 1H), 2.33-2.17 (m, 1H), 2.12-1.86 (m, 4H), 1.47-1.24 (m, 4H).

Intermediate I-3B: 2-((1r,4r)-4-(dibenzylamino)cyclohexyl)propan-2-ol

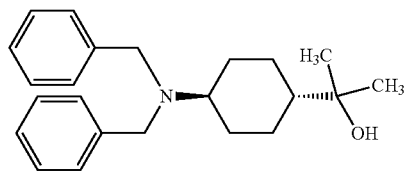

To a stirred solution of (1R,4R)-benzyl 4-(dibenzylamino)cyclohexanecarboxylate (12.8 g, 31.0 mmol) in dry tetrahydrofuran (130 mL) was added methylmagnesium bromide (36.1 mL, 108 mmol) dropwise at 0° C. for 20 min. The reaction mixture was allowed to reach room temperature and stirred for an additional 3 hrs. The reaction mixture was cooled to 0° C., quenched with saturated NH$_4$Cl solution and EtOAc was added. The layers were separated and the organic layer was washed with water followed by brine, dried over Na$_2$SO$_4$, filtered and concentrated in vacuo. The crude residue obtained was purified via column chromatography (10% ethylacetate/pet ether) to afford 2-((1R,4R)-4-(dibenzylamino)cyclohexyl)propan-2-ol (10.5 g, 86% yield). LCMS m/z 339 (M+H); $^1$H NMR (400 MHz, DMSO-$d_6$) δ 7.40-7.25 (m, 8H), 7.24-7.13 (m, 2H), 3.94 (s, 1H), 3.58 (s, 4H), 2.34 (d, J=3.0 Hz, 1H), 1.84 (t, J=13.3 Hz, 4H), 1.33 (d, J=12.0 Hz, 2H), 1.18-1.07 (m, 1H), 0.97 (s, 6H), 0.84 (d, J=12.5 Hz, 2H).

Intermediate I-3

2-((1R,4R)-4-(dibenzylamino)cyclohexyl)propan-2-ol (11.2 g, 33.2 mmol) was dissolved in methanol (120 mL). Pd/C (3.53 g, 3.32 mmol) was added and the reaction mixture was stirred for 16 hrs at 25° C. under a balloon of hydrogen. The reaction mixture was filtered through a bed of celite and the bed of celite was washed with methanol. The combined filtrate was concentrated in vacuo to afford 2-((1R,4R)-4-aminocyclohexyl) propan-2-ol (4.8 g, 92% yield) as an off-white solid. $^1$H NMR (300 MHz, DMSO-$d_6$) δ 3.97 (br. s., 1H), 2.47-2.34 (m, 1H), 1.85-1.62 (m, 4H), 1.15-0.82 (m, 10H).

Intermediate I-4

6-chloro-N-((1R,4R)-4-(cyclopropylcarbamoyl)cyclohexyl)-4-(oxetan-3-ylamino)nicotinamide

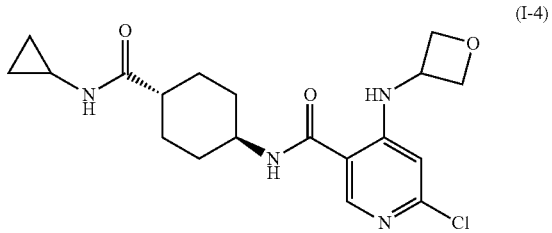 [SMILES: O=C(N[C@H]1CC[C@H](C(=O)NC2CC2)CC1)c1cnc(Cl)cc1NC1COC1]

(I-4)

Intermediate I-4A: (1r,4r)-4-((tert-butoxycarbonyl)amino)cyclohexanecarboxylic acid

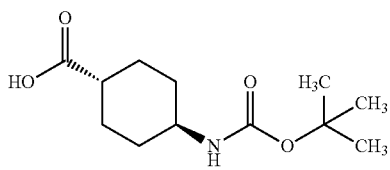

(I-4A)

(1R,4R)-4-aminocyclohexanecarboxylic acid (2 g, 13.97 mmol) was dissolved in tert-butanol (10 mL). A solution of sodium hydroxide (0.670 g, 16.76 mmol) in water was added to this mixture followed by di-tert-butyl dicarbonate (3.89 mL, 16.76 mmol). The reaction mixture was stirred at room temperature overnight. The reaction mixture was acidified with 6N HCl at 0° C. to get to pH 7. The mixture was extracted with EtOAc (3×30 mL). The combined organic extracts were dried over anhydrous Na$_2$SO$_4$, filtered and concentrated in vacuo to afford (1R,4R)-4-((tert-butoxycarbonyl)amino)cyclohexanecarboxylic acid which was used as is in the next reaction.

Intermediate I-4B: tert-butyl ((1r,4r)-4-(cyclopropylcarbamoyl)cyclohexyl)carbamate

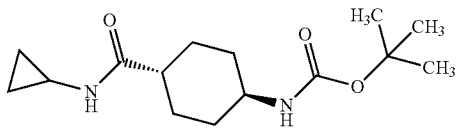

(I-4B)

To a solution of (1R,4R)-4-((tert-butoxycarbonyl)amino)cyclohexanecarboxylic acid (1.5 g, 6.17 mmol) in DCM (20 mL) at 0° C. was added HATU (2.344 g, 6.17 mmol), DIPEA (2.154 mL, 12.33 mmol) and cyclopropanamine (0.352 g, 6.17 mmol). The reaction mixture was stirred at room temperature overnight. The mixture was concentrated in vacuo. To the residue obtained was added a solution of saturated sodium bicarbonate (10 mL) and the aqueous layer was extracted with MTBE (3×30 mL). The combined organic extracts were dried over anhydrous sodium sulphate, filtered and concentrated in vacuo to afford tert-butyl ((1R,4R)-4-(cyclopropylcarbamoyl)cyclohexyl) carbamate which was used as is in the next reaction.

Intermediate I-4C: (1r,4r)-4-amino-N-cyclopropylcyclohexanecarboxamide

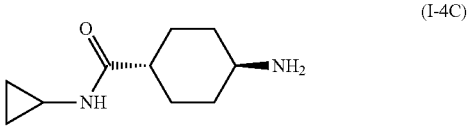 [SMILES: N[C@H]1CC[C@H](C(=O)NC2CC2)CC1]

(I-4C)

To a solution of tert-butyl ((1R,4R)-4-(cyclopropylcarbamoyl)cyclohexyl) carbamate (1.4 g, 4.96 mmol) in methanol (10 mL) at 0° C. was added HCl in dioxane (15 mL, 60.0 mmol, 4M). The reaction mixture was stirred at room temperature overnight. The reaction mixture was concentrated in vacuo. The crude residue was triturated with diethyl ether (5 mL) and dried under reduced pressure. This procedure afforded 6-chloro-4-(oxetan-3-ylamino)nicotinic acid which was used as is in the next reaction.

Intermediate I-4

To a stirred solution of 6-chloro-4-(oxetan-3-ylamino)nicotinic acid (0.25 g, 1.093 mmol) in DMF (10 mL) at 0° C. was added DIPEA (0.955 mL, 5.47 mmol) and HATU (0.832 g, 2.187 mmol) followed by (1R,4R)-4-amino-N-cyclopropylcyclohexane carboxamide (0.199 g, 1.093 mmol). The reaction mixture was stirred at 25° C. for 16 hrs. The reaction mixture was diluted with ethyl acetate, washed with water and brine, dried over anhydrous Na$_2$SO$_4$, filtered and concentrated in vacuo. The crude residue was purified by column chromatography (3.5% MeOH/Chloroform) to afford 6-chloro-N-((1R,4R)-4-(cyclopropylcarbamoyl)cyclohexyl)-4-(oxetan-3-ylamino)nicotinamide (0.23 g, 45% yield) as an off-white solid. LCMS m/z 393.1 (M+H); $^1$H NMR (400 MHz, DMSO-d$_6$) δ 0.32-0.40 (m, 2H), 0.55-0.63 (m, 2H), 1.30-1.50 (m, 4H), 1.74 (d, J=11.04 Hz, 2H), 1.89 (d, J=9.04 Hz, 2H), 1.94-2.05 (m, 1H), 2.60 (tq, J=7.47, 3.89 Hz, 1H), 2.86-2.93 (m, 1H), 3.68-3.78 (m, 1H), 4.43 (t, J=6.02 Hz, 2H), 4.72 (dq, J=12.86, 6.09 Hz, 1H), 4.85-4.92 (m, 2H), 6.46-6.51 (m, 1H), 7.77 (d, J=4.02 Hz, 1H), 8.34-8.42 (m, 2H), 8.89 (d, J=6.53 Hz, 1H).

Intermediate I-5

Ethyl 6-chloro-4-(((3R,4S)-4-fluorotetrahydrofuran-3-yl)amino)nicotinate

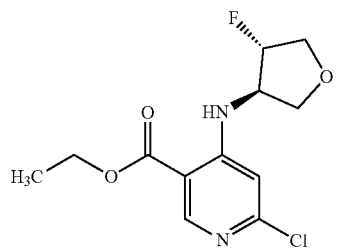

(I-5)

To a stirred solution of ethyl 6-chloro-4-(((3R,4S)-4-hydroxytetrahydrofuran-3-yl)amino)nicotinate (1 g, 3.49 mmol) (trans racemate) in DCM (10 mL) at −78° C. was added DAST (0.922 mL, 6.98 mmol) and the reaction mixture was allowed to warm up to 0° C. over a period of 1 hr. The reaction mixture was poured dropwise into a saturated aqueous solution of NaHCO$_3$ at 0° C. The organic layer was separated and the aqueous layer was extracted with DCM (2×50 mL). The combined organic extracts were dried over Na$_2$SO$_4$, filtered and concentrated in vacuo. The crude product was purified via column chromatography (0-15% ethyl acetate/pet ether) to afford ethyl 6-chloro-4-(((3R,4S)-4-fluorotetrahydrofuran-3-yl)amino)nicotinate as the trans racemate (730 mg, 63% yield). LCMS m/z 289 (M+H); $^1$H NMR (400 MHz, DMSO-d$_6$) δ 8.55-8.64 (m, 1H), 8.08 (d, J=7.03 Hz, 1H), 6.95 (s, 1H), 5.13-5.34 (m, 1H), 4.46 (ddd, J=6.53, 9.79, 16.31 Hz, 1H), 4.32 (q, J=7.03 Hz, 2H), 4.12-4.23 (m, 1H), 3.87-4.08 (m, 2H), 3.73 (dd, J=3.51, 9.54 Hz, 1H), 1.32 (t, J=7.03 Hz, 3H).

Intermediate I-6

1-(oxetan-3-yl)-1H-pyrazol-4-amine

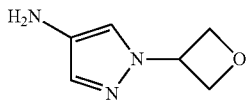

(I-6)

Intermediate I-6A:
4-nitro-1-(oxetan-3-yl)-1H-pyrazole

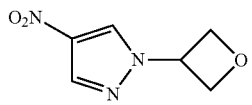

(I-6A)

To a stirred solution of 4-nitro-1H-pyrazole (1.0 g, 8.84 mmol) and oxetan-3-ol (0.655 g, 8.84 mmol) in tetrahydrofuran (20 mL) was added triphenylphosphine (2.78 g, 10.61 mmol) followed by di-tert-butyl azodicarboxylate (2.65 g, 11.50 mmol) at room temperature. The reaction mixture was stirred at room temperature overnight. The reaction mixture was concentrated in vacuo. The crude compound obtained was purified via column chromatography (60% ethyl acetate/pet ether) to afford 4-nitro-1-(oxetan-3-yl)-1H-pyrazole (1.2 g, 80% yield). $^1$H NMR (400 MHz, DMSO-d$_6$) δ 9.05-9.01 (s, 1H), 8.43-8.39 (s, 1H), 5.63 (m, 2H), 4.98-4.85 (m, 2H), 4.61 (m, 1H).

Intermediate I-6

To a stirred solution of 4-nitro-1-(oxetan-3-yl)-1H-pyrazole (1.2 g, 7.09 mmol) in MeOH (15 mL) was added Pd/C (0.755 g, 0.709 mmol). The reaction mixture was put under an atmosphere of hydrogen (balloon) and stirred at room temperature overnight. The reaction mixture was filtered through a bed of celite which was washed with methanol. The filtrate was concentrated in vacuo to afford 1-(oxetan-3-yl)-1H-pyrazol-4-amine as an oil. The crude compound was used as is in the next reaction. $^1$H NMR (300 MHz, DMSO-d$_6$) δ 7.17 (s, 1H), 7.04 (s, 1H), 5.36 (q, J=7.1 Hz, 1H), 4.91-4.75 (m, 4H), 3.89 (br. s., 2H).

Intermediate I-7

2-((1S,3S)-3-aminocyclopentyl)propan-2-ol, HCl

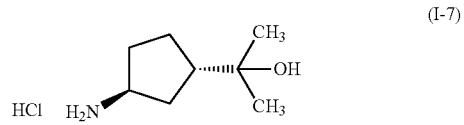

(I-7)

Intermediate I-7A: tert-butyl ((1S,3S)-3-(2-hydroxypropan-2-yl)cyclopentyl)carbamate

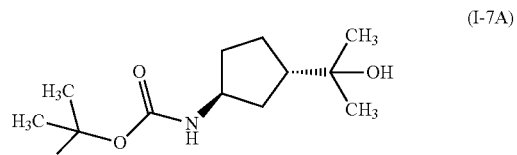

(I-7A)

To a solution of (1S,3S)-methyl 3-((tert-butoxycarbonyl)amino)cyclopentane carboxylate (600 mg, 2.466 mmol) in THF (15 mL) at −78° C. was added 3M methyllithium in diethoxymethane (3.29 mL, 9.86 mmol) dropwise. After completion of the addition, the reaction mixture was allowed to stir at room temperature for 3 h. The mixture was cooled to 0° C. and quenched with methanol. The mixture was concentrated in vacuo to afford tert-butyl ((1S,3S)-3-(2-hydroxypropan-2-yl)cyclopentyl)carbamate (550 mg, 82% yield) as a white solid. LCMS m/z 487.3 (M+H)$^+$.

Intermediate I-7

To a stirred solution of tert-butyl ((1S,3S)-3-(2-hydroxypropan-2-yl)cyclopentyl) carbamate (550 mg, 2.034 mmol) in dioxane (5 mL) at room temperature was added 4N HCl in dioxane (2.54 mL, 10.17 mmol). After 72 hrs, the reaction mixture was concentrated in vacuo from methylene chloride (5×) to provide 2-((1S,3S)-3-aminocyclopentyl)propan-2-ol, HCl (300 mg, 74% yield) as an oil. LCMS m/z 144.2 (M+H)$^+$.

Intermediate I-8

1-(Aminomethyl)cyclobutanol

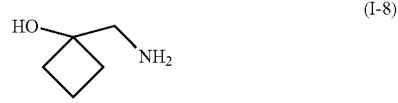

(I-8)

Intermediate I-8A:
1-hydroxycyclobutanecarbonitrile

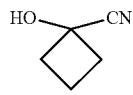
(I-8A)

A solution of cyclobutanone (5.000 g, 71.3 mmol) in CH$_2$Cl$_2$ (50 mL) was cooled to 0° C. To this solution was added TMS-CN (11.48 mL, 86 mmol) and zinc iodide (0.023 g, 0.071 mmol). The reaction mixture was allowed to warm up to room temperature and stirred for 3 hrs. The reaction mixture was quenched by the addition of water (20 mL) and was extracted with DCM (2×50 mL). The combined organic extracts were washed with water (50 mL), brine (20 mL), dried over Na$_2$SO$_4$, filtered and concentrated in vacuo. The crude product was purified via column chromatography (10% ethyl acetate/pet ether) to provide 1-hydroxycyclobutanecarbonitrile (2.8 g, 40% yield) as a colorless oil. $^1$H NMR (400 MHz, DMSO-d$_6$) δ 2.76 (s, 1H) 2.62-2.69 (m, 2H) 2.30-2.38 (m, 2H) 1.94-2.01 (m, 2H).

Intermediate I-8

To a solution of 1-hydroxycyclobutanecarbonitrile (2.0 g, 20.59 mmol) in dry THF (40 mL) at 0° C. was added lithium aluminum hydride (15.45 mL, 30.9 mmol, 2.0M solution) dropwise. The reaction mixture was allowed to warm up to room temperature over 1 h and the stirring was continued for 16 h. The reaction mixture was quenched with water (2 mL), 2M NaOH solution (5 mL) and water (1 mL) and stirred at room temperature for 1 hrs. The mixture was filtered through celite and washed with THF. The filtrate was dried over Na$_2$SO$_4$, filtered and concentrated in vacuo. This procedure afforded 1-(aminomethyl)cyclobutanol which was used as is in the next reaction. $^1$H NMR (400 MHz, DMSO-d$_6$) δ 4.90 (s, 1H) 1.80-1.94 (m, 6H) 1.55-1.60 (m, 2H) 1.37-1.40 (m, 2H).

Intermediate I-9

1-(tetrahydro-2H-pyran-4-yl)-1H-pyrazol-4-amine

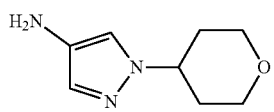
(I-9)

Intermediate I-9A: 4-nitro-1-(tetrahydro-2H-pyran-4-yl)-1H-pyrazole

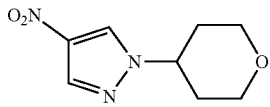
(I-9A)

To a stirred solution of 4-nitro-1H-pyrazole (1.0 g, 8.84 mmol) and tetrahydro-2H-pyran-4-ol (0.903 g, 8.84 mmol) in tetrahydrofuran (20 mL) was added triphenylphosphine (2.78 g, 10.61 mmol) followed by di-tert-butyl azodicarboxylate (2.65 g, 11.50 mmol) at room temperature. The reaction mixture was stirred at room temperature overnight. The reaction mixture was concentrated in vacuo and the residue obtained was purified via column chromatography (60% ethyl acetate/pet ether) to afford 4-nitro-1-(tetrahydro-2H-pyran-4-yl)-1H-pyrazole (1.3 g, 75% yield). LCMS m/z 198.1 (M+H). $^1$H NMR (400 MHz, DMSO-d$_6$) δ 8.95 (s, 1H), 8.29 (s, 1H), 7.67-7.59 (m, 4H), 7.59-7.50 (m, 4H), 4.52 (tt, J=10.5, 5.3 Hz, 1H).

Intermediate I-9

To a stirred solution of 4-nitro-1-(tetrahydro-2H-pyran-4-yl)-1H-pyrazole (1.2 g, 6.09 mmol) in MeOH (25 mL) was added Pd/C (0.648 g, 0.609 mmol) at room temperature. The reaction mass was put under an atmosphere of hydrogen (balloon) and stirred at room temperature overnight. The reaction mixture was filtered through a bed of celite which was washed with methanol. The filtrate was concentrated in vacuo to afford 1-(tetrahydro-2H-pyran-4-yl)-1H-pyrazol-4-amine which was used as is in the next reaction. LCMS m/z 168.0 (M+H).

Intermediate I-10

(R)-2-fluoro-3-deutero-methoxypropan-1-amine

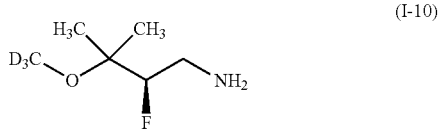
(I-10)

Intermediate I-10A: (R)-4-(dibenzylamino)-3-fluoro-2-methylbutan-2-ol

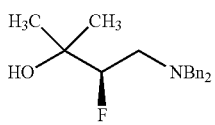
(I-10A)

(R)-methyl 3-(dibenzylamino)-2-fluoropropanoate (2.0 g, 6.64 mmol) was dissolved in THF (20 mL) and the solution was cooled to 0° C. Next, 1.4M methyl magnesium bromide (10.43 mL, 14.60 mmol) was added dropwise to this solution over 5 minutes. The reaction mixture was allowed to warm up to room temperature and stirred for an additional 2 hrs. The reaction mixture was then cooled to 0° C. and quenched with a saturated ammonium chloride solution. The aqueous layer was extracted with methylene chloride, dried over Na$_2$SO$_4$, filtered and concentrated in vacuo. This procedure afforded (R)-4-(dibenzylamino)-3-fluoro-2-methylbutan-2-ol (1.8 g, 80% yield). LCMS m/z 301.5 (M+H)$^+$.

Intermediate I-10B: (R)-4-(dibenzylamino)-3-fluoro-2-trideuteromethylbutan-2-ol

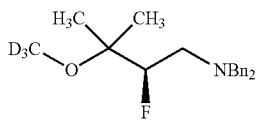

(I-10B)

(R)-4-(dibenzylamino)-3-fluoro-2-methylbutan-2-ol (900 mg, 2.99 mmol) was dissolved in THF (10 mL) and DMF (10 mL). The solution obtained was put under nitrogen and cooled to 0° C. NaH (143 mg, 3.58 mmol) was added and the mixture stirred at 0° C. for 10 min. Deutero-iodomethane (0.185 mL, 2.99 mmol) was then added and the mixture was stirred at 0° C. for 1 hrs. Another 0.5 equiv. of NaH (60 mg, 1.50 mmol) and deutero-iodomethane (0.09 mL, 1.50 mmol) were added. After 1 hrs, another 0.5 equiv. of NaH (60 mg, 1.50 mmol) and deutero-iodomethane (0.09 mL, 1.50 mmol) were added. The reaction was carefully quenched with the dropwise addition of water. The mixture was diluted with ethyl acetate and washed with 10% LiCl (2×), saturated sodium bicarbonate (1×) and 10% LiCl (1×). The organic layer was dried over Na₂SO₄, filtered and concentrated in vacuo. This procedure afforded (R)—N,N-dibenzyl-2-fluoro-3-deutero-methoxypropan-1-amine (900 mg, 85%) of a colorless oil. LCMS m/z 319.4 (M+H)⁺.

Intermediate I-10

Under a nitrogen atmosphere, a Parr bottle was carefully charged with 10% Pd/C (135 mg, 0.127 mmol) and methanol (10 mL). The vessel was charged with a solution of (R)—N,N-dibenzyl-2-fluoro-3-deutero-methoxypropan-1-amine (900 mg, 2.54 mmol) in methanol (10 mL). A small amount of DCM was added to improve solubility. The mixture was hydrogenated under a pressure of 50 psi for 16 hours. The mixture was then degassed and filtered under nitrogen through fiberglass filter paper. The filter cake was thoroughly rinsed with methanol (25 mL) and the filtrate was concentrated in vacuo to provide (R)-2-fluoro-3-deutero-methoxypropan-1-amine (350 mg, 90% yield) as a colorless oil which was used as is in the next reaction.

Intermediate I-11

2-((1R,3R)-3-Aminocyclobutyl)propan-2-ol, HCl

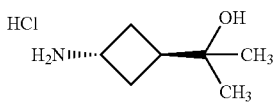

(I-11)

Intermediate I-11A: tert-butyl ((1r,3r)-3-(2-hydroxypropan-2-yl)cyclobutyl)carbamate

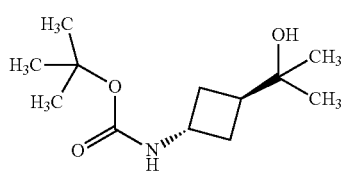

(I-11A)

(1R,3R)-methyl 3-((tert-butoxycarbonyl)amino)cyclobutanecarboxylate (600 mg, 2.224 mmol) was dissolved in THF (15 mL) and the solution was cooled to −78° C. Next, 3M methyl lithium in diethoxymethane (2.97 mL, 8.90 mmol) was added dropwise. After completion of the addition, the reaction mixture was stirred at 0° C. for 2 hrs, then at room temperature for 16 hrs. The mixture was quenched with methanol and concentrated in vacuo. This procedure afforded tert-butyl ((1R,3R)-3-(2-hydroxypropan-2-yl)cyclobutyl)carbamate (500 mg, 74% yield) as a tan solid. LCMS m/z 215.0 (M+H)⁺.

Intermediate I-11

To a stirred solution of tert-butyl ((1R,3R)-3-(2-hydroxypropan-2-yl)cyclobutyl) carbamate (500 mg, 1.635 mmol) in dioxane (5 mL) at room temperature was added 4N HCl in dioxane (2.044 mL, 8.18 mmol). After 20 h, the reaction mixture was concentrated in vacuo from methylene chloride (5×) to provide 2-((1R,3R)-3-aminocyclobutyl)propan-2-ol, HCl (250 mg, 0.755 mmol, 46.1% yield).

Intermediate I-12

(S)-Ethyl 6-chloro-4-((2-hydroxypropyl)amino)nicotinate

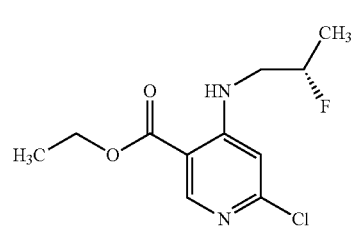

(I-12)

Intermediate I-12A: (S)-ethyl 6-chloro-4-((2-hydroxypropyl)amino)nicotinate

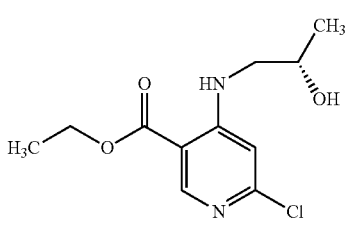

(I-12A)

To a solution of ethyl 4,6-dichloronicotinate (500 mg, 2.272 mmol) and (S)-1-aminopropan-2-ol (171 mg, 2.272 mmol) in DMF (10 mL) was added DIPEA (1.191 mL, 6.82 mmol) and the reaction mixture was heated to 120° C. After 20 hours, the reaction mixture was diluted with ethyl acetate and rinsed with 10% LiCl (2×), saturated sodium bicarbonate (1×) and 10% LiCl (1×). The organic layer was dried over Na₂SO₄, filtered and concentrated in vacuo to provide (S)-ethyl 6-chloro-4-((2-hydroxypropyl)amino) nicotinate (600 mg, 77% yield) as an amber oil. LCMS m/z 259.0 (M+H)⁺.

Intermediate I-12

A solution of (S)-ethyl 6-chloro-4-((2-hydroxypropyl)amino)nicotinate (600 mg, 1.739 mmol) in DCM (10 mL) was cooled to −40° C. DAST (0.460 mL, 3.48 mmol) was added dropwise over 5 min. The mixture was allowed to warm up to room temperature. The reaction mixture was then rinsed with 2M potassium phosphate dibasic and brine. The organic layer was dried over $Na_2SO_4$, filtered and concentrated in vacuo to provide (S)-ethyl 6-chloro-4-((2-hydroxypropyl)amino)nicotinate (450 mg, 84% yield) as an amber oil. LCMS m/z 261.1 (M+H)$^+$.

Intermediate I-13

3-amino-1-morpholinopropan-1-one

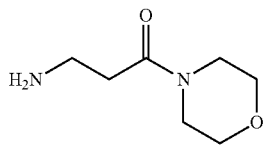
(I-13)

Intermediate I-13A: ethyl 3-((tert-butoxycarbonyl)amino)propanoate

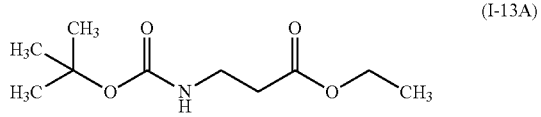
(I-13A)

To a stirred solution of ethyl 3-aminopropanoate (10 g, 85 mmol) in DCM (10 mL) at 0° C. was added triethylamine (35.7 mL, 256 mmol) followed by di-tert-butyl dicarbonate (21.80 mL, 94 mmol). The reaction mixture was allowed to warm up to room temperature and the stirring was continued for 15 hrs. The reaction mixture was diluted with DCM (15 mL), washed with water and 10% $NaHCO_3$. The organic layer was dried over $Na_2SO_4$, filtered and concentrated in vacuo. The crude residue obtained was purified via column chromatography using ethyl acetate/pet ether to afford ethyl 3-((tert-butoxycarbonyl)amino)propanoate (15 g, 81% yield) as a colorless syrup. $^1$H NMR (400 MHz, $CDCl_3$) δ 5.04 (s, 1H), 4.10-4.21 (m, 2H), 3.38-3.44 (m, 2H), 2.51-2.55 (m, 2H), 1.46-1.49 (m, 9H), 1.25-1.31 (m, 3H).

Intermediate I-13B: 3-((tert-butoxycarbonyl)amino)propanoic acid

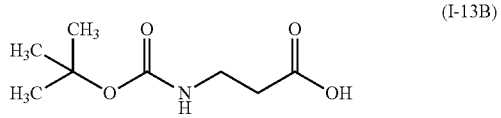
(I-13B)

Ethyl 3-((tert-butoxycarbonyl)amino)propanoate (1.4, 6.44 mmol) was dissolved in ethanol (10 mL) and a solution of lithium hydroxide (0.154 g, 6.44 mmol) in water (10 mL) was added. The reaction mixture was stirred at room temperature for 5 hrs. The reaction mixture was concentrated in vacuo to provide a crude residue which was dissolved in water and washed with DCM. The aqueous layer was neutralized with 6N HCl and the solid obtained was filtered and dried under vacuum to afford 3-((tert-butoxycarbonyl)amino) propanoic acid (1.1 g, 90% yield) as a white solid. LCMS m/z 188.2 (M–H); $^1$H NMR (400 MHz, MeOD) δ 3.29 (t, J=11.20 Hz, 2H), 2.47 (t, J=13.60 Hz, 2H), 1.43 (s, 9H).

Intermediate I-13C: tert-butyl (3-morpholino-3-oxopropyl)carbamate

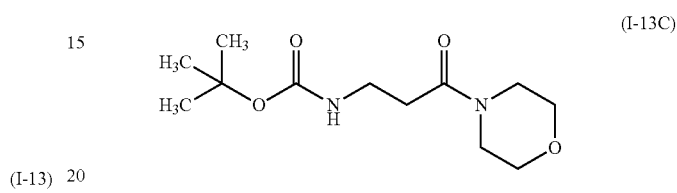
(I-13C)

To a stirred solution of 3-((tert-butoxycarbonyl)amino) propanoic acid (0.6 g, 3.17 mmol) in DMF (5.0 mL) was added morpholine (0.276 g, 3.17 mmol), triethylamine (0.464 mL, 3.33 mmol) and HATU (1.206 g, 3.17 mmol). The reaction mixture was stirred at room temperature for 2 hrs. The reaction mixture was concentrated in vacuo to provide a crude residue, which was dissolved in ethyl acetate and washed with water (5 mL) and 10% $NaHCO_3$ (10 mL). The organic extract was dried over $Na_2SO_4$, filtered and concentrated in vacuo. The crude residue obtained was purified via column chromatography using MeOH/$CHCl_3$ to afford tert-butyl (3-morpholino-3-oxopropyl) carbamate (0.77 g, 94% yield) as a white solid. LCMS m/z 259.2 (M+H); $^1$H NMR (400 MHz, MeOD) δ 3.52-3.63 (m, 4H), 3.64-3.69 (m, 4H), 3.11-3.15 (m, 2H), 2.55-2.63 (m, 2H), 1.43 (m, 9H).

Intermediate I-13

Tert-butyl (3-morpholino-3-oxopropyl)carbamate (0.8 g, 3.10 mmol) was dissolved in DCM (5.0 mL) and cooled to 0° C. TFA (3.58 mL, 46.5 mmol) was then added and the reaction mixture was allowed to warm to room temperature and stirred for an additional 2 hrs. The reaction mixture was concentrated in vacuo to afford 3-amino-1-morpholinopropan-1-one (0.48 g, 98% yield) as a TFA salt. LCMS m/z 159.2 (M+H); $^1$H NMR (400 MHz, MeOD) δ 3.45-3.75 (m, 8H), 3.19-3.24 (m, 2H), 2.75-2.82 (m, 2H).

Intermediate I-14

6-chloro-4-(isopropylamino)-N-(2-oxo-2-(2-oxa-7-azaspiro[3.5]nonan-7-yl)ethyl)nicotinamide

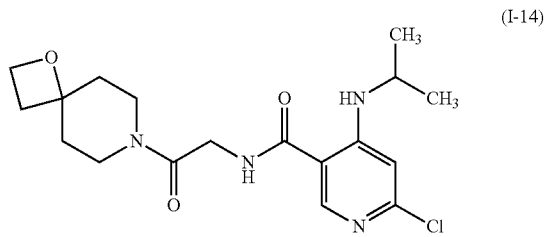 [SMILES: CC(C)Nc1cc(Cl)ncc1C(=O)NCC(=O)N1CCC2(CCO2)CC1]
(I-14)

Intermediate I-14A: tert-butyl 1-oxa-7-azaspiro[3.5]nonane-7-carboxylate

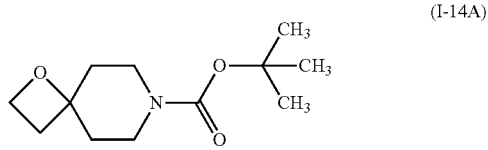 [SMILES: CC(C)(C)OC(=O)N1CCC2(CCO2)CC1]

To a solution of trimethylsulfoxonium iodide (13.81 g, 62.7 mmol) in t-BuOH (20 mL) was added potassium tert-butoxide (7.04 g, 62.7 mmol) and the reaction mixture was heated to 50° C. for 1 hr. To this mixture was added a solution of tert-butyl 4-oxopiperidine-1-carboxylate (5.0 g, 25.09 mmol) in t-BuOH (20 mL) and the reaction mixture was heated to 50° C. for 48 hrs. The reaction mixture was quenched with 1 N HCl. The aqueous layer was extracted with ethyl acetate, dried over $Na_2SO_4$, filtered and concentrated in vacuo. The crude product obtained was purified via column chromatography using 15% ethyl acetate/pet ether to afford tert-butyl 1-oxa-7-azaspiro[3.5]nonane-7-carboxylate (2.3 g, 40% yield). LCMS m/z 128.2 (M-Boc); $^1$H NMR (400 MHz, $CDCl_3$) δ 4.51-4.55 (m, 2H), 3.40-3.42 (m, 4H), 2.36-2.40 (m, 2H), 1.86-1.90 (m, 2H), 1.73-1.78 (m, 2H), 1.44-1.46 (m, 9H).

Intermediate I-14B: 1-oxa-7-azaspiro[3.5]nonane

A solution of tert-butyl 1-oxa-7-azaspiro[3.5]nonane-7-carboxylate (2.0 g, 8.80 mmol) in DCM (2.0 mL) was cooled to 0° C. TFA (0.452 mL, 5.87 mmol) was then added and the reaction mixture was stirred at 25° C. for 1 hr. The reaction mixture was concentrated in vacuo to afford 1-oxa-7-azaspiro[3.5]nonane (0.72 g, 97% yield) as a TFA salt and a brown liquid. $^1$H NMR (400 MHz, MeOD) δ 5.62 (s, 1H), 4.51-4.60 (m, 2H), 3.64-3.69 (m, 2H), 3.20-3.30 (m, 2H), 3.53-3.56 (m, 2H), 2.38-2.40 (m, 2H), 1.76-1.83 (m, 2H).

Intermediate I-14C: methyl 2-(6-chloro-4-(isopropylamino)nicotinamido)acetate

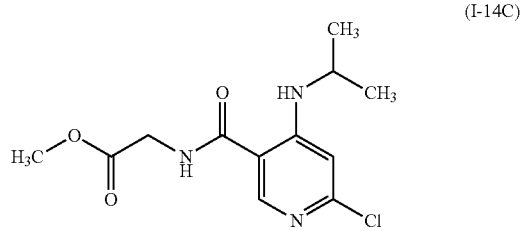 [SMILES: COC(=O)CNC(=O)c1cnc(Cl)cc1NC(C)C]

To a solution of 6-chloro-4-(isopropylamino)nicotinic acid (1.0 g, 4.66 mmol) and methyl 2-aminoacetate (0.415 g, 4.66 mmol) in DMF (10 mL) was added triethylamine (0.682 mL, 4.89 mmol) and HATU (1.771 g, 4.66 mmol). The reaction mixture was stirred at room temperature for 2 hrs. The reaction mixture was concentrated in vacuo. The residue obtained was dissolved in ethyl acetate, washed with water (5 mL) and 10% $NaHCO_3$ (10 mL). The organic layer was dried over $Na_2SO_4$, filtered and concentrated in vacuo. The crude product was purified via column chromatography using MeOH/$CHCl_3$ to afford methyl 2-(6-chloro-4-(isopropylamino)nicotinamido)acetate (0.72 g, 54% yield) as a yellow solid. LCMS m/z 286.0 (M+H); $^1$H NMR (400 MHz, MeOD) δ 8.30 (s, 1H), 6.72 (s, 1H), 4.09 (s, 2H), 3.75 (s, 3H), 3.74 (m, 1H), 1.22-1.22 (m, 6H).

Intermediate I-14D: 2-(6-chloro-4-(isopropylamino)nicotinamido)acetic acid

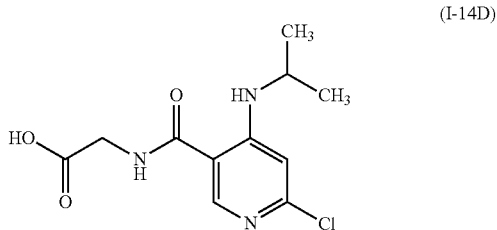 [SMILES: CC(C)Nc1cc(Cl)ncc1C(=O)NCC(=O)O]

To a solution of methyl 2-(6-chloro-4-(isopropylamino)nicotinamido)acetate (1.0 g, 3.50 mmol) in ethanol (10 mL) was added a solution of lithium hydroxide (0.251 g, 10.50 mmol) in water (10 mL) and the reaction mixture was stirred at room temperature for 3 h. The reaction mixture was concentrated in vacuo. The crude residue obtained was dissolved in water and washed with DCM. The aqueous layer was neutralized using 6N HCl and the solid obtained was filtered and dried under vacuum to afford 2-(6-chloro-4-(isopropylamino)nicotinamido)acetic acid (0.55 g, 58% yield) as a white solid. LCMS m/z 272.0 (M+H).

Intermediate I-14

To a stirred solution of 2-(6-chloro-4-(isopropylamino)nicotinamido)acetic acid (0.3 g, 1.104 mmol) and 1-oxa-7-azaspiro[3.5]nonane (0.140 g, 1.104 mmol) in DMF (2.0 mL) was added DIPEA (0.771 mL, 4.42 mmol) and HATU (0.672 g, 1.767 mmol). The reaction mixture was stirred at room temperature for 2 h. The mixture was then concentrated in vacuo. The crude residue obtained was dissolved in ethyl acetate, washed with water (5 mL) and 10% $NaHCO_3$ (10 mL). The organic layer was dried over $Na_2SO_4$, filtered and concentrated in vacuo. The crude product obtained was purified via column chromatography using 3% MeOH/$CHCl_3$ to obtain 6-chloro-4-(isopropylamino)-N-(2-oxo-2-(2-oxa-7-azaspiro[3.5]nonan-7-yl)ethyl)nicotinamide (0.41 g, 97% yield) as a pale yellow solid. LCMS m/z 381 (M+H); $^1$H NMR (400 MHz, MeOD) δ 8.74-8.76 (m, 1H), 8.43 (s, 1H), 6.75 (s, 1H), 5.53 (s, 2H), 4.30 (d, J=4.00 Hz, 1H), 4.19-4.19 (m, 1H), 4.05-4.10 (m, 2H), 3.65-3.80 (m, 6H), 2.27-2.29 (m, 2H), 1.23-1.28 (m, 6H).

Intermediate I-15

(R)-6-chloro-4-((1-(2,2-difluoroethyl)-1H-pyrazol-4-yl)amino)-N-(2-fluoro-3-hydroxy-3-methylbutyl)nicotinamide

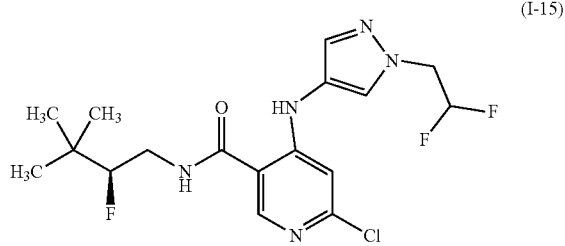 [SMILES: CC(C)(C)[C@H](F)CNC(=O)c1cnc(Cl)cc1Nc1cnn(CC(F)F)c1]

(I-15)

Intermediate I-15A: 1-(2,2-difluoroethyl)-4-nitro-1H-pyrazole

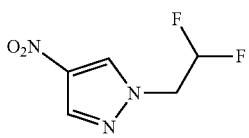

(I-15A)

To a stirred solution of 4-nitro-1H-pyrazole (5 g, 44.2 mmol) in DMF (60 mL) was added K$_2$CO$_3$ (12.22 g, 88 mmol) over a period of 5 minutes. The reaction mixture was stirred at ambient temperature for 10 minutes. 1,1-difluoro-2-iodoethane (11.03 g, 57.5 mmol) was added and the reaction mixture was stirred for 12 hrs at 90° C. The reaction mixture was then partitioned between water (150 mL) and EtOAc (150 mL) and the aqueous layer was extracted with EtOAc (2×100 mL). The combined EtOAc extracts were washed with water (2×100 mL) and brine (100 mL), dried over sodium sulfate, filtered and concentrated in vacuo. The crude product was purified via column chromatography to afford 1-(2,2-difluoroethyl)-4-nitro-1H-pyrazole (5.2 g, 60% yield) as a tan solid. $^1$H NMR (400 MHz, DMSO-d$_6$) δ 8.95 (s, 1H), 8.35 (s, 1H), 6.45 (m, 1H), 4.75 (td, J=15, 3.5 Hz, 2H).

Intermediate I-15B: 1-(2,2-difluoroethyl)-1H-pyrazol-4-amine

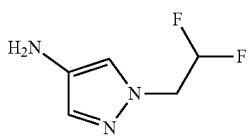

(I-15B)

Under a nitrogen atmosphere, a Parr bottle was carefully charged with 10% Pd on carbon (1.56 g, 1.47 mmol) and the catalyst was carefully wetted with MeOH (50 mL). The vessel was charged with a solution of 1-(2,2-difluoroethyl)-4-nitro-1H-pyrazole (5.2 g, 29.4 mmol) and the mixture was degassed by evacuating the vessel under vacuum and repressurizing with hydrogen. The mixture was hydrogenated at 15 psi for 6 hours. The mixture was degassed, and the reaction mixture was filtered under nitrogen through fiberglass filter paper. The filter cake was thoroughly rinsed with methanol (200 mL total rinse volume), and the combined filtrate and rinsings were concentrated in vacuo to obtain 1-(2,2-difluoroethyl)-4-amino-1H-pyrazole (5.2 g, 62% yield). $^1$H NMR (400 MHz, DMSO-d$_6$) δ 7.07 (s, 1H), 6.99 (d, J=0.9 Hz, 1H), 6.38-6.10 (m, 1H), 4.40 (td, J=15.1, 4.0 Hz, 2H), 3.18 (m, 2H).

Intermediate I-15C: ethyl 6-chloro-4-((1-(2,2-difluoroethyl)-1H-pyrazol-4-yl)amino) nicotinate

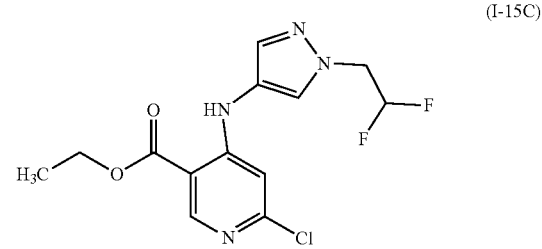 [SMILES: CCOC(=O)c1cnc(Cl)cc1Nc1cnn(CC(F)F)c1]

(I-15C)

A solution of ethyl 4,6-dichloronicotinate (0.6 g, 2.73 mmol), 1-(2,2-difluoroethyl)-1H-pyrazol-4-amine (0.401 g, 2.73 mmol), and DIPEA (2.381 mL, 13.63 mmol) in DMA (12 mL) was heated at 100° C. overnight. The reaction mixture was concentrated to remove DMA and water was added. The product was extracted with ethyl acetate (3×) and the combined extracts were washed with water and brine. The extracts were dried over anhydrous Na$_2$SO$_4$, filtered, and concentrated in vacuo to obtain a brown liquid. This crude product was purified via column chromatography to afford ethyl 6-chloro-4-((1-(2,2-difluoroethyl)-1H-pyrazol-4-yl)amino)nicotinate (0.78 g, 86% yield). LCMS m/z 331.0 (M+H); $^1$H NMR (300 MHz, DMSO-d$_6$) δ 9.29 (s, 1H), 8.63 (s, 1H), 8.02 (s, 1H), 7.66 (s, 1H), 6.67 (s, 1H), 6.61-6.19 (m, 1H), 4.64 (td, J=15.2, 3.6 Hz, 2H), 4.36 (q, J=7.2 Hz, 2H), 1.41-1.29 (m, 3H).

Intermediate I-15D: 6-chloro-4-((1-(2,2-difluoroethyl)-1H-pyrazol-4-yl)amino)nicotinic acid

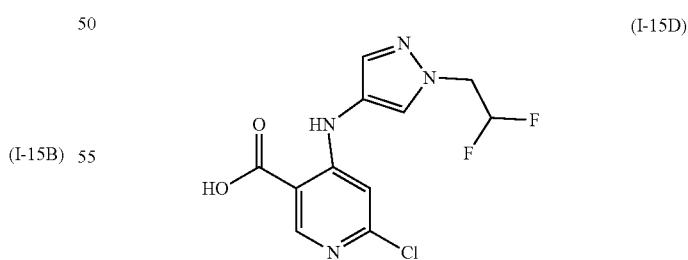

(I-15D)

To a solution of ethyl 6-chloro-4-((1-(2,2-difluoroethyl)-1H-pyrazol-4-yl)amino) nicotinate (0.4 g, 1.21 mmol) in ethanol (10 mL) and water (4 mL) was added LiOH (0.09 g, 3.6 mmol). The reaction mixture was stirred at room temperature overnight. The reaction mixture was concentrated in vacuo to remove ethanol and the residue was acidified with 1.5N HCl. The white solid formed was collected to afford 6-chloro-4-((1-(2,2-difluoroethyl)-1H-pyrazol-4-yl)amino)nicotinic acid (0.35 g, 96% yield) which was used as is in the next reaction. LCMS m/z 303.0 (M+H).

Intermediate I-15

To a solution of 6-chloro-4-((1-(2,2-difluoroethyl)-1H-pyrazol-4-yl)amino) nicotinic acid (0.4 g, 1.322 mmol) in DMF (8 mL), was added HATU (0.75 g, 2 mmol), DIPEA (1.15 mL, 6.6 mmol), and (R)-4-amino-3-fluoro-2-methylbutan-2-ol (0.19 g, 1.6 mmol). The reaction mixture was stirred at room temperature overnight. Sodium bicarbonate was added and the reaction mixture was extracted with ethyl acetate (3×). The combined organic extracts were washed with water and brine then dried over anhydrous $Na_2SO_4$, filtered and concentrated in vacuo. The brown liquid obtained was purified via column chromatography to afford (R)-6-chloro-4-((1-(2,2-difluoroethyl)-1H-pyrazol-4-yl)amino)-N-(2-fluoro-3-hydroxy-3-methylbutyl)nicotinamide (0.51 g, 95% yield). LCMS m/z 406.0 (M+H); $^1$H NMR (300 MHz, DMSO-$d_6$) δ 9.83 (s, 1H), 8.95 (t, J=5.5 Hz, 1H), 8.49 (s, 1H), 8.00 (s, 1H), 7.63 (d, J=0.8 Hz, 1H), 6.66 (s, 1H), 6.60-6.18 (m, 1H), 4.85 (s, 1H), 4.62 (td, J=15.1, 3.8 Hz, 2H), 4.48-4.25 (m, 1H), 3.85-3.61 (m, 1H), 3.50-3.36 (m, 1H), 1.20-1.12 (m, 6H).

Intermediate I-16

6-chloro-4-(isopropylamino)-N-(1-(isopropylsulfonyl)piperidin-4-yl)nicotinamide

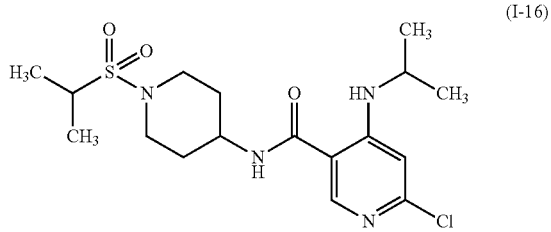 [SMILES: CC(C)Nc1cc(Cl)ncc1C(=O)NC1CCN(S(=O)(=O)C(C)C)CC1]

(I-16)

Intermediate I-16A: tert-butyl 4-(6-chloro-4-(isopropylamino)nicotinamido)piperidine-1-carboxylate

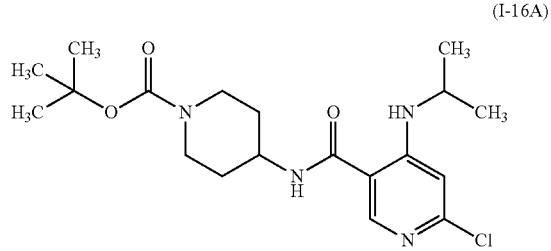 [SMILES: CC(C)Nc1cc(Cl)ncc1C(=O)NC1CCN(C(=O)OC(C)(C)C)CC1]

(I-16A)

To a stirred solution of 6-chloro-4-(isopropylamino)nicotinic acid (1 g, 4.66 mmol) in $CHCl_3$ (20 mL) was added DIPEA (2.441 mL, 13.98 mmol) and HATU (2.126 g, 5.59 mmol) followed by tert-butyl 4-aminopiperidine-1-carboxylate (0.933 g, 4.66 mmol). The reaction mixture was allowed to stir for 18 hrs at 25° C. The reaction mixture was diluted with DCM and washed with water. The organic layer was dried over $Na_2SO_4$, filtered and concentrated in vacuo. The crude material was purified via column chromatography using 20-30% EtOAc/pet ether to afford tert-butyl 4-(6-chloro-4-(isopropylamino)nicotinamido)piperidine-1-carboxylate (1.5 g, 81% yield). LCMS m/z 397.2 (M+H); $^1$H NMR (400 MHz, METHANOL-$d_4$) δ 8.31-8.19 (m, 1H), 6.71 (s, 1H), 4.11 (d, J=13.6 Hz, 2H), 4.02 (tt, J=11.2, 4.1 Hz, 1H), 3.84-3.69 (m, 1H), 3.11-2.72 (m, 2H), 2.00-1.87 (m, 2H), 1.57-1.42 (m, 11H), 1.27 (d, J=6.5 Hz, 6H).

Intermediate I-16B: 6-chloro-4-(isopropylamino)-N-(piperidin-4-yl)nicotinamide

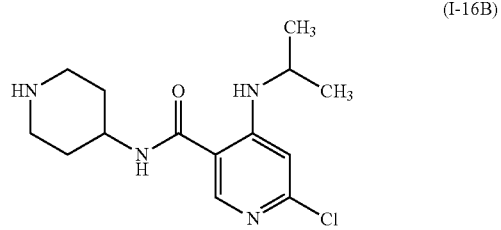 [SMILES: CC(C)Nc1cc(Cl)ncc1C(=O)NC1CCNCC1]

(I-16B)

A solution of tert-butyl 4-(6-chloro-4-(isopropylamino)nicotinamido)piperidine-1-carboxylate (1.5 g, 3.78 mmol) in DCM (10 mL) was cooled to 0° C. HCl in diethyl ether (18.90 mL, 18.90 mmol) was added and the mixture was stirred at 0° C. for 30 min. The reaction mixture was then allowed to warm up to room temperature over 1 hr. The reaction mixture was concentrated in vacuo to afford 6-chloro-4-(isopropylamino)-N-(piperidin-4-yl)nicotinamide (1.1 g, 98% yield). LCMS m/z 297.1 (M+H); $^1$H NMR (400 MHz, DMSO-$d_6$) δ 8.61 (s, 1H), 6.97 (s, 1H), 4.14-3.76 (m, 2H), 3.29 (d, J=12.5 Hz, 2H), 2.95 (d, J=10.5 Hz, 2H), 2.04-1.69 (m, 4H), 1.27-1.11 (m, 6H).

Intermediate I-16

To a solution of 6-chloro-4-(isopropylamino)-N-(piperidin-4-yl)nicotinamide (200 mg, 0.674 mmol) in DCM (2 mL) at 0° C. was added isopropylsulfonyl chloride (96 mg, 0.674 mmol) and triethylamine (0.188 mL, 1.348 mmol). The reaction mixture was stirred at 0° C. for 2 hrs. The reaction mixture was poured into water and extracted with DCM. The organic layer was dried over $Na_2SO_4$, filtered and concentrated in vacuo. The crude material was purified via column chromatography using 40-50% EtOAc/pet ether to afford 6-chloro-4-(isopropylamino)-N-(1-(isopropylsulfonyl)piperidin-4-yl) nicotinamide (124 mg, 46% yield). LCMS m/z 403.2 (M+H); $^1$H NMR (300 MHz, DMSO-$d_6$) δ 8.59-8.24 (m, 3H), 6.70 (s, 1H), 3.93 (d, J=7.2 Hz, 2H), 3.75 (dd, J=13.8, 6.6 Hz, 1H), 3.66 (d, J=12.5 Hz, 2H), 3.00 (t, J=11.1 Hz, 2H), 1.84 (d, J=9.4 Hz, 2H), 1.62-1.41 (m, 2H), 1.19 (m, 12H).

Intermediate I-17

6-chloro-N-((3R,6S)-6-(hydroxymethyl)tetrahydro-2H-pyran-3-yl)-4-(isopropylamino)nicotinamide

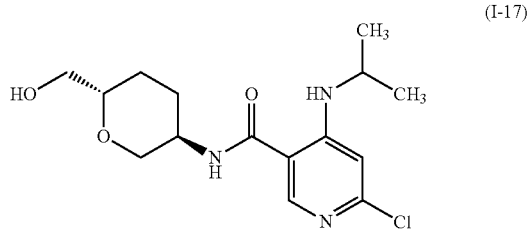 [SMILES: CC(C)Nc1cc(Cl)ncc1C(=O)N[C@@H]1CC[C@@H](CO)OC1]

(I-17)

Intermediate I-17A: (3R,6S)-6-(((tert-butyldimethylsilyl)oxy)methyl)-3,6-dihydro-2H-pyran-3-amine

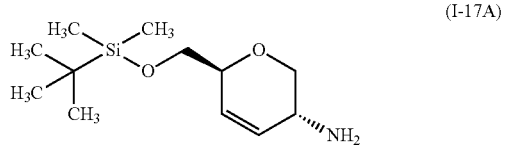 [SMILES: CC(C)(C)[Si](C)(C)OC[C@@H]1C=C[C@@H](N)CO1]

(I-17A)

To a solution of N-((3R,6S)-6-(((tert-butyldimethylsilyl)oxy)methyl)-3,6-dihydro-2H-pyran-3-yl)-2,2,2-trichloroacetamide (6 g, 15.43 mmol) in 2-propanol (50 mL) was added KOH (2.60 g, 46.3 mmol). The mixture was stirred at room temperature for 3 days. The reaction mixture was concentrated in vacuo to afford (3R,6S)-6-(((tert-butyldimethylsilyl)oxy)methyl)-3,6-dihydro-2H-pyran-3-amine which was used as is in the next reaction. $^1$H NMR (400 MHz, DMSO-$d_6$) δ 5.86-5.55 (m, 2H), 4.06-3.82 (m, 2H), 3.64-3.47 (m, 2H), 3.23 (br. s., 1H), 3.05 (dd, J=10.5, 8.8 Hz, 1H), 0.99-0.76 (m, 9H), 0.04-0.01 (m, 6H).

Intermediate I-17B: (3R,6S)-6-(((tert-butyldimethylsilyl)oxy)methyl)tetrahydro-2H-pyran-3-amine

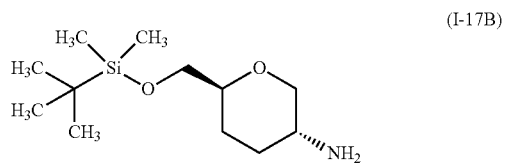 [SMILES: CC(C)(C)[Si](C)(C)OC[C@@H]1CC[C@@H](N)CO1]

(I-17B)

To a solution of (3R,6S)-6-(((tert-butyldimethylsilyl)oxy)methyl)-3,6-dihydro-2H-pyran-3-amine (300 mg, 1.232 mmol) in methanol (5 mL) was added Pd/C (131 mg, 0.123 mmol) and the mixture was stirred under an atmosphere of hydrogen (balloon) for 24 h. The reaction mixture was filtered through a bed of celite and the filtrate was concentrated in vacuo to afford (3R,6S)-6-(((tert-butyldimethylsilyl)oxy)methyl)tetrahydro-2H-pyran-3-amine (220 mg, 73% yield) as a brown syrup which was used as is in the next reaction. $^1$H NMR (400 MHz, DMSO-$d_6$) δ 3.85-3.77 (m, 1H), 3.73 (ddd, J=10.7, 4.6, 2.3 Hz, 1H), 3.61-3.41 (m, 2H), 3.39-3.23 (m, 2H), 3.16 (dtd, J=10.6, 5.3, 2.1 Hz, 1H), 2.82 (t, J=10.5 Hz, 1H), 1.96-1.74 (m, 1H), 1.68-1.55 (m, 1H), 1.28-0.99 (m, 9H), 0.04-0.01 (m, 6H).

Intermediate I-17C: N-((3R,6S)-6-(((tert-butyldimethylsilyl)oxy)methyl)tetrahydro-2H-pyran-3-yl)-6-chloro-4-(isopropylamino)nicotinamide

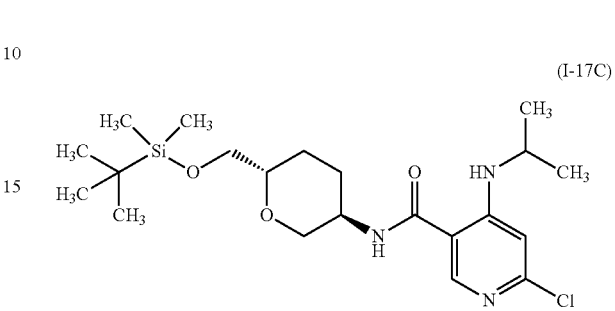

(I-17C)

To a stirred solution of 6-chloro-4-(isopropylamino)nicotinic acid (250 mg, 1.165 mmol) in DMF (2 mL) was added HATU (576 mg, 1.514 mmol), (3R,6S)-6-(((tert-butyldimethylsilyl)oxy)methyl)tetrahydro-2H-pyran-3-amine (286 mg, 1.165 mmol) and DIPEA (0.814 mL, 4.66 mmol). The reaction mixture was stirred at room temperature overnight. The reaction mixture was then concentrated in vacuo and the crude product was suspended in water and filtered out. The residue obtained was dissolved in ethyl acetate and washed with 10% NaHCO$_3$ solution (2×10 mL). The organic extract was dried over Na$_2$SO$_4$, filtered and concentrated in vacuo. The crude product was purified via column chromatography (0-30% ethyl acetate/pet ether) to afford N-((3R,6S)-6-(((tert-butyldimethylsilyl)oxy)methyl)tetrahydro-2H-pyran-3-yl)-6-chloro-4-(isopropylamino)nicotinamide (250 mg, 49% yield) as pale brown solid. LCMS m/z 442 (M+H); $^1$H NMR (300 MHz, DMSO-$d_6$) δ 8.42-8.26 (m, 1H), 6.69 (s, 1H), 3.95-3.66 (m, 3H), 3.64-3.38 (m, 3H), 3.19-3.06 (m, 1H), 1.95 (d, J=13.6 Hz, 1H), 1.79-1.66 (m, 1H), 1.57 (s, 2H), 1.42-1.03 (m, 7H), 0.91-0.79 (m, 6H), 0.11-0.02 (m, 6H).

Intermediate I-17: 6-chloro-N-((3R,6S)-6-(hydroxymethyl)tetrahydro-2H-pyran-3-yl)-4-(isopropylamino)nicotinamide To a stirred solution of N-((3R,6S)-6-(((tert-butyldimethylsilyl)oxy)methyl)tetrahydro-2H-pyran-3-yl)-6-chloro-4-(isopropylamino)nicotinamide (250 mg, 0.566 mmol) in DCM (1 mL) was added TFA (0.4 mL, 5.19 mmol) dropwise. The reaction mixture was stirred at room temperature for 30 min. The reaction mixture was concentrated in vacuo. The residue obtained was dissolved in ethyl acetate and washed with 10% NaHCO$_3$ solution (4×15 mL). The organic extract was dried over Na$_2$SO$_4$, filtered and concentrated in vacuo. The crude product was purified via column chromatography (0-3% methanol/CHCl$_3$) to afford 6-chloro-N-((3R,6S)-6-(hydroxymethyl)tetrahydro-2H-pyran-3-yl)-4-(isopropylamino)nicotinamide (150 mg, 81% yield) as a pale brown solid. LCMS m/z 328 (M+H). $^1$H NMR (300 MHz, DMSO-$d_6$) δ 8.52-8.18 (m, 1H), 6.74-6.58 (m, 1H), 4.62 (t, J=5.7 Hz, 1H), 4.03 (q, J=7.2 Hz, 2H), 3.94-3.67 (m, 4H), 3.47-3.35 (m, 2H), 2.13-1.86 (m, 6H), 1.79-1.44 (m, 4H), 1.37-0.91 (m, 19H).

Intermediate I-18

6-chloro-N-((1R,4R)-4-(2-hydroxy-2-methylpropanamido)cyclohexyl)-4-(isopropylamino)nicotinamide

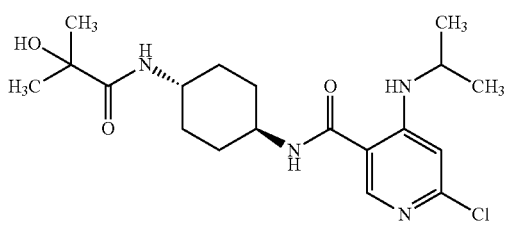

(I-18)

Intermediate I-18A: N-((1r,4r)-4-aminocyclohexyl)-6-chloro-4-(isopropylamino)nicotinamide

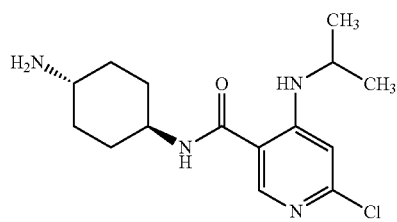

(I-18A)

A stirred solution of tert-butyl ((1R,4R)-4-(6-chloro-4-(isopropylamino) nicotinamido)cyclohexyl)carbamate (475 mg, 1.156 mmol) in DCM (2 mL) was cooled to 0° C. To this solution was added TFA (0.5 mL, 6.49 mmol). The reaction mixture was allowed to warm up to room temperature and stirred for 12 hrs. The reaction mixture was concentrated in vacuo to afford an off-white semi-solid which was co-evaporated with CHCl$_3$ two times. This procedure provided N-((1R,4R)-4-aminocyclohexyl)-6-chloro-4-(isopropylamino)nicotinamide as an off-white solid which was used as is in the next reaction. LCMS m/z 311 (M+H); $^1$H NMR (300 MHz, DMSO-d$_6$) δ 8.47-8.29 (m, 1H), 7.82 (m, 2H), 6.70 (s, 1H), 4.66 (br. s., 2H), 3.74 (m, 1H), 2.97 (br. s., 1H), 2.03-1.83 (m, 4H), 1.45-1.27 (m, 4H), 1.16 (d, J=6.3 Hz, 6H).

Intermediate I-18B: 1-(((1r,4r)-4-(6-chloro-4-(isopropylamino)nicotinamido)cyclohexyl)amino)-2-methyl-1-oxopropan-2-yl acetate

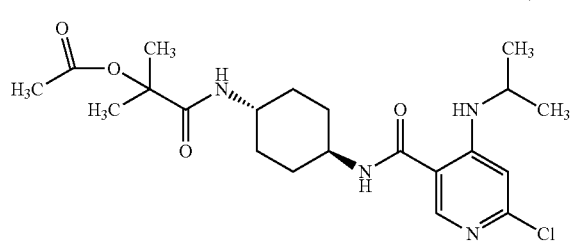

(I-18B)

To a stirred solution of N-((1R,4R)-4-aminocyclohexyl)-6-chloro-4-(isopropylamino)nicotinamide (200 mg, 0.643 mmol) in DCM was added Et$_3$N (269 μl, 1.930 mmol). The mixture was cooled to 0° C. and 1-chloro-2-methyl-1-oxopropan-2-yl acetate (106 mg, 0.643 mmol) was added dropwise. The reaction mixture was allowed to warm up to 25° C. and stirred for 4 hrs. The reaction mixture was diluted with DCM and washed with water (2×10 mL). The organic layer was dried over Na$_2$SO$_4$, filtered and concentrated in vacuo. This procedure afforded 1-(((1R,4R)-4-(6-chloro-4-(isopropylamino)nicotinamido)cyclohexyl)amino)-2-methyl-1-oxopropan-2-yl acetate (280 mg, 99% yield) as an off-white solid, which was used as is in the next reaction. LCMS m/z 439 (M+H); $^1$H NMR (300 MHz, DMSO-d$_6$) δ 8.42-34 (m, 2H), 7.44 (dd, J=12.5, 8.4 Hz, 2H), 6.68 (s, 1H), 4.41 (s, 1H), 3.83-3.59 (m, 1H), 3.49 (br. s., 1H), 2.09 (s, 3H), 1.91-1.77 (m, 4H), 1.75-1.57 (m, 6H), 1.53-1.20 (m, 4H), 1.20-1.06 (m, 6H).

Intermediate I-18

To a stirred solution of 1-(((1R,4R)-4-(6-chloro-4-(isopropylamino)nicotinamido)cyclohexyl)amino)-2-methyl-1-oxopropan-2-yl acetate (280 mg, 0.638 mmol) in methanol (5 mL) was added potassium carbonate (176 mg, 1.276 mmol) and the mixture was stirred at room temperature for 1 hr. The reaction mixture was concentrated in vacuo. The crude residue obtained was suspended in water and extracted with ethyl acetate (3×10 mL). The combined organic extracts were dried over Na$_2$SO$_4$, filtered and concentrated in vacuo. The crude product was purified via column chromatography (25% ethyl acetate/pet ether) to afford 6-chloro-N-((1R,4R)-4-(2-hydroxy-2-methylpropanamido)cyclohexyl)-4-(isopropylamino)nicotinamide (200 mg, 79% yield) as a pale pink solid. LCMS m/z 397.1 (M+H); $^1$H NMR (300 MHz, DMSO-d$_6$) δ 8.42-8.32 (m, 2H), 7.37-7.30 (m, 2H), 6.68 (s, 1H), 5.33 (d, J=4.3 Hz, 1H), 4.41 (s, 1H), 3.89-3.62 (m, 2H), 3.60-3.38 (m, 1H), 1.93-1.61 (m, 4H), 1.38 (m, 4H), 1.22 (d, J=2.7 Hz, 3H), 1.15 (m, 6H).

Intermediate I-19

6-Chloro-N—((R)-2-fluoro-3-hydroxy-3-methylbutyl)-4-((3-fluorocyclopentyl)amino)nicotinamide

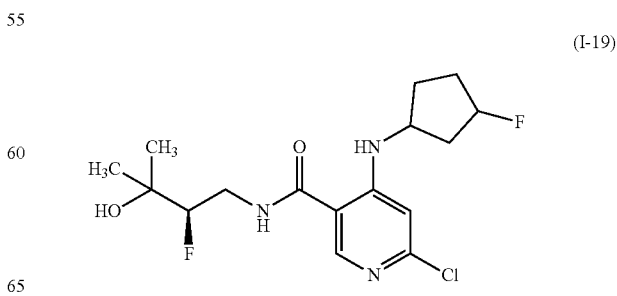

(I-19)

Intermediate I-19A: ethyl 6-chloro-4-((3-hydroxycyclopentyl)amino)nicotinate

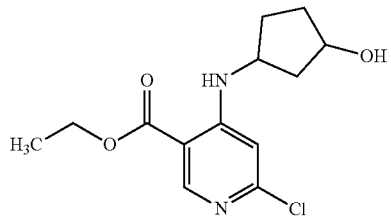

(I-19A)

To a solution of 3-aminocyclopentanol hydrochloride (1.05 g, 7.63 mmol) and ethyl 4,6-dichloronicotinate (1.679 g, 7.63 mmol) in DMA (10 mL) was added DIPEA (6.66 mL, 38.2 mmol), then reaction mixture was heated at 100° C. for 4 hr. Water (50 mL) was added and the mixture was extracted with ethyl acetate (2×150 mL). The combined organic layers were washed with cold water (2×50 mL) and brine solution (40 mL) then dried over $Na_2SO_4$. The filtrate was concentrated and the product was purified using silica gel eluting 40% ethyl acetate in hexane to afford ethyl 6-chloro-4-((3-hydroxycyclopentyl)amino)nicotinate (1.5 g, 5.27 mmol, 69% yield), which was taken for the next step without chiral separation. $^1$H NMR (400 MHz, DMSO-$d_6$) δ ppm 8.54 (br. s., 1H) 8.03-8.42 (m, 1H) 6.78 (d, J=9.54 Hz, 1H) 4.62-4.77 (m, 1H) 3.99-4.33 (m, 4H) 1.86-2.29 (m, 3H) 1.38-1.78 (m, 3H) 1.31 (td, J=7.03, 1.00 Hz, 3H); LCMS (M+H) 285.0.

Intermediate I-19B: ethyl 6-chloro-4-((3-fluorocyclopentyl)amino)nicotinate

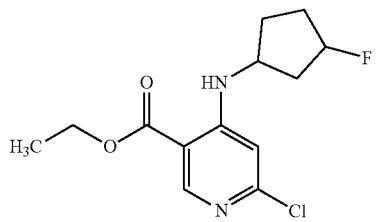

(I-19B)

To a solution of ethyl 6-chloro-4-((3-hydroxycyclopentyl)amino)nicotinate (1.5 g, 5.27 mmol) in DCM (20 mL) was added DAST (1.392 mL, 10.54 mmol) slowly at −20° C. The reaction mixture was stirred at room temperature for 2 hrs. After the reaction was complete, the mixture was quenched with aqueous $NaHCO_3$ solution and extracted with DCM (50 mL). The organic layer was washed with water (30 mL) and brine (20 mL) then dried over $Na_2SO_4$. The crude compound was purified over silica gel eluting 1:9 EtOAc and hexane to afford two separated diastereomers. Yield: Diastereomer 1: 540 mg, Diastereomer 2: 320 mg.

Diastereomer 1: $^1$H NMR (400 MHz, chloroform-d) δ ppm 8.67 (s, 1H) 8.22 (br. s., 1H) 6.58 (s, 1H) 5.16-5.34 (m, 1H) 4.33 (q, J=7.03 Hz, 2H) 4.06-4.15 (m, 2H) 2.47-2.60 (m, 1H) 2.35 (dq, J=13.18, 7.99 Hz, 1H) 2.00-2.16 (m, 2H) 1.59-1.84 (m, 2H) 1.36-1.41 (m, 3H) LC/MS 287.0 (M+H).

Diastereomer 2: $^1$H NMR (400 MHz, chloroform-d) δ ppm 8.67 (s, 1H) 8.42 (br. s., 1H) 6.52 (s, 1H) 5.16-5.33 (m, 1H) 4.30-4.38 (m, 2H) 3.93-4.00 (m, 1H) 1.81-2.35 (m, 6H) 1.37 (t, J=7.03 Hz, 3H) LC/MS 287.0 (M+H).

Intermediate I-19C: 6-chloro-4-((3-fluorocyclopentyl)amino)nicotinic acid

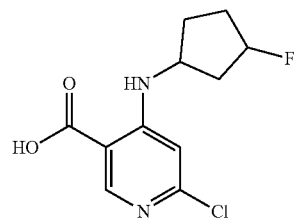

(I-19C)

To a solution of ethyl 6-chloro-4-((3-fluorocyclopentyl)amino)nicotinate (1.0 g, 3.49 mmol) in EtOH (10 mL) was added LiOH (0.167 g, 6.98 mmol) as 2N aq solution at 0° C., then stirred for 3 hrs at room temperature. When the reaction was complete, the EtOH was removed and water (1 mL) was added and acidified to pH 4 with 1.5N HCl. The precipitated solid was collected on a filter and used in the next step without chiral separation. Yield: 88%(0.79 g). $^1$H NMR (400 MHz, DMSO-$d_6$) δ ppm 13.37 (br. s., 1H) 8.52 (d, J=9.04 Hz, 1H) 8.32 (d, J=7.03 Hz, 1H) 6.83 (s, 1H) 5.17-5.35 (m, 1H) 4.19 (dq, J=13.68, 6.99 Hz, 1H) 2.21-2.47 (m, 2H) 1.73-2.17 (m, 3H) 1.47-1.57 (m, 1H) LCMS (M+H) 259.0.

Intermediate I-19

To a solution of 6-chloro-4-((3-fluorocyclopentyl)amino) nicotinic acid (0.91 g, 3.52 mmol) and (R)-4-amino-3-fluoro-2-methylbutan-2-ol (0.511 g, 4.22 mmol) in DMF (10 mL) was added DIPEA (1.843 mL, 10.55 mmol) and HATU (2.68 g, 7.04 mmol). The reaction mixture was stirred for 2 hrs at room temperature. Then reaction mixture was diluted with EtOAc (50 mL) and the organic layer was washed with cold water (3×20 mL) and brine (15 mL). The extracts were dried over $Na_2SO_4$ and concentrated to give the crude compound which was purified over silica gel eluting 60% EtOAc in hexane to afford 6-chloro-N—((R)-2-fluoro-3-hydroxy-3-methylbutyl)-4-((3-fluorocyclopentyl)amino) nicotinamide (0.98 g, 2.71 mmol, 77% yield) as off-white solid, which was taken for the next step without chiral separation. $^1$H NMR 400 MHz, DMSO-$d_6$: δ 8.71 (t, J=7.20 Hz, 2H), 8.38 (s, 1H), 6.71 (s, 1H), 5.14-5.27 (m, 1H), 4.83 (s, 1H), 4.24-4.39 (m, 1H), 4.03 (d, J=2.80 Hz, 1H), 3.60-3.69 (m, 1H), 3.31-3.37 (m, 1H), 2.25-2.42 (m, 1H), 2.14-2.18 (m, 1H), 1.59-1.97 (m, 4H), 1.15 (dd, J=0.80, 6.00 Hz, 6H), LCMS (M+H) 362.2.

The Examples in Table 1 were prepared using the general methods for Example 1-20 using the appropriate starting material and amine. Intermediates described above were used for the synthesis of the examples below and other examples in this application.

TABLE 1

| Ex. No. | Structure | | HPLC rt (min) | HPLC cond. | LCMS |
|---|---|---|---|---|---|
| 22 | (structure) | Abs | 7.19 | B | 433 |
| 23 | (structure) | Abs | 6.92 | B | 470 |
| 24 | (structure) | Abs | 5.11 | A | 502 |
| 25 | (structure) | Abs | 6.71 | B | 468 |
| 26 | (structure) | | 6.6 | A | 514.2 |

TABLE 1-continued

| Ex. No. | Structure | | HPLC rt (min) | HPLC cond. | LCMS |
|---|---|---|---|---|---|
| 27 | 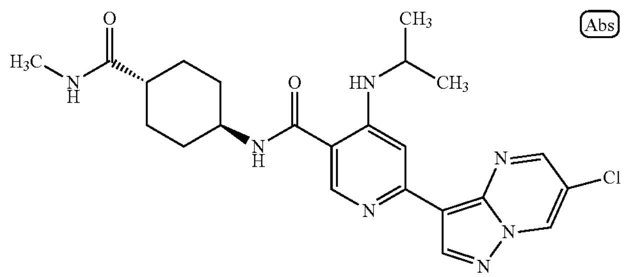 [SMILES: CNC(=O)[C@H]1CC[C@H](NC(=O)c2cnc(-c3cnn4cc(Cl)cnc34)cc2NC(C)C)CC1] | Abs | 6.73 | B | 470 |
| 28 | 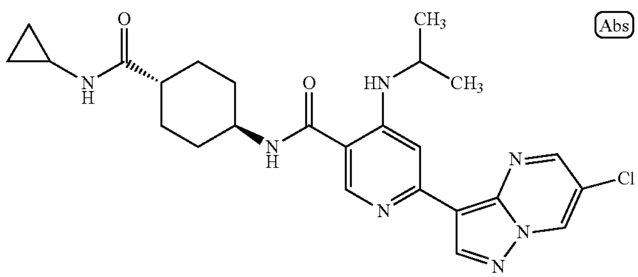 [SMILES: CC(C)Nc1cc(-c2cnn3cc(Cl)cnc23)ncc1C(=O)N[C@H]1CC[C@H](C(=O)NC2CC2)CC1] | Abs | 7.24 | B | 496 |
| 29 | 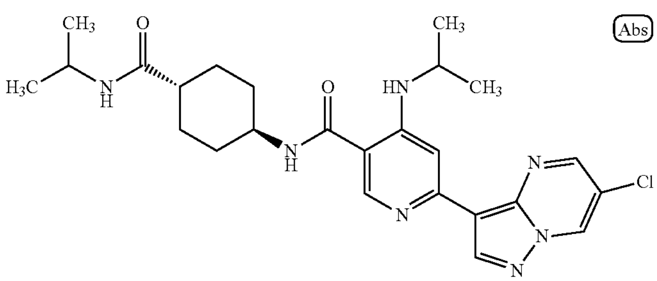 [SMILES: CC(C)Nc1cc(-c2cnn3cc(Cl)cnc23)ncc1C(=O)N[C@H]1CC[C@H](C(=O)NC(C)C)CC1] | Abs | 7.43 | B | 498.1 |
| 30 | 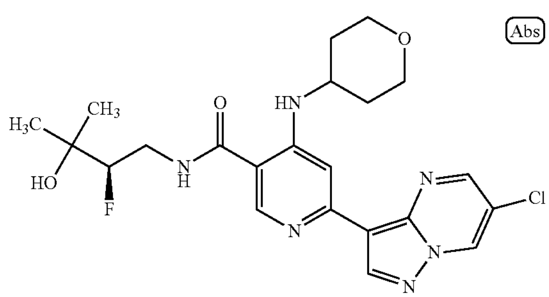 [SMILES: CC(C)(O)[C@H](F)CNC(=O)c1cnc(-c2cnn3cc(Cl)cnc23)cc1NC1CCOCC1] | Abs | 5.61 | A | 477 |
| 31 | 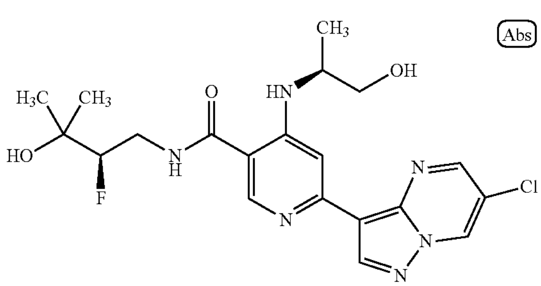 [SMILES: C[C@@H](CO)Nc1cc(-c2cnn3cc(Cl)cnc23)ncc1C(=O)NC[C@@H](F)C(C)(C)O] | Abs | 5.91 | B | 451.2 |

TABLE 1-continued
| Ex. No. | Structure | HPLC rt (min) | HPLC cond. | LCMS |
|---|---|---|---|---|
| 32 | 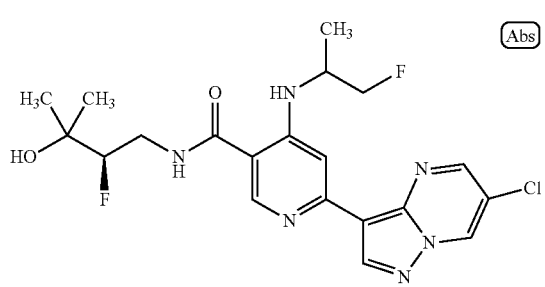 [SMILES: CC(CF)Nc1cc(-c2cnn3cc(Cl)cnc23)ncc1C(=O)NC[C@@H](F)C(C)(C)O] | 6.94 | B | 453.2 |
| 33 | 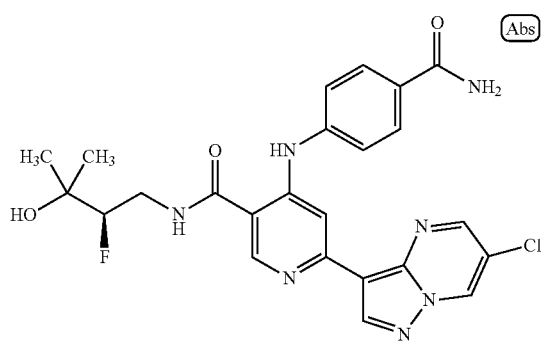 [SMILES: CC(C)(O)[C@H](F)CNC(=O)c1cnc(-c2cnn3cc(Cl)cnc23)cc1Nc1ccc(C(N)=O)cc1] | 5.52 | B | 512.2 |
| 34 | 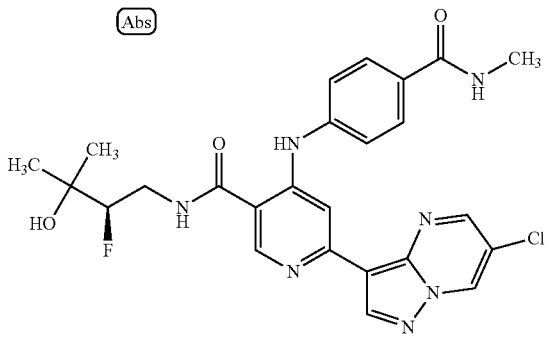 [SMILES: CNC(=O)c1ccc(Nc2cc(-c3cnn4cc(Cl)cnc34)ncc2C(=O)NC[C@@H](F)C(C)(C)O)cc1] | 11.31 | B | 526.2 |
| 35 | 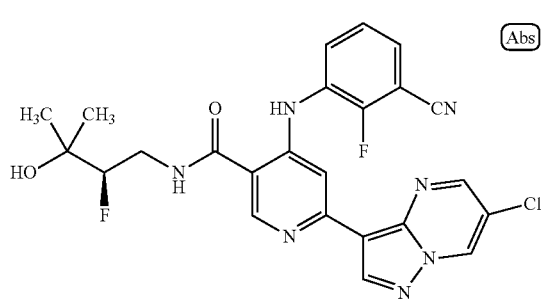 [SMILES: CC(C)(O)[C@H](F)CNC(=O)c1cnc(-c2cnn3cc(Cl)cnc23)cc1Nc1cccc(C#N)c1F] | 1.591 | C | 512.4 |

TABLE 1-continued
| Ex. No. | Structure | HPLC rt (min) | HPLC cond. | LCMS |
|---|---|---|---|---|
| 36 | 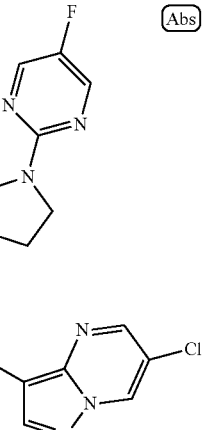 Abs | 1.565 | C | 558.1 |
| 37 | 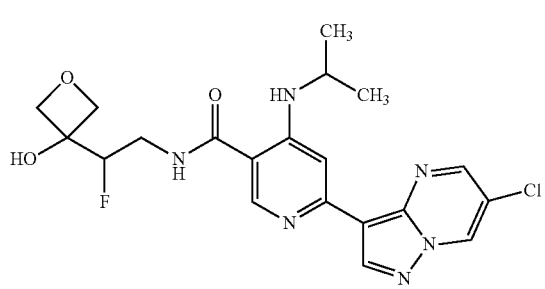 [SMILES: CC(C)Nc1cc(-c2cnn3cc(Cl)cnc23)ncc1C(=O)NCC(F)C1(O)COC1] | 5.17 | A | 449.2 |
| 38 | 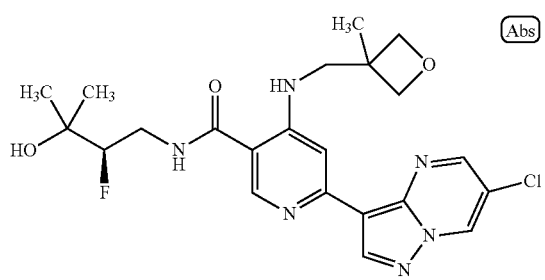 [SMILES: CC1(CNc2cc(-c3cnn4cc(Cl)cnc34)ncc2C(=O)NC[C@@H](F)C(C)(C)O)COC1] Abs | 0.902 | D | 477 |
| 39 | 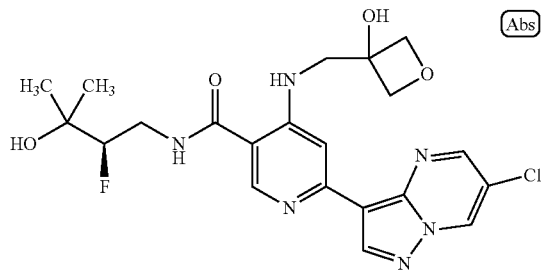 [SMILES: CC(C)(O)[C@H](F)CNC(=O)c1cnc(-c2cnn3cc(Cl)cnc23)cc1NCC1(O)COC1] Abs | 0.739 | D | 479 |
| 40 | 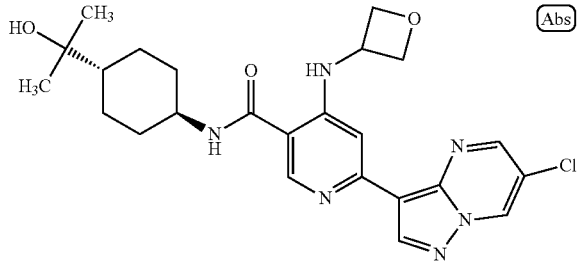 [SMILES: CC(C)(O)[C@H]1CC[C@H](NC(=O)c2cnc(-c3cnn4cc(Cl)cnc34)cc2NC2COC2)CC1] Abs | 6.34 | B | 485.6 |

TABLE 1-continued

| Ex. No. | Structure | | HPLC rt (min) | HPLC cond. | LCMS |
|---|---|---|---|---|---|
| 41 | (structure) | Abs | 5.81 | B | 510.6 |
| 42 | (structure) | Abs | 9.58 | B | 479.3 |
| 43 | (structure) Disastereomer 1 | Abs | 6.48 | B | 481.3 |
| 44 | (structure) Disastereomer 2 | Abs | 5.7 | A | 481.2 |
| 45 | (structure) | | 1.077 | D | 468 |

TABLE 1-continued

| Ex. No. | Structure | HPLC rt (min) | HPLC cond. | LCMS |
|---|---|---|---|---|
| 46 | 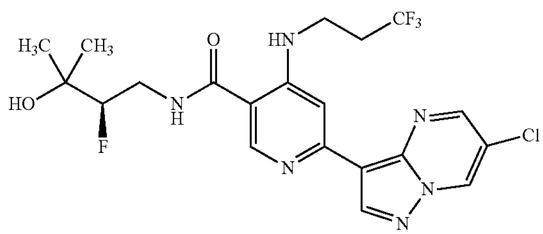 [SMILES: CC(C)(O)[C@H](F)CNC(=O)c1cnc(-c2cnn3cc(Cl)cnc23)cc1NCCC(F)(F)F] | 1.563 | C | 489.2 |
| 47 | 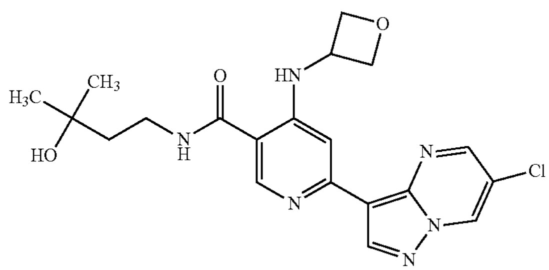 [SMILES: CC(C)(O)CCNC(=O)c1cnc(-c2cnn3cc(Cl)cnc23)cc1NC1COC1] | 10.5 | B | 431.2 |
| 48 | 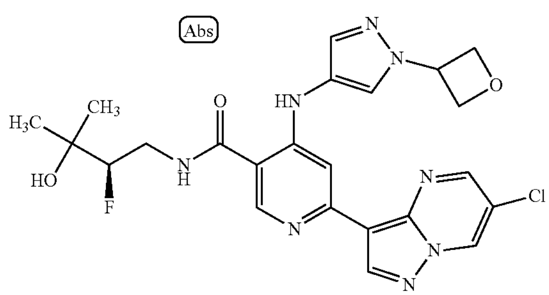 [SMILES: CC(C)(O)[C@H](F)CNC(=O)c1cnc(-c2cnn3cc(Cl)cnc23)cc1Nc1cnn(C2COC2)c1] | 1.16 | C | 515.2 |
| 49 | 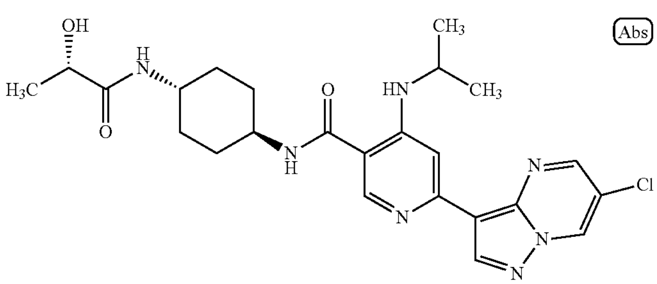 [SMILES: CC(C)Nc1cc(-c2cnn3cc(Cl)cnc23)ncc1C(=O)N[C@H]1CC[C@H](NC(=O)[C@H](C)O)CC1] | 6.186 | A | 500.2 |
| 50 | 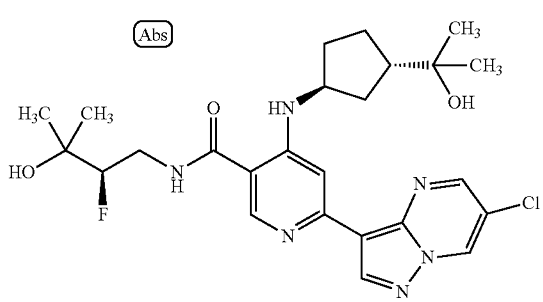 [SMILES: CC(C)(O)[C@H]1CC[C@H](Nc2cc(-c3cnn4cc(Cl)cnc34)ncc2C(=O)NC[C@@H](F)C(C)(C)O)C1] | 1.4 | E | 519.3 |

TABLE 1-continued
| Ex. No. | Structure | HPLC rt (min) | HPLC cond. | LCMS |
|---|---|---|---|---|
| 51 | 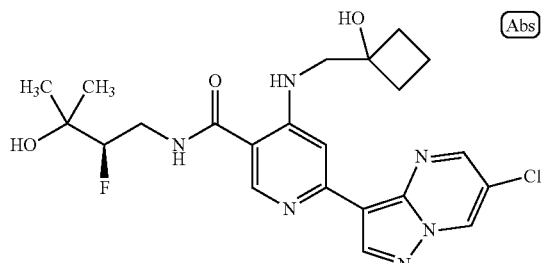 | 1.593 | D | 477.2 |
| 52 | 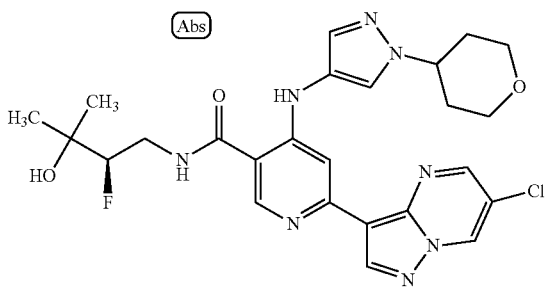 [SMILES: CC(C)(O)[C@H](F)CNC(=O)c1cnc(-c2cnn3cc(Cl)cnc23)cc1Nc1cnn(C2CCOCC2)c1] | 1.924 | C | 543 |
| 53 | 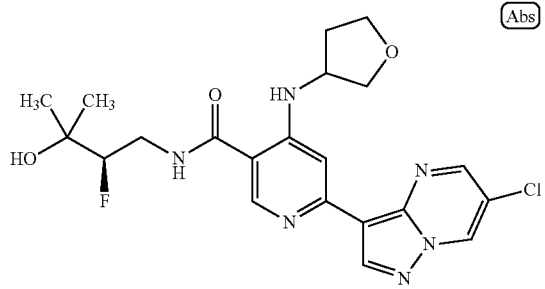<br>Diastereomer 1 | 5.759 | B | 463.2 |
| 54 | 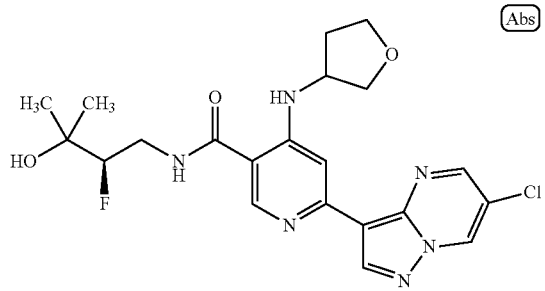<br>Diastereomer 2 | 5.74 | B | 463.2 |
| 55 | 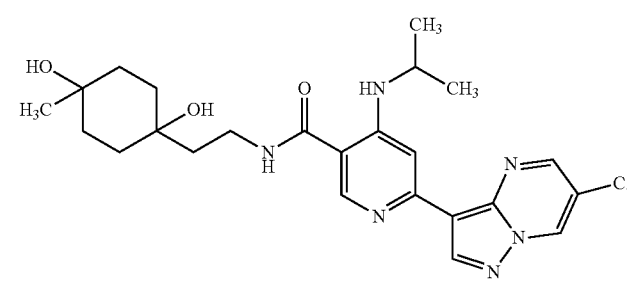 [SMILES: CC(C)Nc1cc(-c2cnn3cc(Cl)cnc23)ncc1C(=O)NCCC1(O)CCC(C)(O)CC1] | 1.58 | F | 487.3 |

TABLE 1-continued
| Ex. No. | Structure | | HPLC rt (min) | HPLC cond. | LCMS |
|---|---|---|---|---|---|
| 56 | 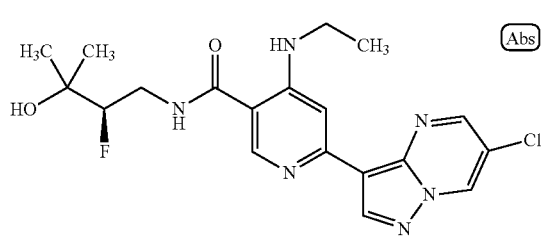 [SMILES: CCNc1cc(-c2cnn3cc(Cl)cnc23)ncc1C(=O)NC[C@@H](F)C(C)(C)O] | (Abs) | 1.46 | E | 421.1 |
| 57 | 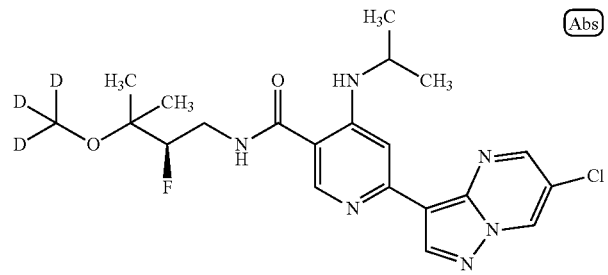 [SMILES: [2H]C([2H])([2H])OC(C)(C)[C@H](F)CNC(=O)c1cnc(-c2cnn3cc(Cl)cnc23)cc1NC(C)C] | (Abs) | 1.82 | E | 452.2 |
| 58 | 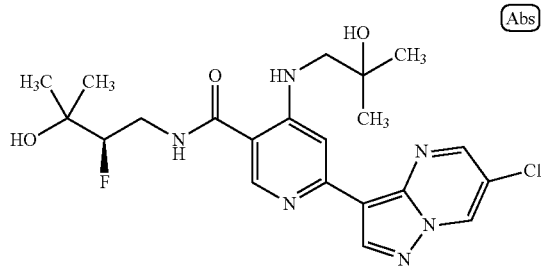 [SMILES: CC(C)(O)CNc1cc(-c2cnn3cc(Cl)cnc23)ncc1C(=O)NC[C@@H](F)C(C)(C)O] | (Abs) | 1.25 | E | 465.1 |
| 59 | 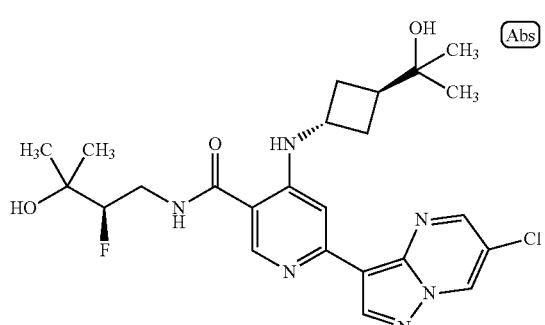 | (Abs) | 1.41 | E | 505.1 |
| 60 | 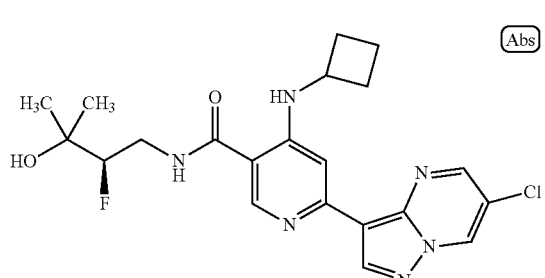 | (Abs) | 1.72 | E | 447.1 |

TABLE 1-continued

| Ex. No. | Structure | HPLC rt (min) | HPLC cond. | LCMS |
|---|---|---|---|---|
| 61 | (Abs) | 1.49 | E | 453.1 |
| 62 | 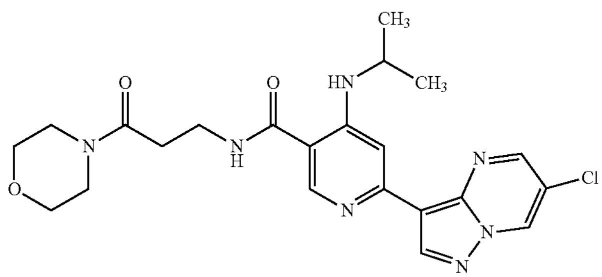 [SMILES: CC(C)Nc1cc(-c2cnn3cc(Cl)cnc23)ncc1C(=O)NCCC(=O)N1CCOCC1] | 1.633 | D | 472.2 |
| 63 | 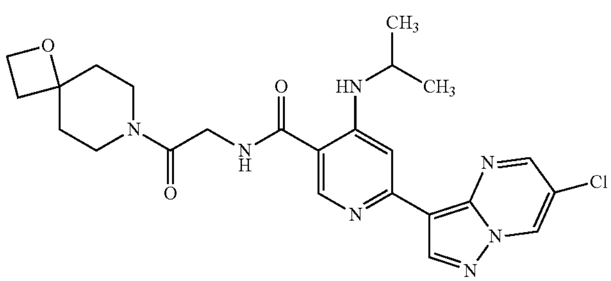 [SMILES: CC(C)Nc1cc(-c2cnn3cc(Cl)cnc23)ncc1C(=O)NCC(=O)N1CCC2(CCO2)CC1] | 1.669 | D | 498.2 |
| 64 | (Abs) | 1.57 | E | 475 |
| 65 | (Abs) | 1.59 | E | 483.1 |

TABLE 1-continued
| Ex. No. | Structure | | HPLC rt (min) | HPLC cond. | LCMS |
|---|---|---|---|---|---|
| 66 | 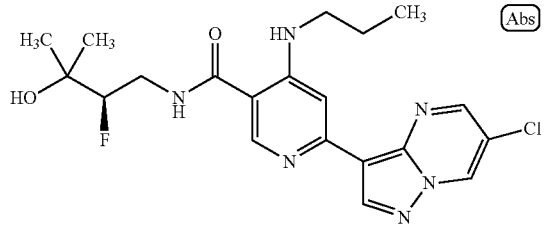 [SMILES: CCCNc1cc(-c2cnn3cc(Cl)cnc23)ncc1C(=O)NC[C@@H](F)C(C)(C)O] | Abs | 1.57 | E | 435.2 |
| 67 | 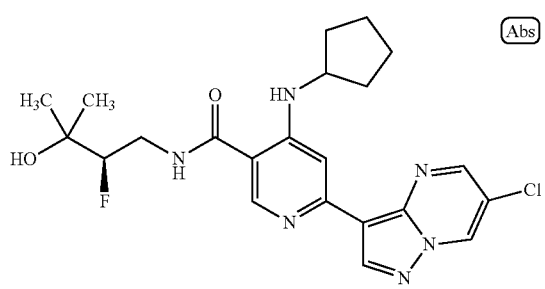 [SMILES: CC(C)(O)[C@H](F)CNC(=O)c1cnc(-c2cnn3cc(Cl)cnc23)cc1NC1CCCC1] | Abs | 1.89 | E | 461.1 |
| 68 | 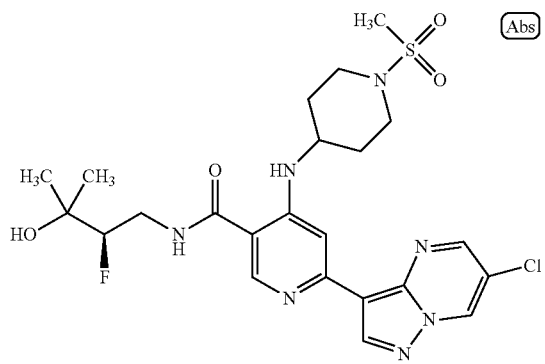 [SMILES: CC(C)(O)[C@H](F)CNC(=O)c1cnc(-c2cnn3cc(Cl)cnc23)cc1NC1CCN(S(C)(=O)=O)CC1] | Abs | 1.25 | E | 554.2 |
| 69 | 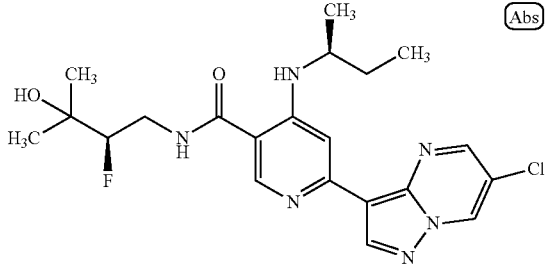 [SMILES: CC[C@H](C)Nc1cc(-c2cnn3cc(Cl)cnc23)ncc1C(=O)NC[C@@H](F)C(C)(C)O] | Abs | 1.83 | F | 449.2 |
| 70 | 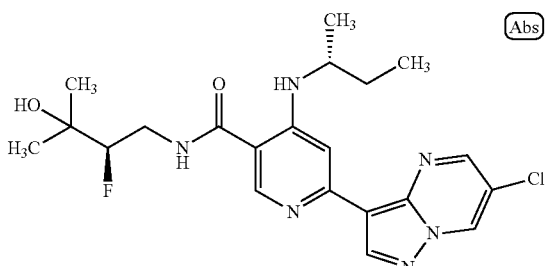 | Abs | 1.82 | F | 449.2 |

TABLE 1-continued
| Ex. No. | Structure | HPLC rt (min) | HPLC cond. | LCMS |
|---|---|---|---|---|
| 71 | 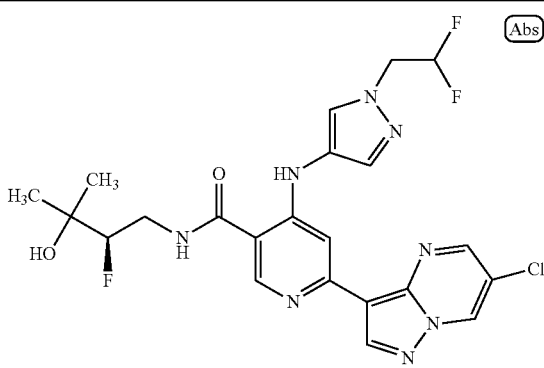 | 2.214 | C | 523.2 |
| 72 | 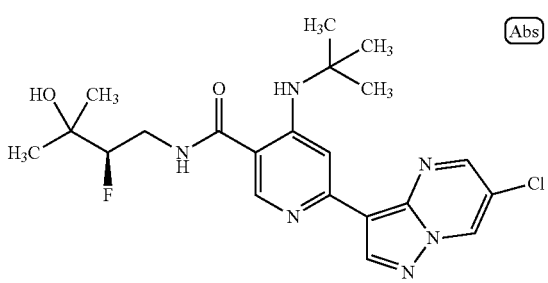 [SMILES: CC(C)(C)Nc1cc(-c2cnn3cc(Cl)cnc23)ncc1C(=O)NC[C@@H](F)C(C)(C)O] | 1.6 | E | 449.2 |
| 73 | 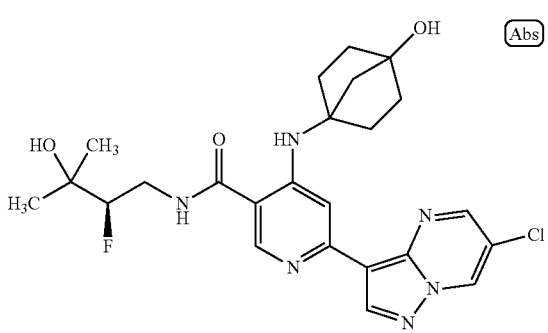 [SMILES: CC(C)(O)[C@H](F)CNC(=O)c1cnc(-c2cnn3cc(Cl)cnc23)cc1NC12CCC(O)(CC1)C2] | 1.31 | E | 503.1 |
| 74 | 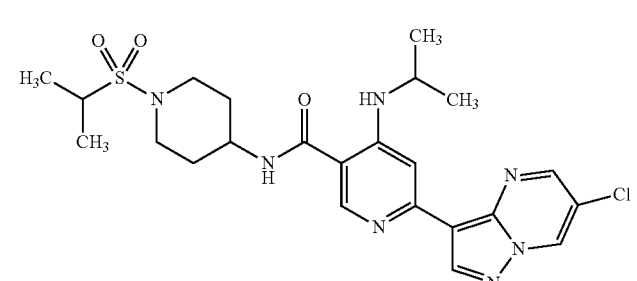 | 7.186 | A | 520.2 |
| 75 | 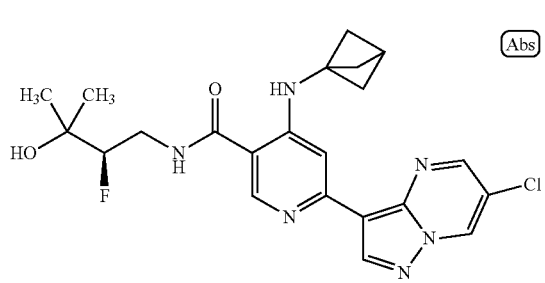 [SMILES: CC(C)(O)[C@H](F)CNC(=O)c1cnc(-c2cnn3cc(Cl)cnc23)cc1NC12CC(C1)C2] | 1.74 | E | 459.2 |

TABLE 1-continued

| Ex. No. | Structure | | HPLC rt (min) | HPLC cond. | LCMS |
|---|---|---|---|---|---|
| 76 | 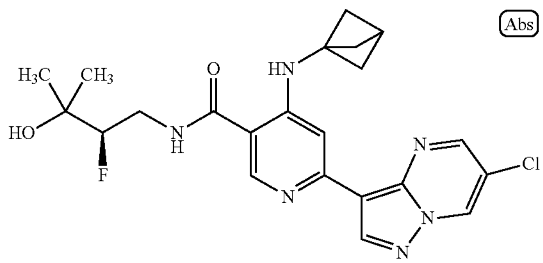 [SMILES: CC(C)(O)[C@H](F)CNC(=O)c1cnc(-c2cnn3cc(Cl)cnc23)cc1NC12CC(C1)C2] | Abs | 1.3 | F | 431.2 |
| 77 | 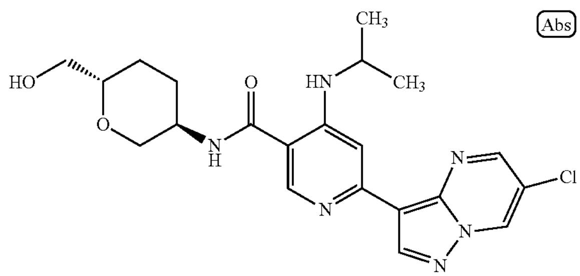 [SMILES: CC(C)Nc1cc(-c2cnn3cc(Cl)cnc23)ncc1C(=O)N[C@@H]1CC[C@@H](CO)OC1] | Abs | 1.396 | C | 445.3 |
| 78 | 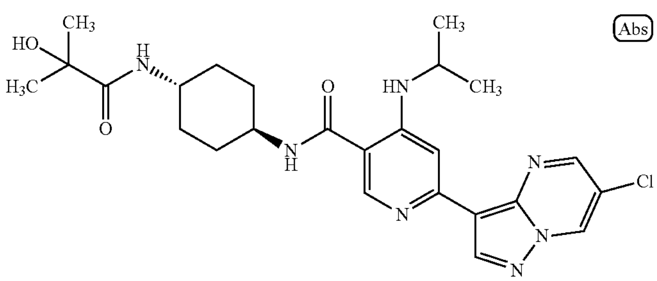 [SMILES: CC(C)Nc1cc(-c2cnn3cc(Cl)cnc23)ncc1C(=O)N[C@H]1CC[C@H](NC(=O)C(C)(C)O)CC1] | Abs | 2.378 | D | 514.2 |
| 79 | 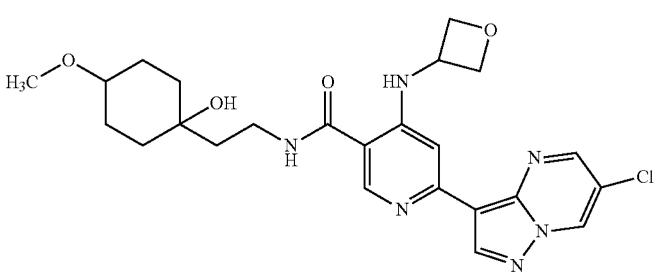 [SMILES: COC1CCC(O)(CCNC(=O)c2cnc(-c3cnn4cc(Cl)cnc34)cc2NC2COC2)CC1] | | 1.36 | F | 501.3 |
| 80 | 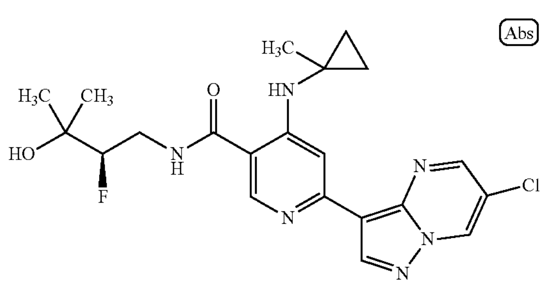 [SMILES: CC1(Nc2cc(-c3cnn4cc(Cl)cnc34)ncc2C(=O)NC[C@@H](F)C(C)(C)O)CC1] | Abs | 1.58 | E | 447.1 |

TABLE 1-continued

| Ex. No. | Structure | HPLC rt (min) | HPLC cond. | LCMS |
|---|---|---|---|---|
| 81 | 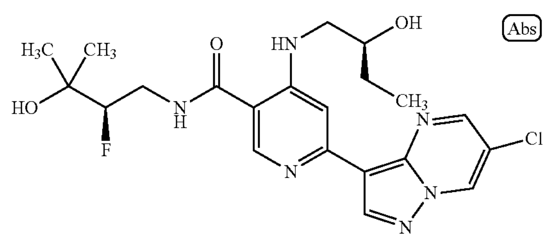 [SMILES: CC[C@H](O)CNc1cc(-c2cnn3cc(Cl)cnc23)ncc1C(=O)NC[C@@H](F)C(C)(C)O] | 1.261 | C | 465.3 |
| 82 | 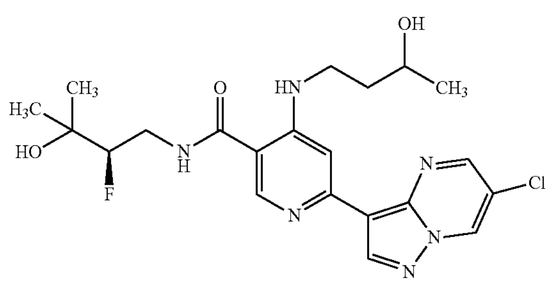 [SMILES: CC(O)CCNc1cc(-c2cnn3cc(Cl)cnc23)ncc1C(=O)NC[C@@H](F)C(C)(C)O] | 1.27 | F | 465.2 |
| 83 | 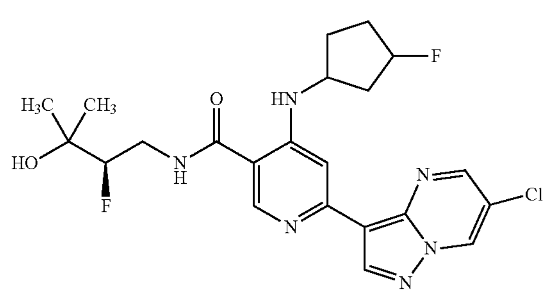 [SMILES: CC(C)(O)[C@H](F)CNC(=O)c1cnc(-c2cnn3cc(Cl)cnc23)cc1NC1CCC(F)C1] | 1.79 | D | 479.2 |
| 84 | 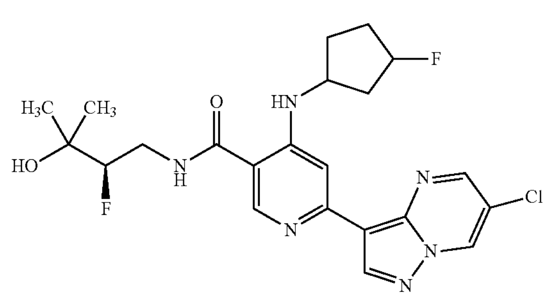 [SMILES: CC(C)(O)[C@H](F)CNC(=O)c1cnc(-c2cnn3cc(Cl)cnc23)cc1NC1CCC(F)C1] | 1.72 | D | 479.2 |
| 85 | 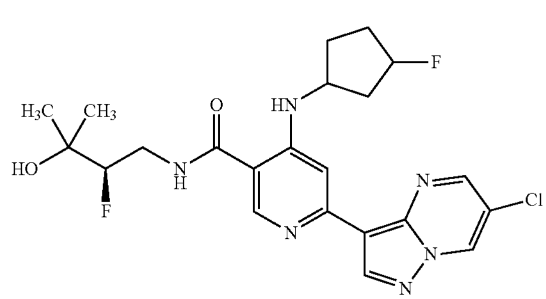 [SMILES: CC(C)(O)[C@H](F)CNC(=O)c1cnc(-c2cnn3cc(Cl)cnc23)cc1NC1CCC(F)C1] | 1.72 | D | 479.2 |

TABLE 1-continued

| Ex. No. | Structure | HPLC rt (min) | HPLC cond. | LCMS |
|---|---|---|---|---|
| 86 | 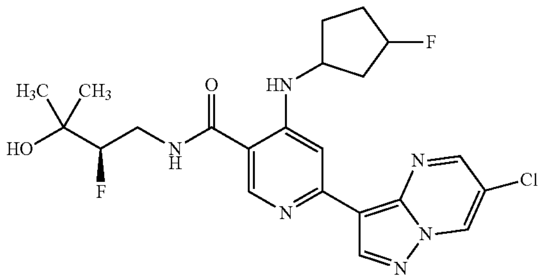 [SMILES: CC(C)(O)[C@H](F)CNC(=O)c1cnc(-c2cnn3cc(Cl)cnc23)cc1NC1CCC(F)C1] | 2.07 | D | 479.2 |

The Examples in Table 2 were prepared using the general methods for Example 1-20 using the appropriate starting material and amine.

TABLE 2

| Ex. No. | Structure | HPLC rt (min) | HPLC cond. | LCMS |
|---|---|---|---|---|
| 87 | 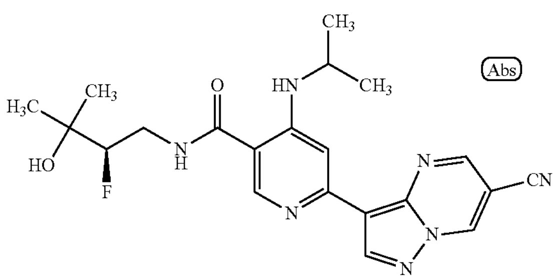 [SMILES: CC(C)Nc1cc(-c2cnn3cc(C#N)cnc23)ncc1C(=O)NC[C@@H](F)C(C)(C)O] | 6.493 | B | 426.2 |
| 88 | 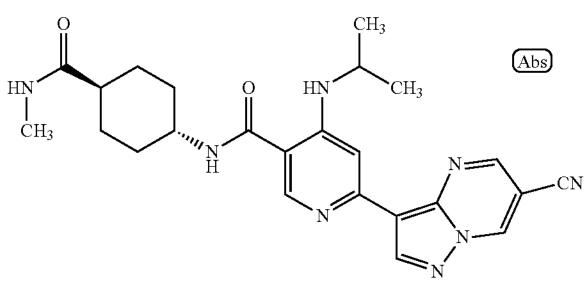 [SMILES: CNC(=O)[C@H]1CC[C@H](NC(=O)c2cnc(-c3cnn4cc(C#N)cnc34)cc2NC(C)C)CC1] | 6.85 | I | 461.2 |
| 89 | 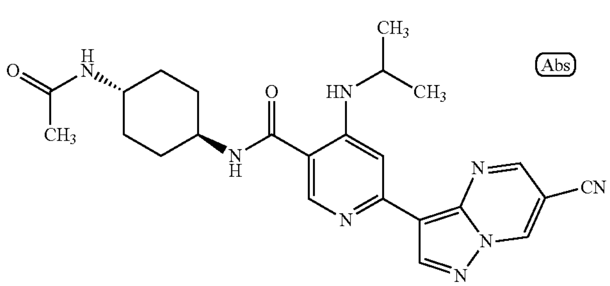 [SMILES: CC(=O)N[C@H]1CC[C@H](NC(=O)c2cnc(-c3cnn4cc(C#N)cnc34)cc2NC(C)C)CC1] | 6.41 | B | 459 |

TABLE 2-continued

| Ex. No. | Structure | HPLC rt (min) | HPLC cond. | LCMS |
|---|---|---|---|---|
| 90 | 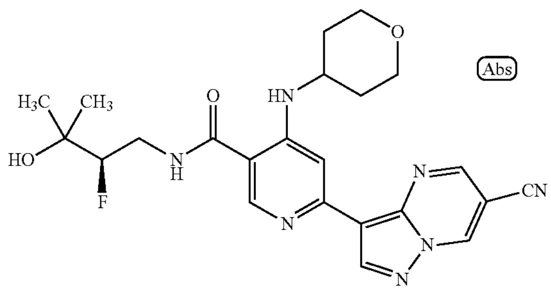 [SMILES: CC(C)(O)[C@H](F)CNC(=O)c1cnc(-c2cnn3cc(C#N)cnc23)cc1NC1CCOCC1] | 14.84 | B | 468 |
| 91 | 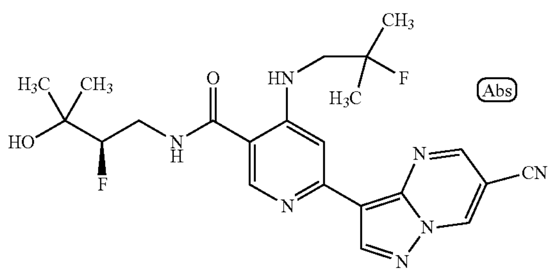 [SMILES: CC(C)(F)CNc1cc(-c2cnn3cc(C#N)cnc23)ncc1C(=O)NC[C@@H](F)C(C)(C)O] | 5.95 | A | 456.7 |
| 92 | 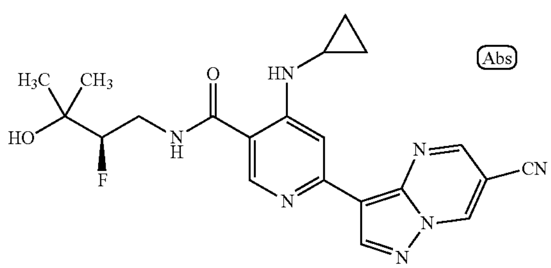 [SMILES: CC(C)(O)[C@H](F)CNC(=O)c1cnc(-c2cnn3cc(C#N)cnc23)cc1NC1CC1] | 6.43 | B | 424.4 |
| 93 | 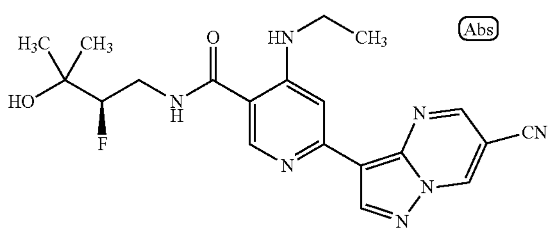 [SMILES: CCNc1cc(-c2cnn3cc(C#N)cnc23)ncc1C(=O)NC[C@@H](F)C(C)(C)O] | 11.45 | B | 412.4 |
| 94 (Diastereomer 1) | | 5.5 | A | 468 |

TABLE 2-continued
| Ex. No. | Structure | HPLC rt (min) | HPLC cond. | LCMS |
|---|---|---|---|---|
| 95 |  Diastereomer 2 | 5.5 | A | 468 |
| 96 | 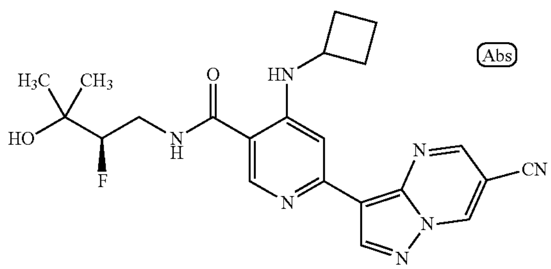 [SMILES: CC(C)(O)[C@H](F)CNC(=O)c1cnc(-c2cnn3cc(C#N)cnc23)cc1NC1CCC1] | 8.09 | B | 435.8 |
| 97 | 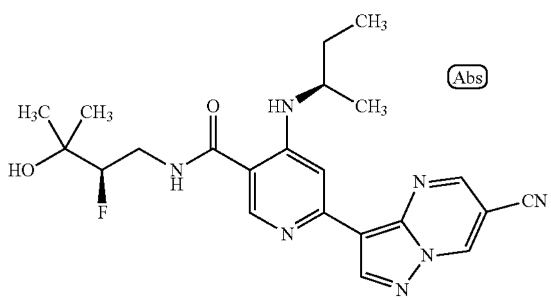 [SMILES: CC[C@@H](C)Nc1cc(-c2cnn3cc(C#N)cnc23)ncc1C(=O)NC[C@@H](F)C(C)(C)O] | 6.31 | A | 440 |
| 98 | 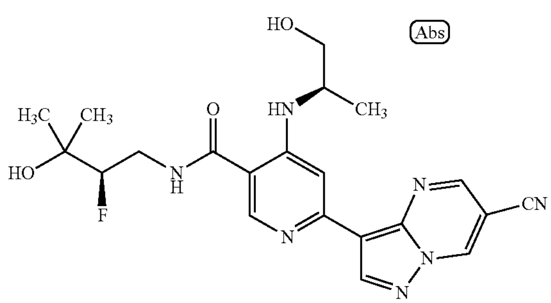 [SMILES: C[C@H](CO)Nc1cc(-c2cnn3cc(C#N)cnc23)ncc1C(=O)NC[C@@H](F)C(C)(C)O] | 9.13 | A | 442 |
| 99 | 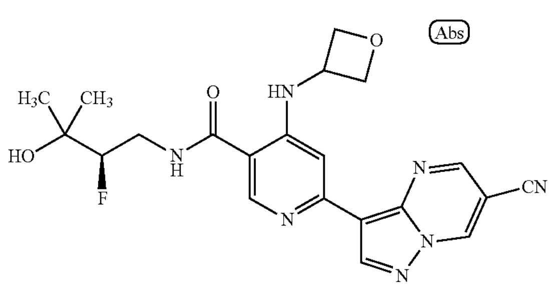 [SMILES: CC(C)(O)[C@H](F)CNC(=O)c1cnc(-c2cnn3cc(C#N)cnc23)cc1NC1COC1] | 9.84 | B | 440 |

TABLE 2-continued
| Ex. No. | Structure | HPLC rt (min) | HPLC cond. | LCMS |
|---|---|---|---|---|
| 100 | 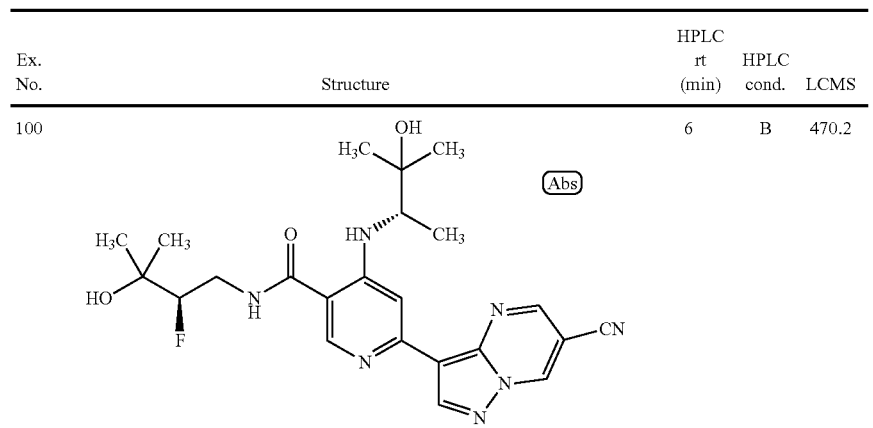 | 6 | B | 470.2 |
| 101 | 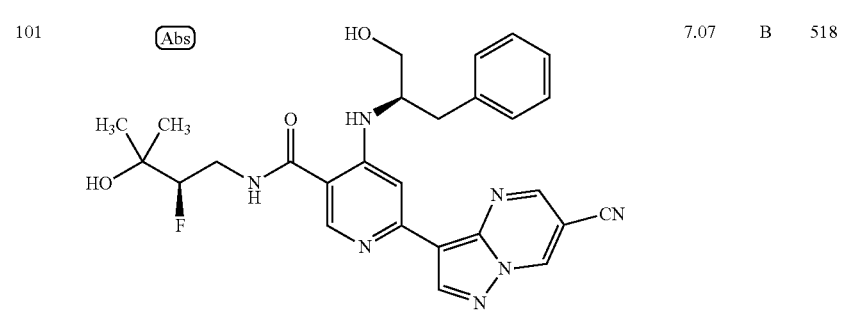 | 7.07 | B | 518 |
| 102 | 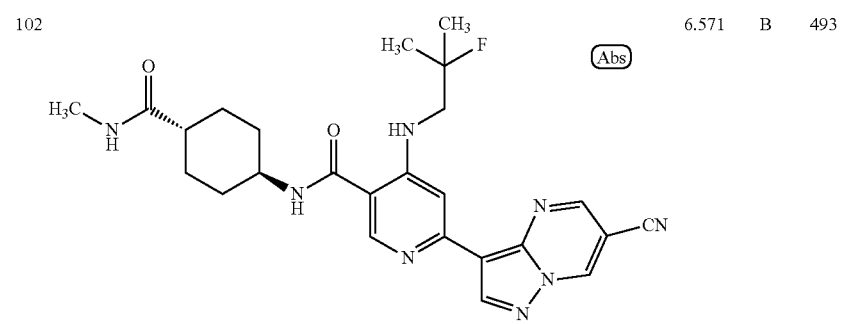 | 6.571 | B | 493 |
| 103 | 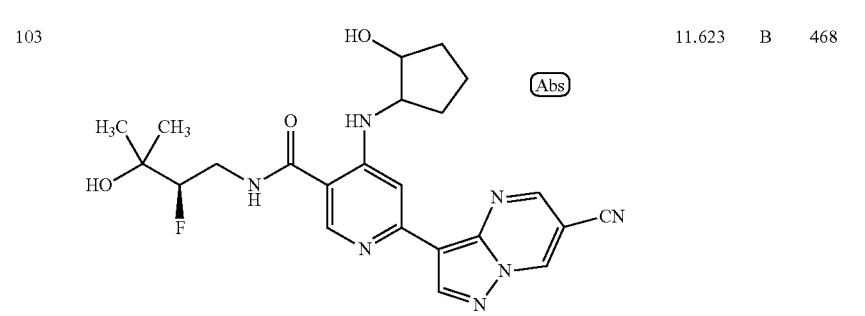 | 11.623 | B | 468 |
| 104 | 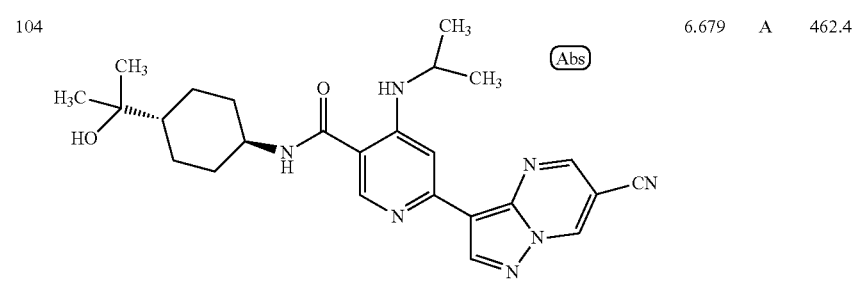 | 6.679 | A | 462.4 |

TABLE 2-continued
| Ex. No. | Structure | HPLC rt (min) | HPLC cond. | LCMS |
|---|---|---|---|---|
| 105 | 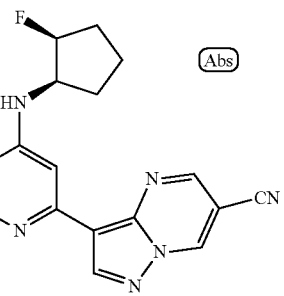 | 6.329 | A | 470.2 |
| 106 | 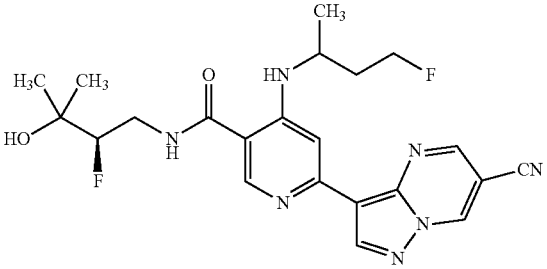 [SMILES: CC(CCF)Nc1cc(-c2cnn3cc(C#N)cnc23)ncc1C(=O)NC[C@@H](F)C(C)(C)O] | 6.843 | B | 458.2 |
| 107 | 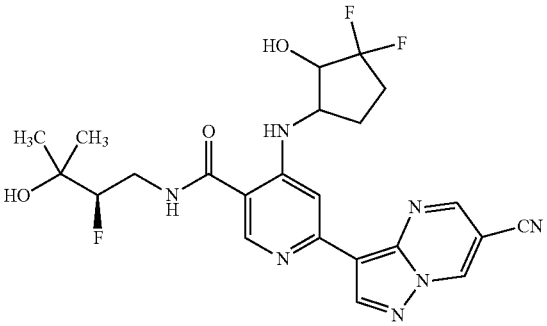 [SMILES: CC(C)(O)[C@H](F)CNC(=O)c1cnc(-c2cnn3cc(C#N)cnc23)cc1NC1CCC(F)(F)C1O] | 6.355 | B | 502 |
| 108 | 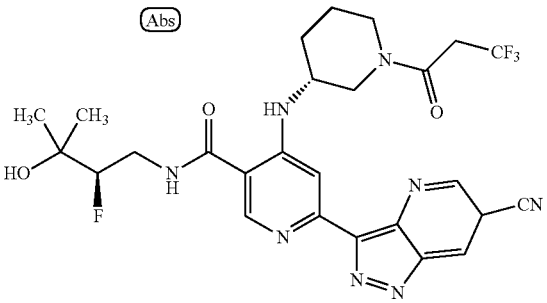 [SMILES: CC(C)(O)[C@H](F)CNC(=O)c1cnc(C2=C3N=CC(C#N)C=C3N=N2)cc1N[C@@H]1CCCN(C(=O)CC(F)(F)F)C1] | 6.868 | B | 577.2 |

TABLE 2-continued
| Ex. No. | Structure | HPLC rt (min) | HPLC cond. | LCMS |
|---|---|---|---|---|
| 109 | 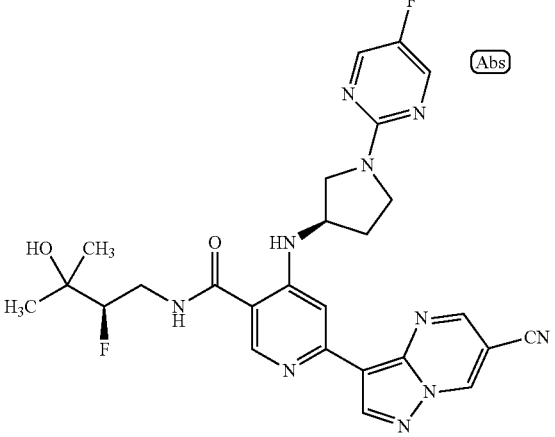 | 6.777 | B | 549.2 |
| 110 | 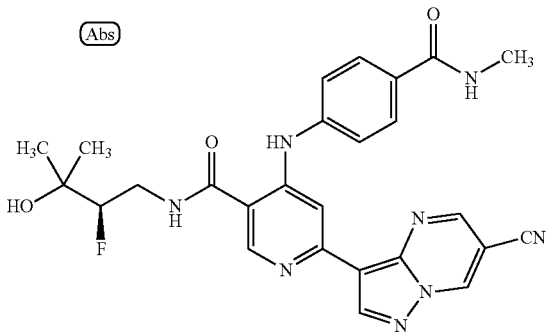 [SMILES: CNC(=O)c1ccc(Nc2cc(-c3cnn4cc(C#N)cnc34)ncc2C(=O)NC[C@@H](F)C(C)(C)O)cc1] | 5.22 | A | 517 |
| 111 | 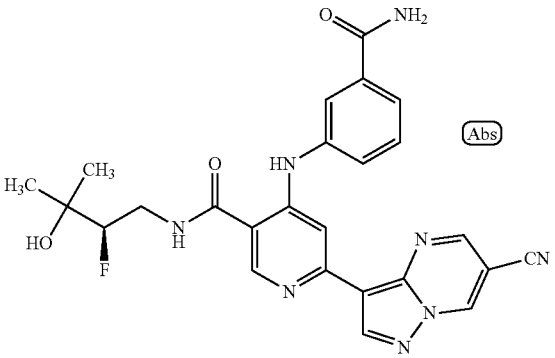 [SMILES: CC(C)(O)[C@H](F)CNC(=O)c1cnc(-c2cnn3cc(C#N)cnc23)cc1Nc1cccc(C(N)=O)c1] | 9.71 | A | 503 |
| 112 | 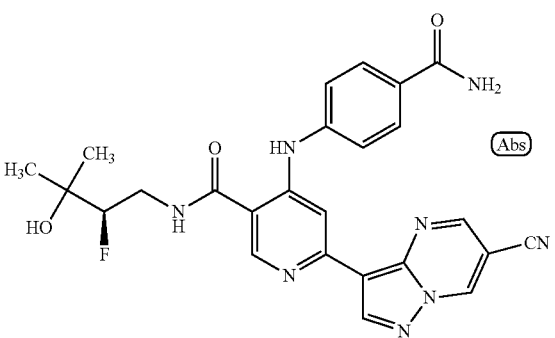 [SMILES: CC(C)(O)[C@H](F)CNC(=O)c1cnc(-c2cnn3cc(C#N)cnc23)cc1Nc1ccc(C(N)=O)cc1] | 4.91 | A | 502 |

TABLE 2-continued
| Ex. No. | Structure | HPLC rt (min) | HPLC cond. | LCMS |
|---|---|---|---|---|
| 113 | 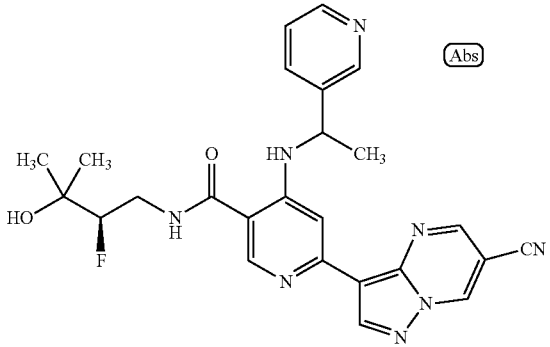 [SMILES: CC(Nc1cc(-c2cnn3cc(C#N)cnc23)ncc1C(=O)NC[C@@H](F)C(C)(C)O)c1cccnc1] | 9.426 | A | 489.2 |
| 114 | 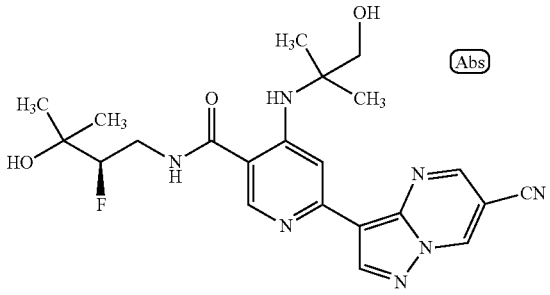 [SMILES: CC(C)(CO)Nc1cc(-c2cnn3cc(C#N)cnc23)ncc1C(=O)NC[C@@H](F)C(C)(C)O] | 1.037 | C | 456 |
| 115 | 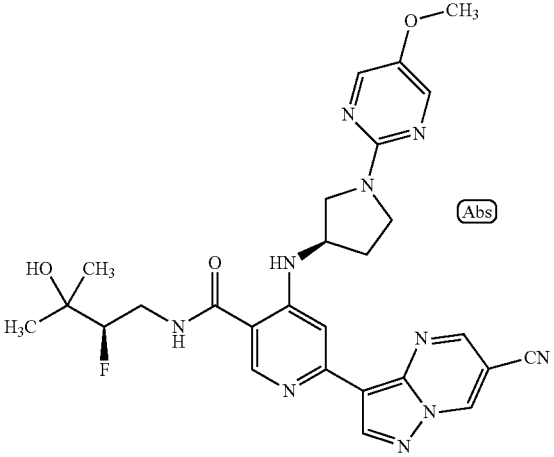 [SMILES: COc1cnc(N2CC[C@@H](Nc3cc(-c4cnn5cc(C#N)cnc45)ncc3C(=O)NC[C@@H](F)C(C)(C)O)C2)nc1] | 6.263 | B | 560.9 |
| 116 | 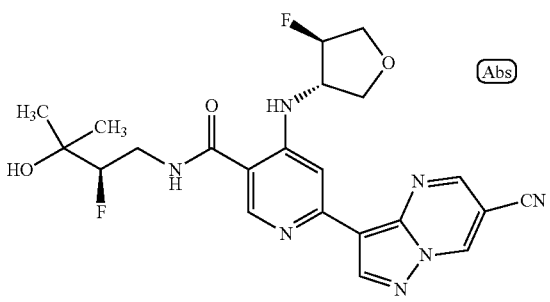 Diastereomer 1 | 6.065 | B | 472.3 |

TABLE 2-continued
| Ex. No. | Structure | HPLC rt (min) | HPLC cond. | LCMS |
|---|---|---|---|---|
| 117 | 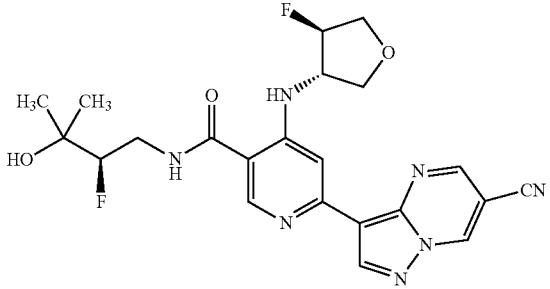 Diastereomer 2 | 6.14 | B | 472.2 |
| 118 | 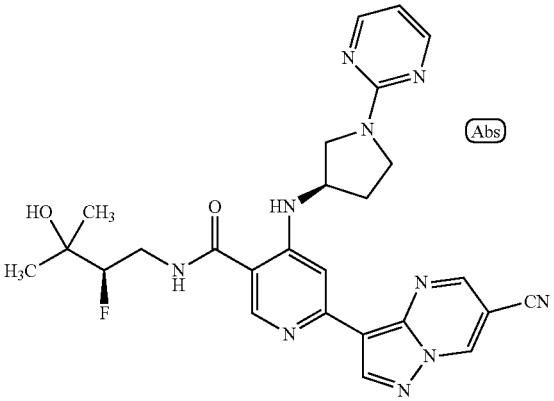 [SMILES: CC(C)(O)[C@H](F)CNC(=O)c1cnc(-c2cnn3cc(C#N)cnc23)cc1N[C@@H]1CCN(c2ncccn2)C1] | 9.302 | A | 531.3 |
| 119 | 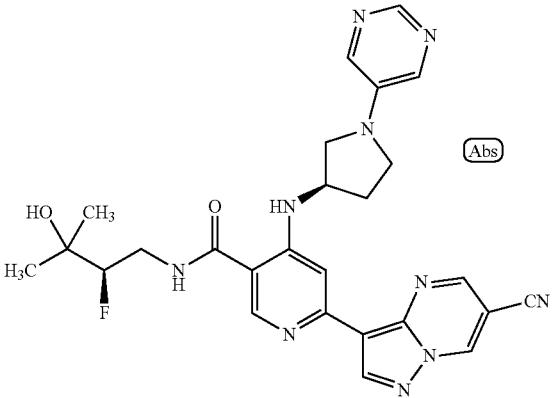 [SMILES: CC(C)(O)[C@H](F)CNC(=O)c1cnc(-c2cnn3cc(C#N)cnc23)cc1N[C@@H]1CCN(c2cncnc2)C1] | 1.095 | C | 531.2 |
| 120 | 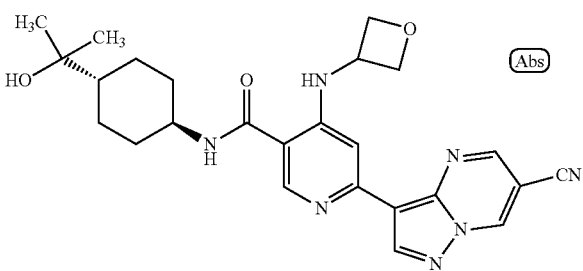 [SMILES: CC(C)(O)[C@H]1CC[C@H](NC(=O)c2cnc(-c3cnn4cc(C#N)cnc34)cc2NC2COC2)CC1] | 0.891 | D | 476.2 |

TABLE 2-continued
| Ex. No. | Structure | HPLC rt (min) | HPLC cond. | LCMS |
|---|---|---|---|---|
| 121 | 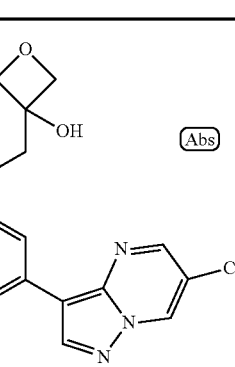 | 8.599 | A | 470.2 |
| 122 | 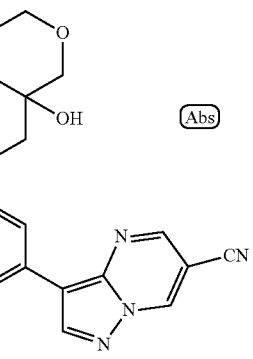<br>Diastereomer 1 | 10.149 | B | 498.2 |
| 123 | 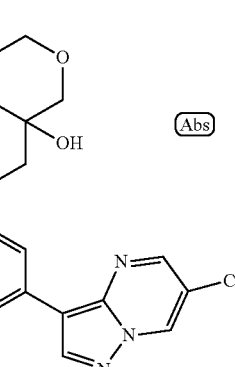<br>Diastereomer 2 | 10.17 | B | 498.2 |
| 124 | 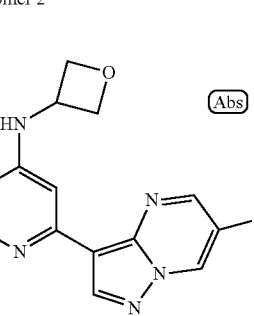 | 10.045 | A | 448.2 |

TABLE 2-continued
| Ex. No. | Structure | HPLC rt (min) | HPLC cond. | LCMS |
|---|---|---|---|---|
| 125 | 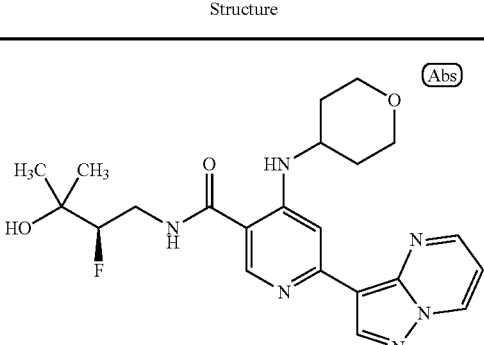 | 1.108 | C | 456.3 |
The Examples in Table 3 were prepared using the general methods for Example 1-20 using the appropriate starting material and amine.
TABLE 3
| Ex. No. | Structure | HPLC rt (min) | HPLC cond. | LCMS |
|---|---|---|---|---|
| 126 | 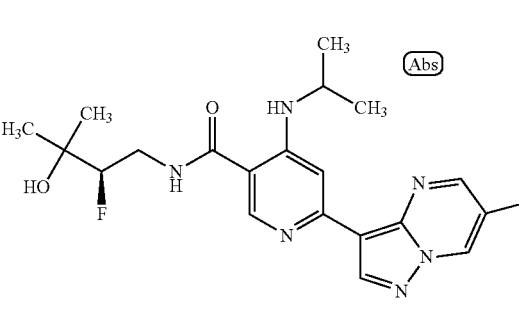 | 10.25 | B | 443.2 |
| 127 | 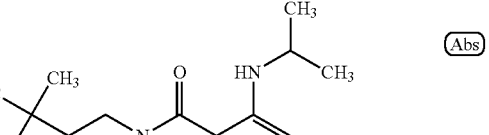 | 6.19 | B | 400 |
| 128 | 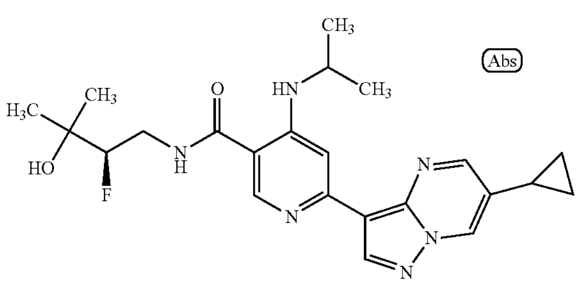 [SMILES: CC(C)Nc1cc(-c2cnn3cc(C4CC4)cnc23)ncc1C(=O)NC[C@@H](F)C(C)(C)O] | 1.566 | C | 441.2 |

TABLE 3-continued
| Ex. No. | Structure | HPLC rt (min) | HPLC cond. | LCMS |
|---|---|---|---|---|
| 129 | 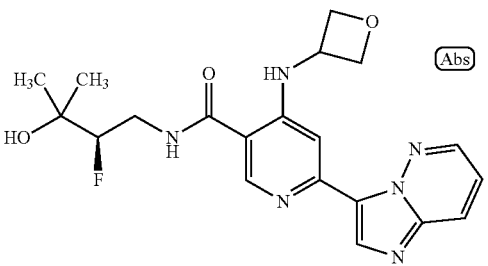 | 11.78 | B | 434.2 |
| 130 | 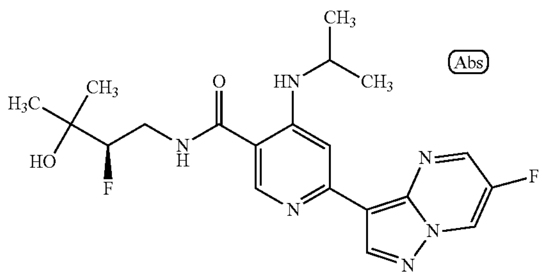 [SMILES: CC(C)Nc1cc(-c2cnn3cc(F)cnc23)ncc1C(=O)NC[C@@H](F)C(C)(C)O] | 8.59 | B | 419.3 |
The Examples in Table 4 were prepared using the general methods for Example 1-21 using the appropriate starting material and amine.
TABLE 4
| Ex. No. | Structure | HPLC rt (min) | HPLC cond. | LCMS |
|---|---|---|---|---|
| 131 | 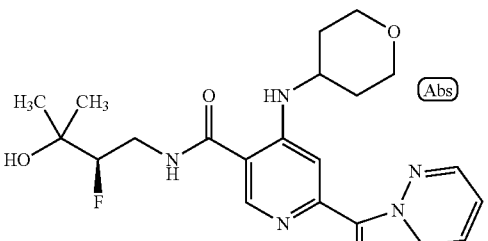 | 8.522 | B | 415.3 |
| 132 | 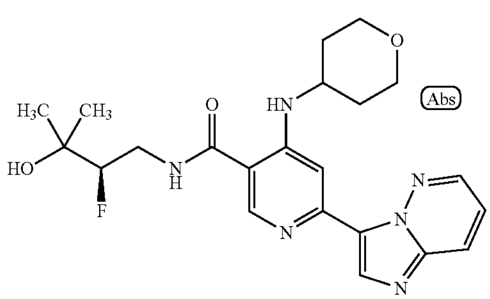 [SMILES: CC(C)(O)[C@H](F)CNC(=O)c1cnc(-c2cnc3cccnn23)cc1NC1CCOCC1] | 1.655 | C | 443.2 |

TABLE 4-continued
| Ex. No. | Structure | HPLC rt (min) | HPLC cond. | LCMS |
|---|---|---|---|---|
| 133 | 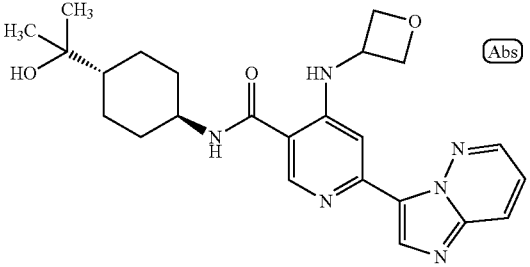 [SMILES: CC(C)(O)[C@H]1CC[C@H](NC(=O)c2cnc(-c3cnc4cccnn34)cc2NC2COC2)CC1] (Abs) | 1.757 | C | 451.2 |
| 134 | 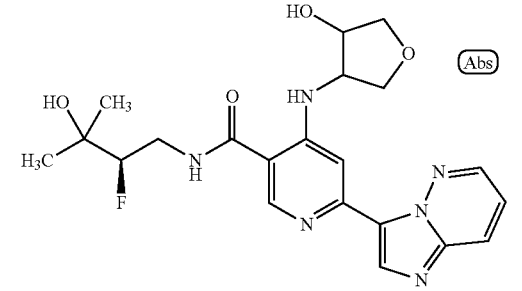 (Abs) Diastereomer 1 | 7.902 | A | 445.2 |
| 135 | 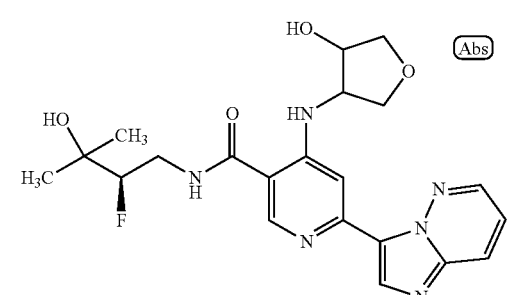 (Abs) Diastereomer 2 | 7.916 | A | 445.2 |
| 136 | 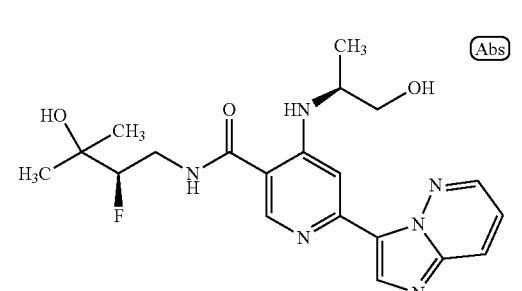 (Abs) | 0.888 | C | 417.2 |
| 137 | 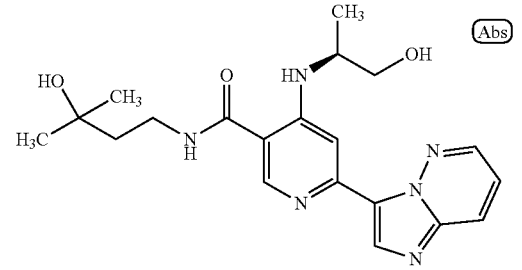 [SMILES: C[C@@H](CO)Nc1cc(-c2cnc3cccnn23)ncc1C(=O)NCCC(C)(C)O] (Abs) | 0.885 | C | 399 |

TABLE 4-continued

| Ex. No. | Structure | HPLC rt (min) | HPLC cond. | LCMS |
|---|---|---|---|---|
| 138 | 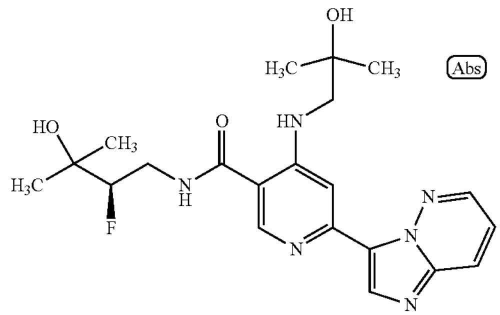 [SMILES: CC(C)(O)CNc1cc(-c2cnc3cccnn23)ncc1C(=O)NC[C@@H](F)C(C)(C)O] | 0.954 | C | 431.3 |
| 139 | 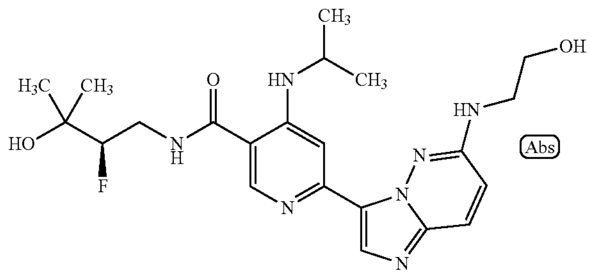 [SMILES: CC(C)Nc1cc(-c2cnc3ccc(NCCO)nn23)ncc1C(=O)NC[C@@H](F)C(C)(C)O] | 1.657 | C | 460.2 |
| 140 | 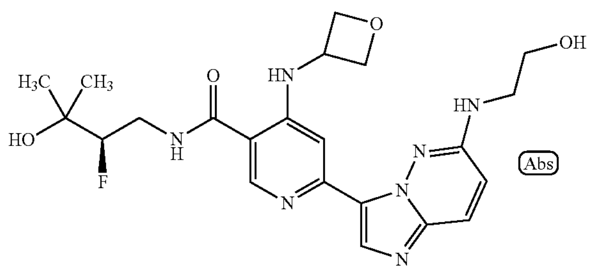 [SMILES: CC(C)(O)[C@H](F)CNC(=O)c1cnc(-c2cnc3ccc(NCCO)nn23)cc1NC1COC1] | 1.452 | C | 474.2 |
| 141 | 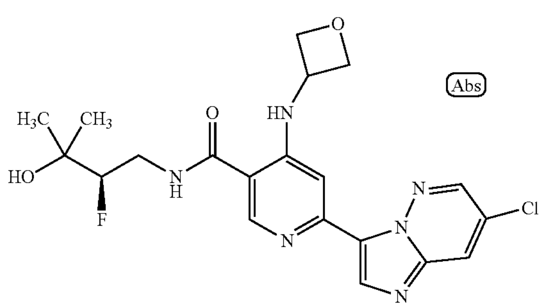 [SMILES: CC(C)(O)[C@H](F)CNC(=O)c1cnc(-c2cnc3cc(Cl)cnn23)cc1NC1COC1] | 9.318 | A | 449.2 |
| 142 | 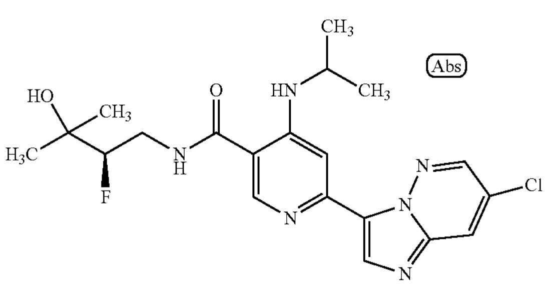 [SMILES: CC(C)Nc1cc(-c2cnc3cc(Cl)cnn23)ncc1C(=O)NC[C@@H](F)C(C)(C)O] | 1.447 | C | 435 |

TABLE 4-continued
| Ex. No. | Structure | HPLC rt (min) | HPLC cond. | LCMS |
|---|---|---|---|---|
| 143 | 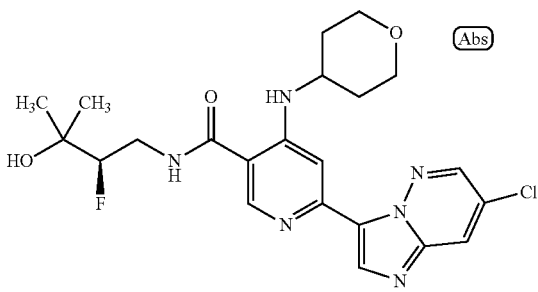 [SMILES: CC(C)(O)[C@H](F)CNC(=O)c1cnc(-c2cnc3cc(Cl)cnn23)cc1NC1CCOCC1] | 1.89 | C | 477 |
| 144 | 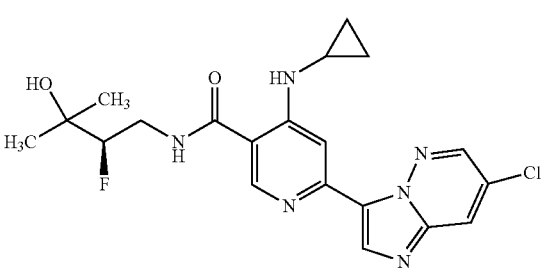 [SMILES: CC(C)(O)[C@H](F)CNC(=O)c1cnc(-c2cnc3cc(Cl)cnn23)cc1NC1CC1] | 1.413 | C | 433.2 |
| 145 | 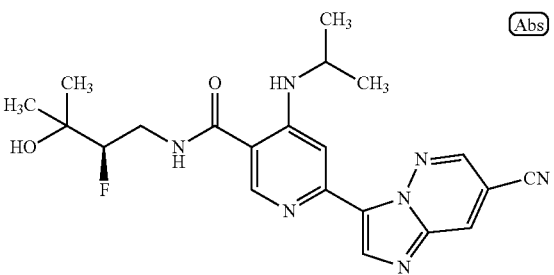 [SMILES: CC(C)Nc1cc(-c2cnc3cc(C#N)cnn23)ncc1C(=O)NC[C@@H](F)C(C)(C)O] | 1.575 | D | 426.2 |
| 146 | 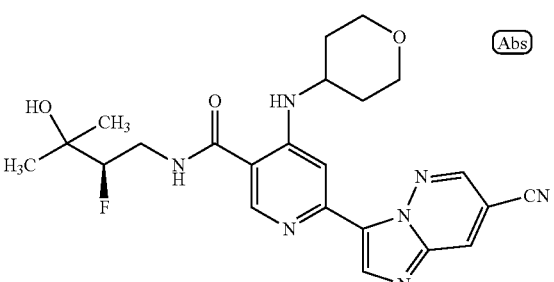 | 1.767 | C | 468.2 |
| 147 | 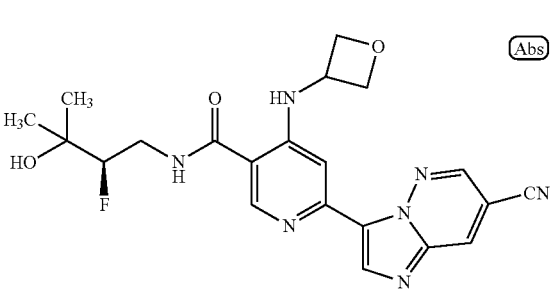 [SMILES: CC(C)(O)[C@H](F)CNC(=O)c1cnc(-c2cnc3cc(C#N)cnn23)cc1NC1COC1] | 1.269 | D | 440 |

TABLE 4-continued

| Ex. No. | Structure | | HPLC rt (min) | HPLC cond. | LCMS |
|---|---|---|---|---|---|
| 148 | [Structure with isopropylamino pyridine carboxamide, fluoro-hydroxy butyl group, imidazo[1,2-b]pyridazine with methyl] | Abs | 2.086 | C | 415.2 |
| 149 | [Structure with isopropylamino pyridine carboxamide, fluoro-hydroxy butyl group, methoxy-imidazo[1,2-b]pyridazine] | Abs | 1.637 | D | 431.2 |
| 150 | [Structure with isopropylamino pyridine carboxamide, fluoro-hydroxy butyl group, amino-imidazo[1,2-b]pyridazine] | Abs | 2.014 | C | 416.2 |
| 151 | [Structure with isopropylamino pyridine carboxamide, fluoro-hydroxy butyl group, (hydroxy-dimethyl-ethyl)amino-imidazo[1,2-b]pyridazine] | Abs | 1.2 | C | 488.4 |
| 152 | [Structure with isopropylamino pyridine carboxamide, fluoro-hydroxy butyl group, hydroxypyrrolidinyl-imidazo[1,2-b]pyridazine] | Abs | 1.146 | C | 486.4 |

TABLE 4-continued

| Ex. No. | Structure | | HPLC rt (min) | HPLC cond. | LCMS |
|---|---|---|---|---|---|
| 153 | [structure] | (Abs) | 11.14 | A | 431.2 |
| 154 | [structure] | (Abs) | 1.01 | C | 445.3 |

The Examples in Table 5 were prepared using the general methods for Example 1-21 using the appropriate starting material and amine.

TABLE 5

| Ex. No. | Structure | | HPLC rt (min) | HPLC cond. | LCMS |
|---|---|---|---|---|---|
| 155 | [structure] | (Abs) | 6.845 | A | 452 |
| 156 | [structure] | (Abs) | 1.4 | E | 427.1 |

Example 157

(R)-6-(6-chloropyrazolo[1,5-a]pyrimidin-3-yl)-N-(3-(difluoromethoxy)-2-fluoro-3-methylbutyl)-4-(isopropylamino)nicotinamide

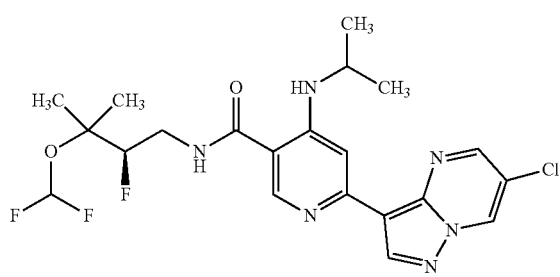
(157)

Intermediate 157A: (R)-6-bromo-N-(3-(difluoromethoxy)-2-fluoro-3-methylbutyl)-4-(isopropylamino)nicotinamide

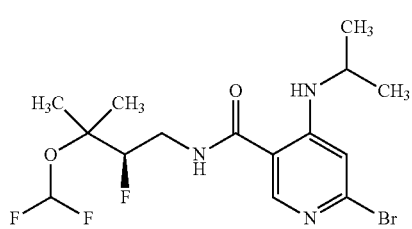
(157A)

A solution of (R)-6-bromo-N-(2-fluoro-3-hydroxy-3-methylbutyl)-4-(isopropylamino)nicotinamide (0.6 g, 1.66 mmol) in acetonitrile (10 mL) was purged with nitrogen for 5 min. Cu(I)I (0.32 g, 1.66 mmol) was added and the reaction mixture was heated at reflux. 2,2-Difluoro-2-(fluorosulfonyl)acetic acid (0.295 g, 1.66 mmol) (dissolved in 10 mL of acetonitrile) was added dropwise over a period of 10 min. After being stirred for additional 1 h, the reaction mixture was cooled to room temperature and quenched by the addition of solid NaHCO$_3$. The mixture was diluted with water (50 mL), and extracted with ethyl acetate (2×20 mL). The combined organic layers were dried over Na$_2$SO$_4$, filtered, and concentrated. The product was purified via column chromatography (30% EtOAc:hexane) to afford (R)-6-bromo-N-(3-(difluoromethoxy)-2-fluoro-3-methylbutyl)-4-(isopropylamino)nicotinamide (0.4 g, 59% yield). $^1$H NMR (300 MHz, DMSO-d$_6$) δ 8.85 (t, J=5.7 Hz, 1H), 8.40 (d, J=7.9 Hz, 1H), 8.35-8.24 (m, 1H), 7.18-6.62 (m, 2H), 4.71-4.39 (m, 1H), 3.87-3.56 (m, 2H), 3.38 (d, J=2.6 Hz, 1H), 1.39 (d, J=5.3 Hz, 6H), 1.16 (d, J=6.4 Hz, 6H); LCMS m/z 412.0 (M+H).

Intermediate 157B: (R)—N-(3-(difluoromethoxy)-2-fluoro-3-methylbutyl)-4-(isopropylamino)-6-(trimethylstannyl)nicotinamide

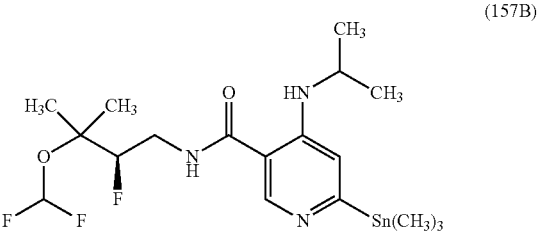
(157B)

A solution of (R)-6-bromo-N-(3-(difluoromethoxy)-2-fluoro-3-methylbutyl)-4-(isopropylamino)nicotinamide (0.18 g, 0.44 mmol) and hexamethylditin (0.26 g, 0.79 mmol) in toluene (10 mL) was purged with nitrogen for 10 min. Pd(PPh$_3$)$_4$ (0.1 g, 0.09 mmol) was added and purging continued for an additional 5 min. The pressure tube was closed and stirred at 110° C. for 10 h. The reaction mixture was cooled and filtered through celite which was washed with ethyl acetate. The combined filtrates were concentrated in vacuo to afford (R)—N-(3-(difluoromethoxy)-2-fluoro-3-methylbutyl)-4-(isopropylamino)-6-(trimethylstannyl)nicotinamide (0.3 g); LCMS m/z 498 (M+H).

Example 157

In a microwave reactor vial, (R)—N-(3-(difluoromethoxy)-2-fluoro-3-methylbutyl)-4-(isopropylamino)-6-(trimethylstannyl)nicotinamide (0.1 g, 0.20 mmol) and 7-chloro-3-iodoimidazo[1,2-b]pyridazine (0.056 g, 0.20 mmol) were dissolved in dioxane (10 mL) and purged with nitrogen for 10 min. Pd(PPh$_3$)$_4$ (0.047 g, 0.040 mmol) was added and purging was continued for an additional 5 minutes. The vessel was sealed and heated in a microwave reactor at 150° C. for 1 h. The reaction mixture was cooled and filtered through celite with ethyl acetate (3×15 mL). The combined filtrates were concentrated the product was purified via preparative HPLC to afford (R)-6-(7-chloroimidazo[1,2-b]pyridazin-3-yl)-N-(3-(difluoromethoxy)-2-fluoro-3-methylbutyl)-4-(isopropylamino)nicotinamide (15 mg, 15% yield). $^1$H NMR (400 MHz, DMSO-d$_6$) δ 1.28 (dd, J=6.02, 1.0 Hz, 6H), 1.42 (d, J=6.5 Hz, 6H), 3.36-3.47 (m, 1H), 3.64-3.85 (m, 2H), 4.49-4.68 (m, 1H), 6.69-7.09 (m, 1H), 7.90-7.94 (m, 1H), 8.46 (s, 1H), 8.52-8.56 (m, 1H), 8.58-8.61 (m, 1H), 8.69 (s, 1H), 8.79-8.84 (m, 1H), 8.87-8.91 (m, 1H); LCMS m/z 485.3 (M+H).

The Examples in Table 6 were prepared using the general methods for Example 1-20 using the appropriate starting material and amine. Intermediates described above were used for the synthesis of the examples below and other examples in this application.

TABLE 6

| Ex. No. | Structure | HPLC rt (min) | HPLC cond. | LCMS |
|---|---|---|---|---|
| 158 | 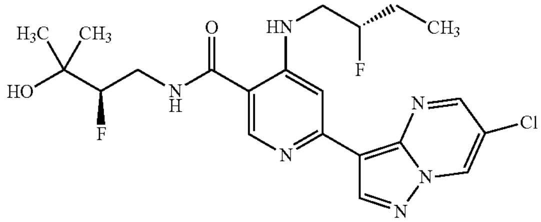 [SMILES: CC[C@H](F)CNc1cc(-c2cnn3cc(Cl)cnc23)ncc1C(=O)NC[C@@H](F)C(C)(C)O] | 1.58 | C | 467.3 |
| 159 | 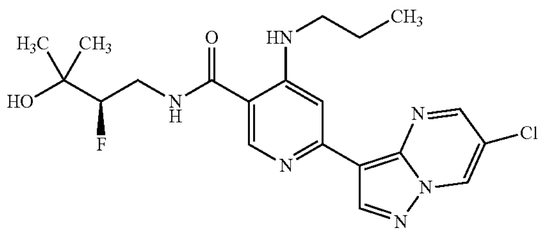 | 1.42 | E | 453.2 |
| 160 | 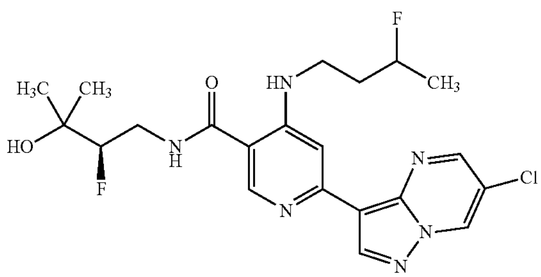 [SMILES: CC(F)CCNc1cc(-c2cnn3cc(Cl)cnc23)ncc1C(=O)NC[C@@H](F)C(C)(C)O] | 1.54 | E | 467.2 |
| 161 | 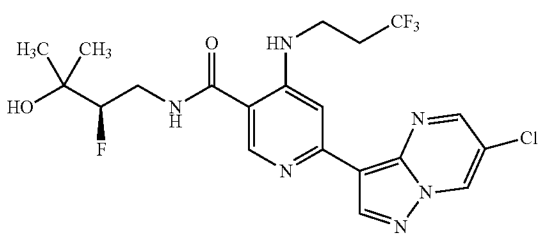 [SMILES: CC(C)(O)[C@H](F)CNC(=O)c1cnc(-c2cnn3cc(Cl)cnc23)cc1NCCC(F)(F)F] | 1.47 | C | 489.2 |
| 163 | 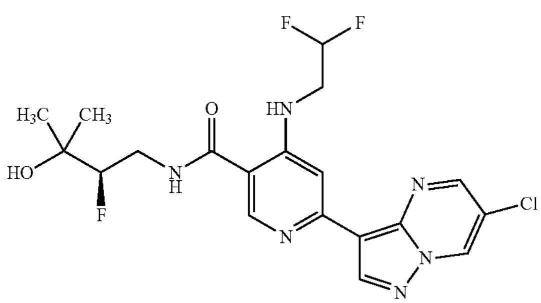 [SMILES: CC(C)(O)[C@H](F)CNC(=O)c1cnc(-c2cnn3cc(Cl)cnc23)cc1NCC(F)F] | 10.93 | A, 18 MIN GRADIENT | 457.0 |
| 164 | 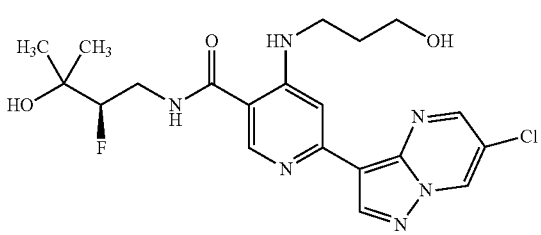 [SMILES: CC(C)(O)[C@H](F)CNC(=O)c1cnc(-c2cnn3cc(Cl)cnc23)cc1NCCCO] | 1.07 | E | 451.2 |

TABLE 6-continued

| Ex. No. | Structure | HPLC rt (min) | HPLC cond. | LCMS |
|---|---|---|---|---|
| 165 | 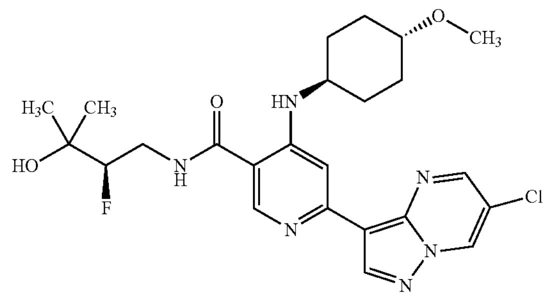 [SMILES: CO[C@H]1CC[C@H](Nc2cc(-c3cnn4cc(Cl)cnc34)ncc2C(=O)NC[C@@H](F)C(C)(C)O)CC1] | 1.51 | C | 505.3 |
| 166 | 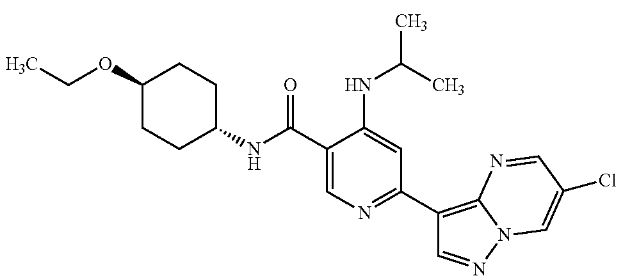 [SMILES: CCO[C@H]1CC[C@H](NC(=O)c2cnc(-c3cnn4cc(Cl)cnc34)cc2NC(C)C)CC1] | 2.18 | C | 457.2 |
| 167 | 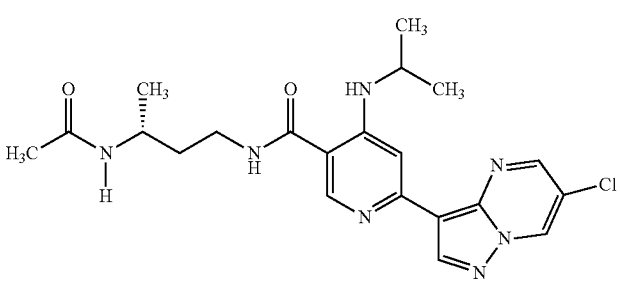 [SMILES: CC(=O)N[C@H](C)CCNC(=O)c1cnc(-c2cnn3cc(Cl)cnc23)cc1NC(C)C] | 1.43 | E | 444.0 |
| 168 | 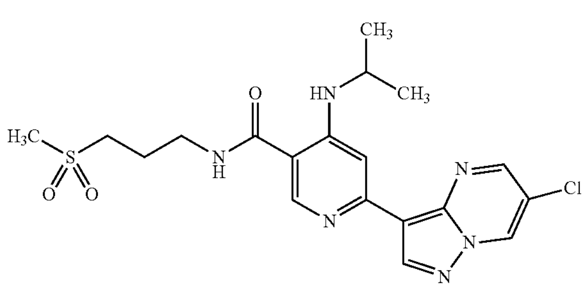 [SMILES: CC(C)Nc1cc(-c2cnn3cc(Cl)cnc23)ncc1C(=O)NCCCS(C)(=O)=O] | 1.53 | E | 451.2 |

Example 169

N-(3-cyano-3-methylbutyl)-6-(6-cyanopyrazolo[1,5-a]pyrimidin-3-yl)-4-(isopropylamino)nicotinamide

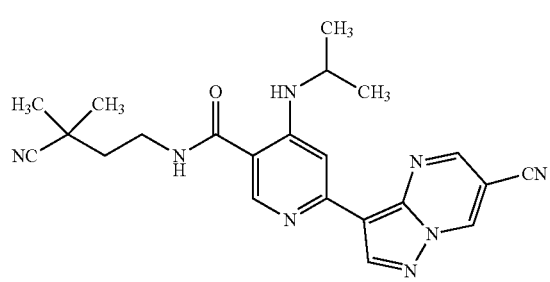

(169)

Intermediate 169A: tert-butyl (3-cyano-3-methylbutyl)carbamate

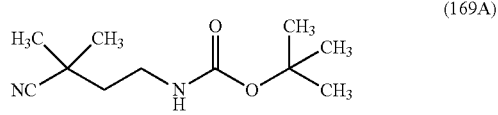

(169A)

To a stirred solution of LDA (2.68 mL, 5.35 mmol) in THF (20 mL) at −78° C. was added a solution of isobutyronitrile (0.370 g, 5.35 mmol) in THF (10 mL) over period of 15 mins. The reaction mixture was stirred for 1 h at room temperature then added tert-butyl (2-bromoethyl)carbamate (1 g, 4.46 mmol) in THF (10 mL) drop wise at −78° C. over a period of 15 min. The cooling bath was removed and the reaction mixture was stirred at room temperature for 17 h. The reaction mixture was quenched with NH$_4$Cl solution and extracted with ethyl acetate (2×60 mL). The organic layer was dried over Na$_2$SO$_4$, filtered, and concentrated to an oil. The product was purified via column chromatography (10% ethyl acetate/pet ether) to afford tert-butyl (3-cyano-3-methylbutyl)carbamate (0.5 g, 53% yield) as pale yellow liquid. $^1$H NMR (400 MHz, CDCl$_3$) δ=4.67 (br s, 1H), 3.37-3.21 (m, 2H), 1.81-1.69 (m, 2H), 1.51-1.42 (m, 9H), 1.41-1.32 (m, 6H); LCMS m/z 213.2 (M+H).

Intermediate 169B: 4-amino-2,2-dimethylbutanenitrile

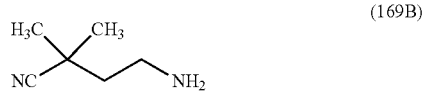

(169B)

A stirred solution of tert-butyl (3-cyano-3-methylbutyl)carbamate (450 mg, 2.12 mmol) in DCM (1 mL) was added TFA (0.6 mL, 7.8 mmol) and stirred for 1 h. The reaction mixture was evaporated to remove excess TFA and the crude compound 4-amino-2,2-dimethylbutanenitrile (225 mg, 95% yield) was used without further purification. $^1$H NMR (300 MHz, DMSO-d$_6$) δ 7.87 (br s, 2H), 3.03-2.80 (m, 2H), 1.89-1.73 (m, 2H), 1.41-1.30 (m, 6H).

Intermediate 169C: 6-chloro-N-(3-cyano-3-methylbutyl)-4-(isopropylamino)nicotinamide

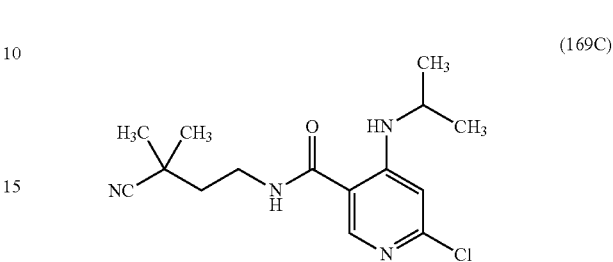

(169C)

To a stirred solution of 6-chloro-4-(isopropylamino)nicotinic acid (420 mg, 1.96 mmol) in DMF (2 mL) was added HATU (1488 mg, 3.91 mmol), 4-amino-2,2-dimethylbutanenitrile (219 mg, 1.96 mmol) and DIPEA (1.03 mL, 5.87 mmol) successively at 27° C. and stirred for 2 h. The reaction mixture was concentrated to dryness and diluted with 100 mL of EtOAc. The organic layer was washed with NaHCO$_3$ solution, dried over Na$_2$SO$_4$, filtered, and concentrated. The product was purified via column chromatography (30% ethyl acetate/pet ether) to afford 6-chloro-N-(3-cyano-3-methylbutyl)-4-(isopropylamino)nicotinamide (350 mg, 58% yield). LCMS: m/z 309.1 (M+H).

Example 169

To a stirred solution of 6-chloro-N-(3-cyano-3-methylbutyl)-4-(isopropylamino) nicotinamide (50 mg, 0.16 mmol) in 1,4-dioxane (2 mL) was added 3-(4,4,5,5-tetramethyl-1,3,2-dioxaborolan-2-yl)pyrazolo[1,5-a]pyrimidine-6-carbonitrile (87 mg, 0.324 mmol) and potassium acetate (48 mg, 0.486 mmol). The reaction mixture was degassed by bubbling nitrogen gas for 5 min. Pd(PPh$_3$)$_4$ (37.4 mg, 0.032 mmol) was added and further degassed for 5 min. The reaction mixture was heated at 120° C. for 70 min in a microwave reactor. The reaction mixture was filtered through celite bed, and washed with 50 mL of ethyl acetate. The filtrate was concentrated and diluted with 1.5N HCl (20 mL) and extracted with DCM (2×20 mL). The aqueous layer was basified using NaHCO$_3$ solution and extracted with ethyl acetate (2×30 mL). The organic extracts were dried over Na$_2$SO$_4$, filtered, evaporated in vacuo. Purification via preparative HPLC afforded N-(3-cyano-3-methylbutyl)-6-(6-cyanopyrazolo[1,5-a]pyrimidin-3-yl)-4-isopropylamino) nicotinamide (4 mg, 6% yield). $^1$H NMR (400 MHz, DMSO-d$_6$) δ 13.74 (br s, 1H), 10.24 (d, J=2.0 Hz, 1H), 9.41 (br s, 1H), 9.14-9.25 (m, 2H), 9.07 (br s, 1H), 8.59 (s, 1H), 7.69-7.82 (m, 1H), 4.00 (dq, J=13.2, 6.5 Hz, 1H), 3.32-3.49 (m, 3H), 1.78-1.91 (m, 2H), 1.37 (d, 6H), 1.32 (d, J=6.5 Hz, 6H); LCMS: m/z 417.0 (M+H).

The Examples in Table 7 were prepared using the general methods for Example 169 using the appropriate starting material and amine. Intermediates described above were used for the synthesis of the examples below and other examples in this application.

TABLE 7

| Ex. No. | Structure | HPLC rt (min) | HPLC cond. | LCMS |
|---|---|---|---|---|
| 170 | 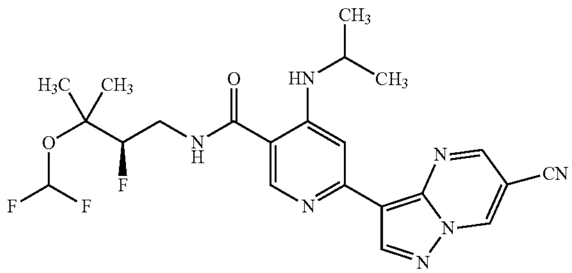 [SMILES: CC(C)Nc1cc(-c2cnn3cc(C#N)cnc23)ncc1C(=O)NC[C@@H](F)C(C)(C)OC(F)F] | 1.34 | C | 476.3 |
| 171 | 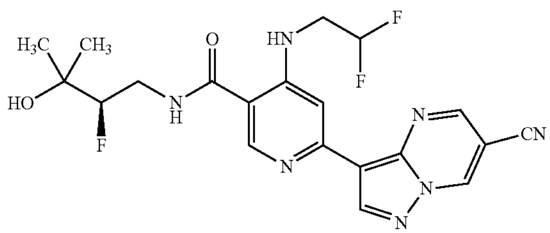 [SMILES: CC(C)(O)[C@H](F)CNC(=O)c1cnc(-c2cnn3cc(C#N)cnc23)cc1NCC(F)F] | 10.15 | A, 18 MIN GRADIENT | 448.2 |
| 172 | 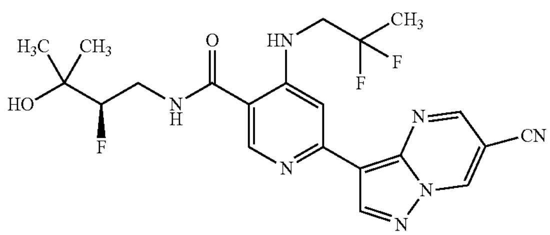 [SMILES: CC(F)(F)CNc1cc(-c2cnn3cc(C#N)cnc23)ncc1C(=O)NC[C@@H](F)C(C)(C)O] | 12.21 | B, 18 MIN GRADIENT | 462.2 |

Example 173

6-(7-cyanoimidazo[1,2-b]pyridazin-3-yl)-N-(2,2-difluoro-3-hydroxy-3-methylbutyl)-4-(isopropylamino)nicotinamide

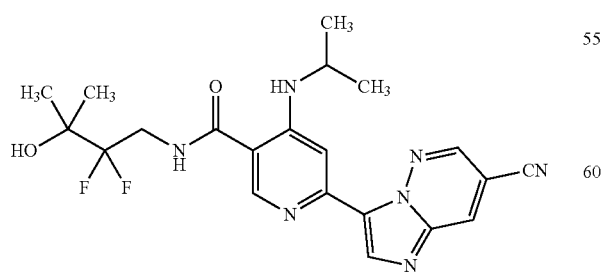
(173)

Intermediate 173A: ethyl 3-(dibenzylamino)-2,2-difluoropropanoate

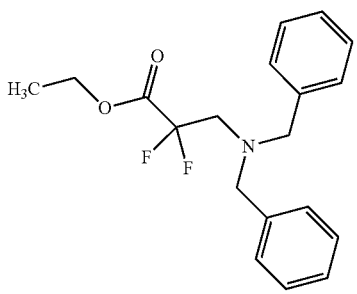
(173A)

To a stirred suspension of Zn dust (4.98 g, 76 mmol) in THF (100 mL) was added TMS-Cl (9.73 mL, 76 mmol) followed by the addition of ethyl 2-bromo-2,2-difluoroacetate (3.40 g, 16.8 mmol). The mixture was stirred for 15 minutes, then a solution of N-((1H-benzo[d][1,2,3]triazol-1-yl)methyl)-N-benzyl-1-phenylmethanamine (5 g, 15.22 mmol) in THF (50 mL) was added slowly. The reaction mixture was stirred for 2 hours. The reaction was quenched slowly by the addition of 10% sodium-bicarbonate solution. The reaction mixture was extracted with ethyl acetate (3×200 mL). The combined organic layers were washed with water, dried over sodium sulfate and concentrated. The crude material was purified via column chromatography to afford ethyl 3-(dibenzylamino)-2,2-difluoropropanoate (5 g, 95% yield) as a pale yellow oil. LCMS 334.2 (M+H).

Intermediate 173B: 4-(dibenzylamino)-3,3-difluoro-2-methylbutan-2-ol

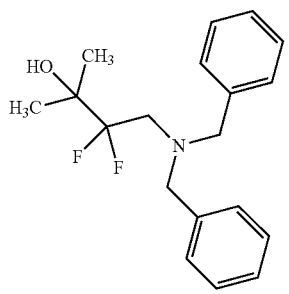

(173B)

To a solution of ethyl 3-(dibenzylamino)-2,2-difluoropropanoate (5.5 g, 16.5 mmol) in THF (50 mL) at 0° C. was added methyl magnesium bromide (3M in diethyl ether) (16.50 mL, 49.5 mmol) dropwise. After completion of the addition, the reaction mixture was allowed to stir at room temperature for 2 h. The mixture was then cooled to 0° C. and quenched with saturated ammonium chloride solution. The aqueous layer was extracted with ethyl acetate, dried over Na$_2$SO$_4$ and concentrated to afford 4-(dibenzylamino)-3,3-difluoro-2-methylbutan-2-ol (5 g, 90% yield). LC/MS: 320.2 (M+H).

Intermediate 173C: 4-amino-3,3-difluoro-2-methylbutan-2-ol

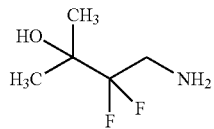

(173C)

A solution of 4-(dibenzylamino)-3,3-difluoro-2-methylbutan-2-ol (5 g, 15.65 mmol) in MeOH (50 mL) was added Pd/C (2.5 g, 23.5 mmol) and Pd(OH)$_2$ (2.5 g, 15.7 mmol) and hydrogenated at 1 atm pressure for 4 hrs. The reaction mixture was diluted with ethyl acetate and passed through a small plug of CELITE®. The filtrate was concentrated to afford 4-amino-3,3-difluoro-2-methylbutan-2-ol (2 g, 91% yield). The product was used without further purification. $^1$H NMR (400 MHz, methanol-d$_4$) δ 3.14 (t, J=16.3 Hz, 2H), 1.30 (t, J=1.1 Hz, 6H).

Example 173

To a stirred solution of 6-(7-cyanoimidazo[1,2-b]pyridazin-3-yl)-4-(isopropylamino)nicotinic acid (20 mg, 0.062 mmol) in DMF (1 mL) was added HATU (47.2 mg, 0.124 mmol). A solution of 4-amino-3,3-difluoro-2-methylbutan-2-ol (9.50 mg, 0.068 mmol) in DMF (0.5 mL) was then added and the reaction mixture was stirred for 3 h. The product was purified directly via preparative HPLC to afford 6-(7-cyanoimidazo[1,2-b]pyridazin-3-yl)-N-(2,2-difluoro-3-hydroxy-3-methylbutyl)-4-(isopropylamino)nicotinamide (6 mg, 20% yield). $^1$H NMR (400 MHz, DMSO-d$_6$) δ 9.11 (q, J=2.01 Hz, 2H), 8.68-8.79 (m, 3H), 8.46 (d, J=7.5 Hz, 1H), 7.98 (s, 1H), 5.39 (s, 1H), 3.76-3.98 (m, 3H), 1.21-1.34 (m, 12H); LCMS m/z 444.3 (M+H).

Example 174

6-(7-cyanoimidazo[1,2-b]pyridazin-3-yl)-4-(isopropylamino)-N-((1r,4r)-4-(2-methoxypropan-2-yl)cyclohexyl)nicotinamide

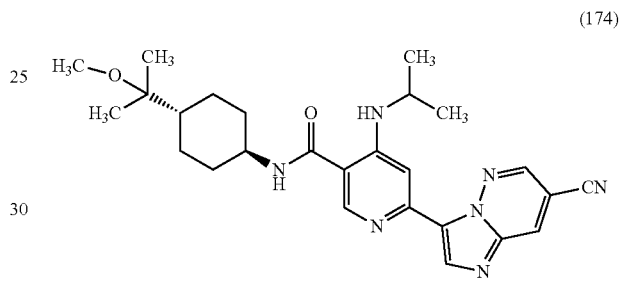

(174)

Intermediate 174A: 2-((1R,4R)-4-(dibenzylamino)cyclohexyl)propan-2-ol

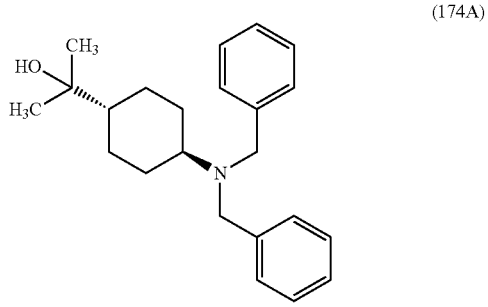 [SMILES: CC(C)(O)[C@H]1CC[C@H](N(Cc2ccccc2)Cc2ccccc2)CC1]

(174A)

To a stirred solution of (1R,4R)-benzyl 4-(dibenzylamino)cyclohexane carboxylate (11 g, 26.6 mmol) in THF (110 mL) was added methylmagnesium bromide (26.6 mL, 80 mmol) at 0° C. The reaction mixture was warmed to 25° C. and stirred for 2 h. The reaction mixture was cooled to 0° C., quenched with saturated NH$_4$Cl, and the aqueous layer was extracted with EtOAc. The organic layer was washed with brine, dried over Na$_2$SO$_4$, filtered, and concentrated. The product was purified via column chromatography (12% EtOAc:PE) to provide 2-((1R,4R)-4-(dibenzylamino)cyclohexyl) propan-2-ol (6.5 g, 67% yield). LCMS: 338.2 (M+H).

Intermediate 174B: (1R,4R)—N,N-dibenzyl-4-(2-methoxypropan-2-yl)cyclohexanamine

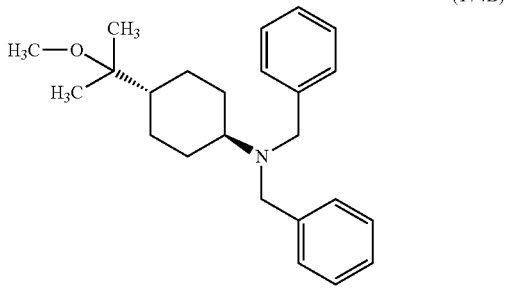

(174B)

To a stirred solution of 2-((1R,4R)-4-(dibenzylamino)cyclohexyl)propan-2-ol (500 mg, 1.48 mmol) in THF (10 mL) was added NaH (148 mg, 3.7 mmol) portion wise at 0° C. The reaction mixture was allowed to warm to 25° C. and stirred for 15 min. The reaction mixture was then cooled to 0° C. and added methyl iodide (0.23 mL, 3.7 mmol) and stirring was continued at room temperature for 16 h. The reaction was quenched by pouring into ice and extracted with EtOAc (2×20 mL). The combined organic layers were washed with brine, dried over $Na_2SO_4$, filtered, and concentrated to an oil. The product was purified via column chromatography (10% EtOAc:PE) to provide (1R,4R)—N,N-dibenzyl-4-(2-methoxypropan-2-yl)cyclohexanamine (450 mg, 71% yield) as an off-white solid. $^1$H NMR (300 MHz, DMSO-$d_6$) δ 7.41-7.24 (m, 8H), 7.23-7.13 (m, 2H), 3.58 (s, 4H), 3.03 (s, 3H), 1.94-1.81 (m, 2H), 1.80-1.66 (m, 2H), 1.46-1.20 (m, 4H), 0.97 (s, 6H), 0.92-0.78 (m, 2H); LCMS m/z 352.3 (M+H).

Intermediate 174C: (1R,4R)-4-(2-methoxypropan-2-yl)cyclohexanamine

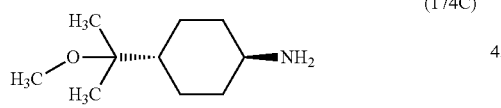

(174C)

To a stirred suspension of (1R,4R)—N,N-dibenzyl-4-(2-methoxypropan-2-yl)cyclohexanamine (400 mg, 1.14 mmol) in MeOH (12 mL) was added Pd/C (121 mg, 0.11 mmol). The reaction vessel was filled with hydrogen gas (bladder pressure) and stirred for 16 h. The mixture was evacuated and the solution was filtered through celite and washed with methanol. The crude product (1R,4R)-4-(2-methoxypropan-2-yl)cyclohexanamine (183 mg, 94% yield) was used without further purification. $^1$H NMR (300 MHz, DMSO-$d_6$) δ 2.47-2.35 (m, 1H), 1.89-1.72 (m, 2H), 1.71-1.54 (m, 2H), 1.44-1.18 (m, 1H), 1.13-0.81 (m, 9H).

Example 174

To a stirred suspension of 6-(7-cyanoimidazo[1,2-b]pyridazin-3-yl)-4-(isopropylamino)nicotinic acid (20 mg, 0.06 mmol) in DMF (1 mL) was added HATU (47.2 mg, 0.12 mmol), DIPEA (0.033 mL, 0.17 mmol), and (1R,4R)-4-(2-methoxypropan-2-yl)cyclohexanamine (13 mg, 0.07 mmol) in DMF (0.2 ml). The reaction mixture was stirred for 3 h at 25° C. and then purified directly via preparative HPLC to afford 6-(7-cyanoimidazo[1,2-b]pyridazin-3-yl)-4-(isopropylamino)-N-((1R,4R)-4-(2-methoxypropan-2-yl)cyclohexyl)nicotinamide (12 mg, 40% yield). $^1$H NMR (400 MHz, DMSO-$d_6$) δ 9.09 (q, J=2.0 Hz, 2H), 8.73-8.65 (m, 2H), 8.52 (d, J=7.5 Hz, 1H), 8.31 (d, J=7.5 Hz, 1H), 7.93 (s, 1H), 4.13-4.06 (m, 1H), 4.05-4.01 (m, 2H), 3.85-3.63 (m, 2H), 3.30 (s, 2H), 3.20-3.14 (m, 2H), 3.08 (s, 3H), 1.91 (d, J=10.0 Hz, 2H), 1.75 (d, J=13.1 Hz, 2H), 1.46-1.30 (m, 3H), 1.29-1.20 (m, 6H), 1.16-1.07 (m, 2H), 1.05 (s, 6H); LCMS: m/z 476.4 (M+H).

Example 175

6-(7-chloroimidazo[1,2-b]pyridazin-3-yl)-N—((R)-2-fluoro-3-hydroxy-3-methylbutyl)-4-(((1r,4R)-4-(2-fluoropropan-2-yl)cyclohexyl)amino)nicotinamide

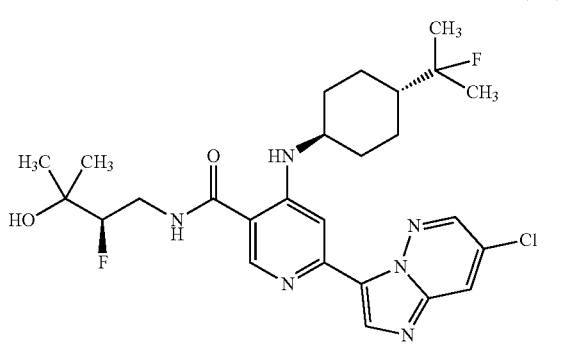

(175)

Intermediate 175A: ethyl 6-bromo-4-(((1R,4R)-4-(2-fluoropropan-2-yl)cyclohexyl)amino)nicotinate

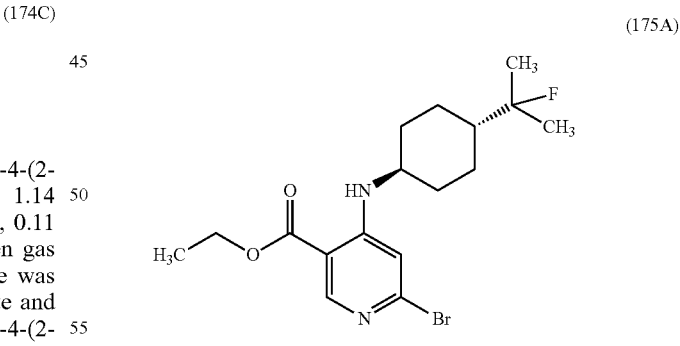

(175A)

To a stirred solution of ethyl 6-bromo-4-(((1R,4R)-4-(2-hydroxypropan-2-yl)cyclohexyl)amino)nicotinate (500 mg, 1.3 mmol) in DCM (10 mL) at −78° C. was added DAST (0.19 mL, 1.43 mmol) and the reaction mixture was allowed to room temperature over 30 minutes. After stirring for additional 1 h, the reaction mixture was diluted with DCM (15 mL), cooled to 0° C., and quenched with saturated $NaHCO_3$ solution. The organic layer was separated and the aqueous layer was extracted with DCM (3×15 mL). The combined organic layers were washed with brine, dried over $Na_2SO_4$, filtered, and concentrated. The product was purified via column chromatography (40% EtOAc:PE) to provide ethyl 6-bromo-4-(((1R,4R)-4-(2-fluoropropan-2-yl)cyclohexyl)amino)nicotinate (360 mg, 71% yield). $^1$H NMR (300 MHz, CDCl$_3$-d) δ 8.62 (s, 1H), 8.12 (d, J=7.9 Hz, 1H), 6.72 (s, 1H), 4.35 (q, J=6.9 Hz, 2H), 3.28 (dd, J=7.6, 3.8 Hz, 1H), 2.31-2.10 (m, 2H), 1.95 (d, J=8.3 Hz, 2H), 1.49-1.13 (m, 14H); LCMS: m/z 389 (M+H).

Intermediate 175B: 6-bromo-4-(((1R,4R)-4-(2-fluoropropan-2-yl)cyclohexyl)amino)nicotinic acid

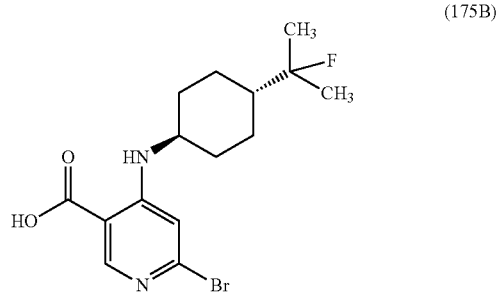 [SMILES: CC(C)(F)[C@H]1CC[C@H](Nc2cc(Br)ncc2C(=O)O)CC1]

(175B)

To a stirred suspension of ethyl 6-bromo-4-(((1R,4R)-4-(2-fluoropropan-2-yl)cyclohexyl)amino)nicotinate (350 mg, 0.90 mmol) in ethanol (6 mL) was added LiOH (65 mg, 2.7 mmol) in water (3 mL) and stirring was continued for 3 h. The reaction mixture was concentrated to remove ethanol and acidified using 1.5N HCl to pH 4-5. The resulting solids were stirred for 5 min, filtered, and washed with water. After drying, 6-bromo-4-(((1R,4R)-4-(2-fluoropropan-2-yl)cyclohexyl)amino)nicotinic acid (270 mg, 80% yield) was obtained as an off-white solid. $^1$H NMR (400 MHz, DMSO-d$_6$) δ 13.34 (br s, 1H), 8.44 (s, 1H), 8.19 (d, J=8.0 Hz, 1H), 7.02 (s, 1H), 3.51 (dd, J=7.5, 3.5 Hz, 1H), 2.01 (d, J=11.0 Hz, 2H), 1.77 (d, J=11.5 Hz, 2H), 1.54 (d, J=11.0 Hz, 1H), 1.39-1.11 (m, 10H); LCMS m/z 361 (M+H).

Intermediate 175C: 6-bromo-N—((R)-2-fluoro-3-hydroxy-3-methylbutyl)-4-(((1R,4R)-4-(2-fluoropropan-2-yl)cyclohexyl)amino)nicotinamide

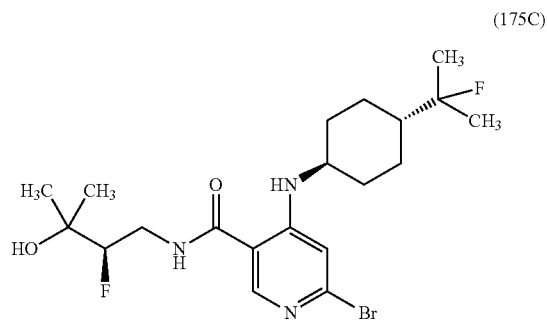 [SMILES: CC(C)(O)[C@H](F)CNC(=O)c1cnc(Br)cc1N[C@H]1CC[C@H](C(C)(C)F)CC1]

(175C)

To a stirred solution of 6-bromo-4-(((1R,4R)-4-(2-fluoropropan-2-yl)cyclohexyl)amino)nicotinic acid (270 mg, 0.75 mmol) in DMF (4 mL) were added HATU (572 mg, 1.50 mmol), DIPEA (0.394 mL, 2.26 mmol) and (R)-4-amino-3-fluoro-2-methylbutan-2-ol (109 mg, 0.90 mmol) in DMF (1 mL). The reaction mixture was stirred for 3 h, diluted with water, and extracted with EtOAc (2×20 mL). The combined organic layers were washed with saturated NaHCO$_3$ (20 mL), water (20 mL), and brine (30 mL). The extracts were then dried over Na$_2$SO$_4$, filtered, and concentrated to an residue. The product was purified via column chromatography (60% EtOAc/PE) to provide 6-bromo-N—((R)-2-fluoro-3-hydroxy-3-methylbutyl)-4-(((1R,4R)-4-(2-fluoropropan-2-yl)cyclohexyl)amino)nicotinamide (310 mg, 87% yield) as an off-white solid. $^1$H NMR (300 MHz, DMSO-d$_6$) δ 8.75 (t, J=5.5 Hz, 1H), 8.43 (d, J=8.3 Hz, 1H), 8.32 (s, 1H), 6.93 (s, 1H), 4.83 (s, 1H), 4.47-4.16 (m, 1H), 3.80-3.54 (m, 2H), 3.52-3.37 (m, 2H), 2.06-1.91 (m, 2H), 1.76 (d, J=12.1 Hz, 2H), 1.53 (d, J=11.7 Hz, 1H), 1.41-1.04 (m, 15H); LCMS m/z 464 (M+H).

Intermediate 175D: N—((R)-2-fluoro-3-hydroxy-3-methylbutyl)-4-(((1r,4R)-4-(2-fluoropropan-2-yl)cyclohexyl)amino)-6-(trimethylstannyl)nicotinamide

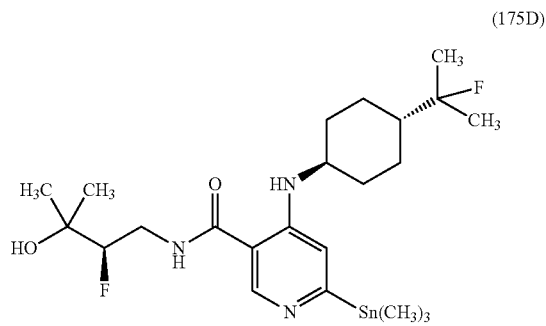

(175D)

To a stirred suspension of 6-bromo-N—((R)-2-fluoro-3-hydroxy-3-methylbutyl)-4-(((1R,4R)-4-(2-fluoropropan-2-yl)cyclohexyl)amino)nicotinamide (150 mg, 0.32 mmol) in toluene (10 mL) was added Pd(PPh$_3$)$_4$ (37.5 mg, 0.032 mmol). The mixture was degassed with nitrogen for 5 min, added hexamethylditin (0.135 mL, 0.65 mmol), and further degassed for 2 min. The reaction mixture was then heated at 120° C. for 2 h, cooled to 25° C., and filtered through celite. The celite pad was washed with THF and the combined filtrates were concentrated to obtain N—((R)-2-fluoro-3-hydroxy-3-methylbutyl)-4-(((1r,4R)-4-(2-fluoropropan-2-yl)cyclohexyl)amino)-6-(trimethylstannyl) nicotinamide (550 mg), which was used further without purification. LCMS: m/z 548 (M+H)$^+$.

Example 175

To a stirred solution of N—((R)-2-fluoro-3-hydroxy-3-methylbutyl)-4-(((1R,4R)-4-(2-fluoropropan-2-yl)cyclohexyl)amino)-6-(trimethylstannyl)nicotinamide (100 mg, 0.183 mmol) in 1,4-dioxane (10 mL) was added 7-chloro-3-iodoimidazo[1,2-b]pyridazine (61.4 mg, 0.22 mmol), CuI (3.5 mg, 0.018 mmol), and Pd(PPh$_3$)$_4$ (21 mg, 0.018 mmol). The mixture was degassed with nitrogen for 5 min then heated at 110° C. for 12 h. The reaction mixture was cooled to 25° C., filtered through celite pad, and washed with 5% MeOH:CHCl$_3$. The combined filtrates were concentrated and the residue was suspended in MeOH (10 mL) and stirred for 5 minutes. The supernatant solution was decanted, and the solids were further purified by preparative HPLC to afford 6-(7-chloroimidazo[1,2-b]pyridazin-3-yl)-N—((R)-2-fluoro-3-hydroxy-3-methylbutyl)-4-(((1R,4R)-4-(2-fluoropropan-2-yl)cyclohexyl)amino)nicotinamide (8.1 mg, 8% yield) as pale yellow solid. ¹H NMR (400 MHz, DMSO-d₆) δ 8.92 (d, J=2.5 Hz, 1H), 8.77-8.65 (m, 2H), 8.61-8.52 (m, 2H), 8.45 (s, 1H), 7.94 (s, 1H), 4.86 (br s, 1H), 4.48-4.21 (m, 1H), 3.82-3.55 (m, 2H), 2.20 (br s, 2H), 1.93-1.79 (m, 2H), 1.59 (d, J=11.0 Hz, 2H), 1.42-1.21 (m, 10H), 1.20-1.11 (m, 6H); LCMS m/z 535.0 (M+H)⁺.

Example 176 (Enantiomer 1)

6-(7-cyanoimidazo[1,2-b]pyridazin-3-yl)-N-(2-(2,6-dimethyltetrahydro-2H-pyran-4-yl)-2-fluoroethyl)-4-(isopropylamino)nicotinamide

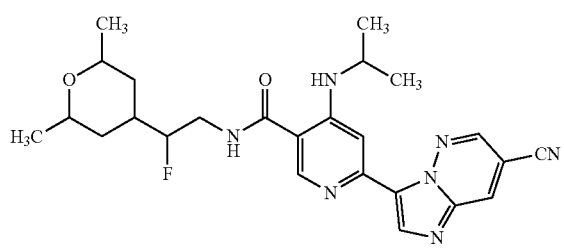

(176)

Intermediate 176A: ethyl 2-(diethoxyphosphoryl)-2-fluoroacetate

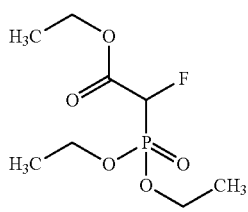

(176A)

A stirred solution of ethyl 2-bromo-2-fluoroacetate (10 g, 54.1 mmol) in triethyl phosphite (25 mL, 143 mmol) was heated at 130° C. for 24 h. The reaction mixture was distilled under vacuum at 110° C. with a downward distillation condenser to obtain ethyl 2-(diethoxyphosphoryl)-2-fluoroacetate as colorless liquid. ¹H NMR (300 MHz, DMSO-d₆) 5.97-5.70 (m, 1H), 4.31-4.06 (m, 6H), 1.32-1.18 (m, 9H).

Intermediate 176B: ethyl 2-(2,6-dimethyldihydro-2H-pyran-4(3H)-ylidene)-2-fluoroacetate

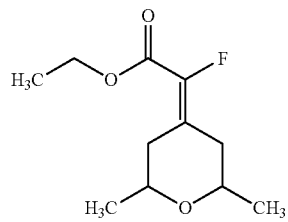

(176B)

To a stirred solution of ethyl 2-(diethoxyphosphoryl)-2-fluoroacetate (3.78 g, 15.6 mmol) in THF (30 mL) at 0° C. was added NaH (1.12 g, 47 mmol) and stirred for 10 min. The reaction mixture was transferred to a solution of 2,6-dimethyldihydro-2H-pyran-4(3H)-one (2 g, 15.6 mmol) in THF (30 mL) and continued stirring for 16 h. The reaction mixture was quenched with water and extracted with ethyl acetate (2×50 mL). The combined organic layers were dried over Na₂SO₄, filtered, and concentrated. The resulting residue was purified by passing through a small pad of silica gel using 10% ethyl acetate/pet ether to afford ethyl 2-(2,6-dimethyldihydro-2H-pyran-4(3H)-ylidene)-2-fluoroacetate (2.5 g, 74% yield). ¹H NMR (400 MHz, DMSO-d₆) δ 4.27-4.17 (m, 1H), 3.49-3.28 (m, 2H), 2.75-2.67 (m, 1H), 1.87-1.66 (m, 2H), 1.29-1.22 (m, 3H), 1.21-1.13 (m, 6H).

Intermediate 176C: ethyl 2-(2,6-dimethyltetrahydro-2H-pyran-4-yl)-2-fluoroacetate

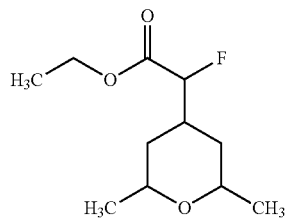

(176C)

To a solution of ethyl 2-(2,6-dimethyldihydro-2H-pyran-4(3H)-ylidene)-2-fluoroacetate (2.5 g, 11.6 mmol)) in ethanol (20 mL) was added Pd/C (1.23 g, 11.6 mmol). The reaction vessel was backfilled with H₂ and stirred for 16 h. The hydrogen gas was evacuated and the reaction mixture was filtered through celite. The filtrate was concentrated to afford ethyl 2-(2,6-dimethyltetrahydro-2H-pyran-4-yl)-2-fluoroacetate (2.3 g, 91% yield).

Intermediate 176D: 2-(2,6-dimethyltetrahydro-2H-pyran-4-yl)-2-fluoroethanol

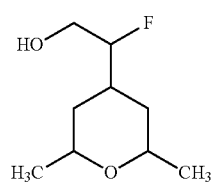

(176D)

A stirred solution of ethyl 2-(2,6-dimethyltetrahydro-2H-pyran-4-yl)-2-fluoroacetate (2.3 g, 10.5 mmol) in THF (20 mL) at 0° C. was added LAH (10.5 mL, 10.5 mmol). The reaction mixture was stirred for 1 h then quenched by the addition of ethyl acetate followed by Na₂SO₄ solution. The organic layer was separated, dried over Na₂SO₄, filtered and concentrated to afford 2-(2,6-dimethyltetrahydro-2H-pyran-4-yl)-2-fluoroethanol (1.6 g, 86% yield). ¹H NMR (400 MHz, DMSO-d₆) δ 4.86 (t, J=5.5 Hz, 1H), 4.25 (br s, 1H), 4.16-4.09 (m, 1H), 3.65-3.46 (m, 4H), 3.39 (dddd, J=10.8, 6.3, 4.0, 2.0 Hz, 4H), 1.99 (s, 2H), 1.67 (dt, J=13.1, 2.0 Hz, 2H), 1.53-1.46 (m, 2H), 1.11-1.04 (m, 12H), 0.93-0.82 (m, 4H).

Intermediate 176E: 2-(2,6-dimethyltetrahydro-2H-pyran-4-yl)-2-fluoroethyl methanesulfonate

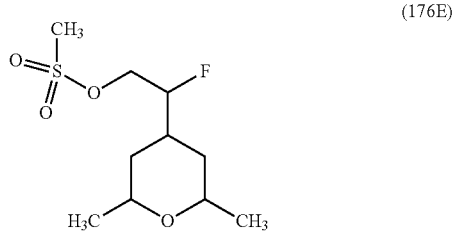 [SMILES: CC1CC(C(F)COS(C)(=O)=O)CC(C)O1]

(176E)

A solution of 2-(2,6-dimethyltetrahydro-2H-pyran-4-yl)-2-fluoroethanol (1.8 g, 10.2 mmol) in DCM (20 mL) was added methanesulfonyl chloride (1.2 mL, 15.3 mmol) followed by Et$_3$N (4.3 mL, 31 mmol) and stirred at room temperature for 3 h. The reaction was quenched with water and extracted with ethyl acetate. The organic extracts were dried over Na$_2$SO$_4$, filtered, and concentrated. The crude residue was purified by silica gel column chromatography (2% MeOH/CHCl$_3$) to afford 2-(2,6-dimethyltetrahydro-2H-pyran-4-yl)-2-fluoroethyl methanesulfonate (2 g, 77% yield) as white solid.

Intermediate 176F: 4-(2-azido-1-fluoroethyl)-2,6-dimethyltetrahydro-2H-pyran

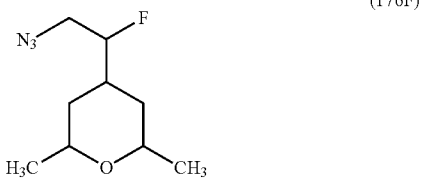

(176F)

A stirred solution of 2-(2,6-dimethyltetrahydro-2H-pyran-4-yl)-2-fluoroethyl methanesulfonate (2 g, 7.86 mmol) in DMF (5 mL) was added sodium azide (1.53 g, 23.6 mmol). The reaction mixture was heated at 100° C. for 16 h, then cooled and concentrated. The crude material was partitioned between water and extracted with ethyl acetate. The organic extracts were dried over Na$_2$SO$_4$, filtered, and concentrated to afford 4-(2-azido-1-fluoroethyl)-2,6-dimethyltetrahydro-2H-pyran (1.3 g, 82% yield). $^1$H NMR (400 MHz, DMSO-d$_6$) δ 4.55-4.48 (m, 1H), 4.54-4.48 (m, 1H), 4.39 (d, J=7.0 Hz, 1H), 3.62-3.57 (m, 1H), 3.53 (d, J=4.5 Hz, 1H), 3.45-3.34 (m, 4H), 2.01-1.86 (m, 2H), 1.69 (dt, J=12.8, 1.9 Hz, 2H), 1.51-1.42 (m, 2H), 1.09 (dd, J=6.3, 4.8 Hz, 1H), 0.97-0.82 (m, 1H).

Intermediate 176G: 2-(2,6-dimethyltetrahydro-2H-pyran-4-yl)-2-fluoroethanamine

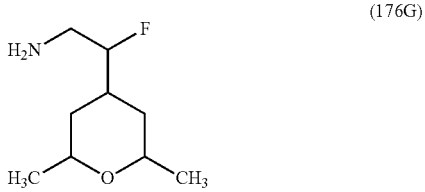

(176G)

To a solution of 4-(2-azido-1-fluoroethyl)-2,6-dimethyltetrahydro-2H-pyran (1.3 g, 6.5 mmol) in ethanol (20 mL) was added Pd/C (60 mg, 0.56 mmol). The vessel was backfilled with H$_2$ and stirred for 16 h. The reaction vessel was then evacuated of H$_2$. The reaction mixture was filtered through celite, and concentrated to obtain 2-(2,6-dimethyltetrahydro-2H-pyran-4-yl)-2-fluoroethanamine (1 g, 88% yield) as colorless liquid. $^1$H NMR (400 MHz, DMSO-d$_6$) δ 4.25-4.16 (m, 1H), 4.11-4.05 (m, 1H), 3.38 (dtd, J=17.0, 6.1, 2.0 Hz, 9H), 2.78-2.62 (m, 4H), 1.99-1.83 (m, 3H), 1.67 (dt, J=12.7, 1.9 Hz, 3H), 1.60-1.53 (m, 2H), 1.51-1.44 (m, 2H), 1.12-1.06 (m, 16H), 0.93-0.82 (m, 5H).

Intermediate 176H: tert-butyl 6-chloro-4-(isopropylamino)nicotinate

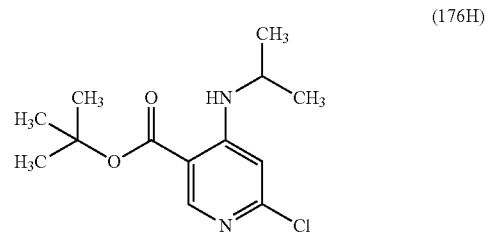 [SMILES: CC(C)Nc1cc(Cl)ncc1C(=O)OC(C)(C)C]

(176H)

To a solution of 6-chloro-4-(isopropylamino)nicotinic acid (6.0 g, 28 mmol), TEA (11.7 mL, 84 mmol), and DMAP (1.71 g, 14 mmol) in toluene (60 mL) at 0° C. was added BOC$_2$O (32.4 mL, 140 mmol) and heated at 100° C. for 16 h. The reaction cooled to room temperature, concentrated on a rotary evaporator and partitioned between water and EtOAc. The layers were separated and the organic layer was washed with water and brine. The organic layer was dried over Na$_2$SO$_4$, filtered, and concentrated to an oily residue. The crude material was purified via silica gel chromatography (20% EA in hexane) to afford tert-butyl 6-chloro-4-(isopropylamino)nicotinate (6.1 g, 81% yield) as colorless oil. $^1$H NMR (400 MHz, DMSO-d$_6$) δ 8.48 (s, 1H), 7.97 (d, J=5.7 Hz, 1H), 6.80 (s, 1H), 3.84 (m, 1H), 1.51 (s, 9H), 1.20 (s, 3H), 1.19 (s, 3H); LCMS m/z 271.2 (M+H)$^+$.

Intermediate 176I: tert-butyl 4-(isopropylamino)-6-(trimethylstannyl)nicotinate

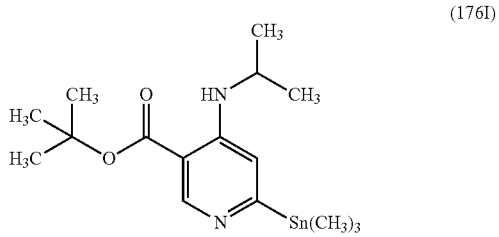

(176I)

A stirred solution of tert-butyl 6-chloro-4-(isopropylamino)nicotinate (3.0 g, 11.1 mmol) in 1,4-dioxane (40 mL) was degassed with nitrogen for 5 min then 1,1'-bis(di-tert-butylphosphino)ferrocene palladium dichloride (0.36 g, 0.55 mmol) was added. The mixture was degassed for an additional 5 min and added hexamethylditin (3.45 mL, 16.62 mmol). The reaction mixture was heated at 115° C. for 3 h, then cooled to room temperature. The mixture was filtered through a bed of celite and rinsed with ethyl acetate. The filtrates were concentrated to afford the crude stannane which was used without further purification. LCMS m/z 401.4 (M+H)$^+$.

Intermediate 176J: tert-butyl 6-(7-cyanoimidazo[1,2-b]pyridazin-3-yl)-4-(isopropylamino)nicotinate

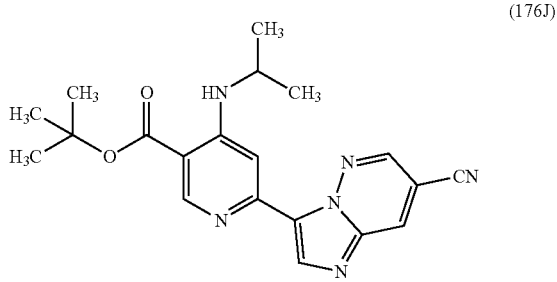 [SMILES: CC(C)Nc1cc(-c2cnc3cc(C#N)cnn23)ncc1C(=O)OC(C)(C)C]

(176J)

A solution of tert-butyl 4-(isopropylamino)-6-(trimethylstannyl)nicotinate (3.5 g, 8.8 mmol) in 1,4-dioxane (50 mL) was degassed via $N_2$ bubble and 3-bromoimidazo[1,2-b]pyridazine-7-carbonitrile (1.956 g, 8.77 mmol) was added. The mixture was degassed for 5 min, Pd(PPh$_3$)$_4$ (1.01 g, 0.9 mmol) was added, and then the mixture was heated at 120° C. in a sealed tube for 18 h. The reaction mixture was cooled and filtered through small pad of celite. The filtrate was concentrated and the crude material was purified by column chromatography (40% EA in hexane) to afford tert-butyl 6-(7-cyanoimidazo[1,2-b]pyridazin-3-yl)-4-(isopropylamino)nicotinate (1.7 g, 51% yield) as yellow solid. $^1$H NMR (300 MHz, DMSO-d$_6$) δ 9.10 (m, 2H), 8.80 (s, 1H), 8.69 (s, 1H), 8.04 (s, 1H), 3.85 (m, 1H), 1.57 (s, 9H), 1.33 (s, 3H), 1.30 (s, 3H); LCMS m/z 379.3 (M+H)$^+$.

Intermediate 176K: 6-(7-cyanoimidazo[1,2-b]pyridazin-3-yl)-4-(isopropylamino)nicotinic acid

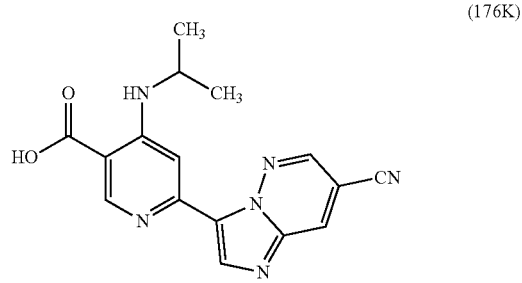 [SMILES: CC(C)Nc1cc(-c2cnc3cc(C#N)cnn23)ncc1C(=O)O]

(176K)

A solution of tert-butyl 6-(7-cyanoimidazo[1,2-b]pyridazin-3-yl)-4-(isopropylamino)nicotinate (1.7 g, 4.5 mmol) in 1,2-dichloroethane (20 mL) at 0° C. was added a solution of TFA (3.5 mL, 45 mmol) in 1 mL 1,2-dichloroethane. The mixture was stirred at 45° C. for 18 h. The reaction mixture was concentrated and the residue was washed with ether (2x) to afford 6-(7-cyanoimidazo[1,2-b]pyridazin-3-yl)-4-(isopropylamino)nicotinic acid (1.3 g, 90% yield) as pale yellow solid. $^1$H NMR (400 MHz, DMSO-d$_6$) δ 9.19 (m, 2H), 8.93 (s, 1H), 8.91 (s, 1H), 7.97 (s, 1H), 4.02 (m, 1H), 1.33 (m, 6H); LCMS m/z 323.2 (M+H)$^+$.

Example 176

To a solution of 6-(7-cyanoimidazo[1,2-b]pyridazin-3-yl)-4-(isopropylamino) nicotinic acid (0.05 g, 0.155 mmol) in DMF (3 mL) were added HATU (0.118 g, 0.31 mmol) and DIPEA (0.081 mL, 0.465 mmol) followed by 2-(2,6-dimethyltetrahydro-2H-pyran-4-yl)-2-fluoroethanamine (0.033 g, 0.186 mmol). The mixture was stirred at room temperature for 3 h. The reaction mixture was then concentrated to remove DMF and the crude residue was purified by flash column by using 5% methanol/chloroform. Further purification via preparative HPLC followed by chiral separation of enantiomers by SFC to provide the two enantiomers 6-(7-cyanoimidazo[1,2-b]pyridazin-3-yl)-N-(2-(2,6-dimethyltetrahydro-2H-pyran-4-yl)-2-fluoroethyl)-4-(isopropylamino)nicotinamide. Enantiomer 1: $^1$H NMR (300 MHz, DMSO-d$_6$) δ 9.13-9.06 (m, 2H), 8.82-8.75 (m, 1H), 8.73-8.67 (m, 2H), 8.51-8.44 (m, 1H), 7.98-7.95 (m, 1H), 4.56-4.46 (m, 1H), 3.88-3.75 (m, 1H), 3.48-3.35 (m, 4H), 1.97-1.88 (m, 2H), 1.79-1.69 (m, 1H), 1.67-1.56 (m, 1H), 1.28 (d, J=6.0 Hz, 6H), 1.15-1.08 (m, 1H), 1.01-0.88 (m, 1H). LCMS 480.2 m/z (M+H)$^+$.

The Examples in Table 8 were prepared using the general methods for Examples 173-176 using the appropriate starting material and amine. Intermediates described above were used for the synthesis of the examples below and other examples in this application.

TABLE 8

| Ex. No. | Structure | HPLC rt (min) | HPLC cond. | LCMS |
|---|---|---|---|---|
| 177 | 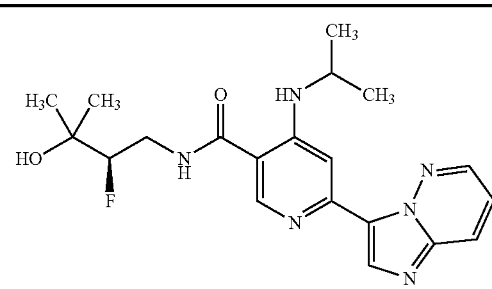 | 5.28 | A | 401.3 |

TABLE 8-continued
| Ex. No. | Structure | HPLC rt (min) | HPLC cond. | LCMS |
|---|---|---|---|---|
| 178 | 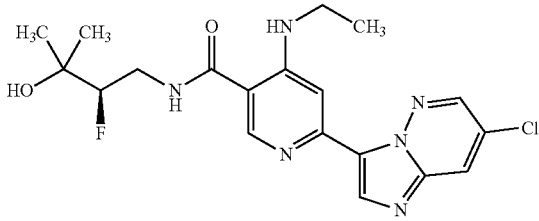 [SMILES: CCNc1cc(-c2cnc3cc(Cl)cnn23)ncc1C(=O)NC[C@@H](F)C(C)(C)O] | 1.36 | C | 421.2 |
| 179 | 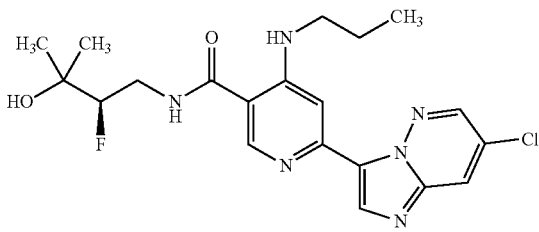 [SMILES: CCCNc1cc(-c2cnc3cc(Cl)cnn23)ncc1C(=O)NC[C@@H](F)C(C)(C)O] | 1.04 | C | 435.3 |
| 180 | 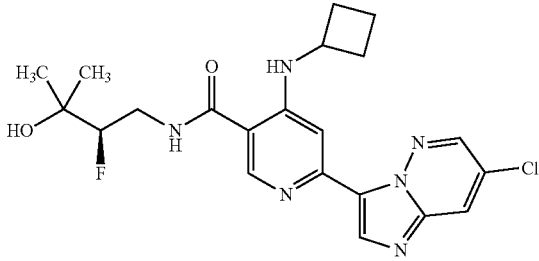 [SMILES: CC(C)(O)[C@H](F)CNC(=O)c1cnc(-c2cnc3cc(Cl)cnn23)cc1NC1CCC1] | 1.58 | C | 447.3 |
| 181 | 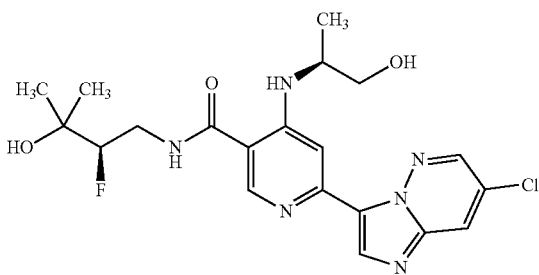 [SMILES: C[C@@H](CO)Nc1cc(-c2cnc3cc(Cl)cnn23)ncc1C(=O)NC[C@@H](F)C(C)(C)O] | 1.08 | C | 451.3 |
| 182 | 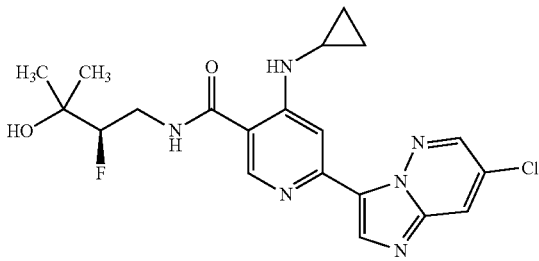 [SMILES: CC(C)(O)[C@H](F)CNC(=O)c1cnc(-c2cnc3cc(Cl)cnn23)cc1NC1CC1] | 1.29 | C | 424.3 |

TABLE 8-continued

| Ex. No. | Structure | HPLC rt (min) | HPLC cond. | LCMS |
|---|---|---|---|---|
| 183 | 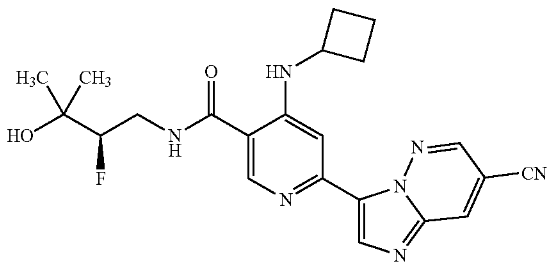 [SMILES: CC(C)(O)[C@H](F)CNC(=O)c1cnc(-c2cnc3cc(C#N)cnn23)cc1NC1CCC1] | 1.42 | C | 438.3 |
| 184 | 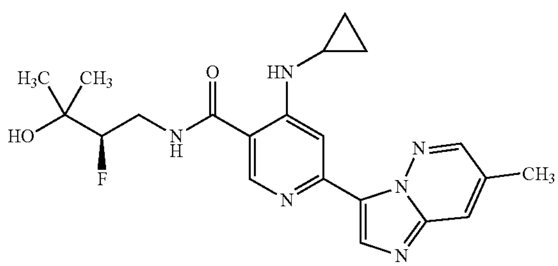 [SMILES: Cc1cnn2c(-c3cc(NC4CC4)c(C(=O)NC[C@@H](F)C(C)(C)O)cn3)cnc2c1] | 1.27 | C | 413.3 |
| 185 | 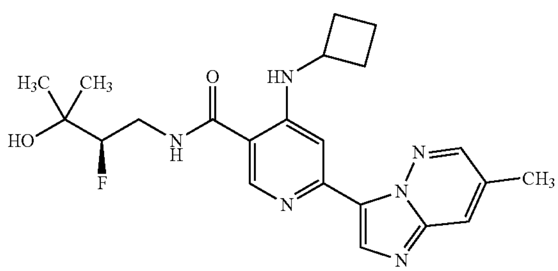 [SMILES: Cc1cnn2c(-c3cc(NC4CCC4)c(C(=O)NC[C@@H](F)C(C)(C)O)cn3)cnc2c1] | 1.44 | C | 427.3 |
| 186 | 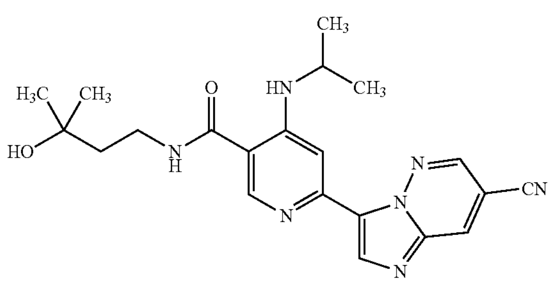 [SMILES: CC(C)Nc1cc(-c2cnc3cc(C#N)cnn23)ncc1C(=O)NCCC(C)(C)O] | 1.43 | C | 408.3 |
| 187 | 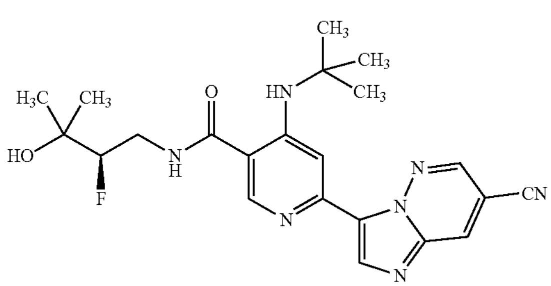 [SMILES: CC(C)(C)Nc1cc(-c2cnc3cc(C#N)cnn23)ncc1C(=O)NC[C@@H](F)C(C)(C)O] | 12.85 | B, 18 min gradient | 441.2 |

TABLE 8-continued

| Ex. No. | Structure | HPLC rt (min) | HPLC cond. | LCMS |
|---|---|---|---|---|
| 188 | 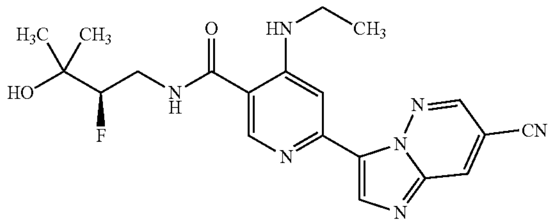 [SMILES: CCNc1cc(-c2cnc3cc(C#N)cnn23)ncc1C(=O)NC[C@@H](F)C(C)(C)O] | 0.82 | C | 412.3 |
| 189 | 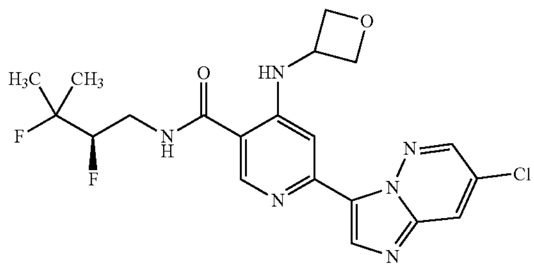 [SMILES: CC(C)(F)[C@H](F)CNC(=O)c1cnc(-c2cnc3cc(Cl)cnn23)cc1NC1COC1] | 5.80 | A | 451.0 |
| 190 | 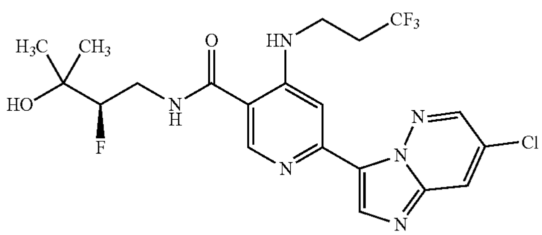 [SMILES: CC(C)(O)[C@H](F)CNC(=O)c1cnc(-c2cnc3cc(Cl)cnn23)cc1NCCC(F)(F)F] | 5.95 | A, 12 MIN GRADIENT | 489.2 |
| 191 | 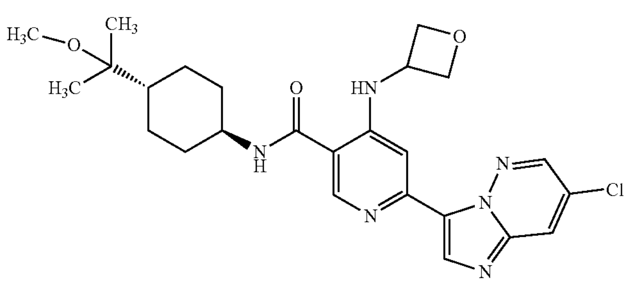 [SMILES: COC(C)(C)[C@H]1CC[C@H](NC(=O)c2cnc(-c3cnc4cc(Cl)cnn34)cc2NC2COC2)CC1] | 1.59 | C | 500.3 |
| 192 | 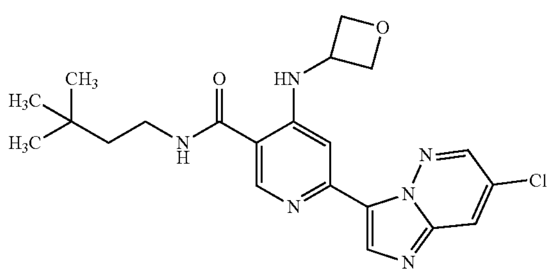 [SMILES: CC(C)(C)CCNC(=O)c1cnc(-c2cnc3cc(Cl)cnn23)cc1NC1COC1] | 1.31 | C | 429.3 |
| 193 | 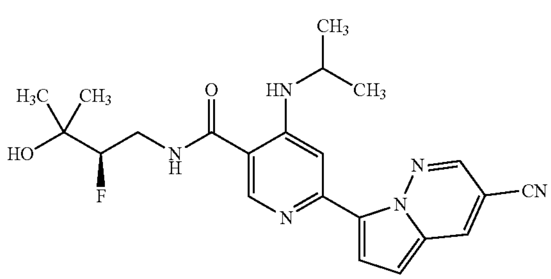 [SMILES: CC(C)Nc1cc(-c2ccc3cc(C#N)cnn23)ncc1C(=O)NC[C@@H](F)C(C)(C)O] | 1.17 | C | 425.3 |

TABLE 8-continued

| Ex. No. | Structure | HPLC rt (min) | HPLC cond. | LCMS |
|---|---|---|---|---|
| 194 | 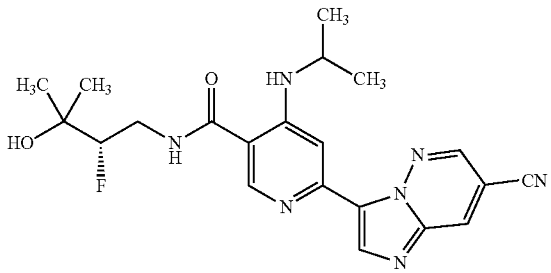 [SMILES: CC(C)Nc1cc(-c2cnc3cc(C#N)cnn23)ncc1C(=O)NC[C@H](F)C(C)(C)O] | 1.05 | C | 426.3 |
| 195 | 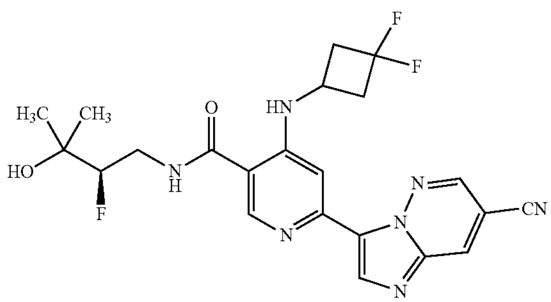 [SMILES: CC(C)(O)[C@H](F)CNC(=O)c1cnc(-c2cnc3cc(C#N)cnn23)cc1NC1CC(F)(F)C1] | 1.09 | C | 474.3 |
| 196 | 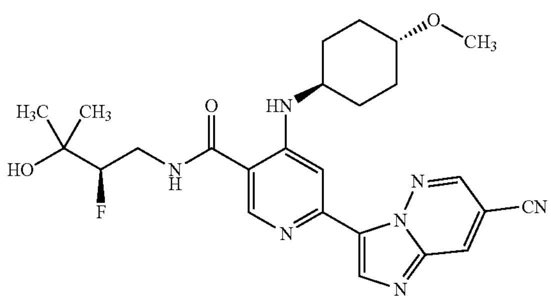 [SMILES: CO[C@H]1CC[C@H](Nc2cc(-c3cnc4cc(C#N)cnn34)ncc2C(=O)NC[C@@H](F)C(C)(C)O)CC1] | 1.40 | C | 496.3 |
| 197 | 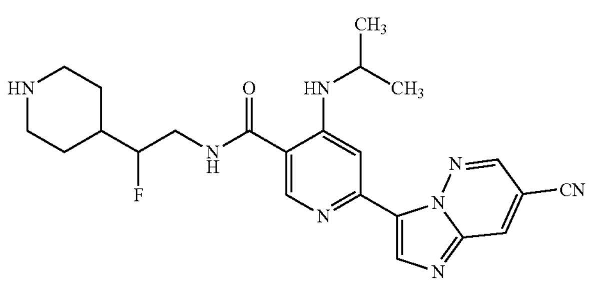 [SMILES: CC(C)Nc1cc(-c2cnc3cc(C#N)cnn23)ncc1C(=O)NCC(F)C1CCNCC1] | 7.90 | A | 451.3 |
| 198 | 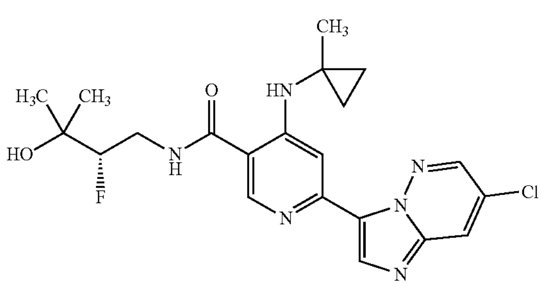 [SMILES: CC1(Nc2cc(-c3cnc4cc(Cl)cnn34)ncc2C(=O)NC[C@H](F)C(C)(C)O)CC1] | 1.54 | C | 447.3 |

TABLE 8-continued

| Ex. No. | Structure | HPLC rt (min) | HPLC cond. | LCMS |
|---|---|---|---|---|
| 199 | 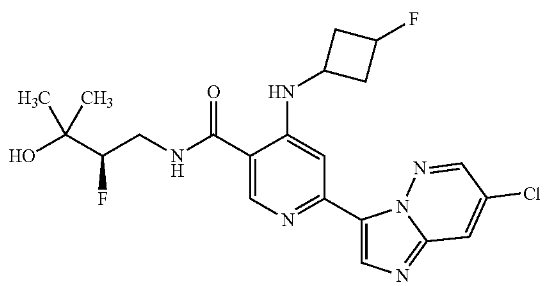 [SMILES: CC(C)(O)[C@H](F)CNC(=O)c1cnc(-c2cnc3cc(Cl)cnn23)cc1NC1CC(F)C1] | 5.66 | A, 12 MIN GRADIENT | 465.2 |
| 200 | 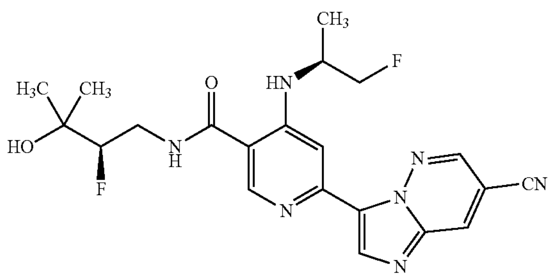 [SMILES: C[C@@H](CF)Nc1cc(-c2cnc3cc(C#N)cnn23)ncc1C(=O)NC[C@@H](F)C(C)(C)O] | 10.18 | A, 18 MIN GRADIENT | 444.2 |
| 201 | 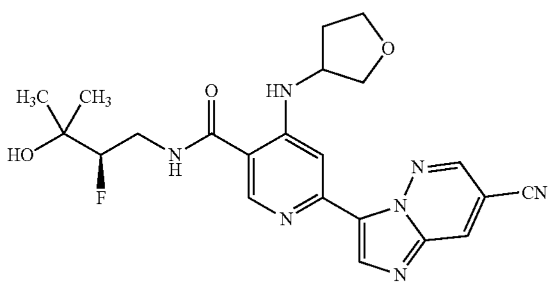 [SMILES: CC(C)(O)[C@H](F)CNC(=O)c1cnc(-c2cnc3cc(C#N)cnn23)cc1NC1CCOC1] | 10.16 | B, 18 MIN GRADIENT | 454.0 |
| 202 | 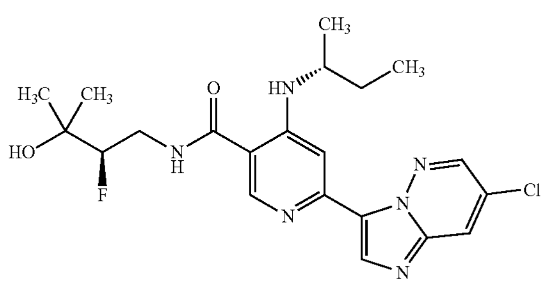 [SMILES: CC[C@@H](C)Nc1cc(-c2cnc3cc(Cl)cnn23)ncc1C(=O)NC[C@@H](F)C(C)(C)O] | 1.69 | C | 449.3 |
| 203 | Enantiomer 2 | 6.69 | A | 480.2 |

TABLE 8-continued

| Ex. No. | Structure | HPLC rt (min) | HPLC cond. | LCMS |
|---|---|---|---|---|
| 204 | 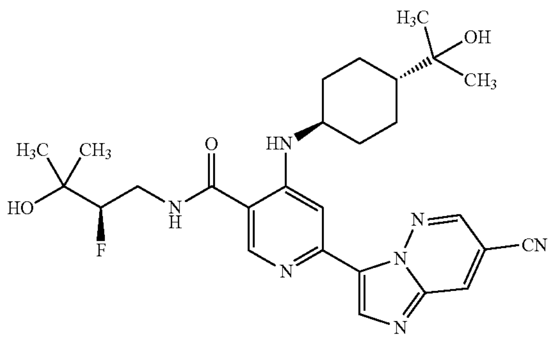 [SMILES: CC(C)(O)[C@H](F)CNC(=O)c1cnc(-c2cnc3cc(C#N)cnn23)cc1N[C@H]1CC[C@H](C(C)(C)O)CC1] | 1.40 | C | 524.4 |
| 205 | 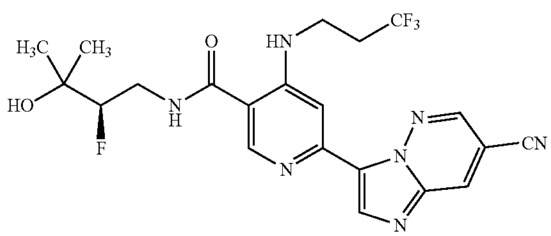 [SMILES: CC(C)(O)[C@H](F)CNC(=O)c1cnc(-c2cnc3cc(C#N)cnn23)cc1NCCC(F)(F)F] | 1.43 | C | 480.3 |
| 206 | 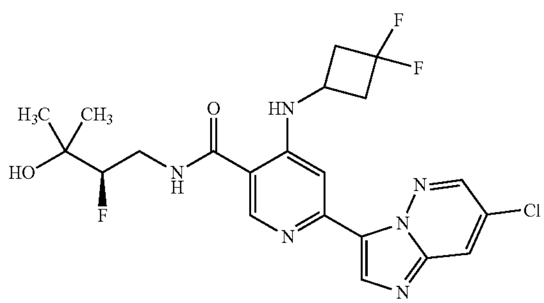 [SMILES: CC(C)(O)[C@H](F)CNC(=O)c1cnc(-c2cnc3cc(Cl)cnn23)cc1NC1CC(F)(F)C1] | 1.52 | C | 483.3 |
| 207 | 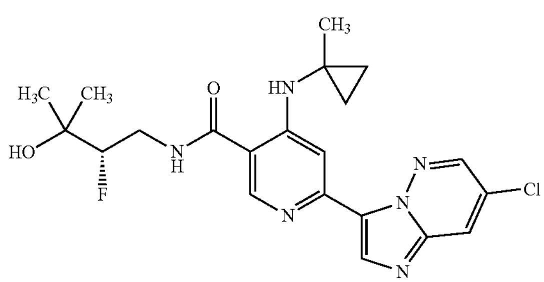 [SMILES: CC1(Nc2cc(-c3cnc4cc(Cl)cnn34)ncc2C(=O)NC[C@H](F)C(C)(C)O)CC1] | 1.39 | C | 438.3 |
| 208 | 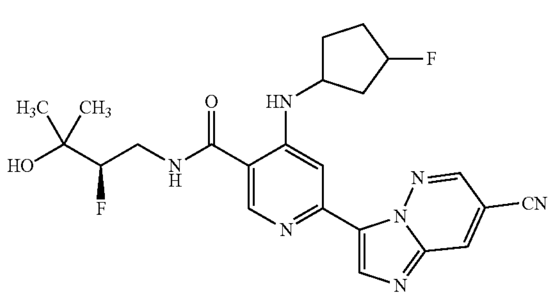 [SMILES: CC(C)(O)[C@H](F)CNC(=O)c1cnc(-c2cnc3cc(C#N)cnn23)cc1NC1CCC(F)C1] | 1.41 | C | 470.3 |

TABLE 8-continued

| Ex. No. | Structure | HPLC rt (min) | HPLC cond. | LCMS |
|---|---|---|---|---|
| 209 | 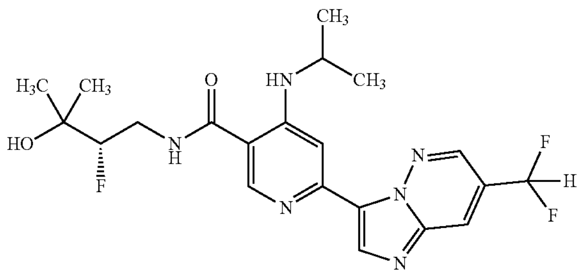 [SMILES: CC(C)Nc1cc(-c2cnc3cc(C(F)F)cnn23)ncc1C(=O)NC[C@H](F)C(C)(C)O] | 1.74 | C | 451.2 |
| 210 | 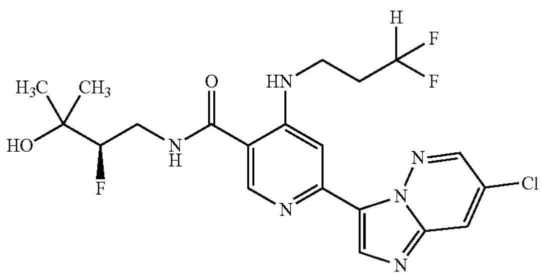 [SMILES: CC(C)(O)[C@H](F)CNC(=O)c1cnc(-c2cnc3cc(Cl)cnn23)cc1NCCC(F)F] | 1.25 | C | 471.1 |
| 211 | 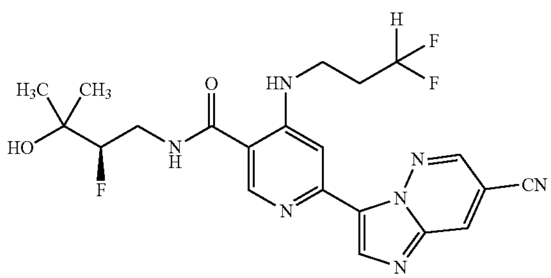 [SMILES: CC(C)(O)[C@H](F)CNC(=O)c1cnc(-c2cnc3cc(C#N)cnn23)cc1NCCC(F)F] | 1.17 | C | 462.1 |
| 212 | 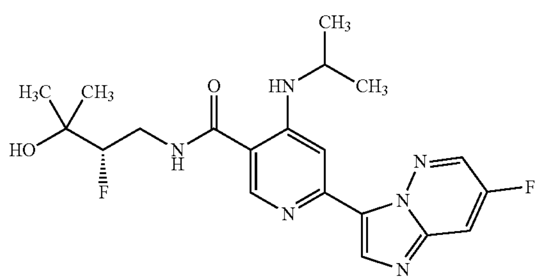 [SMILES: CC(C)Nc1cc(-c2cnc3cc(F)cnn23)ncc1C(=O)NC[C@H](F)C(C)(C)O] | 1.64 | C | 419.2 |
| 213 | 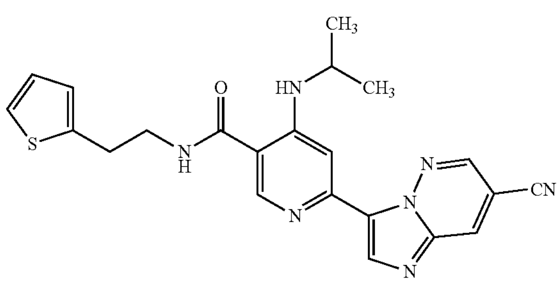 [SMILES: CC(C)Nc1cc(-c2cnc3cc(C#N)cnn23)ncc1C(=O)NCCc1cccs1] | 2.08 | C | 432.1 |

TABLE 8-continued

| Ex. No. | Structure | HPLC rt (min) | HPLC cond. | LCMS |
|---|---|---|---|---|
| 214 | 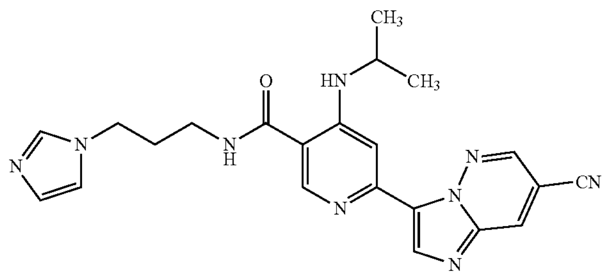 [SMILES: CC(C)Nc1cc(-c2cnc3cc(C#N)cnn23)ncc1C(=O)NCCCn1ccnc1] | 1.53 | C | 430.1 |
| 215 | 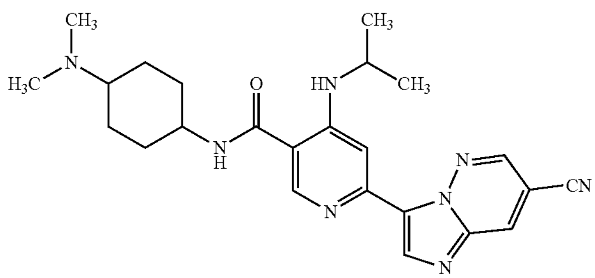 [SMILES: CC(C)Nc1cc(-c2cnc3cc(C#N)cnn23)ncc1C(=O)NC1CCC(N(C)C)CC1] | 1.35 | C | 447.2 |
| 216 | 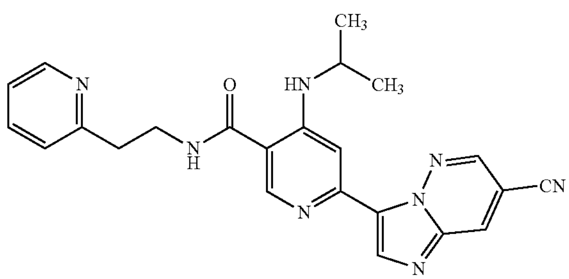 [SMILES: CC(C)Nc1cc(-c2cnc3cc(C#N)cnn23)ncc1C(=O)NCCc1ccccn1] | 1.72 | C | 427.2 |
| 217 | 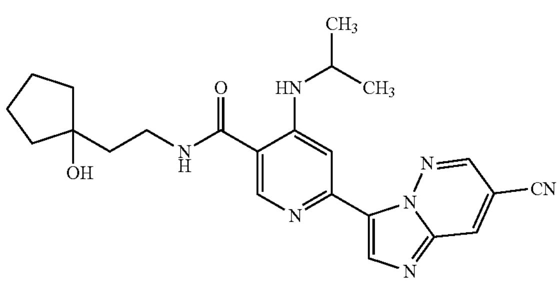 [SMILES: CC(C)Nc1cc(-c2cnc3cc(C#N)cnn23)ncc1C(=O)NCCC1(O)CCCC1] | 1.81 | C | 434.2 |
| 218 | 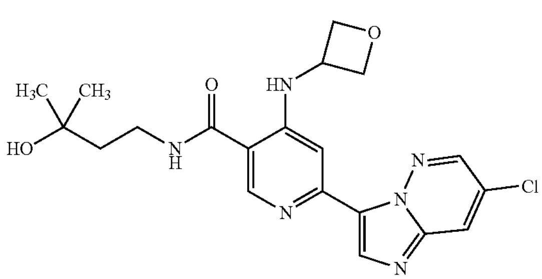 [SMILES: CC(C)(O)CCNC(=O)c1cnc(-c2cnc3cc(Cl)cnn23)cc1NC1COC1] | 1.10 | C | 431.0 |

TABLE 8-continued

| Ex. No. | Structure | HPLC rt (min) | HPLC cond. | LCMS |
|---|---|---|---|---|
| 219 | 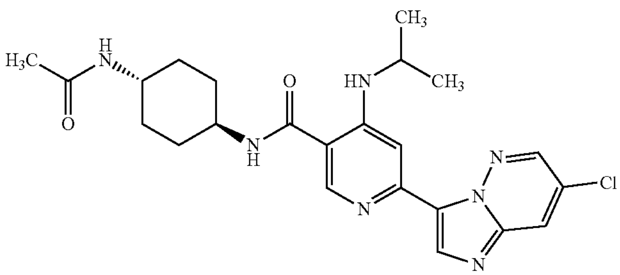 [SMILES: CC(=O)N[C@H]1CC[C@H](NC(=O)c2cnc(-c3cnc4cc(Cl)cnn34)cc2NC(C)C)CC1] | 1.69 | C | 470.2 |
| 220 | 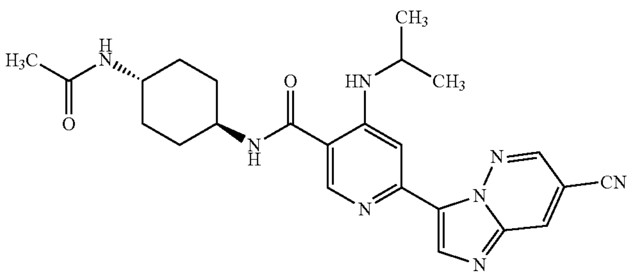 [SMILES: CC(=O)N[C@H]1CC[C@H](NC(=O)c2cnc(-c3cnc4cc(C#N)cnn34)cc2NC(C)C)CC1] | 1.54 | C | 461.2 |
| 221 | 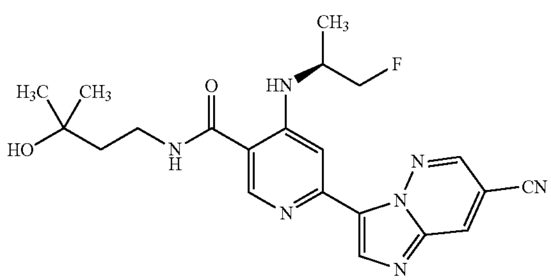 [SMILES: C[C@@H](CF)Nc1cc(-c2cnc3cc(C#N)cnn23)ncc1C(=O)NCCC(C)(C)O] | 1.20 | C | 426.2 |
| 222 | 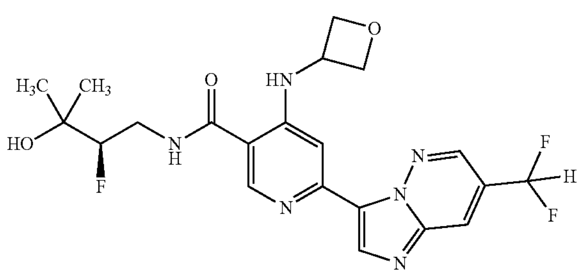 [SMILES: CC(C)(O)[C@H](F)CNC(=O)c1cnc(-c2cnc3cc(C(F)F)cnn23)cc1NC1COC1] | 10.86 | A, 18 MIN GRADIENT | 464.9 (M+) |
| 223 | 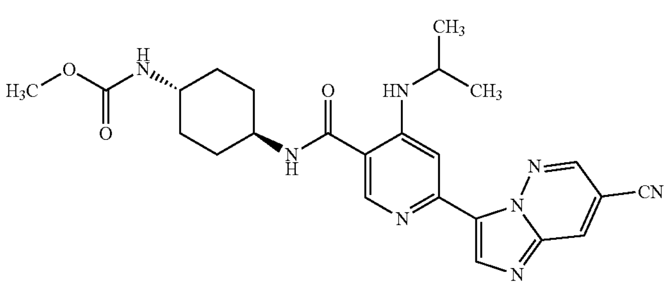 [SMILES: COC(=O)N[C@H]1CC[C@H](NC(=O)c2cnc(-c3cnc4cc(C#N)cnn34)cc2NC(C)C)CC1] | 1.73 | C | 477.2 |

TABLE 8-continued

| Ex. No. | Structure | HPLC rt (min) | HPLC cond. | LCMS |
|---|---|---|---|---|
| 224 | 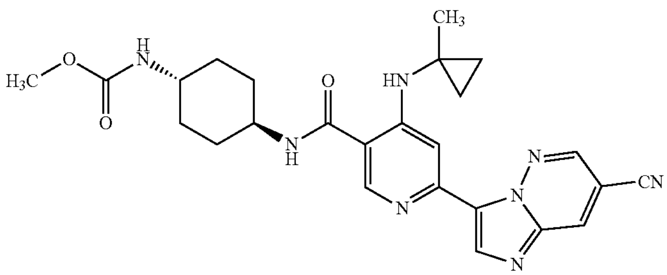 [SMILES: COC(=O)N[C@H]1CC[C@H](NC(=O)c2cnc(-c3cnc4cc(C#N)cnn34)cc2NC2(C)CC2)CC1] | 1.76 | C | 489.2 |

The Examples in Table 9 were prepared using the general methods for Example XXXX using the appropriate starting material and amine. Intermediates described above were used for the synthesis of the examples below and other examples in this application.

TABLE 9

| Ex. No. | Structure | HPLC rt (min) | HPLC cond. | LCMS |
|---|---|---|---|---|
| 225 | 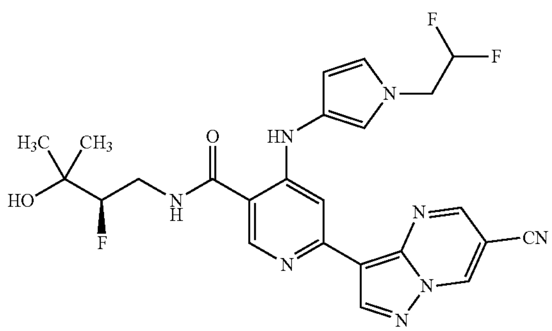 [SMILES: CC(C)(O)[C@H](F)CNC(=O)c1cnc(-c2cnn3cc(C#N)cnc23)cc1Nc1ccn(CC(F)F)c1] | 1.18 | C | 514.3 |
| 226 | 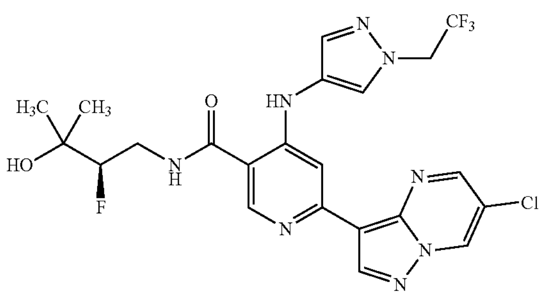 [SMILES: CC(C)(O)[C@H](F)CNC(=O)c1cnc(-c2cnn3cc(Cl)cnc23)cc1Nc1cnn(CC(F)(F)F)c1] | 1.49 | C | 541.3 |
| 227 | 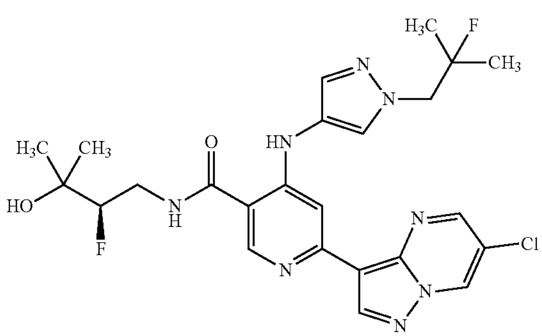 [SMILES: CC(C)(F)Cn1cc(Nc2cc(-c3cnn4cc(Cl)cnc34)ncc2C(=O)NC[C@@H](F)C(C)(C)O)cn1] | 1.45 | C | 533.3 |

TABLE 9-continued

| Ex. No. | Structure | HPLC rt (min) | HPLC cond. | LCMS |
|---|---|---|---|---|
| 228 | 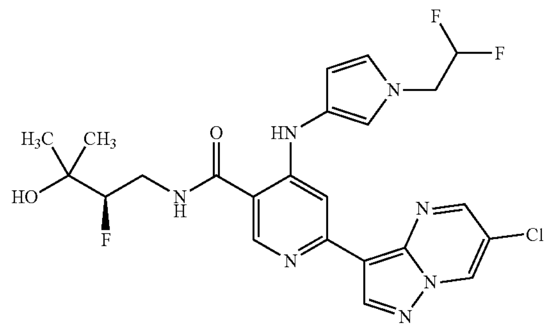 [SMILES: CC(C)(O)[C@H](F)CNC(=O)c1cnc(-c2cnn3cc(Cl)cnc23)cc1Nc1ccn(CC(F)F)c1] | 1.46 | C | 523.3 |
| 229 | 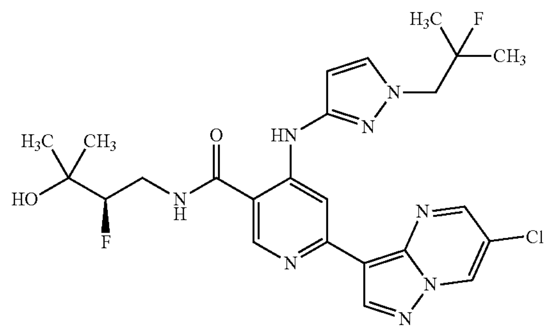 [SMILES: CC(C)(F)Cn1ccc(Nc2cc(-c3cnn4cc(Cl)cnc34)ncc2C(=O)NC[C@@H](F)C(C)(C)O)n1] | 1.59 | C | 533.3 |
| 230 | 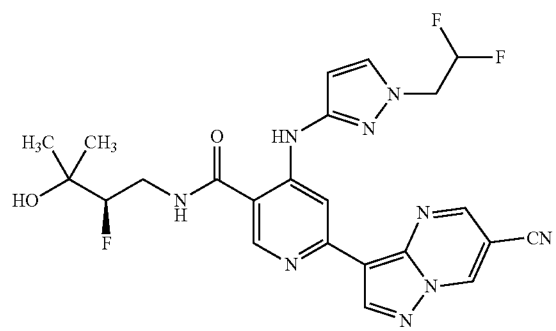 [SMILES: CC(C)(O)[C@H](F)CNC(=O)c1cnc(-c2cnn3cc(C#N)cnc23)cc1Nc1ccn(CC(F)F)n1] | 1.34 | C | 514.3 |
| 231 | 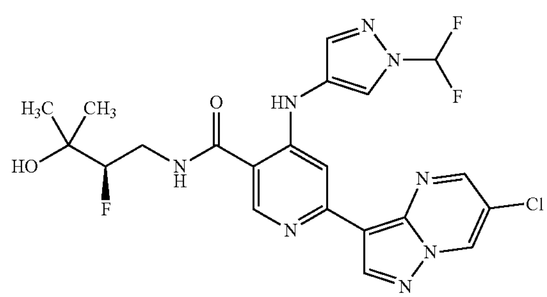 [SMILES: CC(C)(O)[C@H](F)CNC(=O)c1cnc(-c2cnn3cc(Cl)cnc23)cc1Nc1cnn(C(F)F)c1] | 1.45 | C | 509.2 |
| 232 | 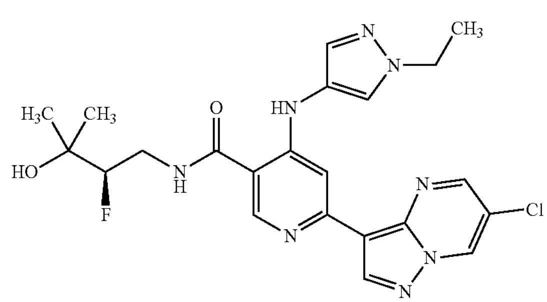 | 1.30 | C | 487.3 |

TABLE 9-continued

| Ex. No. | Structure | HPLC rt (min) | HPLC cond. | LCMS |
|---|---|---|---|---|
| 233 | 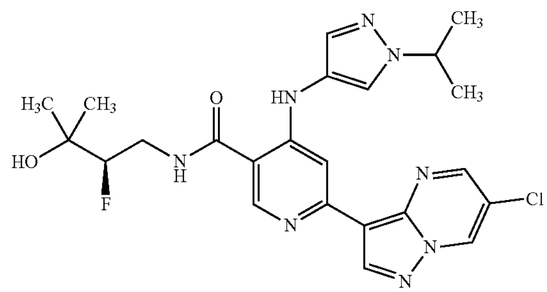 [SMILES: CC(C)n1cc(Nc2cc(-c3cnn4cc(Cl)cnc34)ncc2C(=O)NC[C@@H](F)C(C)(C)O)cn1] | 1.42 | C | 501.3 |
| 234 | 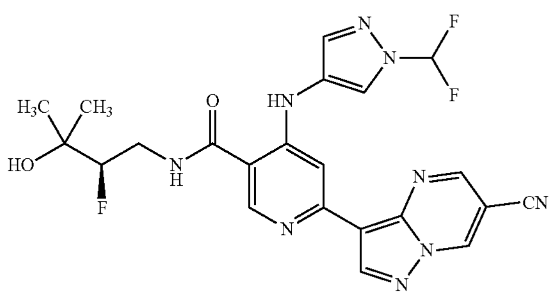 [SMILES: CC(C)(O)[C@H](F)CNC(=O)c1cnc(-c2cnn3cc(C#N)cnc23)cc1Nc1cnn(C(F)F)c1] | 1.27 | C | 500.3 |
| 235 | 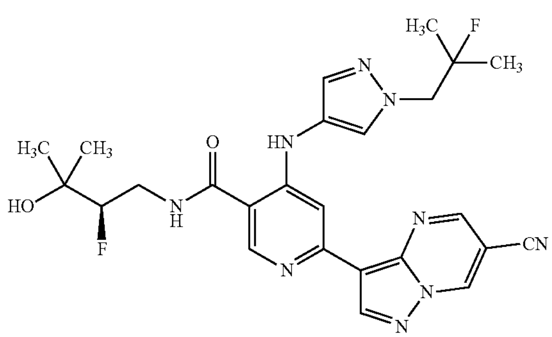 [SMILES: CC(C)(F)Cn1cc(Nc2cc(-c3cnn4cc(C#N)cnc34)ncc2C(=O)NC[C@@H](F)C(C)(C)O)cn1] | 1.29 | C | 524.3 |
| 236 | 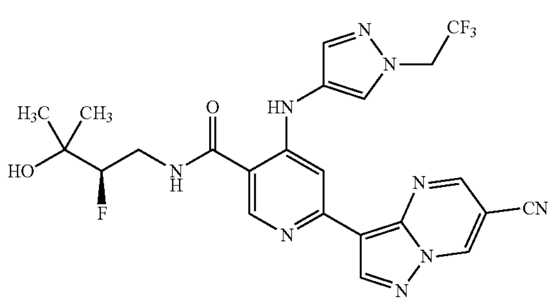 [SMILES: CC(C)(O)[C@H](F)CNC(=O)c1cnc(-c2cnn3cc(C#N)cnc23)cc1Nc1cnn(CC(F)(F)F)c1] | 1.38 | C | 532.3 |
| 237 | 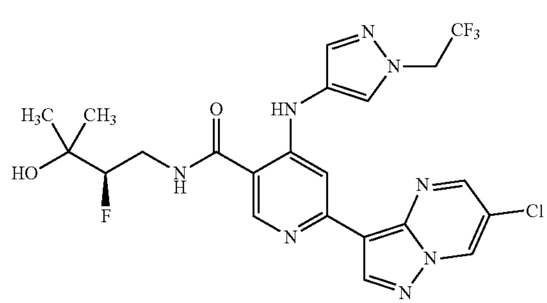 [SMILES: CC(C)(O)[C@H](F)CNC(=O)c1cnc(-c2cnn3cc(Cl)cnc23)cc1Nc1cnn(CC(F)(F)F)c1] | 1.49 | C | 541.3 |

TABLE 9-continued

| Ex. No. | Structure | HPLC rt (min) | HPLC cond. | LCMS |
|---|---|---|---|---|
| 238 | 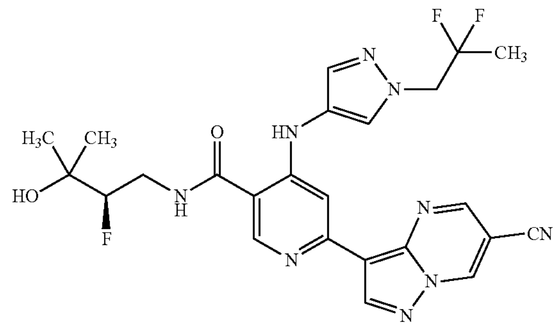 [SMILES: CC(F)(F)Cn1cc(Nc2cc(-c3cnn4cc(C#N)cnc34)ncc2C(=O)NC[C@@H](F)C(C)(C)O)cn1] | 1.29 | C | 528.3 |
| 239 | 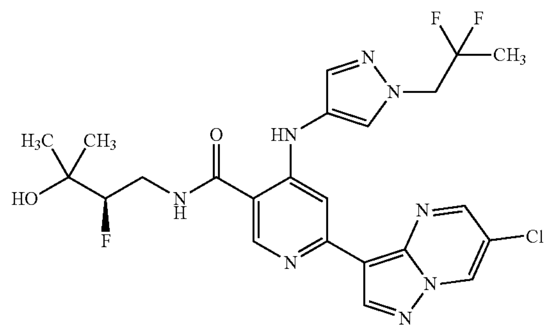 [SMILES: CC(F)(F)Cn1cc(Nc2cc(-c3cnn4cc(Cl)cnc34)ncc2C(=O)NC[C@@H](F)C(C)(C)O)cn1] | 1.39 | C | 537.3 |
| 240 | 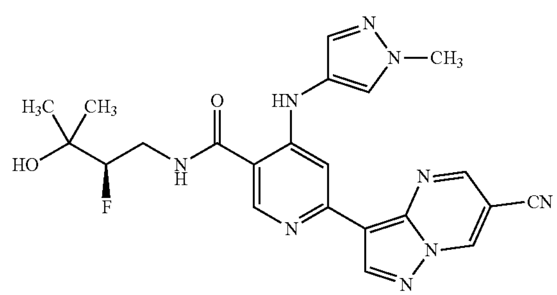 [SMILES: Cn1cc(Nc2cc(-c3cnn4cc(C#N)cnc34)ncc2C(=O)NC[C@@H](F)C(C)(C)O)cn1] | 1.03 | C | 464.3 |
| 241 | 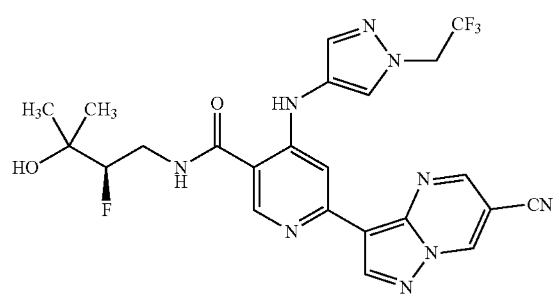 [SMILES: CC(C)(O)[C@H](F)CNC(=O)c1cnc(-c2cnn3cc(C#N)cnc23)cc1Nc1cnn(CC(F)(F)F)c1] | 1.29 | C | 532.3 |
| 242 | 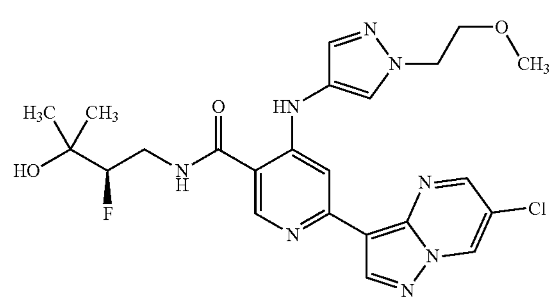 [SMILES: COCCn1cc(Nc2cc(-c3cnn4cc(Cl)cnc34)ncc2C(=O)NC[C@@H](F)C(C)(C)O)cn1] | 1.20 | C | 517.3 |

TABLE 9-continued
| Ex. No. | Structure | HPLC rt (min) | HPLC cond. | LCMS |
|---|---|---|---|---|
| 243 | 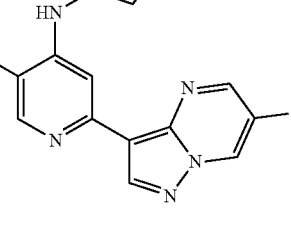 | | | NO DATA in ELN |
| 244 | 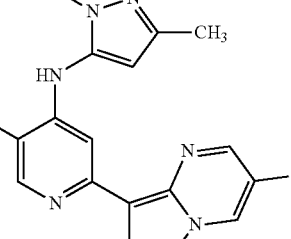 | 10.18 | A, 18 MIN GRADIENT | 478.2 |
| 245 | 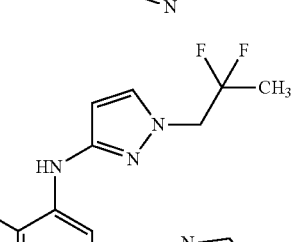 | 1.49 | C | 528.3 |
| 246 | 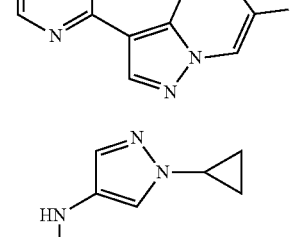 | 1.15 | C | 499.3 |
| 247 | 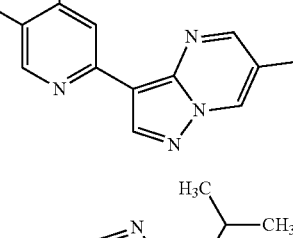 | 1.27 | C | 515.3 |

TABLE 9-continued

| Ex. No. | Structure | HPLC rt (min) | HPLC cond. | LCMS |
|---|---|---|---|---|
| 248 | 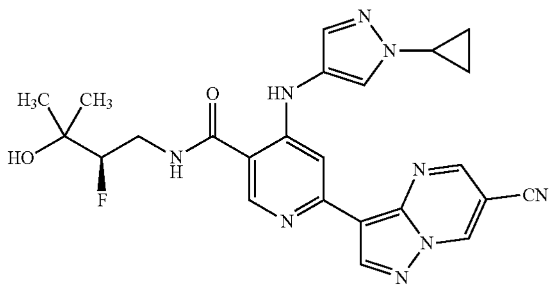 [SMILES: CC(C)(O)[C@H](F)CNC(=O)c1cnc(-c2cnn3cc(C#N)cnc23)cc1Nc1cnn(C2CC2)c1] | 1.01 | C | 490.3 |
| 249 | 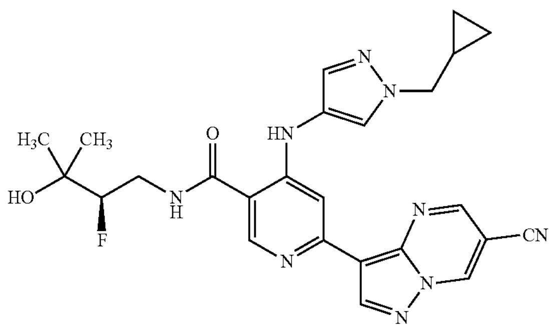 [SMILES: CC(C)(O)[C@H](F)CNC(=O)c1cnc(-c2cnn3cc(C#N)cnc23)cc1Nc1cnn(CC2CC2)c1] | 1.32 | C | 504.3 |
| 250 | 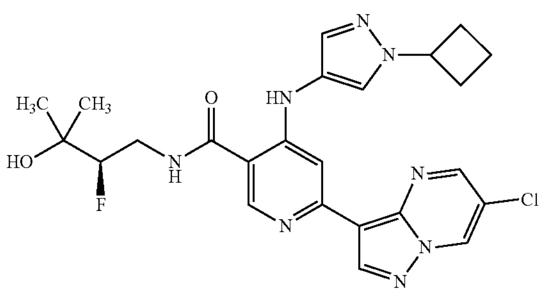 [SMILES: CC(C)(O)[C@H](F)CNC(=O)c1cnc(-c2cnn3cc(Cl)cnc23)cc1Nc1cnn(C2CCC2)c1] | 1.18 | C | 513.3 |
| 251 | 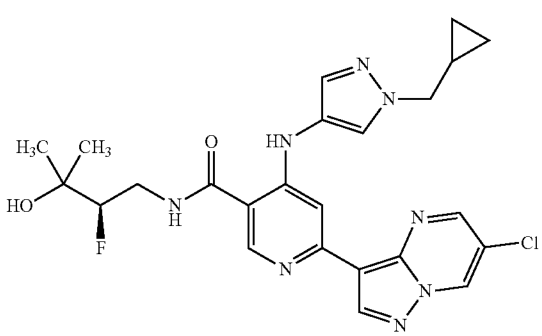 [SMILES: CC(C)(O)[C@H](F)CNC(=O)c1cnc(-c2cnn3cc(Cl)cnc23)cc1Nc1cnn(CC2CC2)c1] | 1.76 | C | 513.1 |
| 252 | 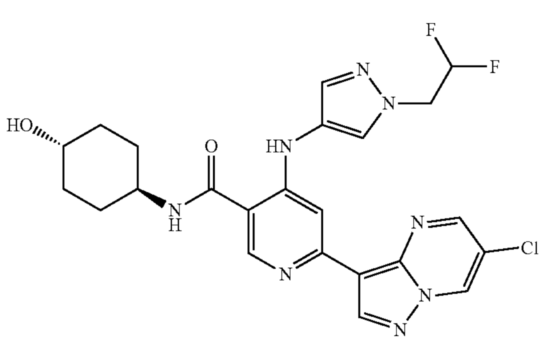 [SMILES: O=C(N[C@H]1CC[C@H](O)CC1)c1cnc(-c2cnn3cc(Cl)cnc23)cc1Nc1cnn(CC(F)F)c1] | 1.53 | C | 517.7 |

TABLE 9-continued
| Ex. No. | Structure | HPLC rt (min) | HPLC cond. | LCMS |
|---|---|---|---|---|
| 253 | 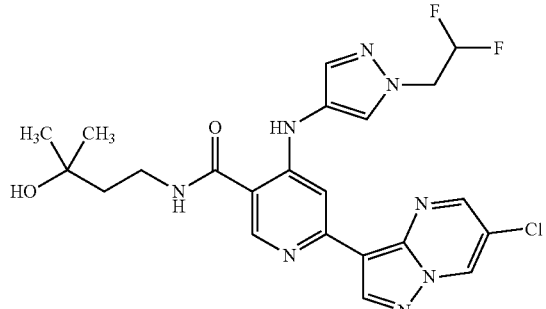 | 1.62 | C | 505.2 |
| 254 | 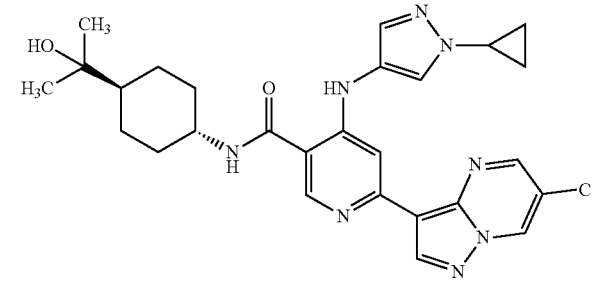 [SMILES: CC(C)(O)[C@H]1CC[C@H](NC(=O)c2cnc(-c3cnn4cc(Cl)cnc34)cc2Nc2cnn(C3CC3)c2)CC1] | 1.60 | C | 535.2 (m+) |
| 255 | 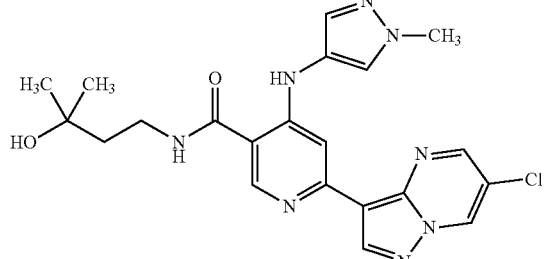 | 1.44 | C | 455.2 |
| 256 | 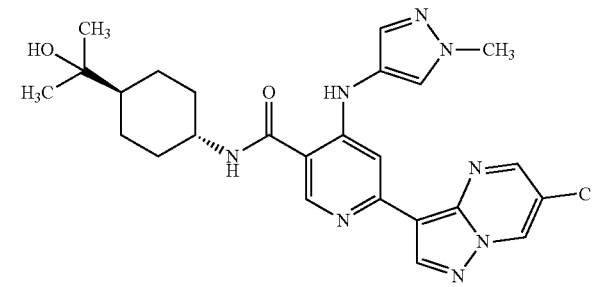 [SMILES: Cn1cc(Nc2cc(-c3cnn4cc(Cl)cnc34)ncc2C(=O)N[C@H]2CC[C@H](C(C)(C)O)CC2)cn1] | 1.36 | C | 509.2 (M+) |
| 257 | 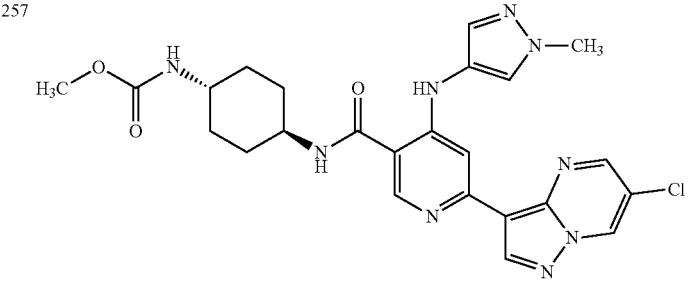 | 1.26 | C | 524.2 |

Example 258

(R)-6-(7-cyanoimidazo[1,2-b]pyridazin-3-yl)-N-(2,3-difluoro-3-methylbutyl)-4-((1-(2,2-difluoroethyl)-1H-pyrazol-4-yl)amino)nicotinamide

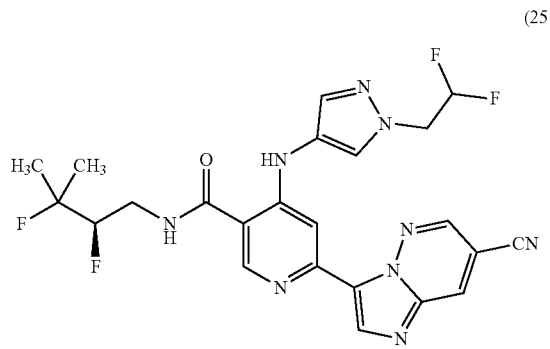
(258)

Intermediate 258A: (R)-tert-butyl (2-fluoro-3-hydroxy-3-methylbutyl)carbamate

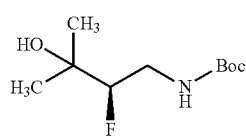
(258A)

To a stirred solution of (R)-4-amino-3-fluoro-2-methylbutan-2-ol (500 mg, 4.1 mmol) in DCM (10 mL), were added DMAP (504 mg, 4.1 mmol) and BOC$_2$O (1.44 mL, 6.2 mmol) at room temperature. The mixture was stirred for 14 h then diluted with 50 mL of DCM. The organic layer was washed with water (2×20 mL), dried over Na$_2$SO$_4$, filtered, and concentrated. The product was purified by silica gel chromatography (20% ethyl acetate/pet ether) to afford (R)-tert-butyl (2-fluoro-3-hydroxy-3-methylbutyl) carbamate (820 mg, 90% yield). $^1$H NMR (300 MHz, CHLOROFORM-d) δ 4.95 (br s, 1H), 4.47-4.19 (m, 1H), 3.83-3.53 (m, 1H), 3.35-3.13 (m, 1H), 2.08-1.97 (m, 1H), 1.55-1.40 (m, 9H), 1.36-1.22 (m, 6H).

Intermediate 258B: (R)-tert-butyl (2,3-difluoro-3-methylbutyl)carbamate

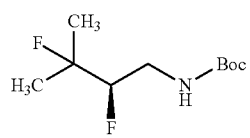
(258B)

A stirred solution of (R)-tert-butyl (2-fluoro-3-hydroxy-3-methylbutyl)carbamate (800 mg, 3.62 mmol) in dichloromethane (10 mL) at 0° C. was added DAST (0.956 mL, 7.24 mmol). The reaction mixture was stirred for 30 min then basified using NaHCO$_3$ solution. The product was extracted with DCM (2×20 mL) and the organic layer was dried over Na$_2$SO$_4$, filtered, and concentrated. The product was purified by silica gel chromatography (10% ethyl acetate/pet ether) to afford (R)-tert-butyl (2,3-difluoro-3-methylbutyl)carbamate (220 mg, 27% yield). $^1$H NMR (400 MHz, CHLOROFORM-d) δ 4.86 (br s, 1H), 4.51-4.29 (m, 1H), 3.80-3.58 (m, 1H), 3.28-3.11 (m, 1H), 1.59-1.52 (m, 6H), 1.51-1.42 (m, 9H).

Intermediate 258C: (R)-2,3-difluoro-3-methylbutan-1-amine

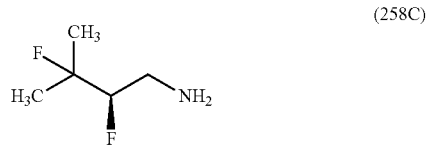
(258C)

A stirred solution of (R)-tert-butyl (2,3-difluoro-3-methylbutyl)carbamate (220 mg, 0.985 mmol) in DCM (5 mL) was added TFA (0.5 mL, 6.5 mmol) and the mixture was stirred for 1 h. The reaction mixture was concentrated and co-evaporated with chloroform to afford (R)-2,3-difluoro-3-methylbutan-1-amine (120 mg, 99% yield). $^1$H NMR (400 MHz, CHLOROFORM-d) δ 4.77-4.50 (m, 1H), 3.49-3.22 (m, 4H), 1.53-1.35 (m, 6H).

Intermediate 258D: ethyl 6-chloro-4-((1-(2,2-difluoroethyl)-1H-pyrazol-4-yl)amino) nicotinate

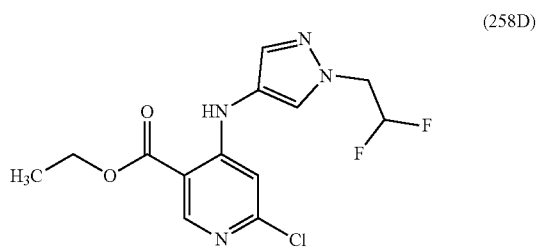 [SMILES: CCOC(=O)c1cnc(Cl)cc1Nc1cnn(CC(F)F)c1]
(258D)

To a stirred solution of ethyl 4,6-dichloronicotinate (2.5 g, 11.4 mmol) in DMA (10 mL) in a pressure tube was added 1-(2,2-difluoroethyl)-1H-pyrazol-4-amine (2.01 g, 13.6 mmol) followed by DIPEA (1.98 mL, 11.4 mmol). The vessel was sealed and heated at 120° C. for 16 h. The solvent was evaporated and the product was purified by silica gel column chromatography (30-40% EtOAc:hexane) to afford ethyl 6-chloro-4-((1-(2,2-difluoroethyl)-1H-pyrazol-4-yl)amino)nicotinate (2.8 g, 75%). $^1$H NMR (400 MHz, DMSO-d$_6$) δ 9.29 (s, 1H), 8.63 (s, 1H), 8.02 (s, 1H), 7.65 (s, 1H), 6.67 (s, 1H), 6.58-6.18 (m, 1H), 4.64 (td, J=15.1, 4.0 Hz, 2H), 4.35 (q, J=7.0 Hz, 2H), 1.34 (t, J=7.3 Hz, 3H); LCMS: m/z 331 (M+H).

Intermediate 258E: 6-chloro-4-((1-(2,2-difluoro-ethyl)-1H-pyrazol-4-yl)amino)nicotinic acid

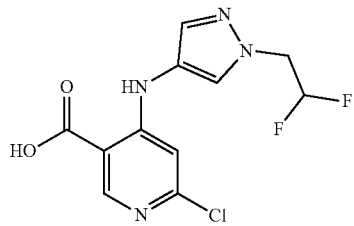
(258E)

To a stirred solution of ethyl 6-chloro-4-((1-(2,2-difluoroethyl)-1H-pyrazol-4-yl)amino)nicotinate (2.8 g, 8.47 mmol) in ethanol (40 mL) was added lithium hydroxide (0.608 g, 25.4 mmol) in water (15 mL) and stirred at 70° C. for 3 h. The reaction mixture was concentrated in vacuo and the residue was diluted with water (20 mL) and cooled to 0° C. 6N HCl was added to acidify the mixture and the resulting solids were filtered and dried to afford 6-chloro-4-((1-(2,2-difluoroethyl)-1H-pyrazol-4-yl)amino)nicotinic acid (2.3 g, 90% yield) as white solid. $^1$H NMR (400 MHz, Acetonitrile-$d_3$) δ 9.96 (br s, 1H), 9.24 (s, 1H), 8.27 (s, 1H), 8.09 (d, J=0.5 Hz, 1H), 7.28 (s, 1H), 6.98-6.52 (m, 1H), 5.08 (td, J=14.7, 3.8 Hz, 2H); LCMS m/z 303 (M+H).

Intermediate 258F: (R)-6-chloro-N-(2,3-difluoro-3-methylbutyl)-4-((1-(2,2-difluoroethyl)-1H-pyrazol-4-yl)amino)nicotinamide

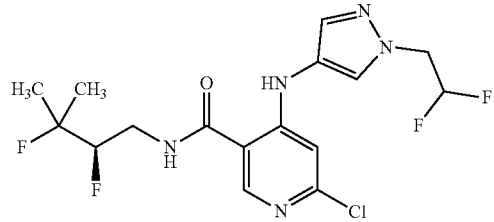
(258F)

To a stirred solution of 6-chloro-4-((1-(2,2-difluoroethyl)-1H-pyrazol-4-yl)amino)nicotinic acid (300 mg, 0.99 mmol) in DMF (15 mL) was added DIPEA (0.52 mL, 2.97 mmol), HATU (415 mg, 1.090 mmol), and (R)-2,3-difluoro-3-methylbutan-1-amine (134 mg, 1.09 mmol). The reaction mixture was stirred for 18 h. The reaction mixture was diluted with brine and extracted with ethyl acetate. The organic layer was washed with water, dried over $Na_2SO_4$ and concentrated. The product was purified by silica gel column chromatography (45% EtOAc:pet ether) to afford (R)-6-chloro-N-(2,3-difluoro-3-methylbutyl)-4-((1-(2,2-difluoroethyl)-1H-pyrazol-4-yl)amino)nicotinamide (150 mg, 37% yield) as pale yellow liquid. LCMS m/z 408.1 (M+H).

Intermediate 258G: (R)—N-(2,3-difluoro-3-methylbutyl)-4-((1-(2,2-difluoroethyl)-1H-pyrazol-4-yl)amino)-6-(trimethylstannyl)nicotinamide

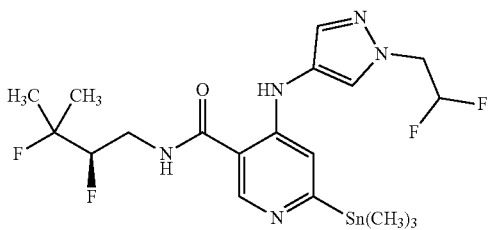
(258G)

A solution of (R)-6-chloro-N-(2,3-difluoro-3-methylbutyl)-4-((1-(2,2-difluoroethyl)-1H-pyrazol-4-yl)amino)nicotinamide (0.1 g, 0.25 mmol) and hexamethylditin (0.145 g, 0.44 mmol) in toluene (10 mL) was purged with nitrogen for 10 min. Pd(PPh$_3$)$_4$ (0.057 g, 0.05 mmol) was added and nitrogen purging was continued for additional 5 min. The mixture was stirred at 110° C. for 10 h, cooled to room temperature, and filtered through a celite bed. The celite was washed with ethyl acetate (2×15 mL) and the filtrate was concentrated to give (R)—N-(2,3-difluoro-3-methylbutyl)-4-((1-(2,2-difluoroethyl)-1H-pyrazol-4-yl)amino)-6-(trimethylstannyl)nicotinamide (240 mg), which was used further without purification. LCMS m/z 538.1 (M+H).

Example 258

In a microwave vial, (R)—N-(2,3-difluoro-3-methylbutyl)-4-((1-(2,2-difluoroethyl)-1H-pyrazol-4-yl)amino)-6-(trimethylstannyl)nicotinamide (0.2 g, 0.373 mmol) and 3-bromoimidazo[1,2-b]pyridazine-7-carbonitrile (0.083 g, 0.373 mmol) were dissolved in 1,4 dioxane (10 mL) and purged with nitrogen for 5 min. Pd(PPh$_3$)$_4$ (0.086 g, 0.08 mmol) was added and purging continued for additional 5 min. The reaction mixture was heated in a microwave reactor at 150° C. for 1 h. The reaction mixture was cooled, filtered through celite, and the filtrate was concentrated. The product was purified via preparative TLC (5% methanol/CHCl$_3$) then preparative HPLC to afford (R)-6-(7-cyanoimidazo[1,2-b]pyridazin-3-yl)-N-(2,3-difluoro-3-methylbutyl)-4-((1-(2,2-difluoroethyl)-1H-pyrazol-4-yl)amino)nicotinamide (2.5 mg, 1.3% yield). $^1$H NMR (400 MHz, DMSO-$d_6$) δ 1.37-1.49 (m, 6H), 3.35-3.52 (m, 2H), 3.69-3.86 (m, 1H), 4.57-4.78 (m, 3H), 6.28-6.60 (m, 1H), 7.64-7.70 (m, 1H), 7.97-8.04 (m, 1H), 8.24-8.30 (m, 1H), 8.68-8.74 (m, 1H), 8.81-8.86 (m, 1H), 8.93-8.96 (m, 1H), 9.03-9.12 (m, 1H), 10.01-10.07 (m, 1H); LCMS: m/z 516.2 (M+H)$^+$.

Example 259

(R)-6-(7-cyanoimidazo[1,2-b]pyridazin-3-yl)-4-((1-(3,3-difluorocyclobutyl)-1H-pyrazol-4-yl)amino)-N-(2-fluoro-3-hydroxy-3-methylbutyl)nicotinamide

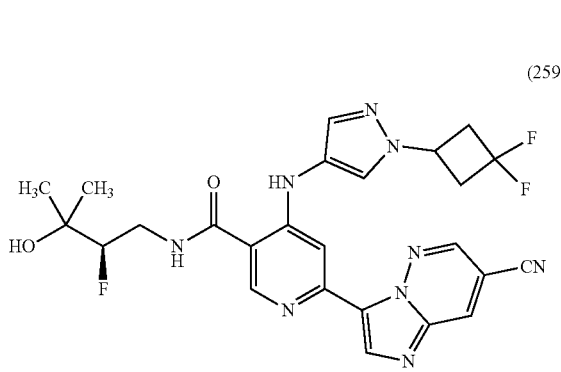
(259)

Intermediate 259A: 1-(3,3-dimethoxycyclobutyl)-4-nitro-1H-pyrazole

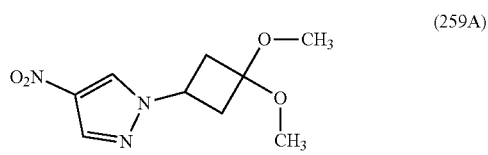
(259A)

To a stirred solution of 4-nitro-1H-pyrazole (900 mg, 7.96 mmol) in THF (15 mL), was added 3,3-dimethoxybutanol (1.05 g, 7.96 mmol) and triphenylphosphine (2.7 g, 10.4 mmol) at room temperature. The reaction mixture was cooled to 0° C. and DTBAD (2.38 g, 10.4 mmol) was added. The reaction mixture was allowed room temperature and stir for 16 h. The reaction mixture was evaporated and the crude residue was purified by silica gel column chromatography (15% ethylacetate/pet ether) to afford 1-(3,3-dimethoxycyclobutyl)-4-nitro-1H-pyrazole (1.1 g, 61% yield).

Intermediate 259B: 1-(3,3-dimethoxycyclobutyl)-1H-pyrazol-4-amine

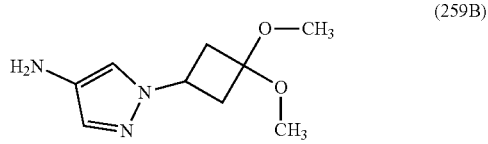 [SMILES: COC1(OC)CC(n2cc([N+](=O)[O-])cn2)C1]
(259B)

To a stirred solution of 1-(3,3-dimethoxycyclobutyl)-4-nitro-1H-pyrazole (1.1 g, 4.84 mmol) in methanol (12 mL) was added palladium on carbon 10% (80 mg, 0.75 mmol) under $N_2$ atmosphere. The reaction mixture was stirred under hydrogen (balloon) atmosphere for 2 h. The mixture was filtered through celite, washed with MeOH, and the combined filtrates were concentrated to afford 1-(3,3-dimethoxycyclobutyl)-1H-pyrazol-4-amine (900 mg, 94% yield). LCMS m/z 198.2 (M+H)+.

Intermediate 259C: ethyl 6-chloro-4-((1-(3,3-dimethoxycyclobutyl)-1H-pyrazol-4-yl)amino)nicotinate

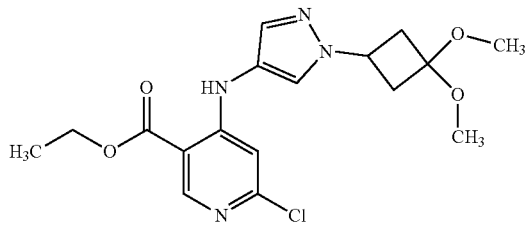
(259C)

To a stirred solution of ethyl 4,6-dichloronicotinate (500 mg, 2.72 mmol) in DMA (10 mL) in a pressure tube, was added 1-(3,3-dimethoxycyclobutyl)-1H-pyrazol-4-amine (448 mg, 2.72 mmol) and DIPEA (1.19 mL, 6.8 mmol). The reaction mixture was heated at 120° C. for 5 h. The reaction mixture was cooled and concentrated and the resulting residue was partitioned between EtOAc and water. The layers were separated and the organic layer was dried over $Na_2SO_4$, filtered, and concentrated. The residue was purified by silica gel column chromatography (20% ethylacetate/pet ether) to afford ethyl 6-chloro-4-((1-(3,3-dimethoxycyclobutyl)-1H-pyrazol-4-yl)amino)nicotinate (250 mg, 28% yield); $^1$H NMR (400 MHz, DMSO-$d_6$) δ 9.27 (s, 1H), 8.62 (s, 1H), 8.04 (s, 1H), 7.61 (s, 1H), 6.69 (s, 1H), 4.67 (t, J=8.0 Hz, 1H), 4.35 (q, J=7.2 Hz, 2H), 3.20-3.06 (m, 6H), 2.80-2.65 (m, 2H), 2.60-2.52 (m, 2H), 1.34 (t, J=7.0 Hz, 3H) LCMS: m/z 381.4 (M+H).

Intermediate 259D: ethyl 6-chloro-4-((1-(3-oxocyclobutyl)-1H-pyrazol-4-yl)amino) nicotinate

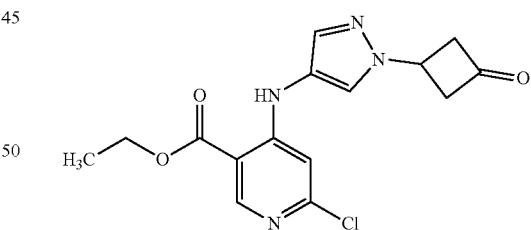
(259D)

Ethyl 6-chloro-4-((1-(3,3-dimethoxycyclobutyl)-1H-pyrazol-4-yl)amino) nicotinate (350 mg, 0.92 mmol) and HCl (10 mL, 30 mmol) were treated at 27° C. for 14 hours in a 100 mL flask. The reaction mixture was basified using 10% $NaHCO_3$ solution and extracted with DCM (2×20 mL). The organic layer was dried over $Na_2SO_4$, filtered, and concentrated to afford ethyl 6-chloro-4-((1-(3-oxocyclobutyl)-1H-pyrazol-4-yl)amino)nicotinate (280 mg, 85% yield). $^1$H NMR (400 MHz, DMSO-$d_6$) δ 9.31 (s, 1H), 8.63 (s, 1H), 8.20 (s, 1H), 7.66 (s, 1H), 6.75 (s, 1H), 5.29-5.12 (m, 1H), 4.35 (q, J=7.4 Hz, 2H), 3.64-3.53 (m, 4H), 1.40-1.26 (m, 3H) LCMS: m/z 335.3 (M−H).

Intermediate 259E: ethyl 6-chloro-4-((1-(3,3-difluorocyclobutyl)-1H-pyrazol-4-yl)amino)nicotinate

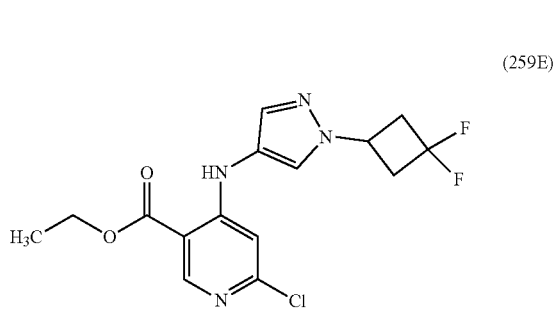 [SMILES: CCOC(=O)c1cnc(Cl)cc1Nc1cnn(C2CC(F)(F)C2)c1]

(259E)

To a stirred solution of ethyl 6-chloro-4-((1-(3-oxocyclobutyl)-1H-pyrazol-4-yl)amino)nicotinate (260 mg, 0.78 mmol) in DCM (15 mL) was added DAST (0.23 mL, 1.71 mmol) at room temperature and stirred for 14 h. The reaction mixture was cooled to 0° C., basified using 10% NaHCO$_3$ solution, and extracted with DCM (2×20 mL). The organic layer was dried over Na$_2$SO$_4$, filtered, and concentrated. The resulting crude material was purified using silica gel column chromatography (10% ethyl acetate/pet ether) to afford ethyl 6-chloro-4-((1-(3,3-difluorocyclobutyl)-1H-pyrazol-4-yl)amino) nicotinate (200 mg, 72% yield). $^1$H NMR (300 MHz, DMSO-d$_6$) δ 9.29 (s, 1H), 8.63 (s, 1H), 8.09 (s, 1H), 7.68 (s, 1H), 6.72 (s, 1H), 5.01-4.83 (m, 1H), 4.35 (q, J=7.2 Hz, 2H), 3.27-3.06 (m, 4H), 1.34 (t, J=7.2 Hz, 3H); LCMS: m/z=357.3 (M+H).

Intermediate 259F: 6-chloro-4-((1-(3,3-difluorocyclobutyl)-1H-pyrazol-4-yl)amino) nicotinic acid

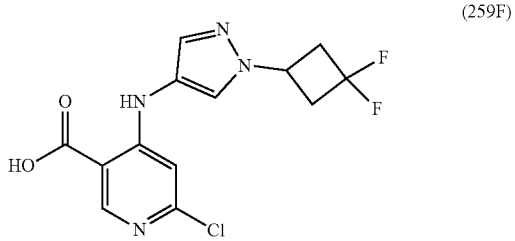 [SMILES: O=C(O)c1cnc(Cl)cc1Nc1cnn(C2CC(F)(F)C2)c1]

(259F)

To a stirred solution of ethyl 6-chloro-4-((1-(3,3-difluorocyclobutyl)-1H-pyrazol-4-yl)amino)nicotinate (200 mg, 0.56 mmol) in ethanol (3 mL), THF (6 mL), and water (3 mL) was added LiOH (40 mg, 1.68 mmol). The reaction mixture was stirred for 2 h. The reaction mixture was concentrated and the crude salt was acidified to pH 6-7. The resulting solids were filtered and dried in vacuo to afford 6-chloro-4-((1-(3,3-difluorocyclobutyl)-1H-pyrazol-4-yl) amino)nicotinic acid (165 mg, 82% yield). $^1$H NMR (300 MHz, DMSO-d$_6$) δ 13.92-13.41 (m, 1H), 9.55 (s, 1H), 8.61 (s, 1H), 8.10 (s, 1H), 7.68 (s, 1H), 6.71 (s, 1H), 5.03-4.81 (m, 1H), 3.24-3.06 (m, 4H); LCMS: m/z 329.3 (M+H).

Intermediate 259G: (R)-6-chloro-4-((1-(3,3-difluorocyclobutyl)-1H-pyrazol-4-yl)amino)-N-(2-fluoro-3-hydroxy-3-methylbutyl)nicotinamide

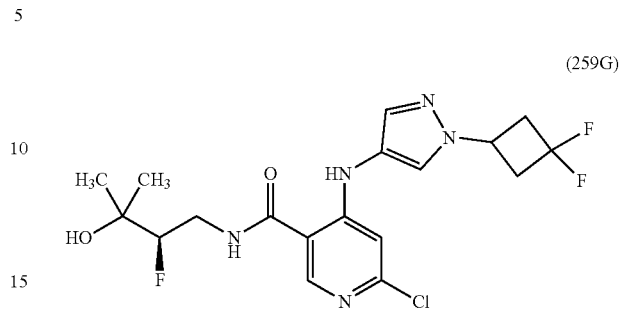

(259G)

To a stirred solution of 6-chloro-4-((1-(3,3-difluorocyclobutyl)-1H-pyrazol-4-yl)amino)nicotinic acid (160 mg, 0.49 mmol) in DMF (6 mL) were added DIPEA (0.26 mL, 1.46 mmol) and HATU (185 mg, 0.49 mmol) followed by (R)-4-amino-3-fluoro-2-methylbutan-2-ol (59 mg, 0.49 mmol). The mixture was stirred for 14 h then concentrated. The residue was diluted with 30 mL of EtOAc and washed with water (2×10 mL). The organic layer was dried over Na$_2$SO$_4$, filtered, and concentrated. The crude residue was purified by silica gel column chromatography (3% MeOH/DCM) to afford (R)-6-chloro-4-((1-(3,3-difluorocyclobutyl)-1H-pyrazol-4-yl)amino)-N-(2-fluoro-3-hydroxy-3-methylbutyl)nicotinamide (180 mg, 75% yield). LCMS: m/z 432.3 (M+H).

Intermediate 259H: (R)-4-((1-(3,3-difluorocyclobutyl)-1H-pyrazol-4-yl)amino)-N-(2-fluoro-3-hydroxy-3-methylbutyl)-6-(trimethylstannyl)nicotinamide

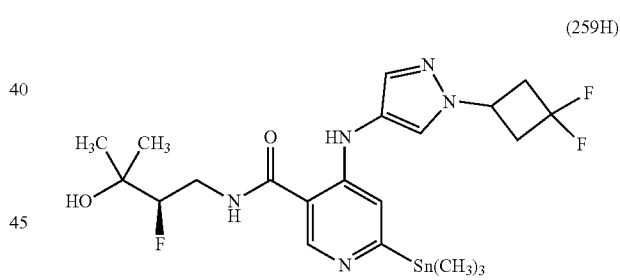

(259H)

To a stirred solution of (R)-6-chloro-4-((1-(3,3-difluorocyclobutyl)-1H-pyrazol-4-yl)amino)-N-(2-fluoro-3-hydroxy-3-methylbutyl)nicotinamide (80 mg, 0.19 mmol) in toluene (10 mL) was added hexamethylditin (0.077 mL, 0.371 mmol). The mixture was degassed via nitrogen bubble for 5 mins then added 1,1'-bis(di-tert-butylphosphino) ferrocene palladium dichloride (12 mg, 0.02 mmol). The reaction mixture was further degassed with nitrogen then heated at 115° C. for 3 h. The reaction mixture was cooled to room temperature, filtered through celite, and washed with ethyl acetate. The combined filtrates were concentrated to afford (R)-4-((1-(3,3-difluorocyclobutyl)-1H-pyrazol-4-yl) amino)-N-(2-fluoro-3-hydroxy-3-methylbutyl)-6-(trimethylstannyl)nicotinamide (100 mg, 96% yield) which was used further without purification. LCMS: m/z 562.2 (M−H).

Example 259

To a stirred solution of (R)-4-((1-(3,3-difluorocyclobutyl)-1H-pyrazol-4-yl)amino)-N-(2-fluoro-3-hydroxy-3- methylbutyl)-6-(trimethylstannyl)nicotinamide (50 mg, 0.09 mmol) in 1,4-dioxane (7 mL) was added CuI (1.7 mg, 8.9 µmol). The mixture was degassed by bubbling nitrogen for 5 min. Pd(PPh$_3$)$_4$ (10.3 mg, 9 µmol) was added. The reaction mixture was degassed for additional 5 min, then heated at 110° C. for 15 h. The reaction mixture was cooled to room temperature, filtered through celite, washed with ethyl acetate. The combined filtrates were concentrated then suspended in 20 mL of 1.5 N HCl and extracted with DCM (2×20 mL). The aqueous layer was basified using NaHCO$_3$ solution and extracted with ethyl acetate (2×30 mL). The combined organic layers were dried over Na$_2$SO$_4$, filtered, and concentrated. The residue was purified via preparative HPLC to afford (R)-6-(7-cyanoimidazo[1,2-b]pyridazin-3-yl)-4-((1-(3,3-difluorocyclobutyl)-1H-pyrazol-4-yl)amino)-N-(2-fluoro-3-hydroxy-3-methylbutyl) nicotinamide (9 mg, 19% yield). $^1$H NMR: (400 MHz, DMSO-d$_6$) δ 10.13 (s, 1H), 9.10 (d, J=2.01 Hz, 1H), 9.01 (d, J=2.01 Hz, 1H), 8.95 (t, J=5.27 Hz, 1H), 8.83 (s, 1H), 8.72 (s, 1H), 8.26 (s, 1H), 8.08 (s, 1H), 7.72 (s, 1H), 4.94-5.07 (m, 1H), 4.87 (s, 1H), 4.29-4.51 (m, 1H), 3.66-3.88 (m, 1H), 3.39-3.53 (m, 2H), 3.10-3.28 (m, 5H), 1.11-1.23 (m, 6H); LCMS: m/z 540.0 (M+H).

The Examples in Table 10 were prepared using the general methods for Example 259 using the appropriate starting material and amine. Intermediates described above were used for the synthesis of the examples below and other examples in this application.

TABLE 10

| Ex. No. | Structure | HPLC rt (min) | HPLC cond. | LCMS |
|---|---|---|---|---|
| 260 | 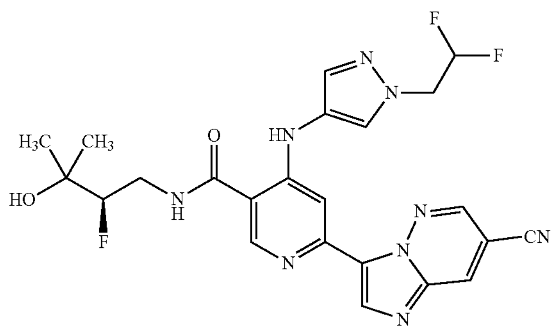 [SMILES: CC(C)(O)[C@H](F)CNC(=O)c1cnc(-c2cnc3cc(C#N)cnn23)cc1Nc1cnn(CC(F)F)c1] | 11.39 | B, 18 MIN GRADIENT | 514.2 |
| 261 | 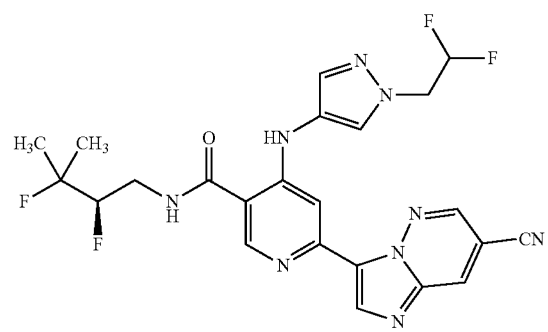 [SMILES: CC(C)(F)[C@H](F)CNC(=O)c1cnc(-c2cnc3cc(C#N)cnn23)cc1Nc1cnn(CC(F)F)c1] | 7.44 | B, 18 MIN GRADIENT | 516.2 |
| 262 | 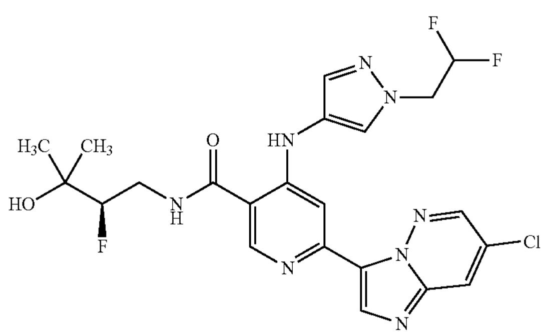 [SMILES: CC(C)(O)[C@H](F)CNC(=O)c1cnc(-c2cnc3cc(Cl)cnn23)cc1Nc1cnn(CC(F)F)c1] | 1.24 | C | 523.3 |

TABLE 10-continued
| Ex. No. | Structure | HPLC rt (min) | HPLC cond. | LCMS |
|---|---|---|---|---|
| 263 | 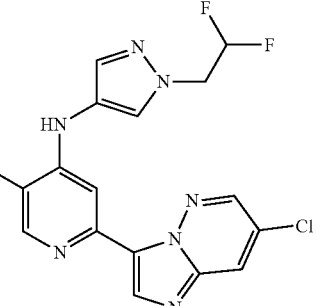 | 1.52 | C | 525.3 |
| 264 | 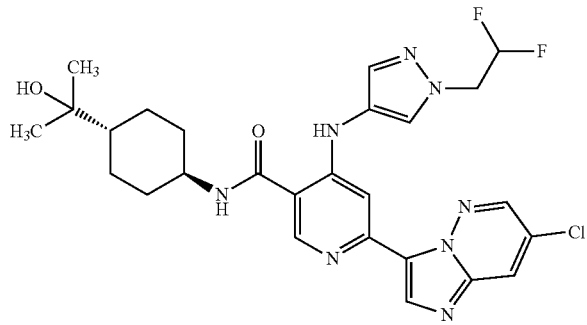 [SMILES: CC(C)(O)[C@H]1CC[C@H](NC(=O)c2cnc(-c3cnc4cc(Cl)cnn34)cc2Nc2cnn(CC(F)F)c2)CC1] | 1.43 | C | 559.3 (M+) |
| 265 | 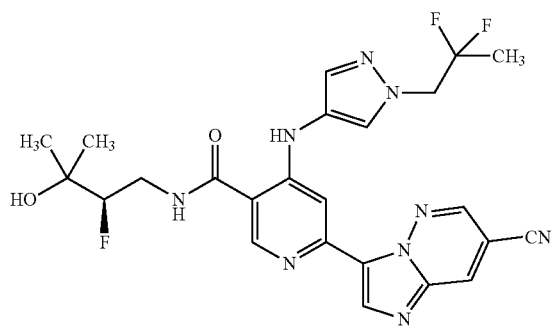 [SMILES: CC(F)(F)Cn1cc(Nc2cc(-c3cnc4cc(C#N)cnn34)ncc2C(=O)NC[C@@H](F)C(C)(C)O)cn1] | 11.04 | A, 18 MIN GRADIENT | 528.2 |
| 266 | 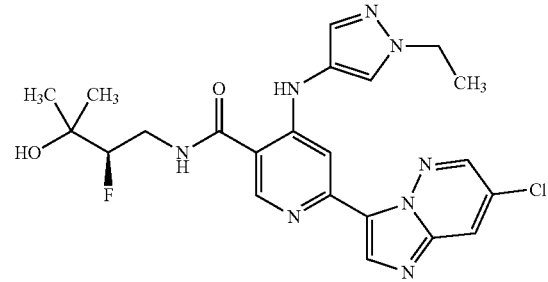 [SMILES: CCn1cc(Nc2cc(-c3cnc4cc(Cl)cnn34)ncc2C(=O)NC[C@@H](F)C(C)(C)O)cn1] | 11.29 | B, 18 MIN GRADIENT | 487.0 (M+) |
| 267 | 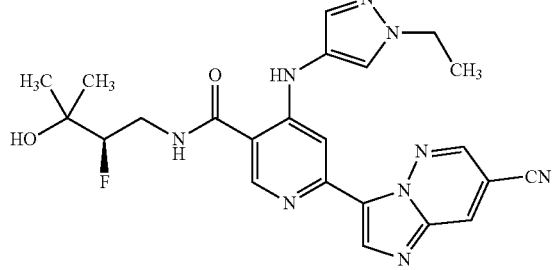 | 10.80 | B, 18 MIN GRADIENT | 478.2 |

TABLE 10-continued
| Ex. No. | Structure | HPLC rt (min) | HPLC cond. | LCMS |
|---|---|---|---|---|
| 268 | 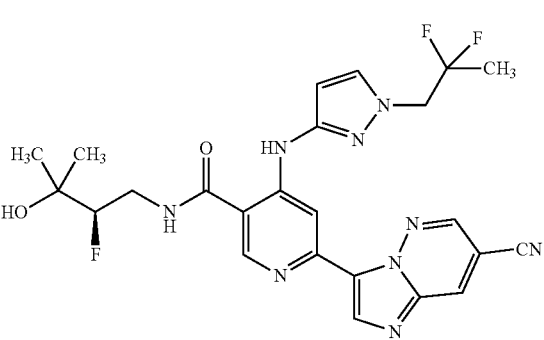 [SMILES: CC(F)(F)Cn1ccc(Nc2cc(-c3cnc4cc(C#N)cnn34)ncc2C(=O)NC[C@@H](F)C(C)(C)O)n1] | 1.21 | C | 528.3 |
| 269 | 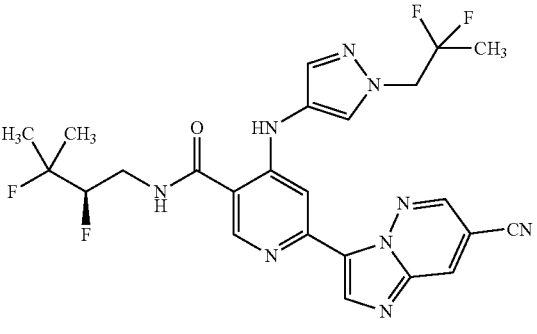 [SMILES: CC(F)(F)Cn1cc(Nc2cc(-c3cnc4cc(C#N)cnn34)ncc2C(=O)NC[C@@H](F)C(C)(C)F)cn1] | 6.78 | A | 530.2 |
| 270 | 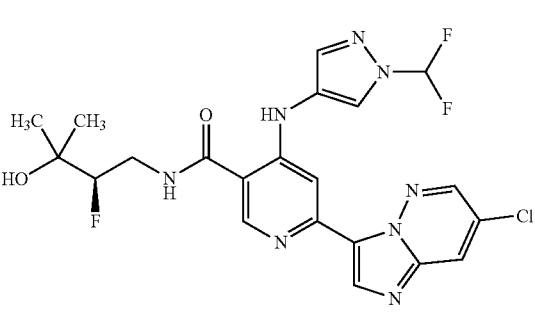 [SMILES: CC(C)(O)[C@H](F)CNC(=O)c1cnc(-c2cnc3cc(Cl)cnn23)cc1Nc1cnn(C(F)F)c1] | 1.42 | C | 509.3 |
| 271 | 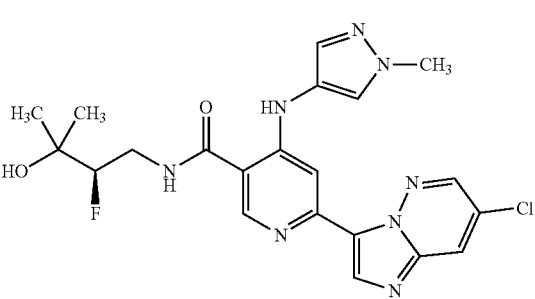 [SMILES: Cn1cc(Nc2cc(-c3cnc4cc(Cl)cnn34)ncc2C(=O)NC[C@@H](F)C(C)(C)O)cn1] | 1.23 | C | 473.2 |

TABLE 10-continued

| Ex. No. | Structure | HPLC rt (min) | HPLC cond. | LCMS |
|---|---|---|---|---|
| 272 | 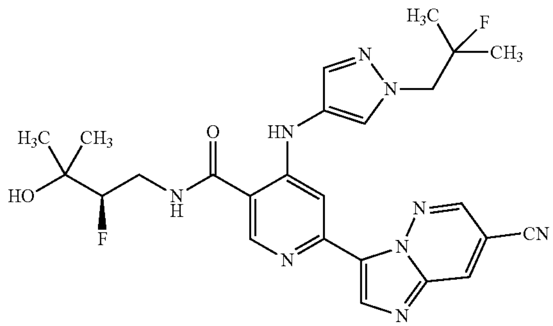 [SMILES: CC(C)(F)Cn1cc(Nc2cc(-c3cnc4cc(C#N)cnn34)ncc2C(=O)NC[C@@H](F)C(C)(C)O)cn1] | 1.40 | C | 524.3 |
| 273 | 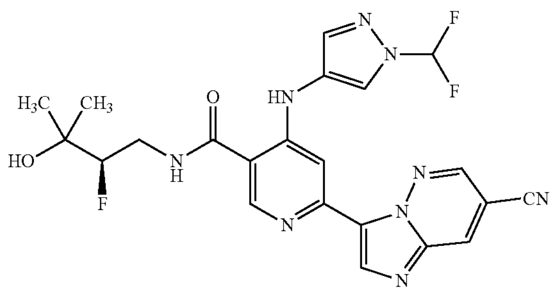 [SMILES: CC(C)(O)[C@H](F)CNC(=O)c1cnc(-c2cnc3cc(C#N)cnn23)cc1Nc1cnn(C(F)F)c1] | 1.06 | C | 500.3 |
| 274 | 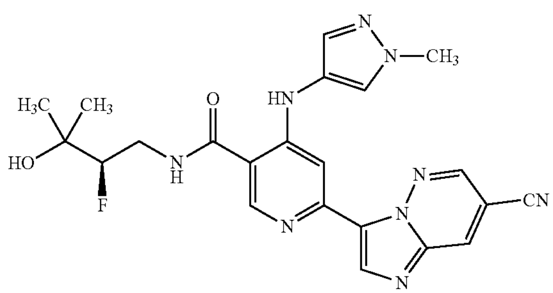 [SMILES: Cn1cc(Nc2cc(-c3cnc4cc(C#N)cnn34)ncc2C(=O)NC[C@@H](F)C(C)(C)O)cn1] | 1.10 | C | 464.3 |
| 275 | 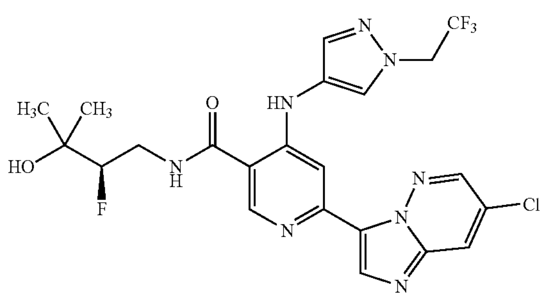 [SMILES: CC(C)(O)[C@H](F)CNC(=O)c1cnc(-c2cnc3cc(Cl)cnn23)cc1Nc1cnn(CC(F)(F)F)c1] | 1.42 | C | 541.3 |
| 276 | 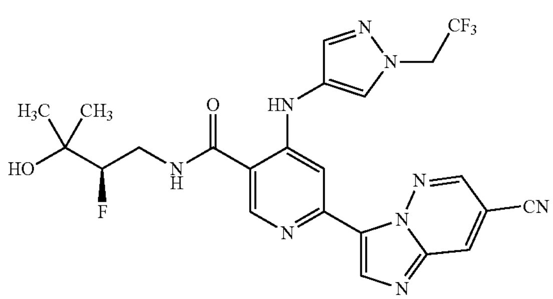 [SMILES: CC(C)(O)[C@H](F)CNC(=O)c1cnc(-c2cnc3cc(C#N)cnn23)cc1Nc1cnn(CC(F)(F)F)c1] | 1.33 | C | 532.3 |

TABLE 10-continued
| Ex. No. | Structure | HPLC rt (min) | HPLC cond. | LCMS |
|---|---|---|---|---|
| 277 | 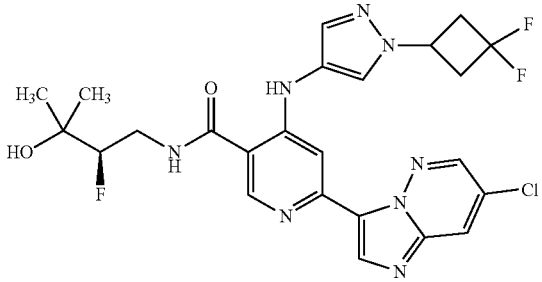 [SMILES: CC(C)(O)[C@H](F)CNC(=O)c1cnc(-c2cnc3cc(Cl)cnn23)cc1Nc1cnn(C2CC(F)(F)C2)c1] | 1.58 | C | 549.3 |
| 278 | 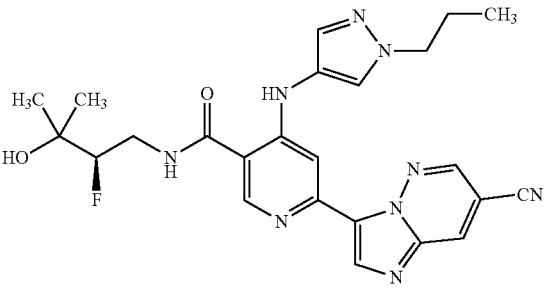 [SMILES: CCCn1cc(Nc2cc(-c3cnc4cc(C#N)cnn34)ncc2C(=O)NC[C@@H](F)C(C)(C)O)cn1] | 1.35 | C | 492.3 |
| 279 | 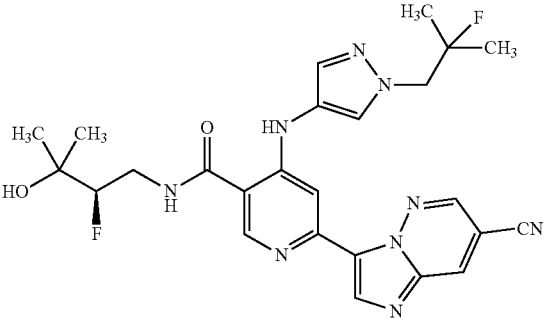 [SMILES: CC(C)(F)Cn1cc(Nc2cc(-c3cnc4cc(C#N)cnn34)ncc2C(=O)NC[C@@H](F)C(C)(C)O)cn1] | 5.67 | A | 524.2 |
| 280 | 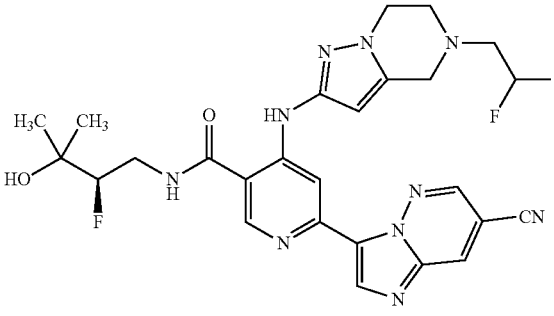 | 1.41 | C | 569.4 |
| 281 | 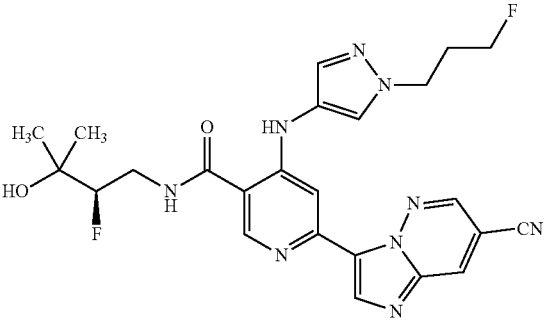 [SMILES: CC(C)(O)[C@H](F)CNC(=O)c1cnc(-c2cnc3cc(C#N)cnn23)cc1Nc1cnn(CCCF)c1] | 1.29 | C | 510.3 |

TABLE 10-continued
| Ex. No. | Structure | HPLC rt (min) | HPLC cond. | LCMS |
|---|---|---|---|---|
| 282 | 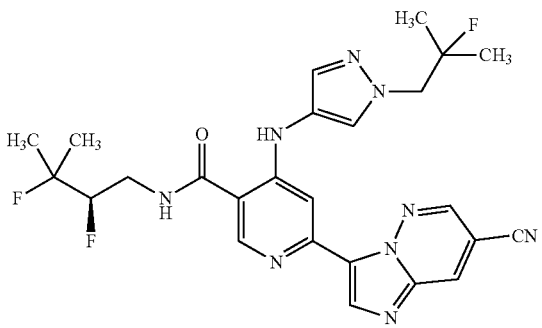 [SMILES: CC(C)(F)Cn1cc(Nc2cc(-c3cnc4cc(C#N)cnn34)ncc2C(=O)NC[C@@H](F)C(C)(C)F)cn1] | 7.73 | B | 526.2 |
| 283 | 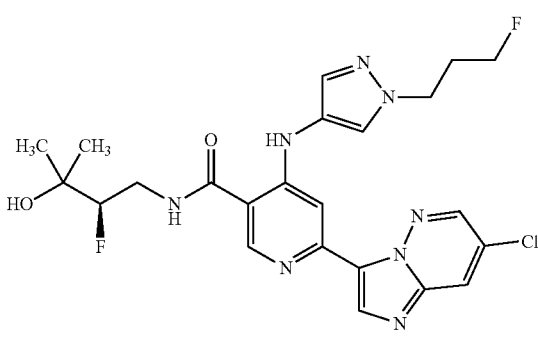 [SMILES: CC(C)(O)[C@H](F)CNC(=O)c1cnc(-c2cnc3cc(Cl)cnn23)cc1Nc1cnn(CCCF)c1] | 1.29 | C | 519.3 |
| 284 | 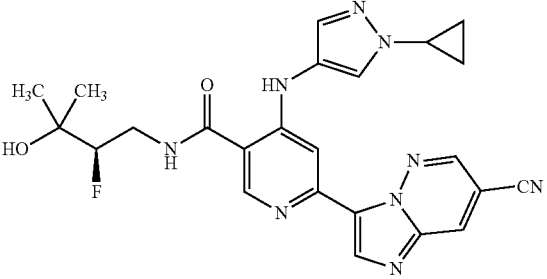 [SMILES: CC(C)(O)[C@H](F)CNC(=O)c1cnc(-c2cnc3cc(C#N)cnn23)cc1Nc1cnn(C2CC2)c1] | 0.98 | C | 490.3 |
| 285 | 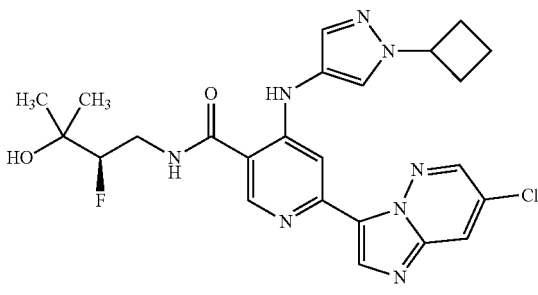 [SMILES: CC(C)(O)[C@H](F)CNC(=O)c1cnc(-c2cnc3cc(Cl)cnn23)cc1Nc1cnn(C2CCC2)c1] | 1.41 | C | 513.2 |
| 286 | 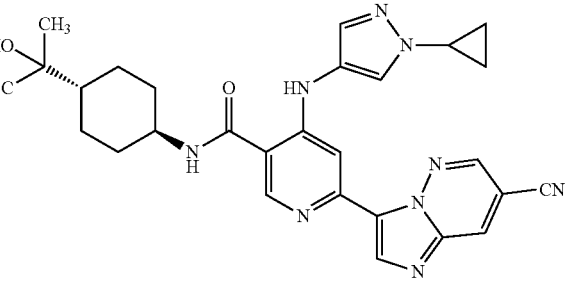 | 1.36 | C | 526.2 |

TABLE 10-continued

| Ex. No. | Structure | HPLC rt (min) | HPLC cond. | LCMS |
|---|---|---|---|---|
| 287 | 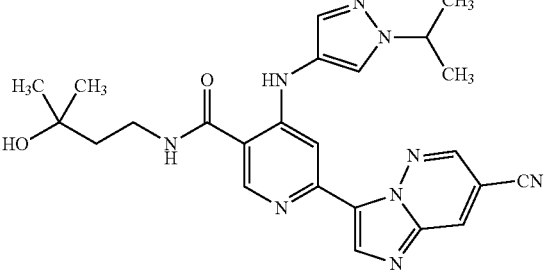 | 1.60 | C | 474.2 |
| 288 | 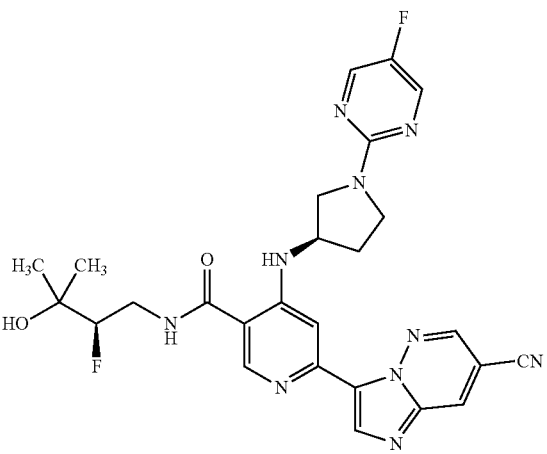 [SMILES: CC(C)(O)[C@H](F)CNC(=O)c1cnc(-c2cnc3cc(C#N)cnn23)cc1N[C@@H]1CCN(c2ncc(F)cn2)C1] | 1.40 | C | 549.3 |

Biological Assays

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 µL prepared from 15 µL additions of enzyme and substrates (fluoresceinated peptide and ATP) and test compounds in assay buffer (20 mM HEPES pH 7.2, 10 mM $MgCl_2$, 0.015% Brij 35 and 4 mM DTT). The reaction was initiated by the combination of IRAK4 with substrates and test compounds. The reaction mixture was incubated at room temperature for 60 min. and terminated by adding 45 µL of 35 mM EDTA to each sample. The reaction mixture was analyzed on the Caliper LAB-CHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 µM; FL-IPTSPITT-TYFFFKKK peptide 1.5 µM; IRAK4, 0.6 nM; and DMSO, 1.6%.

Caco Permeability Assay

Thirteen to 27 days prior to assay, Caco-2 cells were seeded onto collagen-coated polycarbonate filter membranes in 24-well transwell plates at a density of $1.45 \times 10^5$ cells/$cm^2$, approximately $4.8 \times 10^4$ cells per well. The cells were grown in a culture medium consisting of DMEM supplemented with 10% fetal bovine serum, 10 mM HEPES, 1% nonessential amino acids, 2 mM L-glutamine, 100 U/mL penicillin-G, and 100 µg/mL streptomycin. The culture medium was replaced every 3 days and the cells were maintained at 37° C. in a 95% relative humidity and 5% $CO_2$ atmosphere. The cells were evaluated for tight junction formation just prior to assay. The test compound was solubilized to 10 mM in 100% DMSO and diluted to 3 µM in assay buffer. Permeability studies were initiated by adding 200 µL assay buffer plus/minus compound to the apical transwell compartment and 600 µL assay buffer plus/minus compound to the basolateral compartment of the 24-well transwell low-binding cluster plate. For apical-to-basolateral (A to B) permeability (absorptive direction), buffer containing compound was placed in the apical compartment (donor wells), while buffer alone was placed in the corresponding basolateral compartments (receiver wells). For basolateral-to-apical (B to A) permeability (secretive direction), buffer containing compound was placed in the basolateral compartment (donor wells), while buffer alone was placed in the corresponding apical compartments (receiver wells). Transwells were then incubated for 2 hours at 37° C. in a 95% relative humidity and 5% $CO_2$ atmosphere with gentle agitation. Following incubation, 100 µL was removed from each apical and basolateral compartment and transferred to 96-well low binding plates that had been previously loaded with 100 L/well of acetonitrile containing 250 nM propranolol, 250 nM diclofenac, and 500 nM tolbutamide as internal standards. The samples were subsequently analyzed by LC-MS/MS to determine concentrations of compound.

IRAK4 Whole Blood Assay

Human whole blood containing the anti-coagulant ACD-A was plated in 384-well plate (25 μL/well) and incubated with compounds for 60 minutes at 37° C. in a 5% $CO_2$ incubator. The blood was stimulated with a TLR2 agonist, 10 μg/mL final concentration of lipoteichoic acid (Invivogen, San Diego, Calif.) in 25 μL RPMI (Gibco) for 5 hours in a 5% $CO_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, Calif.).

PBMC TLR2 Induced IL-6 assay

Peripheral blood mononuclear cells (PBMCs) were isolated from human blood containing the anti-coagulant EDTA (2.5 mM) by centrifugation over a Ficoll gradient. PBMCs (250000 cells/well) were cultured in assay media (RPMI with 10% heat inactivated FCS) with compounds for 30 minutes at 37° C. in a 5% $CO_2$ incubator. Following pretreatment with compounds, cells were stimulated for 5 hours with 10 μg/ml lipoteichoic acid (Invivogen, San Diego, Calif.), a TLR2 agonist. At the end of the culture, plates were centrifuged at 1800 rpm for 10 minutes to pellet the cells. Supernatants were harvested and analyzed for IL-6 levels by ELISA (BD Biosciences, San Jose, Calif.).

The table below lists the IRAK4 $IC_{50}$ values, the Whole Blood $EC_{50}$ values, and Caco-2 Permeability values for the following examples of this invention measured in the IRAK4 Inhibition Assay, IRAK4 Whole Blood Assay and the Caco-2 Permeability assay. The compounds of the present invention, as exemplified by the following examples, showed IRAK $IC_{50}$ inhibition values of less than 0.1 μM.

TABLE 11

| Example No. | IRAK4 $IC_{50}$ (μM) | Whole Blood $EC_{50}$ (μM) | Caco-2 Permeability (nm/s) |
|---|---|---|---|
| 1 | 0.003 | 0.40 | 248 |
| 2 | 0.008 | 0.88 | <15 |
| 3 | 0.006 | 0.38 | — |
| 4 | 0.013 | 0.68 | — |
| 5 | 0.003 | 0.10 | 175 |
| 6 | 0.010 | — | — |
| 7 | 0.002 | 0.57 | — |
| 8 | 0.024 | — | — |
| 9 | 0.005 | — | — |
| 10 | 0.099 | — | — |
| 11 | 0.014 | — | — |
| 12 | 0.092 | — | — |
| 13 | 0.007 | 4.45 | — |
| 14 | 0.022 | — | — |
| 15 | 0.004 | 0.66 | 65 |
| 16 | 0.006 | 1.09 | — |
| 17 | 0.019 | — | — |
| 18 | 0.008 | 1.15 | — |
| 19 | 0.003 | 0.62 | 49 |
| 20 | 0.007 | 2.53 | — |
| 21 | 0.007 | 2.53 | — |
| 22 | 0.002 | 11.14 | 162 |
| 23 | 0.010 | 0.72 | 18 |
| 24 | 0.035 | — | — |
| 25 | 0.005 | 0.46 | — |
| 26 | 0.008 | — | — |
| 27 | 0.007 | 1.05 | — |
| 28 | 0.005 | 1.92 | — |
| 29 | 0.024 | — | — |
| 30 | 0.004 | 0.38 | 142 |
| 31 | 0.007 | 0.14 | <15 |
| 32 | 0.004 | 0.71 | 241 |
| 33 | 0.002 | 0.35 | <15 |
| 34 | 0.002 | 0.36 | <15 |
| 35 | 0.002 | 2.44 | — |
| 36 | 0.005 | — | — |
| 37 | 0.006 | 0.70 | 48 |
| 38 | 0.007 | — | — |
| 39 | 0.018 | — | — |
| 40 | 0.004 | 1.72 | 221 |
| 41 | 0.007 | 0.35 | — |
| 42 | 0.008 | — | — |
| 43 | 0.017 | — | — |
| 44 | 0.007 | 2.73 | 53 |
| 45 | 0.034 | — | — |
| 46 | 0.005 | 1.97 | 241 |
| 47 | 0.008 | 0.35 | 173 |
| 48 | 0.001 | 0.30 | 26 |
| 49 | 0.018 | 2.92 | <15 |
| 50 | 0.002 | 0.69 | 30 |
| 51 | 0.010 | 1.25 | — |
| 52 | 0.003 | 0.28 | <15 |
| 53 | 0.004 | — | — |
| 54 | 0.003 | — | — |
| 55 | 0.009 | — | — |
| 56 | 0.005 | 0.36 | 143 |
| 57 | 0.003 | 2.34 | — |
| 58 | 0.014 | 0.35 | <15 |
| 59 | 0.006 | — | — |
| 60 | 0.004 | 4.93 | 270 |
| 61 | 0.006 | 1.82 | 197 |
| 62 | 0.047 | — | — |
| 63 | 0.008 | — | — |
| 64 | 0.005 | — | — |
| 65 | 0.004 | 3.47 | 126 |
| 66 | 0.003 | — | 212 |
| 67 | 0.002 | 3.08 | 184 |
| 68 | 0.002 | 0.42 | <15 |
| 69 | 0.002 | 3.17 | — |
| 70 | 0.003 | 0.84 | 73 |
| 71 | 0.001 | 0.07 | 17 |
| 72 | 0.002 | — | — |
| 73 | 0.002 | 0.71 | <15 |
| 74 | 0.026 | — | — |
| 75 | 0.002 | 1.46 | — |
| 76 | 0.009 | — | — |
| 77 | 0.099 | — | — |
| 78 | 0.029 | — | — |
| 79 | 0.014 | — | — |
| 80 | 0.006 | 0.84 | — |
| 81 | 0.026 | — | — |
| 82 | 0.006 | 0.58 | <15 |
| 83 | 0.001 | 0.81 | 159 |
| 84 | 0.002 | 0.32 | 120 |
| 85 | 0.002 | — | — |
| 86 | 0.004 | — | — |
| 87 | 0.002 | 0.25 | 56 |
| 88 | 0.034 | — | — |
| 89 | 0.015 | 2.96 | <15 |
| 90 | 0.004 | 0.40 | 28 |
| 91 | 0.012 | 2.97 | 50 |
| 92 | 0.020 | 0.72 | 74 |
| 93 | 0.006 | 1.66 | 72 |
| 94 | 0.010 | 0.37 | — |
| 95 | 0.006 | 1.16 | — |
| 96 | 0.002 | 0.27 | 83 |
| 97 | 0.004 | 1.60 | 80 |
| 98 | 0.006 | 0.86 | — |
| 99 | 0.004 | 0.60 | — |
| 100 | 0.094 | — | — |
| 101 | 0.007 | 1.64 | — |
| 102 | 0.080 | — | — |
| 103 | 0.044 | — | — |
| 104 | 0.007 | 0.80 | 162 |
| 105 | 0.007 | 0.24 | 86 |
| 106 | 0.004 | 1.03 | 70 |
| 107 | 0.013 | 0.43 | <15 |
| 108 | 0.067 | — | — |
| 109 | 0.005 | 0.44 | — |
| 110 | 0.003 | 0.27 | <15 |
| 111 | 0.003 | 0.90 | — |
| 112 | 0.001 | 0.82 | — |

TABLE 11-continued

| Example No. | IRAK4 IC$_{50}$ (μM) | Whole Blood EC$_{50}$ (μM) | Caco-2 Permeability (nm/s) |
|---|---|---|---|
| 113 | 0.053 | — | — |
| 114 | 0.003 | 0.48 | — |
| 115 | 0.006 | 2.03 | <15 |
| 116 | 0.021 | — | — |
| 117 | 0.039 | — | — |
| 118 | 0.009 | 0.71 | — |
| 119 | 0.009 | — | — |
| 120 | 0.009 | 0.80 | — |
| 121 | 0.052 | — | — |
| 122 | 0.030 | — | — |
| 123 | 0.042 | — | — |
| 124 | 0.012 | — | — |
| 125 | 0.056 | — | — |
| 126 | 0.022 | — | — |
| 127 | 0.081 | — | — |
| 128 | 0.075 | — | — |
| 129 | 0.003 | — | — |
| 130 | 0.017 | 1.89 | 221 |
| 131 | 0.013 | — | — |
| 132 | 0.009 | — | — |
| 133 | 0.036 | — | — |
| 134 | 0.092 | — | — |
| 135 | 0.044 | — | — |
| 136 | 0.019 | — | — |
| 137 | 0.075 | — | — |
| 138 | 0.062 | — | — |
| 139 | 0.003 | — | — |
| 140 | 0.006 | — | — |
| 141 | 0.004 | 0.49 | 52 |
| 142 | 0.003 | 0.10 | 190 |
| 143 | 0.002 | 1.08 | 82 |
| 144 | 0.003 | 0.23 | 134 |
| 145 | 0.002 | 0.24 | 123 |
| 146 | 0.002 | 0.15 | <15 |
| 147 | 0.003 | 0.09 | <15 |
| 148 | 0.007 | 0.35 | 89 |
| 149 | 0.018 | — | — |
| 150 | 0.012 | — | — |
| 151 | 0.011 | — | — |
| 152 | 0.029 | — | — |
| 153 | 0.013 | — | — |
| 154 | 0.016 | — | — |
| 155 | 0.055 | — | — |
| 156 | 0.014 | 2.34 | — |
| 157 | 0.003 | 0.93 | — |
| 158 | 0.005 | 0.87 | 148 |
| 159 | 0.005 | 1.00 | 95 |
| 160 | 0.006 | 0.81 | — |
| 161 | 0.006 | 0.61 | 153 |
| 163 | 0.006 | 0.76 | 191 |
| 164 | 0.011 | 0.27 | <15 |
| 165 | 0.006 | 0.47 | — |
| 166 | 0.005 | 0.66 | — |
| 167 | 0.005 | 0.55 | — |
| 168 | 0.016 | 0.76 | — |
| 169 | 0.008 | 0.65 | 142 |
| 170 | 0.005 | 0.82 | — |
| 171 | 0.006 | 0.36 | 19 |
| 172 | 0.004 | 0.46 | 42 |
| 173 | 0.006 | 0.83 | — |
| 174 | 0.004 | 0.71 | — |
| 175 | 0.003 | 0.48 | — |
| 176 | 0.003 | 0.54 | — |
| 177 | 0.010 | 0.88 | 126 |
| 178 | 0.004 | 0.71 | 215 |
| 179 | 0.003 | 0.70 | 168 |
| 180 | 0.002 | 0.93 | 165 |
| 181 | 0.003 | 0.10 | <15 |
| 182 | 0.002 | 0.62 | — |
| 183 | 0.002 | 0.75 | 89 |
| 184 | 0.005 | 0.51 | 34 |
| 185 | 0.007 | 0.82 | 47 |
| 186 | 0.005 | 0.25 | 122 |
| 187 | 0.002 | 0.20 | — |
| 188 | 0.005 | 0.24 | 67 |
| 189 | 0.007 | 0.49 | 312 |
| 190 | 0.006 | 0.61 | 153 |
| 191 | 0.007 | 0.63 | — |
| 192 | 0.010 | 0.50 | 299 |
| 193 | 0.004 | 0.26 | — |
| 194 | 0.008 | 0.23 | 42 |
| 195 | 0.004 | 0.70 | 37 |
| 196 | 0.006 | 0.64 | — |
| 197 | 0.002 | 0.28 | <15 |
| 198 | 0.001 | 0.47 | 184 |
| 199 | 0.004 | 0.55 | 158 |
| 200 | 0.002 | 0.43 | — |
| 201 | 0.003 | 0.08 | <15 |
| 202 | 0.002 | 0.75 | — |
| 203 | 0.005 | 0.89 | — |
| 204 | 0.002 | 0.26 | — |
| 205 | 0.004 | 0.21 | 45 |
| 206 | 0.004 | 0.82 | — |
| 207 | 0.002 | 0.26 | 97 |
| 208 | 0.006 | 0.55 | — |
| 209 | 0.004 | 0.61 | — |
| 210 | 0.003 | 0.98 | — |
| 211 | 0.002 | 0.94 | — |
| 212 | 0.003 | 0.98 | — |
| 213 | 0.002 | 0.89 | — |
| 214 | 0.011 | 0.48 | — |
| 215 | 0.004 | 0.60 | — |
| 216 | 0.008 | 0.31 | 239 |
| 217 | 0.002 | 0.30 | 256 |
| 218 | 0.005 | 0.22 | 21 |
| 219 | 0.018 | 0.45 | — |
| 220 | 0.016 | 0.34 | — |
| 221 | 0.014 | 0.57 | — |
| 222 | 0.007 | 0.63 | — |
| 223 | 0.013 | 0.81 | — |
| 224 | 0.007 | 0.57 | — |
| 225 | 0.002 | 0.08 | — |
| 226 | 0.003 | 0.21 | 36 |
| 227 | 0.002 | 0.17 | 40 |
| 228 | 0.002 | 0.25 | — |
| 229 | 0.009 | 0.58 | 113 |
| 230 | 0.003 | 0.43 | <15 |
| 231 | 0.001 | 0.34 | 126 |
| 232 | 0.001 | 0.14 | 37 |
| 233 | 0.006 | 0.57 | — |
| 234 | 0.003 | 0.54 | — |
| 235 | 0.002 | 0.20 | 23 |
| 236 | 0.003 | 0.66 | <15 |
| 237 | 0.002 | 0.69 | — |
| 238 | 0.002 | 0.22 | 21 |
| 239 | 0.001 | 0.35 | 144 |
| 240 | 0.002 | 0.18 | <15 |
| 241 | 0.002 | 0.13 | <15 |
| 242 | 0.002 | 0.06 | 21 |
| 243 | 0.003 | 0.16 | <15 |
| 244 | 0.008 | 0.38 | <15 |
| 245 | 0.004 | 0.41 | 18 |
| 246 | 0.001 | 0.13 | 47 |
| 247 | 0.002 | 0.36 | 81 |
| 248 | 0.002 | 0.37 | <15 |
| 249 | 0.002 | 0.40 | <15 |
| 250 | 0.001 | 0.20 | 66 |
| 251 | 0.001 | 0.41 | 76 |
| 252 | 0.003 | 0.93 | — |
| 253 | 0.001 | 0.16 | 48 |
| 254 | 0.002 | 0.47 | — |
| 255 | 0.005 | 0.72 | — |
| 256 | 0.003 | 0.79 | — |
| 257 | 0.014 | 0.71 | — |
| 258 | 0.002 | 0.18 | 59 |
| 259 | 0.002 | 0.13 | <15 |
| 260 | 0.003 | 0.08 | <15 |
| 261 | 0.002 | 0.18 | 59 |
| 262 | 0.001 | 0.52 | 26 |
| 263 | 0.002 | 0.30 | 213 |
| 264 | 0.002 | 0.91 | — |
| 265 | 0.002 | 0.44 | <15 |

TABLE 11-continued

| Example No. | IRAK4 IC$_{50}$ (μM) | Whole Blood EC$_{50}$ (μM) | Caco-2 Permeability (nm/s) |
|---|---|---|---|
| 266 | 0.003 | 0.57 | 29 |
| 267 | 0.002 | 0.13 | <15 |
| 268 | 0.003 | 0.96 | — |
| 269 | 0.002 | 0.56 | — |
| 270 | 0.003 | 0.82 | 78 |
| 271 | 0.004 | 0.17 | — |
| 272 | 0.006 | 0.85 | 20 |
| 273 | 0.007 | 0.38 | — |
| 274 | 0.009 | 0.59 | — |
| 275 | 0.001 | 0.44 | — |
| 276 | 0.002 | 0.08 | — |
| 277 | 0.002 | 0.49 | 36 |
| 278 | 0.001 | 0.36 | <15 |
| 279 | 0.001 | 0.78 | <15 |
| 280 | 0.006 | 0.33 | <15 |
| 281 | 0.002 | 0.29 | <15 |
| 282 | 0.002 | 0.71 | — |
| 283 | 0.002 | 0.34 | — |
| 284 | 0.002 | 0.21 | <15 |
| 285 | 0.003 | 0.37 | — |
| 286 | 0.002 | 0.18 | 55 |
| 287 | 0.009 | 0.45 | 18 |
| 288 | 0.009 | 0.39 | — |

What is claimed is:

1. A compound of Formula (I)

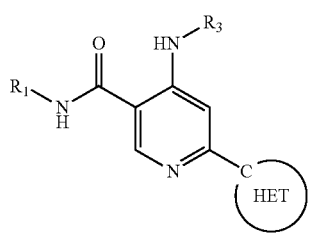

(I)

or a salt thereof, wherein:

HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 $R_b$;

each $R_b$ is independently selected from H, F, Cl, —CN, —NH$_2$, C$_{1-3}$ alkyl, C$_{1-2}$ fluoroalkyl, C$_{1-3}$ alkoxy, C$_{3-6}$ cycloalkyl, —NH(C$_{1-3}$ alkyl), —NH(C$_{1-4}$ hydroxyalkyl), cyanophenyl, pyridinyl, and hydroxypyrrolidinyl;

$R_1$ is:

(i) C$_{3-6}$ alkyl substituted with 1 to 4 substituents independently selected from F, —CN, —OH, —OCH$_3$, —OCD$_3$, —NHC(O)(C$_{1-3}$ alkyl), —S(O)$_2$(C$_{1-3}$ alkyl), and C$_{1-2}$ fluoroalkoxy;

(ii) —(CR$_y$R$_y$)$_{1-3}$R$_x$ or —(CH$_2$)$_{1-3}$C(O)R$_x$, wherein R$_x$ is phenyl, oxetanyl, tetrahydropyranyl, morpholinyl, piperidinyl, imidazolyl, pyridinyl, thiophenyl, or C$_{4-6}$ cycloalkyl, each substituted with zero to 3 substituents independently selected from F, Cl, —OH, C$_{1-3}$ alkyl, C$_{1-2}$ alkoxy, and —S(O)$_2$NH$_2$;

(iii) C$_{4-6}$ cycloalkyl substituted with zero to 2 substituents independently selected from —OH, C$_{1-4}$ hydroxyalkyl, C$_{1-3}$ alkoxy, —(CH$_2$)$_{1-3}$O(C$_{1-3}$ alkyl), —C(O)NH(C$_{1-4}$ alkyl), —C(O)NH(C$_{3-6}$ cycloalkyl), —N(C$_{1-3}$ alkyl)$_2$, —NHC(O)(C$_{1-3}$ alkyl), —NHC(O)O(C$_{1-3}$ alkyl), and —NHC(O)(C$_{1-4}$ hydroxyalkyl);

(iv) tetrahydrofuranyl, tetrahydropyranyl, piperidinyl, piperazinyl, pyrrolyl, pyrazolyl, imidazolyl, or triazolyl, each substituted with zero to 2 substituents independently selected from C$_{1-4}$ hydroxyalkyl, —S(O)$_2$(C$_{1-3}$ alkyl), —CH$_2$C(O)NH(C$_{1-3}$ alkyl), —CH$_2$C(O)NH(C$_{1-6}$ hydroxyalkyl), —CH$_2$C(O)NH(C$_{1-6}$ fluoroalkyl), and —CH$_2$C(O)NH(C$_{1-6}$ hydroxy-fluoroalkyl); or (v) 1-oxa-7-azaspiro[3.5]nonanyl;

each $R_y$ is independently H, F, or —OH; and $R_3$ is:

(i) C$_{2-5}$ alkyl, C$_{2-5}$ fluoroalkyl, C$_{2-5}$ hydroxyalkyl, —(CH$_2$)$_{1-3}$R$_z$, —CH(CH$_3$)R$_z$, or —CH(CH$_2$OH)CH$_2$R$_z$, wherein R$_z$ is C$_{4-6}$ cycloalkyl, oxetanyl, tetrahydrofuranyl, tetrahydropyranyl, or phenyl, each substituted with zero to 1 substituent selected from —OH and —CH$_3$;

(ii) C$_{3-6}$ cycloalkyl substituted with zero to 3 substituents independently selected from F, Cl, —CN, —OH, C$_{1-3}$ alkyl, C$_{1-3}$ fluoroalkyl, C$_{1-4}$ hydroxyalkyl, C$_{1-4}$ alkoxy, —C(O)NH$_2$, —C(O)NH(C$_{1-3}$ alkyl), and —C(O)(C$_{1-3}$ fluoroalkyl);

(iii) oxetanyl, tetrahydrofuranyl, tetrahydropyranyl, pyrrolidinyl, piperidinyl, pyrazolyl, thiazolyl, bicyclo[1.1.1]pentanyl, bicyclo[2.2.1]heptanyl, or 4,5,6,7-tetrahydropyrazolo[1,5-a]pyrazinyl, each substituted with zero to 2 substituents independently selected from F, —OH, C$_{1-4}$ alkyl, C$_{1-3}$ hydroxyalkyl, C$_{1-4}$ fluoroalkyl, —CH$_2$(C$_{3-6}$ cycloalkyl), —(CH$_2$)$_{1-3}$O(C$_{1-3}$ alkyl), —C(O)(C$_{1-3}$ fluoroalkyl), —S(O)$_2$(C$_{1-3}$ alkyl), C$_{3-6}$ cycloalkyl, C$_{3-6}$ fluorocycloalkyl, oxetanyl, tetrahydrofuranyl, tetrahydropyranyl, pyrimidinyl, fluoropyrimidinyl, and methoxypyrimidinyl; or (iv) phenyl substituted with zero to 3 substituents independently selected from F, Cl, —CN, —OH, —C(O)NH$_2$, —C(O)NH(C$_{1-3}$ alkyl), and —C(O)(C$_{1-3}$ fluoroalkyl).

2. The compound according to claim 1 or a salt thereof, wherein:

HET is a heteroaryl selected from oxazolyl, pyrazolyl, imidazo[1,2-b]pyridazin-3-yl, and pyrazolo[1,5-a]pyrimidin-3-yl, wherein said heteroaryl is attached to the pyridinyl group in the compound of Formula (I) by a carbon ring atom in the heteroaryl and wherein said heteroaryl is substituted with zero to 2 $R_b$;

each $R_b$ is independently selected from H, F, Cl, —CN, —NH$_2$, C$_{1-3}$ alkyl, C$_{1-3}$ alkoxy, C$_{3-6}$ cycloalkyl, —NH(C$_{1-3}$ alkyl), —NH(C$_{1-4}$ hydroxyalkyl), cyanophenyl, pyridinyl, and hydroxypyrrolidinyl;

$R_1$ is:

(i) C$_{3-6}$ alkyl substituted with 1 to 4 substituents independently selected from F, —OH, —OCH$_3$, and —OCD$_3$;

(ii) —(CR$_y$R$_y$)$_{1-3}$R$_x$ or —(CH$_2$)$_{1-3}$C(O)R$_x$, wherein R$_x$ is phenyl, tetrahydropyranyl, oxetanyl, morpholinyl, or C$_{4-6}$ cycloalkyl, each substituted with zero to 3 substituents independently selected from F, Cl, —OH, C$_{1-3}$ alkyl, C$_{1-2}$ alkoxy, and —S(O)$_2$NH$_2$;

(iii) C$_{4-6}$ cycloalkyl substituted with C$_{1-4}$ hydroxyalkyl, C$_{1-3}$ alkoxy, —C(O)NH(C$_{1-4}$ alkyl), —C(O)NH(C$_{3-6}$ cycloalkyl), —NHC(O)(C$_{1-3}$ alkyl), or —NHC(O)(C$_{1-4}$ hydroxyalkyl);

255

(iv) tetrahydrofuranyl, tetrahydropyranyl, piperidinyl, piperazinyl, pyrrolyl, pyrazolyl, imidazolyl, or triazolyl, each substituted with zero to 2 substituents independently selected from $C_{1-4}$ hydroxyalkyl, —$S(O)_2(C_{1-3}$ alkyl), —$CH_2C(O)NH(C_{1-3}$ alkyl), —$CH_2C(O)NH(C_{1-6}$ hydroxyalkyl), —$CH_2C(O)NH$ ($C_{1-6}$ fluoroalkyl), and —$CH_2C(O)NH(C_{1-6}$ hydroxy-fluoroalkyl); or (v) 1-oxa-7-azaspiro[3.5]nonanyl;

each $R_y$ is independently H, F, or —OH; and $R_3$ is:
(i) $C_{2-5}$ alkyl, $C_{2-5}$ fluoroalkyl, $C_{2-5}$ hydroxyalkyl, —$(CH_2)_{1-3}R_z$, —$CH(CH_3)R_z$, or —$CH(CH_2OH)CH_2R_z$, wherein $R_z$ is $C_{4-6}$ cycloalkyl, oxetanyl, tetrahydrofuranyl, tetrahydropyranyl, or phenyl, each substituted with zero to 1 substituent selected from —OH and —$CH_3$;

(ii) $C_{3-6}$ cycloalkyl substituted with zero to 3 substituents independently selected from F, Cl, —CN, —OH, $C_{1-3}$ alkyl, $C_{1-3}$ fluoroalkyl, $C_{1-4}$ hydroxyalkyl, $C_{1-4}$ alkoxy, —$C(O)NH_2$, —$C(O)NH(C_{1-3}$ alkyl), and —$C(O)(C_{1-3}$ fluoroalkyl);

(iii) oxetanyl, tetrahydrofuranyl, tetrahydropyranyl, pyrrolidinyl, piperidinyl, pyrazolyl, thiazolyl, bicyclo[1.1.1]pentanyl, or bicyclo[2.2.1]heptanyl, each substituted with zero to 2 substituents independently selected from F, —OH, $C_{1-3}$ alkyl, $C_{1-3}$ hydroxyalkyl, $C_{1-3}$ fluoroalkyl, —$C(O)(C_{1-3}$ fluoroalkyl), —$S(O)_2(C_{1-3}$ alkyl), oxetanyl, tetrahydrofuranyl, tetrahydropyranyl, pyrimidinyl, fluoropyrimidinyl, and methoxypyrimidinyl; or (iv) phenyl substituted with zero to 3 substituents independently selected from F, Cl, —CN, —OH, —$C(O)NH_2$, —$C(O)NH(C_{1-3}$ alkyl), and —$C(O)(C_{1-3}$ fluoroalkyl).

3. The compound according to claim 1 or a salt thereof, wherein:

each $R_b$ is independently selected from H, F, Cl, —CN, —$NH_2$, —$CH_3$, —$CHF_2$, —$OCH_3$, cyclopropyl, —$NHCH_2CH_2OH$, —$NHCH_2C(CH_3)_2OH$, cyanophenyl, pyridinyl, and hydroxypyrrolidinyl;

$R_1$ is:
(i) —$CH_2CH_2C(CH_3)_3$, —$CH_2CH_2C(CH_3)_2OH$, —$CH_2CH_2C(CH_3)_2F$, —$CH_2CHFC(CH_3)_2F$, —$CH_2CH_2C(CH_3)_2CN$, —$CH_2CHFC(CH_3)_2OH$, —$CH_2CHFC(CH_2OH)_2OH$, —$CH_2CF_2C(CH_3)_2OH$, —$CH_2CH_2CH(CH_3)NHC(O)CH_3$, —$CH_2CHFC(CH_3)_2OCD_3$, —$CH_2CHFC(CH_3)_2OCHF_2$, or —$CH_2CH_2CH_2S(O)_2CH_3$;

(ii) —$CH_2CH_2$(sulfamoylphenyl), —$CH_2CH_2$(fluorotetrahydropyranyl), —$CH_2CH_2$(hydrotetrahydropyranyl), —$CH_2CHF$(hydroxyoxetanyl), —$CH_2CH_2C(O)$(morpholinyl), —$CH_2CH_2$(pyridinyl), —$CH_2CH_2$(thiophenyl), —$CH_2CH_2$(hydroxycyclopentyl), —$CH_2CH_2$(hydroxy, methoxycyclohexyl), —$CH_2CH_2$(dihydroxy, methylcyclohexyl), —$CH_2CH_2CH_2$(imidazolyl), —$CH_2CHF$(piperidinyl), or —$CH_2CHF$(dimethyl tetrahydropyranyl);

(iii) cyclohexyl substituted with —OH, —$C(CH_3)_2OH$, —$C(CH_3)_2OCH_3$, —$OCH_3$, —$OCH_2CH_3$, —$N(CH_3)_2$, —$C(O)NHCH_3$, —$C(O)NHCH(CH_3)_2$, —$C(O)NH$(cyclopropyl), —$NHC(O)CH_3$, —$NHC(O)OCH_3$, —$NHC(O)C(CH_3)_2OH$, or —$NHC(O)CH(OH)CH_3$;

256

(iv) piperidinyl, pyrazolyl, or tetrahydropyranyl, each substituted with —$CH_2OH$, —$S(O)_2CH(CH_3)_2$, —$CH_2C(O)NHCH_3$, or —$CH_2C(O)NHCH_2CHFC(CH_3)_2OH$; or (iv) 1-oxa-7-azaspiro[3.5]nonanyl; and $R_3$ is:
(i) —$CH_2CH_3$, —$CH_2CH_2CH_3$, —$CH(CH_3)_2$, —$C(CH_3)_3$, —$CH(CH_3)CH_2CH_3$, —$CH_2CF_3$, —$CH_2CH_2CF_3$, —$CH_2CF_2CH_3$, —$CH_2CHF_2$, —$CH_2CH_2CHF_2$, —$CH_2CH(CH_3)F$, —$CH_2CH_2CHFCH_3$, —$CH_2C(CH_3)_2F$, —$CH(CH_3)CH_2F$, —$CH(CH_3)CH_2CH_2F$, —$CH(CH_3)CH_2OH$, —$C(CH_3)_2CH_2OH$, —$CH_2C(CH_3)_2OH$, —$CH_2CH(OH)CH_2CH_3$, —$CH_2CH_2CH(CH_3)OH$, —$CH(CH_3)C(CH_3)_2OH$, —$CH(CH_3)$phenyl, —$CH_2$(hydroxyoxetanyl), —$CH_2$(methyloxetanyl), —$CH_2$(hydroxycyclobutyl), —$CH_2$(hydroxytetrahydropyranyl), or —$CH(CH_2OH)CH_2$(phenyl);

(ii) $C_{3-6}$ cycloalkyl substituted with zero to 3 substituents independently selected from F, —OH, —$CH_3$, —$C(CH_3)_2OH$, —$C(CH_3)_2F$, —$OCH_3$, and —$OCH(CH_3)_2$;

(iii) oxetanyl, tetrahydrofuranyl, tetrahydropyranyl, pyrrolidinyl, piperidinyl, pyrazolyl, thiazolyl, bicyclo[1.1.1]pentanyl, bicyclo[2.2.1]heptanyl, or 4,5,6,7-tetrahydropyrazolo[1,5-a]pyrazinyl; each substituted with zero to 2 substituents independently selected from F, —OH, $C_{1-4}$ alkyl, $C_{1-4}$ fluoroalkyl, —$C(CH_3)_2OH$, —$CH_2CH_2OCH_3$, —$CH_2$(cyclopropyl), $C_{3-4}$ cycloalkyl, —$S(O)_2CH_3$, difluorocyclobutyl, oxetanyl, tetrahydropyranyl, pyrimidinyl, fluoropyrmidinyl, and methoxypyrimidinyl; or (iv) phenyl substituted with 1 to 2 substituents independently selected from F, —CN, —$C(O)NH_2$, and —$C(O)NHCH_3$.

4. The compound according to any one of claims 1 to 3 or a salt thereof, wherein:

each $R_b$ is independently selected from H, F, Cl, —CN, —$NH_2$, —$CH_3$, —$OCH_3$, cyclopropyl, —$NHCH_2CH_2OH$, —$NHCH_2C(CH_3)_2OH$, cyanophenyl, pyridinyl, and hydroxypyrrolidinyl;

$R_1$ is:
(i) —$CH_2CH_2C(CH_3)_2OH$, —$CH_2CH_2C(CH_3)_2F$, —$CH_2CHFC(CH_3)_2OH$, —$CH_2CHFC(CH_2OH)_2OH$, or —$CH_2CHFC(CH_3)_2OCD_3$;

(ii) —$CH_2CH_2$(sulfamoylphenyl), —$CH_2CH_2$(fluorotetrahydropyranyl), —$CH_2CH_2$(hydrotetrahydropyranyl), —$CH_2CHF$(hydroxyoxetanyl), —$CH_2CH_2C(O)$(morpholinyl), —$CH_2CH_2$(hydroxy, methoxycyclohexyl), or —$CH_2CH_2$(dihydroxy, methylcyclohexyl);

(iii) cyclohexyl substituted with —$C(CH_3)_2OH$, —$OCH_3$, —$C(O)NHCH_3$, —$C(O)NHCH(CH_3)_2$, —$C(O)NH$(cyclopropyl), —$NHC(O)CH_3$, —$NHC(O)C(CH_3)_2OH$, or —$NHC(O)CH(OH)CH_3$;

(iv) piperidinyl, pyrazolyl, or tetrahydropyranyl, each substituted with —$CH_2OH$, —$S(O)_2CH(CH_3)_2$, —$CH_2C(O)NHCH_3$, or —$CH_2C(O)NHCH_2CHFC(CH_3)_2OH$; or (iv) 1-oxa-7-azaspiro[3.5]nonanyl; and $R_3$ is:
(i) —$CH_2CH_3$, —$CH_2CH_2CH_3$, —$CH(CH_3)_2$, —$C(CH_3)_3$, —$CH(CH_3)CH_2CH_3$, —$CH_2CF_3$, —$CH_2CH_2CF_3$, —$CH(CH_3)F$, —$CH_2C(CH_3)_2F$, —$CH(CH_3)CH_2F$, —$CH(CH_3)CH_2CH_2F$, —$CH(CH_3)CH_2OH$, —$C(CH_3)_2CH_2OH$, —CH₂C(CH₃)₂OH, —CH₂CH(OH)CH₂CH₃, —CH₂CH₂CH(CH₃)OH, —CH(CH₃)C(CH₃)₂OH, —CH(CH₃)phenyl, —CH₂(hydroxyoxetanyl), —CH₂(methyloxetanyl), —CH₂(hydroxycyclobutyl), —CH₂(hydroxytetrahydropyranyl), or —CH(CH₂OH)CH₂(phenyl);
(ii) C₃₋₅ cycloalkyl substituted with zero to 3 substituents independently selected from F, —OH, —CH₃, —C(CH₃)₂OH, —OCH₃, and —OCH(CH₃)₂;
(iii) oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, bicyclo[2.2.1]heptanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl; or
(iv) phenyl substituted with 1 to 2 substituents independently selected from F, —CN, —C(O)NH₂, and —C(O)NHCH₃.

5. The compound according to claim 1 or a salt thereof, wherein HET is:

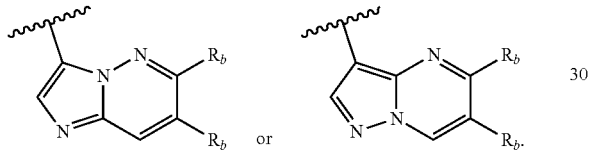

6. The compound according to claim 1 or a salt thereof, wherein R₁ is —CH₂CH₃, —CH₂CH₂CH₃, —CH(CH₃)₂, —C(CH₃)₃, —CH(CH₃)CH₂CH₃, —CH₂CF₃, —CH₂CH₂CF₃, —CH₂CF₂CH₃, —CH₂CHF₂, —CH₂CH₂CHF₂, —CH₂CH(CH₃)F, —CH₂CH₂CHFCH₃, —CH₂C(CH₃)₂F, —CH(CH₃)CH₂F, —CH(CH₃)CH₂CH₂F, —CH(CH₃)CH₂OH, —C(CH₃)₂CH₂OH, —CH₂C(CH₃)₂OH, —CH₂CH(OH)CH₂CH₃, —CH₂CH₂CH(CH₃)OH, —CH(CH₃)C(CH₃)₂OH, —CH(CH₃)phenyl, —CH₂(hydroxyoxetanyl), —CH₂(methyloxetanyl), —CH₂(hydroxycyclobutyl), —CH₂(hydroxytetrahydropyranyl), or —CH(CH₂OH)CH₂(phenyl).

7. The compound according to claim 1 or a salt thereof, wherein R₃ is:
(i) —CH₂CH₃, —CH₂CH₂CH₃, —CH(CH₃)₂, —C(CH₃)₃, —CH(CH₃)CH₂CH₃, —CH₂CF₃, —CH₂CH₂CF₃, —CH₂CF₂CH₃, —CH₂CHF₂, —CH₂CH₂CHF₂, —CH₂CH(CH₃)F, —CH₂CH₂CHFCH₃, —CH₂C(CH₃)₂F, —CH(CH₃)CH₂F, —CH(CH₃)CH₂CH₂F, —CH(CH₃)CH₂OH, —C(CH₃)₂CH₂OH, —CH₂C(CH₃)₂OH, —CH₂CH(OH)CH₂CH₃, —CH₂CH₂CH(CH₃)OH, —CH(CH₃)C(CH₃)₂OH, —CH(CH₃)phenyl, —CH₂(hydroxyoxetanyl), —CH₂(methyloxetanyl), —CH₂(hydroxycyclobutyl), —CH₂(hydroxytetrahydropyranyl), or —CH(CH₂OH)CH₂(phenyl);
(ii) C₃₋₆ cycloalkyl substituted with zero to 3 substituents independently selected from F, —OH, —CH₃, —C(CH₃)₂OH, —C(CH₃)₂F, —OCH₃, and —OCH(CH₃)₂; or
(iii) oxetanyl, tetrahydrofuranyl, tetrahydropyranyl, pyrrolidinyl, piperidinyl, pyrazolyl, thiazolyl, bicyclo[1.1.1]pentanyl, bicyclo[2.2.1]heptanyl, or 4,5,6,7-tetrahydropyrazolo[1,5-a]pyrazinyl; each substituted with zero to 2 substituents independently selected from F, —OH, C₁₋₄ alkyl, C₁₋₄ fluoroalkyl, —C(CH₃)₂OH, —CH₂CH₂OCH₃, —CH₂(cyclopropyl), C₃₋₄ cycloalkyl, —S(O)₂CH₃, difluorocyclobutyl, oxetanyl, tetrahydropyranyl, pyrimidinyl, fluoropyrimidinyl, and methoxypyrimidinyl.

8. The compound according to claim 7 or a salt thereof, wherein R₃ is:
(i) —CH₂CH₃, —CH₂CH₂CH₃, —CH(CH₃)₂, —C(CH₃)₃, —CH(CH₃)CH₂CH₃, —CH₂CF₃, —CH₂CH₂CF₃, —CH₂CH(CH₃)F, —CH₂C(CH₃)₂F, —CH(CH₃)CH₂F, —CH(CH₃)CH₂CH₂F, —CH(CH₃)CH₂OH, —C(CH₃)₂CH₂OH, —CH₂C(CH₃)₂OH, —CH₂CH(OH)CH₂CH₃, —CH₂CH₂CH(CH₃)OH, —CH(CH₃)C(CH₃)₂OH, —CH(CH₃)phenyl, —CH₂(hydroxyoxetanyl), —CH₂(methyloxetanyl), —CH₂(hydroxycyclobutyl), —CH₂(hydroxytetrahydropyranyl), or —CH(CH₂OH)CH₂(phenyl);
(ii) C₃₋₅ cycloalkyl substituted with zero to 3 substituents independently selected from F, —OH, —CH₃, —C(CH₃)₂OH, —OCH₃, and —OCH(CH₃)₂; or
(iii) oxetanyl, tetrahydrofuranyl, fluorotetrahydrofuranyl, difluorotetrahydrofuranyl, hydroxytetrahydrofuranyl, tetrahydropyranyl, fluorotetrahydropyranyl, hydroxypropyl thiazolyl, trifluoropropanoyl-piperidinyl, bicyclo[1.1.1]pentanyl, pyrimidinyl-pyrrolidinyl, fluoropyrimidinyl-pyrrolidinyl, methoxypyrimidinyl-pyrrolidinyl, tetrahydropyranyl-pyrazolyl, oxetanyl-pyrazolyl, difluoroethylpyrazolyl, or methylsulfamylpiperidinyl.

9. The compound according to claim 1 or a salt thereof, wherein said compound is selected from:
(R)-6-(6-chloropyrazolo[1,5-a]pyrimidin-3-yl)-N-(2-fluoro-3-hydroxy-3-methylbutyl)-4-(isopropylamino)nicotinamide (1);
(R)-6-(6-chloropyrazolo[1,5-a]pyrimidin-3-yl)-N-(2-fluoro-3-hydroxy-3-methylbutyl)-4-((5-(2-hydroxypropan-2-yl) thiazol-2-yl)amino)nicotinamide (2);
6-(6-chloropyrazolo[1,5-a]pyrimidin-3-yl)-N—((R)-2-fluoro-3-hydroxy-3-methylbutyl)-4-((tetrahydro-2H-pyran-3-yl)amino)nicotinamide (3 and 4);
(R)-6-(6-chloropyrazolo[1,5-a]pyrimidin-3-yl)-N-(2-fluoro-3-hydroxy-3-methylbutyl)-4-(oxetan-3-ylamino)nicotinamide (5);
N-(2-(4-hydroxytetrahydro-2H-pyran-4-yl)ethyl)-4-(isopropylamino)-6-(pyrazolo[1,5-a]pyrimidin-3-yl)nicotinamide (6);
(R)-6-(6-chloropyrazolo[1,5-a]pyrimidin-3-yl)-N-(2-fluoro-3-hydroxy-3-methylbutyl)-4-((1-hydroxy-2-methylpropan-2-yl)amino)nicotinamide (7);
6-(6-chloropyrazolo[1,5-a]pyrimidin-3-yl)-N-(2-fluoro-2-(3-hydroxyoxetan-3-yl)ethyl)-4-(isopropylamino)nicotinamide (8);
6-(6-chloropyrazolo[1,5-a]pyrimidin-3-yl)-N-(2-fluoro-3,4-dihydroxy-3-(hydroxymethyl) butyl)-4-(isopropylamino)nicotinamide (9);
(R)-6-(6-chloropyrazolo[1,5-a]pyrimidin-3-yl)-N-(1-(2-((2-fluoro-3-hydroxy-3-methylbutyl)amino)-2-oxoethyl)-1H-pyrazol-4-yl)-4-(isopropylamino)nicotinamide (10);
6-(6-chloropyrazolo[1,5-a]pyrimidin-3-yl)-4-(isopropylamino)-N-((1R,4R)-4-methoxycyclohexyl)nicotinamide (11);

6-(6-chloropyrazolo[1,5-a]pyrimidin-3-yl)-N-(3-fluoro-3-methylbutyl)-4-(oxetan-3-ylamino)nicotinamide (12);

6-(6-chloropyrazolo[1,5-a]pyrimidin-3-yl)-4-((3,3-difluoro-4-methoxycyclopentyl) amino)-N—((R)-2-fluoro-3-hydroxy-3-methylbutyl)nicotinamide (13 and 14);

6-(6-chloropyrazolo[1,5-a]pyrimidin-3-yl)-4-((3,3-difluoro-4-isopropoxycyclopentyl) amino)-N—((R)-2-fluoro-3-hydroxy-3-methylbutyl)nicotinamide (15 and 16);

6-(6-chloropyrazolo[1,5-a]pyrimidin-3-yl)-N-(2-(1-fluoro-4-methoxycyclohexyl)ethyl)-4-(oxetan-3-ylamino)nicotinamide (17);

6-(6-chloropyrazolo[1,5-a]pyrimidin-3-yl)-4-((4,4-difluorotetrahydrofuran-3-yl)amino)-N—((R)-2-fluoro-3-hydroxy-3-methylbutyl)nicotinamide (18 and 19);

6-(6-chloropyrazolo[1,5-a]pyrimidin-3-yl)-N-(3-fluoro-3-methylbutyl)-4-(isopropylamino)nicotinamide (20);

(R)—N-(2-fluoro-3-hydroxy-3-methylbutyl)-6-(imidazo[1,2-b]pyridazin-3-yl)-4-(isopropylamino) nicotinamide (21);

(R)-6-(6-chloropyrazolo[1,5-a]pyrimidin-3-yl)-4-(cyclopropylamino)-N-(2-fluoro-3-hydroxy-3-methylbutyl) nicotinamide (22);

N-((1R,4R)-4-acetamidocyclohexyl)-6-(6-chloropyrazolo[1,5-a]pyrimidin-3-yl)-4-(isopropylamino) nicotinamide (23);

6-(6-chloropyrazolo[1,5-a]pyrimidin-3-yl)-4-((2-fluoro-2-methylpropyl)amino)-N-((1R,4R)-4-(methylcarbamoyl)cyclohexyl)nicotinamide (24);

6-(6-chloropyrazolo[1,5-a]pyrimidin-3-yl)-4-(cyclopropylamino)-N-((1R,4R)-4-(methylcarbamoyl)cyclohexyl)nicotinamide (25);

6-(6-chloropyrazolo[1,5-a]pyrimidin-3-yl)-4-(isopropylamino)-N-(4-sulfamoylphenethyl)nicotinamide (26);

6-(6-chloropyrazolo[1,5-a]pyrimidin-3-yl)-4-(isopropylamino)-N-((1R,4R)-4-(methylcarbamoyl)cyclohexyl) nicotinamide (27):

6-(6-chloropyrazolo[1,5-a]pyrimidin-3-yl)-N-((1R,4R)-4-(cyclopropylcarbamoyl) cyclohexyl)-4-(isopropylamino)nicotinamide (28);

6-(6-chloropyrazolo[1,5-a]pyrimidin-3-yl)-4-(isopropylamino)-N-((1R,4R)-4-(isopropylcarbamoyl)cyclohexyl)nicotinamide (29);

(R)-6-(6-chloropyrazolo[1,5-a]pyrimidin-3-yl)-N-(2-fluoro-3-hydroxy-3-methylbutyl)-4-((tetrahydro-2H-pyran-4-yl) amino)nicotinamide (30);

6-(6-chloropyrazolo[1,5-a]pyrimidin-3-yl)-N—((R)-2-fluoro-3-hydroxy-3-methylbutyl)-4-(((S)-1-hydroxypropan-2-yl)amino)nicotinamide (31);

6-(6-chloropyrazolo[1,5-a]pyrimidin-3-yl)-N—((R)-2-fluoro-3-hydroxy-3-methylbutyl)-4-(((S)-1-fluoropropan-2-yl)amino)nicotinamide (32);

(R)-4-((4-carbamoylphenyl)amino)-6-(6-chloropyrazolo[1,5-a]pyrimidin-3-yl)-N-(2-fluoro-3-hydroxy-3-methylbutyl) nicotinamide (33);

(R)-6-(6-chloropyrazolo[1,5-a]pyrimidin-3-yl)-N-(2-fluoro-3-hydroxy-3-methylbutyl)-4-((4-(methylcarbamoyl)phenyl)amino)nicotinamide (34);

(R)-6-(6-chloropyrazolo[1,5-a]pyrimidin-3-yl)-4-((3-cyano-2-fluorophenyl)amino)-N-(2-fluoro-3-hydroxy-3-methylbutyl)nicotinamide (35);

6-(6-chloropyrazolo[1,5-a]pyrimidin-3-yl)-N—((R)-2-fluoro-3-hydroxy-3-methylbutyl)-4-(((R)-1-(5-fluoropyrimidin-2-yl) pyrrolidin-3-yl)amino)nicotinamide (36);

6-(6-chloropyrazolo[1,5-a]pyrimidin-3-yl)-N-(2-fluoro-2-(3-hydroxyoxetan-3-yl)ethyl)-4-(isopropylamino) nicotinamide (37);

(R)-6-(6-chloropyrazolo[1,5-a]pyrimidin-3-yl)-N-(2-fluoro-3-hydroxy-3-methylbutyl)-4-(((3-methyloxetan-3-yl)methyl)amino)nicotinamide (38);

(R)-6-(6-chloropyrazolo[1,5-a]pyrimidin-3-yl)-N-(2-fluoro-3-hydroxy-3-methylbutyl)-4-(((3-hydroxyoxetan-3-yl)methyl) amino)nicotinamide (39);

6-(6-chloropyrazolo[1,5-a]pyrimidin-3-yl)-N-((1R,4R)-4-(2-hydroxypropan-2-yl) cyclohexyl)-4-(oxetan-3-ylamino)nicotinamide (40);

6-(6-chloropyrazolo[1,5-a]pyrimidin-3-yl)-N-((1R,4R)-4-(cyclopropylcarbamoyl) cyclohexyl)-4-(oxetan-3-ylamino)nicotinamide (41);

6-(6-chloropyrazolo[1,5-a]pyrimidin-3-yl)-N—((R)-2-fluoro-3-hydroxy-3-methylbutyl)-4-(((3R,4 S)-4-hydroxytetrahydrofuran-3-yl)amino) nicotinamide (42);

6-(6-chloropyrazolo[1,5-a]pyrimidin-3-yl)-N—((R)-2-fluoro-3-hydroxy-3-methylbutyl)-4-(((3R,4 S)-4-fluorotetrahydrofuran-3-yl)amino)nicotinamide (43);

6-(6-chloropyrazolo[1,5-a]pyrimidin-3-yl)-N—((R)-2-fluoro-3-hydroxy-3-methylbutyl)-4-(((3R,4 S)-4-fluorotetrahydrofuran-3-yl)amino)nicotinamide (44);

6-(6-chloropyrazolo[1,5-a]pyrimidin-3-yl)-4-(isopropylamino)-N-(1-(2-(methylamino)-2-oxoethyl)-1H-pyrazol-4-yl)nicotinamide (45);

(R)-6-(6-chloropyrazolo[1,5-a]pyrimidin-3-yl)-N-(2-fluoro-3-hydroxy-3-methylbutyl)-4-((3,3,3-trifluoropropyl)amino) nicotinamide (46);

6-(6-chloropyrazolo[1,5-a]pyrimidin-3-yl)-N-(3-hydroxy-3-methylbutyl)-4-(oxetan-3-ylamino)nicotinamide (47);

(R)-6-(6-chloropyrazolo[1,5-a]pyrimidin-3-yl)-N-(2-fluoro-3-hydroxy-3-methylbutyl)-4-((1-(oxetan-3-vi)-1H-pyrazol-4-yl) amino)nicotinamide (48);

6-(6-chloropyrazolo[1,5-a]pyrimidin-3-yl)-N-((1 S,4r)-4-((S)-2-hydroxypropanamido) cyclohexyl)-4-(isopropylamino)nicotinamide (49);

6-(6-chloropyrazolo[1,5-a]pyrimidin-3-yl)-N—(R)-2-fluoro-3-hydroxy-3-methylbutyl)-4-(((1S,3 S)-3-(2-hydroxypropan-2-yl)cyclopentyl)amino)nicotinamide (50);

(R)-6-(6-chloropyrazolo[1,5-a]pyrimidin-3-yl)-N-(2-fluoro-3-hydroxy-3-methylbutyl)-4-(((1-hydroxycyclobutyl)methyl) amino)nicotinamide (51);

(R)-6-(6-chloropyrazolo[1,5-a]pyrimidin-3-yl)-N-(2-fluoro-3-hydroxy-3-methylbutyl)-4-((1-(tetrahydro-2H-pyran-4-yl)-1H-pyrazol-4-yl)amino)nicotinamide (52);

6-(6-chloropyrazolo[1,5-a]pyrimidin-3-yl)-N—((R)-2-fluoro-3-hydroxy-3-methylbutyl)-4-((tetrahydrofuran-3-yl)amino)nicotinamide (53 and 54);

6-(6-chloropyrazolo[1,5-a]pyrimidin-3-yl)-N-(2-(1,4-dihydroxy-4-methylcyclohexyl) ethyl)-4-(isopropylamino)nicotinamide (55);

(R)-6-(6-chloropyrazolo[1,5-a]pyrimidin-3-yl)-4-(ethylamino)-N-(2-fluoro-3-hydroxy-3-methylbutyl) nicotinamide (56);

(R)-6-(6-chloropyrazolo[1,5-a]pyrimidin-3-yl)-N-(2-fluoro-3-trideuteromethoxy-3-methylbutyl)-4-(isopropylamino) nicotinamide (57);

(R)-6-(6-chloropyrazolo[1,5-a]pyrimidin-3-yl)-N-(2-fluoro-3-hydroxy-3-methylbutyl)-4-((2-hydroxy-2-methylpropyl)amino)nicotinamide (58);

6-(6-chloropyrazolo[1,5-a]pyrimidin-3-yl)-N—((R)-2-fluoro-3-hydroxy-3-methylbutyl)-4-(((1r,3R)-3-(2-hydroxypropan-2-yl)cyclobutyl)amino) nicotinamide (59);

(R)-6-(6-chloropyrazolo[1,5-a]pyrimidin-3-yl)-4-(cyclobutylamino)-N-(2-fluoro-3-hydroxy-3-methylbutyl) nicotinamide (60);

6-(6-chloropyrazolo[1,5-a]pyrimidin-3-yl)-N—((R)-2-fluoro-3-hydroxy-3-methylbutyl)-4-(((S)-2-fluoropropyl)amino)nicotinamide (61);

6-(6-chloropyrazolo[1,5-a]pyrimidin-3-yl)-4-(isopropylamino)-N-(3-morpholino-3-oxopropyl) nicotinamide (62);

6-(6-chloropyrazolo[1,5-a]pyrimidin-3-yl)-4-(isopropylamino)-N-(2-oxo-2-(1-oxa-7-azaspiro[3.5]nonan-7-yl) ethyl)nicotinamide (63);

(R)-6-(6-chloropyrazolo[1,5-a]pyrimidin-3-yl)-N-(2-fluoro-3-hydroxy-3-methylbutyl)-4-((2,2,2-trifluoroethyl)amino) nicotinamide (64);

(R)-6-(6-chloropyrazolo[1,5-a]pyrimidin-3-yl)-4-((3,3-difluorocyclobutyl) amino)-N-(2-fluoro-3-hydroxy-3-methylbutyl)nicotinamide (65);

(R)-6-(6-chloropyrazolo[1,5-a]pyrimidin-3-yl)-N-(2-fluoro-3-hydroxy-3-methylbutyl)-4-(propylamino) nicotinamide (66);

(R)-6-(6-chloropyrazolo[1,5-a]pyrimidin-3-yl)-4-(cyclopentylamino)-N-(2-fluoro-3-hydroxy-3-methylbutyl) nicotinamide (67);

(R)-6-(6-chloropyrazolo[1,5-a]pyrimidin-3-yl)-N-(2-fluoro-3-hydroxy-3-methylbutyl)-4-((1-(methylsulfonyl)piperidin-4-yl)amino) nicotinamide (68);

4-(((R)-sec-butyl)amino)-6-(6-chloropyrazolo[1,5-a]pyrimidin-3-yl)-N—((R)-2-fluoro-3-hydroxy-3-methylbutyl)nicotinamide (69 and 70);

(R)-6-(6-chloropyrazolo[1,5-a]pyrimidin-3-yl)-4-((1-2,2-difluoroethyl)-1H-pyrazol-4-yl)amino)-N-(2-fluoro-3-hydroxy-3-methylbutyl)nicotinamide (71);

(R)-4-(tert-butylamino)-6-(6-chloropyrazolo[1,5-a]pyrimidin-3-yl)-N-(2-fluoro-3-hydroxy-3-methylbutyl) nicotinamide (72);

(R)-6-(6-chloropyrazolo[1,5-a]pyrimidin-3-yl)-N-(2-fluoro-3-hydroxy-3-methylbutyl)-4-((4-hydroxybicyclo[2.2.1]heptan-1-yl)amino)nicotinamide (73);

6-(6-chloropyrazolo[1,5-a]pyrimidin-3-yl)-4-(isopropylamino)-N-(1-isopropylsulfonyl) piperidin-4-yl)nicotinamide (74);

(R)-4-(bicyclo[1,1,1]pentan-1-ylamino)-6-(6-chloropyrazolo[1,5-a]pyrimidin-3-yl)-N-(2-fluoro-3-hydroxy-3-methylbutyl)nicotinamide (75 and 76);

6-(6-chloropyrazolo[1,5-a]pyrimidin-3-yl)-N-((3R,6S)-6-(hydroxymethyl)tetrahydro-2H-pyran-3-yl)-4-(isopropylamino)nicotinamide (77);

6-(6-chloropyrazolo[1,5-a]pyrimidin-3-yl)-N-((1R,4R)-4-(2-hydroxy-2-methylpropanamido)cyclohexyl)-4-(isopropylamino)nicotinamide (78);

6-(6-chloropyrazolo[1,5-a]pyrimidin-3-yl)-N-(2-(1-hydroxy-4-methoxycyclohexyl) ethyl)-4-(oxetan-3-ylamino)nicotinamide (79);

(R)-6-(6-chloropyrazolo[1,5-a]pyrimidin-3-yl)-N-(2-fluoro-3-hydroxy-3-methylbutyl)-4-((1-methylcyclopropyl)amino)nicotinamide (80);

6-(6-chloropyrazolo[1,5-a]pyrimidin-3-yl)-N—((R)-2-fluoro-3-hydroxy-3-methylbutyl)-4-(((S)-2-hydroxybutyl)amino)nicotinamide (81);

6-(6-chloropyrazolo[1,5-a]pyrimidin-3-yl)-N—((R)-2-fluoro-3-hydroxy-3-methylbutyl)-4-((3-hydroxybutyl)amino)nicotinamide (82);

6-(6-chloropyrazolo[1,5-a]pyrimidin-3-yl)-N—((R)-2-fluoro-3-hydroxy-3-methylbutyl)-4-((3-fluorocyclopentyl)amino)nicotinamide (83 and 84);

6-(6-chloropyrazolo[1,5-a]pyrimidin-3-yl)-N—((R)-2-fluoro-3-hydroxy-3-methylbutyl)-4-((3-fluorocyclopentyl)amino)nicotinamide (85);

6-(6-chloropyrazolo[1,5-a]pyrimidin-3-yl)-N—((R)-2-fluoro-3-hydroxy-3-methylbutyl)-4-((3-fluorocyclopentyl)amino)nicotinamide (86);

(R)-6-(6-cyanopyrazolo[1,5-a]pyrimidin-3-yl)-N-(2-fluoro-3-hydroxy-3-methylbutyl)-4-(isopropylamino) nicotinamide (87);

6-(6-cyanopyrazolo[1,5-a]pyrimidin-3-yl)-4-(isopropylamino)-N-((1R,4R)-4-(methylcarbamoyl)cyclohexyl) nicotinamide (88);

N-((1R,4R)-4-acetamidocyclohexyl)-6-(6-cyanopyrazolo[1,5-a]pyrimidin-3-yl)-4-(isopropylamino)nicotinamide (89);

(R)-6-(6-cyanopyrazolo[1,5-a]pyrimidin-3-yl)-N-(2-fluoro-3-hydroxy-3-methylbutyl)-4-((tetrahydro-2H-pyran-4-yl)amino)nicotinamide (90);

(R)-6-(6-cyanopyrazolo[1,5-a]pyrimidin-3-yl)-4-((2-fluoro-2-methylpropyl)amino)-N-(2-fluoro-3-hydroxy-3-methylbutyl)nicotinamide (91);

(R)-6-(6-cyanopyrazolo[1,5-a]pyrimidin-3-yl)-4-(cyclopropylamino)-N-(2-fluoro-3-hydroxy-3-methylbutyl) nicotinamide (92);

(R)-6-(6-cyanopyrazolo[1,5-a]pyrimidin-3-yl)-4-(ethylamino)-N-(2-fluoro-3-hydroxy-3-methylbutyl) nicotinamide (93);

6-(6-cyanopyrazolo[1,5-a]pyrimidin-3-yl)-N—((R)-2-fluoro-3-hydroxy-3-methylbutyl)-4-((tetrahydro-2H-pyran-3-yl)amino) nicotinamide (94);

6-(6-cyanopyrazolo[1,5-a]pyrimidin-3-yl)-N—((R)-2-fluoro-3-hydroxy-3-methylbutyl)-4-((tetrahydro-2H-pyran-3-vi) amino)nicotinamide (95);

(R)-6-(6-cyanopyrazolo[1,5-a]pyrimidin-3-yl)-4-(cyclobutylamino)-N-(2-fluoro-3-hydroxy-3-methylbutyl) nicotinamide (96);

4-(((R)-sec-butyl)amino)-6-(6-cyanopyrazolo[1,5-a]pyrimidin-3-yl)-N—((R)-2-fluoro-3-hydroxy-3-methylbutyl)nicotinamide (97);

6-(6-cyanopyrazolo[1,5-a]pyrimidin-3-yl)-N—((R)-2-fluoro-3-hydroxy-3-methylbutyl)-4-(((R)-1-hydroxypropan-2-yl)amino)nicotinamide (98);

(R)-6-(6-cyanopyrazolo[1,5-a]pyrimidin-3-yl)-N-(2-fluoro-3-hydroxy-3-methylbutyl)-4-(oxetan-3-ylamino) nicotinamide (99);

6-(6-cyanopyrazolo[1,5-a]pyrimidin-3-yl)-N—((R)-2-fluoro-3-hydroxy-3-methylbutyl)-4-(((S)-3-hydroxy-3-methylbutan-2-yl)amino)nicotinamide (100);

6-(6-cyanopyrazolo[1,5-a]pyrimidin-3-yl)-N—((R)-2-fluoro-3-hydroxy-3-methylbutyl)-4-(((R)-1-hydroxy-3-phenylpropan-2-yl)amino)nicotinamide (101);

6-(6-cyanopyrazolo[1,5-a]pyrimidin-3-yl)-4-((2-fluoro-2-methylpropyl) amino)-N-((1R,4R)-4-(methylcarbamoyl)cyclohexyl)nicotinamide (102);

6-(6-cyanopyrazolo[1,5-a]pyrimidin-3-yl)-N—((R)-2-fluoro-3-hydroxy-3-methylbutyl)-4-((2-hydroxycyclopentyl)amino) nicotinamide (103);

6-(6-cyanopyrazolo[1,5-a]pyrimidin-3-yl)-N-((1R,4R)-4-(2-hydroxypropan-2-yl) cyclohexyl)-4-(isopropylamino)nicotinamide (104);

6-(6-cyanopyrazolo[1,5-a]pyrimidin-3-yl)-N—((R)-2-fluoro-3-hydroxy-3-methylbutyl)-4-(((1R,2S)-2-fluorocyclopentyl)amino) nicotinamide (105);

6-(6-cyanopyrazolo[1,5-a]pyrimidin-3-yl)-N—((R)-2-fluoro-3-hydroxy-3-methylbutyl)-4-((4-fluorobutan-2-yl)amino)nicotinamide (106);

6-(6-cyanopyrazolo[1,5-a]pyrimidin-3-yl)-4-((3,3-difluoro-2-hydroxycyclopentyl) amino)-N—((R)-2-fluoro-3-hydroxy-3-methylbutyl)nicotinamide (107);

6-(6-cyano-6H-pyrazolo[4,3-b]pyridin-3-yl)-N—((R)-2-fluoro-3-hydroxy-3-methylbutyl)-4-(((R)-1-(3,3,3-trifluoropropanoyl)piperidin-3-yl)amino)nicotinamide (108);

6-(6-cyanopyrazolo[1,5-a]pyrimidin-3-yl)-N—((R)-2-fluoro-3-hydroxy-3-methylbutyl)-4-(((R)-1-(5-fluoropyrimidin-2-yl)pyrrolidin-3-yl)amino)nicotinamide (109);

(R)-6-(6-cyanopyrazolo[1,5-a]pyrimidin-3-yl)-N-(2-fluoro-3-hydroxy-3-methylbutyl)-4-((4-(methylcarbamoyl)phenyl)amino)nicotinamide (110);

(R)-4-((3-carbamoylphenyl)amino)-6-(6-cyanopyrazolo[1,5-a]pyrimidin-3-yl)-N-(2-fluoro-3-hydroxy-3-methylbutyl)nicotinamide (111);

(R)-4-((4-carbamoylphenyl)amino)-6-(6-cyanopyrazolo[1,5-a]pyrimidin-3-yl)-N-(2-fluoro-3-hydroxy-3-methylbutyl)nicotinamide (112);

6-(6-cyanopyrazolo[1,5-a]pyrimidin-3-yl)-N—((R)-2-fluoro-3-hydroxy-3-methylbutyl)-4-((1-(pyridin-3-yl)ethyl)amino)nicotinamide (113);

(R)-6-(6-cyanopyrazolo[1,5-a]pyrimidin-3-yl)-N-(2-fluoro-3-hydroxy-3-methylbutyl)-4-((1-hydroxy-2-methylpropan-2-yl)amino)nicotinamide (114);

6-(6-cyanopyrazolo[1,5-a]pyrimidin-3-yl)-N—((R)-2-fluoro-3-hydroxy-3-methylbutyl)-4-(((R)-1-(5-methoxypyrimidin-2-yl)pyrrolidin-3-yl) amino)nicotinamide (115);

6-(6-cyanopyrazolo[1,5-a]pyrimidin-3-yl)-N—((R)-2-fluoro-3-hydroxy-3-methylbutyl)-4-(((3 S,4R)-4-fluorotetrahydrofuran-3-yl)amino)nicotinamide (116 and 117);

6-(6-cyanopyrazolo[1,5-a]pyrimidin-3-yl)-N—((R)-2-fluoro-3-hydroxy-3-methylbutyl)-4-(((R)-1-(pyrimidin-2-yl)pyrrolidin-3-yl)amino)nicotinamide(118);

6-(6-cyanopyrazolo[1,5-a]pyrimidin-3-yl)-N—((R)-2-fluoro-3-hydroxy-3-methylbutyl)-4-(((R)-1-(pyrimidin-5-yl) pyrrolidin-3-yl)amino)nicotinamide (119);

6-(6-cyanopyrazolo[1,5-a]pyrimidin-3-yl)-N-((1R,4R)-4-(2-hydroxypropan-2-yl) cyclohexyl)-4-(oxetan-3-ylamino)nicotinamide (120);

(R)-6-(6-cyanopyrazolo[1,5-a]pyrimidin-3-yl)-N-(2-fluoro-3-hydroxy-3-methylbutyl)-4-(((3-hydroxyoxetan-3-yl)methyl)amino)nicotinamide (121);

6-(6-cyanopyrazolo[1,5-a]pyrimidin-3-yl)-N—((R)-2-fluoro-3-hydroxy-3-methylbutyl)-4-(((3-hydroxytetrahydro-2H-pyran-3-yl)methyl)amino)nicotinamide (122 and 123);

6-(6-cyanopyrazolo[1,5-a]pyrimidin-3-yl)-N-((1R,4R)-4-methoxycyclohexyl)-4-(oxetan-3-ylamino)nicotinamide (124);

6-(6-cyanopyrazolo [1,5-a]pyrimidin-3-yl)-N—((R)-2-fluoro-3-hydroxy-3-methylbutyl)-4-(((S)-2-hydroxybutyl) amino)nicotinamide (125);

(R)—N-(2-fluoro-3-hydroxy-3-methylbutyl)-6-(pyrazolo[1,5-a]pyrimidin-3-yl)-4-((tetrahydro-2H-pyran-4-yl)amino)nicotinamide (126);

(R)—N-(2-fluoro-3-hydroxy-3-methylbutyl)-4-(isopropylamino)-6-(pyrazolo[1,5-a]pyrimidin-3-yl)nicotinamide (127);

(R)-6-(6-cyclopropylpyrazolo[1,5-a]pyrimidin-3-yl)-N-(2-fluoro-3-hydroxy-3-methylbutyl)-4-(isopropylamino)nicotinamide (128);

(R)-6-(5-amino-6-fluoropyrazolo[1,5-a]pyrimidin-3-yl)-N-(2-fluoro-3-hydroxy-3-methylbutyl)-4-(isopropylamino)nicotinamide (129);

(R)—N-(2-fluoro-3-hydroxy-3-methylbutyl)-6-(6-fluoropyrazolo[1,5-a]pyrimidin-3-yl)-4-(isopropylamino) nicotinamide (130);

(R)—N-(2-fluoro-3-hydroxy-3-methylbutyl)-6-(imidazo[1,2-b]pyridazin-3-yl)-4-(oxetan-3-ylamino)nicotinamide (131);

(R)—N-(2-fluoro-3-hydroxy-3-methylbutyl)-6-(imidazo[1,2-b]pyridazin-3-yl)-4-((tetrahydro-2H-pyran-4-yl)amino)nicotinamide (132);

N-((1R,4R)-4-(2-hydroxypropan-2-yl)cyclohexyl)-6-(imidazo[1,2-b]pyridazin-3-yl)-4-(oxetan-3-ylamino) nicotinamide (133);

N—((R)-2-fluoro-3-hydroxy-3-methylbutyl)-4-((4-hydroxytetrahydrofuran-3-yl)amino)-6-(imidazo[1,2-b]pyridazin-3-yl) nicotinamide (134);

N—((R)-2-fluoro-3-hydroxy-3-methylbutyl)-4-((4-hydroxytetrahydrofuran-3-yl)amino)-6-(imidazo[1,2-b]pyridazin-3-yl)nicotinamide (135);

N—((R)-2-fluoro-3-hydroxy-3-methylbutyl)-4-(((S)-1-hydroxypropan-2-yl)amino)-6-(imidazo[1,2-b]pyridazin-3-vi) nicotinamide (136);

(S)—N-3-hydroxy-3-methylbutyl)-4-((1-hydroxypropan-2-yl)amino)-6-(imidazo[1,2-b]pyridazin-3-yl)nicotinamide (137);

(R)—N-(2-fluoro-3-hydroxy-3-methylbutyl)-4-((2-hydroxy-2-methylpropyl)amino)-6-(imidazo[1,2-b]pyridazin-3-yl)nicotinamide (138);

(R)—N-(2-fluoro-3-hydroxy-3-methylbutyl)-6-(6-((2-hydroxyethyl)amino)imidazo[1,2-b]pyridazin-3-yl)-4-(isopropylamino)nicotinamide (139);

(R)—N-(2-fluoro-3-hydroxy-3-methylbutyl)-6-(6-((2-hydroxyethyl)amino)imidazo[1,2-b]pyridazin-3-yl)-4-(oxetan-3-ylamino)nicotinamide (140);

(R)-6-(7-chloroimidazo[1,2-b]pyridazin-3-yl)-N-(2-fluoro-3-hydroxy-3-methylbutyl)-4-(oxetan-3-ylamino)nicotinamide (141);

(R)-6-(7-chloroimidazo[1,2-b]pyridazin-3-yl)-N-(2-fluoro-3-hydroxy-3-methylbutyl)-4-(isopropylamino) nicotinamide (142);

(R)-6-(7-chloroimidazo[1,2-b]pyridazin-3-yl)-N-(2-fluoro-3-hydroxy-3-methylbutyl)-4-((tetrahydro-2H-pyran-4-yl)amino) nicotinamide (143);

(R)-6-(7-chloroimidazo[1,2-b]pyridazin-3-yl)-4-(cyclopropylamino)-N-(2-fluoro-3-hydroxy-3-methylbutyl) nicotinamide (144);

(R)-6-(7-cyanoimidazo[1,2-b]pyridazin-3-yl)-N-(2-fluoro-3-hydroxy-3-methylbutyl)-4-(isopropylamino) nicotinamide (145);

(R)-6-(7-cyanoimidazo[T 1,2-b]pyridazin-3-yl)-N-(2-fluoro-3-hydroxy-3-methylbutyl)-4-((tetrahydro-2H-pyran-4-yl)amino)nicotinamide (146);

(R)-6-(7-cyanoimidazo[1,2-b]pyridazin-3-yl)-N-(2-fluoro-3-hydroxy-3-methylbutyl)-4-(oxetan-3-ylamino) nicotinamide (147);

(R)—N-(2-fluoro-3-hydroxy-3-methylbutyl)-4-(isopropylamino)-6-(7-methylimidazo[1,2-b]pyridazin-3-yl) nicotinamide (148);

(R)—N-(2-fluoro-3-hydroxy-3-methylbutyl)-4-(isopropylamino)-6-(6-methoxyimidazo[1,2-b]pyridazin-3-yl) nicotinamide (149);

(R)-6-(6-aminoimidazo[1,2-b]pyridazin-3-yl)-N-(2-fluoro-3-hydroxy-3-methylbutyl)-4-(isopropylamino)nicotinamide (150);
(R)—N-(2-fluoro-3-hydroxy-3-methylbutyl)-6-(6-((2-hydroxy-2-methylpropyl)amino) imidazo[1,2-b]pyridazin-3-yl)-4-(isopropylamino)nicotinamide (151);
N—((R)-2-fluoro-3-hydroxy-3-methylbutyl)-6-(6-((R)-3-hydroxypyrrolidin-1-yl) imidazo[1,2-b]pyridazin-3-yl)-4-(isopropylamino)nicotinamide (152);
(R)—N-(2-fluoro-3-hydroxy-3-methylbutyl)-4-(isopropylamino)-6-(7-methoxyimidazo[1,2-b]pyridazin-3-yl)nicotinamide (153);
(R)—N-(2-fluoro-3-hydroxy-3-methylbutyl)-6-(7-methoxyimidazo[1,2-b]pyridazo-3-vi)-4-(oxetan-3-ylamino)nicotinamide (154);
(R)-6-(2-(3-cyanophenyl)oxazol-5-yl)-N-(2-fluoro-3-hydroxy-3-methylbutyl)-4-(isopropylamino)nicotinamide (155);
(R)—N-(2-fluoro-3-hydroxy-3-methylbutyl)-4-(isopropylamino)-6-(1-(pyridin-4-yl)-1H-pyrazol-3-yl)nicotinamide (156);
(R)-6-(6-chloropyrazolo[1,5-a]pyrimidin-3-yl)-N-(3-(difluoromethoxy)-2-fluoro-3-methylbutyl)-4-(isopropylamino)nicotinamide (157);
6-(6-chloropyrazolo[1,5-a]pyrimidin-3-yl)-N—((R)-2-fluoro-3-hydroxy-3-methylbutyl)-4-(((S)-2-fluorobutyl)amino)nicotinamide (158);
(R)-6-(6-chloropyrazolo[1,5-a]pyrimidin-3-yl)-N-(2-fluoro-3-hydroxy-3-methylbutyl)-4-(propylamino)nicotinamide (159);
6-(6-chloropyrazolo[1,5-a]pyrimidin-3-yl)-N—((R)-2-fluoro-3-hydroxy-3-methylbutyl)-4-((3-fluorobutyl)amino)nicotinamide (160);
(R)-6-(6-chloropyrazolo[1,5-a]pyrimidin-3-yl)-N-(2-fluoro-3-hydroxy-3-methylbutyl)-4-((3,3,3-trifluoropropyl)amino) nicotinamide (161);
(R)-6-(6-chloropyrazolo[1,5-a]pyrimidin-3-yl)-N-(3-(difluoromethoxy)-2-fluoro-3-methylbutyl)-4-(isopropylamino)nicotinamide (162);
(R)-6-(6-chloropyrazolo[1,5-a]pyrimidin-3-yl)-4-((2,2-difluoroethyl)amino)-N-(2-fluoro-3-hydroxy-3-methylbutyl) nicotinamide (163);
(R)-6-(6-chloropyrazolo[1,5-a]pyrimidin-3-yl)-N-(2-fluoro-3-hydroxy-3-methylbutyl)-4-((3-hydroxypropyl)amino)nicotinamide (164);
6-(6-chloropyrazolo[1,5-a]pyrimidin-3-yl)-N—((R)-2-fluoro-3-hydroxy-3-methylbutyl)-4-(((1R,4R)-4-methoxycyclohexyl) amino)nicotinamide (165);
6-(6-chloropyrazolo[1,5-a]pyrimidin-3-yl)-N-((1R,4R)-4-ethoxycyclohexyl)-4-(isopropylamino)nicotinamide (166);
(R)—N-(3-acetamidobutyl)-6-(6-chloropyrazolo[1,5-a]pyrimidin-3-yl)-4-(isopropylamino) nicotinamide (167);
6-(6-chloropyrazolo[1,5-a]pyrimidin-3-yl)-4-(isopropylamino)-N-(3-(methyl sulfonyl) propyl)nicotinamide (168);
N-(3-cyano-3-methylbutyl)-6-(6-cyanopyrazolo[1,5-a]pyrimidin-3-yl)-4-(isopropylamino)nicotinamide (169);
(R)-6-(6-cyanopyrazolo[1,5-a]pyrimidin-3-yl)-N-(3-(difluoromethoxy)-2-fluoro-3-methylbutyl)-4-(isopropylamino)nicotinamide (170);
(R)-6-(6-cyanopyrazolo[1,5-a]pyrimidin-3-yl)-4-((2,2-difluoroethyl)amino)-N-(2-fluoro-3-hydroxy-3-methylbutyl)nicotinamide (171);
(R)-6-(6-cyanopyrazolo[1,5-a]pyrimidin-3-yl)-4-((2,2-difluoropropyl)amino)-N-(2-fluoro-3-hydroxy-3-methylbutyl)nicotinamide (172);
6-(7-cyanoimidazo[1,2-b]pyridazin-3-yl)-N-(2,2-difluoro-3-hydroxy-3-methylbutyl)-4-(isopropylamino)nicotinamide (173);
6-(7-cyanoimidazo[1,2-b]pyridazin-3-yl)-4-(isopropylamino)-N-((1R,4R)-4-(2-methoxypropan-2-yl)cyclohexyl)nicotinamide (174);
6-(7-chloroimidazo[1,2-b]pyridazin-3-yl)-N—((R)-2-fluoro-3-hydroxy-3-methylbutyl)-4-(((1R,4R)-4-(2-fluoropropan-2-yl)cyclohexyl)amino)nicotinamide (175);
6-(7-cyanoimidazo[1,2-b]pyridazin-3-yl)-N-(2-(2,6-dimethyltetrahydro-2H-pyran-4-yl)-2-fluoroethyl)-4-(isopropylamino) nicotinamide (176);
(R)—N-(2-fluoro-3-hydroxy-3-methylbutyl)-6-(imidazo[1,2-b]pyridazin-3-yl)-4-(isopropylamino)nicotinamide (177);
(R)-6-(7-chloroimidazo[1,2-b]pyridazin-3-yl)-4-(ethylamino)-N-(2-fluoro-3-hydroxy-3-methylbutyl)nicotinamide (178);
(R)-6-(7-chloroimidazo[1,2-b]pyridazin-3-yl)-N-(2-fluoro-3-hydroxy-3-methylbutyl)-4-(propylamino)nicotinamide (179);
(R)-6-(7-chloroimidazo[1,2-b]pyridazin-3-yl)-4-(cyclobutylamino)-N-(2-fluoro-3-hydroxy-3-methylbutyl)nicotinamide (180);
6-(7-chloroimidazo[1,2-b]pyridazin-3-yl)-N—((R)-2-fluoro-3-hydroxy-3-methylbutyl)-4-(((S)-1-hydroxypropan-2-yl)amino)nicotinamide (181);
(R)-6-(7-cyanoimidazo[1,2-b]pyridazin-3-yl)-4-(cyclopropylamino)-N-(2-fluoro-3-hydroxy-3-methylbutyl)nicotinamide (182);
(R)-6-(7-cyanoimidazo[1,2-b]pyridazin-3-yl)-4-(cyclobutylamino)-N-(2-fluoro-3-hydroxy-3-methylbutyl)nicotinamide (183);
(R)-4-(cyclopropylamino)-N-(2-fluoro-3-hydroxy-3-methylbutyl)-6-(7-methylimidazo[1,2-b]pyridazin-3-yl)nicotinamide (184);
(R)-4-(cyclobutylamino)-(2-fluoro-3-hydroxy-3-methylbutyl)-(7-methylimidazo[1,2-b]pyridazin-3-yl)nicotinamide (185);
6-(7-cyanoimidazo[1,2-b]pyridazin-3-yl)-N-(3-hydroxy-3-methylbutyl)-4-(isopropylamino)nicotinamide (186);
(R)-4-(tert-butylamino)-6-(7-cyanoimidazo[1,2-b]pyridazin-3-yl)-N-(2-fluoro-3-hydroxy-3-methylbutyl)nicotinamide (187);
(R)-6-(7-cyanoimidazo[1,2-b]pyridazin-3-yl)-4-(ethylamino)-N-(2-fluoro-3-hydroxy-3-methylbutyl)nicotinamide (188);
(R)-6-(7-chloroimidazo[1,2-b]pyridazin-3-yl)-N-(2,3-difluoro-3-methylbutyl)-4-(oxetan-3-ylamino)nicotinamide (189);
(R)-6-(7-chloroimidazo[1,2-b]pyridazin-3-yl)-N-(2-fluoro-3-hydroxy-3-methylbutyl)-4-((3,3,3-trifluoropropyl)amino)nicotinamide (190);
6-(7-chloroimidazo[1,2-b]pyridazin-3-yl)-N-((1R,4R)-4-(2-methoxypropan-2-yl) cyclohexyl)-4-(oxetan-3-ylamino) nicotinamide (191);
6-(7-chloroimidazo[1,2-b]pyridazin-3-yl)-N-(3,3-dimethylbutyl)-4-(oxetan-3-ylamino)nicotinamide (192);
(R)-6-(3-cyanopyrrolo[1,2-b]pyridazin-7-yl)-N-(2-fluoro-3-hydroxy-3-methylbutyl)-4-(isopropylamino)nicotinamide (193);

(S)-6-(7-cyanoimidazo[1,2-b]pyridazin-3-yl)-N-(2-fluoro-3-hydroxy-3-methylbutyl)-4-(isopropylamino)nicotinamide (194);

(R)-6-(7-cyanoimidazo[1,2-b]pyridazin-3-yl)-4-((3,3-difluorocyclobutyl)amino)-N-(2-fluoro-3-hydroxy-3-methylbutyl)nicotinamide (195);

6-(7-cyanoimidazo[1,2-b]pyridazin-3-yl)-N—((R)-2-fluoro-3-hydroxy-3-methylbutyl)-4-(((1R,4R)-4-methoxycyclohexyl)amino) nicotinamide (196);

6-(7-cyanoimidazo[1,2-b]pyridazin-3-yl)-N-(2-fluoro-2-(piperidin-4-yl)ethyl)-4-(isopropylamino)nicotinamide (197);

(S)-6-(7-chloroimidazo[1,2-b]pyridazin-3-yl)-N-(2-fluoro-3-hydroxy-3-methylbutyl)-4-((1-methylcyclopropyl)amino) nicotinamide (198);

(R)-6-(7-chloroimidazo[1,2-b]pyridazin-3-yl)-N-(2-fluoro-3-hydroxy-3-methylbutyl)-4-((3-fluorocyclobutyl)amino)nicotinamide (199);

6-(7-cyanoimidazo[r 1,2-b]pyridazin-3-yl)-N—((R)-2-fluoro-3-hydroxy-3-methylbutyl)-4-(((S)-1-fluoropropan-2-yl)amino)nicotinamide (200);

6-(7-cyanoimidazo[r 1,2-b]pyridazin-3-yl)-N—((R)-2-fluoro-3-hydroxy-3-methylbutyl)-4-((tetrahydrofuran-3-yl)amino)nicotinamide (201);

4-(((R)-sec-butyl)amino)-6-(7-chloroimidazo[1,2-b]pyridazin-3-yl)-N—((R)-2-fluoro-3-hydroxy-3-methylbutyl)nicotinamide (202);

6-(7-cyanoimidazo[r 1,2-b]pyridazin-3-yl)-N-(2-(2,6-dimethyltetrahydro-2H-pyran-4-yl)-2-fluoroethyl)-4-(isopropylamino)nicotinamide (203);

6-(7-cyanoimidazo[r 1,2-b]pyridazin-3-yl)-N—((R)-2-fluoro-3-hydroxy-3-methylbutyl)-4-(((1R,4R)-4-(2-hydroxypropan-2-yl)cyclohexyl)amino)nicotinamide (204);

(R)-6-(7-cyanoimidazo[1,2-b]pyridazin-3-yl)-N-(2-fluoro-3-hydroxy-3-methylbutyl)-4-((3,3,3-trifluoropropyl)amino)nicotinamide (205);

(R)-6-(7-chloroimidazo[1,2-b]pyridazin-3-yl)-4-((3,3-difluorocyclobutyl)amino)-N-(2-fluoro-3-hydroxy-3-methylbutyl)nicotinamide (206);

(S)-6-(7-chloroimidazo[1,2-b]pyridazin-3-yl)-N-(2-fluoro-3-hydroxy-3-methylbutyl)-4-((1-methylcyclopropyl)amino)nicotinamide (207);

6-(7-cyanoimidazo[r 1,2-b]pyridazin-3-yl)-N—((R)-2-fluoro-3-hydroxy-3-methylbutyl)-4-((3-fluorocyclopentyl)amino) nicotinamide (208);

(S)-6-(7-(difluoromethyl)imidazo[1,2-b]pyridazin-3-yl)-N-(2-fluoro-3-hydroxy-3-methylbutyl)-4-(isopropylamino)nicotinamide (209);

(R)-6-(7-chloroimidazo[1,2-b]pyridazin-3-yl)-4-((3,3-difluoropropyl)amino)-N-(2-fluoro-3-hydroxy-3-methylbutyl) nicotinamide (210);

(R)-6-(7-cyanoimidazo[1,2-b]pyridazin-3-yl)-4-((3,3-difluoropropyl)amino)-N-(2-fluoro-3-hydroxy-3-methylbutyl)nicotinamide (211);

(S)—N-(2-fluoro-3-hydroxy-3-methylbutyl)-6-(7-fluoroimidazo[1,2-b]pyridazin-3-yl)-4-(isopropylamino)nicotinamide (212);

6-(7-cyanoimidazo[1,2-b]pyridazin-3-yl)-4-(isopropylamino)-N-(2-(thiophen-2-yl)ethyl) nicotinamide (213);

N-(3-(1H-imidazol-1-yl)propyl)-6-(7-cyanoimidazo[1,2-b]pyridazin-3-yl)-4-(isopropylamino)nicotinamide (214);

6-(7-cyanoimidazo[1,2-b]pyridazin-3-yl)-N-(4-(dimethylamino)cyclohexyl)-4-(isopropylamino)nicotinamide (215);

6-(7-cyanoimidazo[1,2-b]pyridazin-3-yl)-4-(isopropylamino)-N-(2-(pyridin-2-yl) ethyl)nicotinamide (216);

6-(7-cyanoimidazo[1,2-b]pyridazin-3-yl)-N-(2-(1-hydroxycyclopentyl)ethyl)-4-(isopropylamino)nicotinamide (217);

6-(7-chloroimidazo[1,2-b]pyridazin-3-yl)-N-(3-hydroxy-3-methylbutyl)-4-(oxetan-3-ylamino)nicotinamide (218);

N-((1R,4R)-4-acetamidocyclohexyl)-6-(7-chloroimidazo[1,2-b]pyridazin-3-yl)-4-(isopropylamino)nicotinamide (219);

N-((1R,4R)-4-acetamidocyclohexyl)-6-(7-cyanoimidazo[1,2-b]pyridazin-3-yl)-4-(isopropylamino)nicotinamide (220);

(S)-6-(7-cyanoimidazo[1,2-b]pyridazin-3-yl)-4-((1-fluoropropan-2-yl)amino)-N-(3-hydroxy-3-methylbutyl)nicotinamide (221);

(R)-6-(7-(difluoromethyl)imidazo[1,2-b]pyridazin-3-yl)-N-(2-fluoro-3-hydroxy-3-methylbutyl)-4-(oxetan-3-ylamino)nicotinamide (222);

methyl ((1R,4R)-4-(6-(7-cyanoimidazo[1,2-b]pyridazin-3-yl)-4-(isopropylamino) nicotinamido)cyclohexyl) carbamate (223);

methyl ((1R,4R)-4-(6-(7-cyanoimidazo[1,2-b]pyridazin-3-yl)-4-((1-methylcyclopropyl) amino)nicotinamido)cyclohexyl)carbamate (224);

(R)-6-(6-cyanopyrazolo [1,5-a]pyrimidin-3-yl)-4-((1-2,2-difluoroethyl)-1H-pyrrol-3-yl)amino)-N-(2-fluoro-3-hydroxy-3-methylbutyl)nicotinamide (225);

(R)-6-(6-chloropyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino)nicotinamide (226);

(R)-6-(6-chloropyrazolo[1,5-a]pyrimidin-3-yl)-4-((1-(2-fluoro-2-methylpropyl)-1H-pyrazol-4-yl) amino)-N-(2-fluoro-3-hydroxy-3-methylbutyl)nicotinamide (227);

(R)-6-(6-chloropyrazolo[1,5-a]pyrimidin-3-yl)-4-((1(2,2-difluoroethyl)-1H-pyrrol-3-yl)amino)-N-(2-fluoro-3-hydroxy-3-methylbutyl)nicotinamide (228);

(R)-6-(6-chloropyrazolo[1,5-a]pyrimidin-3-yl)-4-((1-(2-fluoro-2-methylpropyl)-1H-pyrazol-3-yl)amino)-N-(2-fluoro-3-hydroxy-3-methylbutyl)nicotinamide (229);

(R)-6-(6-cyanopyrazolo[1,5-a]pyrimidin-3-yl)-4-((1-2,2-difluoroethyl)-1H-pyrazol-3-yl)amino)-N-(2-fluoro-3-hydroxy-3-methylbutyl)nicotinamide (230);

(R)-6-(6-chloropyrazolo[1,5-a]pyrimidin-3-yl)-4-((1-(difluoromethyl)-1H-pyrazol-4-yl)amino)-N-(2-fluoro-3-hydroxy-3-methylbutyl) nicotinamide (231);

(R)-6-(6-chloropyrazolo[1,5-a]pyrimidin-3-yl)-4-((1-ethyl-1H-pyrazol-4-yl)amino)-N-(2-fluoro-3-hydroxy-3-methylbutyl)nicotinamide (232);

(R)-6-(6-chloropyrazolo[1,5-a]pyrimidin-3-yl)-N-(2-fluoro-3-hydroxy-3-methylbutyl)-4-((1-isopropyl-1H-pyrazol-4-yl)amino)nicotinamide (233);

(R)-6-(6-cyanopyrazolo[1,5-a]pyrimidin-3-yl)-4-((1-difluoromethyl)-1H-pyrazol-4-yl)amino)-N-(2-fluoro-3-hydroxy-3-methylbutyl) nicotinamide (234);

(R)-6-(6-cyanopyrazolo[1,5-a]pyrimidin-3-yl)-4-((1-(2-fluoro-2-methylpropyl)-1H-pyrazol-4-yl)amino)-N-(2-fluoro-3-hydroxy-3-methylbutyl)nicotinamide (235);

(R)-6-(6-cyanopyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino) nicotinamide (236);

(R)-6-(6-chloropyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino)nicotinamide (237);

(R)-6-(6-cyanopyrazolo[1,5-a]pyrimidin-3-yl)-4-((1-2,2-difluoropropyl)-1H-pyrazol-4-yl)amino)-N-(2-fluoro-3-hydroxy-3-methylbutyl) nicotinamide (238);

(R)-6-(6-chloropyrazolo[1,5-a]pyrimidin-3-yl)-4-((1-(2,2-difluoropropyl)-1H-pyrazol-4-yl) amino)-N-(2-fluoro-3-hydroxy-3-methylbutyl)nicotinamide (239);

(R)-6-(6-cyanopyrazolo[1,5-a]pyrimidin-3-yl)-N-(2-fluoro-3-hydroxy-3-methylbutyl)-4-((1-methyl-1H-pyrazol-4-yl)amino)nicotinamide (240);

(R)-6-(6-cyanopyrazolo[1,5-a]pyrimidin-3-yl)-N-(2-fluoro-3-hydroxy-3-methylbutyl)-4-((1-(2,2,2-trifluoroethyl)-1H-pyrazol-4-yl)amino) nicotinamide (241);

(R)-6-(6-chloropyrazolo[1,5-a]pyrimidin-3-yl)-N-(2-fluoro-3-hydroxy-3-methylbutyl)-4-((1-(2-methoxyethyl)-1H-pyrazol-4-yl)amino) nicotinamide (242);

(R)-6-(6-cyanopyrazolo[1,5-a]pyrimidin-3-yl)-N-(2-fluoro-3-hydroxy-3-methylbutyl)-4-((1-(2-methoxyethyl)-1H-pyrazol-4-yl)amino)nicotinamide (243);

(R)-6-(6-cyanopyrazolo[1,5-a]pyrimidin-3-yl)-4-((1,3-dimethyl-1H-pyrazol-5-yl) amino)-N-(2-fluoro-3-hydroxy-3-methylbutyl)nicotinamide (244);

(R)-6-(6-cyanopyrazolo[1,5-a]pyrimidin-3-yl)-4-((1-2,2-difluoropropyl)-1H-pyrazol-3-yl)amino)-N-(2-fluoro-3-hydroxy-3-methylbutyl)nicotinamide (245);

(R)-6-(6-chloropyrazolo[1,5-a]pyrimidin-3-yl)-4-((1-cyclopropyl-1H-pyrazol-4-yl)amino)-N-(2-fluoro-3-hydroxy-3-methylbutyl)nicotinamide (246);

(R)-6-(6-chloropyrazolo[1,5-a]pyrimidin-3-yl)-N-(2-fluoro-3-hydroxy-3-methylbutyl)-4-((1-isobutyl-1H-pyrazol-4-yl)amino)nicotinamide (247);

(R)-6-(6-cyanopyrazolo[1,5-a]pyrimidin-3-yl)-4-((1-cyclopropyl-1H-pyrazol-4-yl)amino)-N-(2-fluoro-3-hydroxy-3-methylbutyl)nicotinamide (248);

(R)-6-(6-cyanopyrazolo[1,5-a]pyrimidin-3-yl)-4(1-(cyclopropylmethyl)-1H-pyrazol-4-yl)amino)-N-(2-fluoro-3-hydroxy-3-methylbutyl)nicotinamide (249);

(R)-6-(6-chloropyrazolo[1,5-a]pyrimidin-3-yl)-4-((1-cyclobutyl-1H-pyrazol-4-yl)amino)-N-(2-fluoro-3-hydroxy-3-methylbutyl)nicotinamide (250);

(R)-6-(6-chloropyrazolo[1,5-a]pyrimidin-3-yl)-4(1-(cyclopropylmethyl)-1H-pyrazol-4-yl)amino)-N-(2-fluoro-3-hydroxy-3-methylbutyl) nicotinamide (251);

6-(6-chloropyrazolo[1,5-a]pyrimidin-3-yl)-4-((1-(2,2-difluoroethyl)-1H-pyrazol-4-yl)amino)-N-((1R,4R)-4-hydroxycyclohexyl) nicotinamide (252);

6-(6-chloropyrazolo[1,5-a]pyrimidin-3-yl)-4-((1-2,2-difluoroethyl)-1H-pyrazol-4-yl)amino)-N-(3-hydroxy-3-methylbutyl)nicotinamide (253);

6-(6-chloropyrazolo[1,5-a]pyrimidin-3-yl)-4-((1-cyclopropyl-1H-pyrazol-4-yl)amino)-N-((1R,4R)-4-(2-hydroxypropan-2-yl)cyclohexyl) nicotinamide (254);

6-(6-chloropyrazolo[1,5-a]pyrimidin-3-yl)-N-(3-hydroxy-3-methylbutyl)-4-((1-methyl-1H-pyrazol-4-yl) amino)nicotinamide (255);

6-(6-chloropyrazolo[1,5-a]pyrimidin-3-yl)-N-((1R,4R)-4-(2-hydroxypropan-2-yl)cyclohexyl)-4-((1-methyl-1H-pyrazol-4-yl) amino)nicotinamide (256);

methyl((1R,4R)-4-(6-(6-chloropyrazolo[1,5-a]pyrimidin-3-yl)-4-((1-methyl-1H-pyrazol-4-yl)amino)nicotinamido)cyclohexyl)carbamate (257);

(R)-6-(7-cyanoimidazo[1,2-b]pyridazin-3-yl)-N-(2,3-difluoro-3-methylbutyl)-4-((1-2,2-difluoroethyl)-1H-pyrazol-4-yl)amino)nicotinamide (258);

(R)-6-(7-cyanoimidazo[1,2-b]pyridazin-3-yl)-4-((1-(3,3-difluorocyclobutyl)-1H-pyrazol-4-yl)amino)-N-(2-fluoro-3-hydroxy-3-methylbutyl) nicotinamide (259);

(R)-6-(7-cyanoimidazo[1,2-b]pyridazin-3-yl)-4-((1-2,2-difluoroethyl)-1H-pyrazol-4-yl)amino)-N-(2-fluoro-3-hydroxy-3-methylbutyl) nicotinamide (260);

(R)-6-(7-cyanoimidazo[1,2-b]pyridazin-3-yl)-N-(2,3-difluoro-3-methylbutyl)-4-((1-(2,2-difluoroethyl)-1H-pyrazol-4-yl)amino)nicotinamide (261);

(R)-6-(7-chloroimidazo[1,2-b]pyridazin-3-yl)-4-((1-2,2-difluoroethyl)-1H-pyrazol-4-yl) amino)-N-(2-fluoro-3-hydroxy-3-methylbutyl) nicotinamide (262);

(R)-6-(7-chloroimidazo[1,2-b]pyridazin-3-yl)-N-(2,3-difluoro-3-methylbutyl)-4-((1-(2,2-difluoroethyl)-1H-pyrazol-4-yl)amino)nicotinamide (263);

6-(7-chloroimidazo[1,2-b]pyridazin-3-yl)-4-((1-(2,2-difluoroethyl)-1H-pyrazol-4-yl)amino)-N-((1R,4R)-4-(2-hydroxypropan-2-yl)cyclohexyl)nicotinamide (264);

(R)-6-(7-cyanoimidazo[1,2-b]pyridazin-3-yl)-4-((1-(2,2-difluoropropyl)-1H-pyrazol-4-yl)amino)-N-(2-fluoro-3-hydroxy-3-methylbutyl)nicotinamide (265);

(R)-6-(7-chloroimidazo[1,2-b]pyridazin-3-yl)-4-((1-ethyl-1H-pyrazol-4-yl)amino)-N-(2-fluoro-3-hydroxy-3-methylbutyl) nicotinamide (266);

(R)-6-(7-cyanoimidazo[1,2-b]pyridazin-3-yl)-4-((1-ethyl-1H-pyrazol-4-yl)amino)-N-(2-fluoro-3-hydroxy-3-methylbutyl)nicotinamide (267);

(R)-6-(7-cyanoimidazo[1,2-b]pyridazin-3-yl)-4-((1-2,2-difluoropropyl)-1H-pyrazol-3-yl)amino)-N-(2-fluoro-3-hydroxy-3-methylbutyl)nicotinamide (268);

(R)-6-(7-cyanoimidazo[1,2-b]pyridazin-3-yl)-N-(2,3-difluoro-3-methylbutyl)-4-((1-(2,2-difluoropropyl)-1H-pyrazol-4-yl)amino)nicotinamide (269);

(R)-6-(7-chloroimidazo[1,2-b]pyridazin-3-yl)-4-((1-difluoromethyl)-1H-pyrazol-4-yl)amino)-N-(2-fluoro-3-hydroxy-3-methylbutyl)nicotinamide (270);

(R)-6-(7-chloroimidazo[1,2-b]pyridazin-3-yl)-N-(2-fluoro-3-hydroxy-3-methylbutyl)-4-((1-methyl-1H-pyrazol-4-yl)amino)nicotinamide (271);

(R)-6-(7-cyanoimidazo[1,2-b]pyridazin-3-yl)-4-((1-(2-fluoro-2-methylpropyl)-1H-pyrazol-3-yl) amino)-N-(2-fluoro-3-hydroxy-3-methylbutyl)nicotinamide (272);

(R)-6-(7-cyanoimidazo[1,2-b]pyridazin-3-yl)-4-((1(difluoromethyl)-1H-pyrazol-4-yl)amino)-N-(2-fluoro-3-hydroxy-3-methylbutyl)nicotinamide (273);

(R)-6-(7-cyanoimidazo[1,2-b]pyridazin-3-yl)-N-(2-fluoro-3-hydroxy-3-methylbutyl)-4-((1-methyl-1H-pyrazol-4-yl) amino)nicotinamide (274);

(R)-6-(7-chloroimidazo[1,2-b]pyridazin-3-yl)-N-(2-fluoro-3-hydroxy-3-methylbutyl)-4-((1-(2,2,2-trifluoroethyl)-1H-pyrazol-4-yl)amino)nicotinamide (275);

(R)-6-(7-cyanoimidazo[1,2-b]pyridazin-3-yl)-N-(2-fluoro-3-hydroxy-3-methylbutyl)-4-((1-(2,2,2-trifluoroethyl)-1H-pyrazol-4-yl)amino)nicotinamide (276);

(R)-6-(7-chloroimidazo[1,2-b]pyridazin-3-yl)-4-((1-3,3-difluorocyclobutyl)-1H-pyrazol-4-yl)amino)-N-(2-fluoro-3-hydroxy-3-methylbutyl)nicotinamide (277);

(R)-6-(7-cyanoimidazo[1,2-b]pyridazin-3-yl)-N-(2-fluoro-3-hydroxy-3-methylbutyl)-4-((1-propyl-1H-pyrazol-4-yl)amino)nicotinamide (278);

(R)-6-(7-cyanoimidazo[1,2-b]pyridazin-3-yl)-4-((1-(2-fluoro-2-methylpropyl)-1H-pyrazol-4-yl)amino)-N-(2-fluoro-3-hydroxy-3-methylbutyl)nicotinamide (279);

(R)-6-(7-cyanoimidazo[1,2-b]pyridazin-3-yl)-4-((5-(2,2-difluoroethyl)-4,5,6,7-tetrahydropyrazolo[1,5-a]pyrazin-2-yl)amino)-N-(2-fluoro-3-hydroxy-3-methylbutyl)nicotinamide (280);

(R)-6-(7-cyanoimidazo[1,2-b]pyridazin-3-yl)-N-(2-fluoro-3-hydroxy-3-methylbutyl)-4-((1-(3-fluoropropyl)-1H-pyrazol-4-yl)amino)nicotinamide (281);

(R)-6-(7-cyanoimidazo[1,2-b]pyridazin-3-yl)-N-(2,3-difluoro-3-methylbutyl)-4-((1-(2-fluoro-2-methylpropyl)-1H-pyrazol-4-yl)amino)nicotinamide (282);

(R)-6-(7-chloroimidazo[1,2-b]pyridazin-3-yl)-N-(2-fluoro-3-hydroxy-3-methylbutyl)-4-((1-(3-fluoropropyl)-1H-pyrazol-4-yl)amino)nicotinamide (283);

(R)-6-(7-cyanoimidazo[1,2-b]pyridazin-3-yl)-4-((1-cyclopropyl-1H-pyrazol-4-yl)amino)-N-(2-fluoro-3-hydroxy-3-methylbutyl)nicotinamide (284);

(R)-6-(7-chloroimidazo[1,2-b]pyridazin-3-yl)-4-((1-cyclobutyl-1H-pyrazol-4-yl)amino)-N-(2-fluoro-3-hydroxy-3-methylbutyl)nicotinamide (285);

6-(7-cyanoimidazo[1,2-b]pyridazin-3-yl)-4-((1-cyclopropyl-1H-pyrazol-4-yl)amino)-N-((1R,4R)-4-(2-hydroxypropan-2-yl)cyclohexyl) nicotinamide (286);

6-(7-cyanoimidazo[r 1,2-b]pyridazin-3-yl)-N-(3-hydroxy-3-methylbutyl)-4-((1-isopropyl-1H-pyrazol-4-yl)amino)nicotinamide (287); and 6-(7-cyanoimidazo[1,2-b]pyridazin-3-yl)-N—((R)-2-fluoro-3-hydroxy-3-methylbutyl)-4-(((R)-1-(5-fluoropyrimidin-2-yl) pyrrolidin-3-yl)amino)nicotinamide (288).

10. A pharmaceutical composition comprising one or more compounds according to claim 1 and a pharmaceutically acceptable carrier or diluent.

* * * * *

UNITED STATES PATENT AND TRADEMARK OFFICE
CERTIFICATE OF CORRECTION

PATENT NO. : 10,618,903 B2
APPLICATION NO. : 16/314574
DATED : April 14, 2020
INVENTOR(S) : Duncia et al.

It is certified that error appears in the above-identified patent and that said Letters Patent is hereby corrected as shown below:

On the Title Page

Item (57), Column 2, Line 1: Delete "Formula (I) Formula (I)" and insert -- Formula (I) --

In the Claims

In Claim 3, Column 256, Line 32-33: delete "fluoropyrmidinyl," and insert -- fluoropyrimidinyl, --

In Claim 7, Column 258, Line 7: delete "fluoropyrmidinyl," and insert -- fluoropyrimidinyl, --

In Claim 9, Column 260, Line 37: delete "vi)" and insert -- yl) --

In Claim 9, Column 261, Line 35: delete "((1-2,2-" and insert -- ((1-(2,2- --

In Claim 9, Column 261, Line 47: delete "[1,1,1]" and insert -- [1.1.1] --

In Claim 9, Column 262, Line 37: delete "vi)" and insert -- yl) --

In Claim 9, Column 263, Line 42: delete "nicotinamide(118);" and insert -- nicotinamide (118); --

In Claim 9, Column 264, Line 28: delete "vi)" and insert -- yl) --

In Claim 9, Column 264, Line 56: delete "[T 1,2-b]" and insert -- [1,2-b] --

In Claim 9, Column 265, Line 15: delete "vi)" and insert -- yl) --

In Claim 9, Column 267, Line 19: delete "[r 1,2-b]" and insert -- [1,2-b] --

In Claim 9, Column 267, Line 22: delete "[r 1,2-b]" and insert -- [1,2-b] --

Signed and Sealed this
Twenty-second Day of December, 2020

Andrei Iancu
*Director of the United States Patent and Trademark Office*

In Claim 9, Column 267, Line 28: delete "[r 1,2-b]" and insert -- [1,2-b] --

In Claim 9, Column 267, Line 31: delete "[r 1,2-b]" and insert -- [1,2-b] --

In Claim 9, Column 267, Line 44: delete "[r 1,2-b]" and insert -- [1,2-b] --

In Claim 9, Column 268, Line 28: delete "((1-2,2-" and insert -- ((1-(2,2- --

In Claim 9, Column 268, Line 44: delete "((1-2,2-" and insert -- ((1-(2,2- --

In Claim 9, Column 269, Line 1: delete "((1-2,2-" and insert -- ((1-(2,2- --

In Claim 9, Column 269, Line 23: delete "((1-2,2-" and insert -- ((1-(2,2- --

In Claim 9, Column 269, Line 47: delete "((1-2,2" and insert -- ((1-(2,2 --

In Claim 9, Column 269, Line 63: delete "((1-2,2" and insert -- ((1-(2,2 --

In Claim 9, Column 270, Line 1: delete "((1-2,2-" and insert -- ((1-(2,2- --

In Claim 9, Column 270, Line 7: delete "((1-2,2-" and insert -- ((1-(2,2- --

In Claim 9, Column 270, Line 13: delete "((1-2,2" and insert -- ((1-(2,2 --

In Claim 9, Column 270, Line 26: delete "((1-2,2-" and insert -- ((1-(2,2- --

In Claim 9, Column 271, Line 19: delete "[r 1,2-b]" and insert -- [1,2-b] --